US012508384B2

(12) United States Patent
Law et al.

(10) Patent No.: US 12,508,384 B2
(45) Date of Patent: Dec. 30, 2025

(54) CUSHION MODULE FOR A PATIENT INTERFACE

(71) Applicant: RESMED PTY LTD, Bella Vista (AU)

(72) Inventors: Kam Man Law, Sydney (AU); Michael Kenneth Truscott, Sydney (AU); Rupert Christian Scheiner, Sydney (AU); Yun Hol Chan, Singapore (SG); Weiyi Chia, Singapore (SG); Chuan Foong Lee, Johor (MY); Beng Hai Tan, Singapore (SG)

(73) Assignee: ResMed Pty Ltd

( * ) Notice: Subject to any disclaimer, the term of this patent is extended or adjusted under 35 U.S.C. 154(b) by 974 days.

(21) Appl. No.: 17/629,180

(22) PCT Filed: Jul. 22, 2020

(86) PCT No.: PCT/AU2020/050749
§ 371 (c)(1),
(2) Date: Jan. 21, 2022

(87) PCT Pub. No.: WO2021/012005
PCT Pub. Date: Jan. 28, 2021

(65) Prior Publication Data

US 2022/0296837 A1 Sep. 22, 2022

(30) Foreign Application Priority Data

Jul. 22, 2019 (AU) ................................ 2019902580
Dec. 20, 2019 (AU) ................................ 2019904852
(Continued)

(51) Int. Cl.
*A61M 16/06* (2006.01)

(52) U.S. Cl.
CPC .... *A61M 16/0622* (2014.02); *A61M 16/0683* (2013.01)

(58) Field of Classification Search
CPC .......................................... A61M 16/06–0694
(Continued)

(56) References Cited

U.S. PATENT DOCUMENTS 2,376,871 A 5/1945 Fink
3,122,171 A 2/1964 Britton et al.
(Continued)

FOREIGN PATENT DOCUMENTS

AU 2017228699 A1 10/2017
CN 101142000 A 3/2008
(Continued)

OTHER PUBLICATIONS

"*Respiratory Physiology*", by John B. West, Lippincott Williams & Wilkins, 9th edition published 2012 (8 pages).
(Continued)

*Primary Examiner* — Paige Kathleen Bugg
(74) *Attorney, Agent, or Firm* — Nixon & Vanderhye P.C.

(57) ABSTRACT

A patient interface is disclosed, comprising a chassis portion having a pair of laterally projecting connection portions configured to connect to gas delivery tubes, a seal-forming structure and a vent. The seal forming structure may comprise a central portion configured to seal in use against an inferior periphery of the patients nose and a pair of lateral posterior regions. Each lateral posterior region may comprise a decoupling portion configured to at least partially decouple the central portion from a respective one of the laterally projecting connection portions. The seal-forming structure may comprise rigidising portions, a central anterior portion having a superior portion stiffer than an inferior portion, mid-lateral anterior portions having superior portions stiffer than inferior portions, and/or a lip superior portion having an anterior portion stiffer than a posterior portion. The chassis portion may be formed from a flexible
(Continued)

material and may comprise chassis superior reinforcing portions.

23 Claims, 111 Drawing Sheets

(30) Foreign Application Priority Data

| | | |
|---|---|---|
| Feb. 27, 2020 | (SG) | 10202001774V |
| May 29, 2020 | (AU) | 2020901769 |
| May 29, 2020 | (AU) | 2020901770 |

(58) Field of Classification Search
USPC .................................................... 128/206.26
See application file for complete search history.

(56) References Cited

U.S. PATENT DOCUMENTS

| | | | |
|---|---|---|---|
| 3,513,844 | A | 5/1970 | Smith |
| 4,535,767 | A | 8/1985 | Tiep et al. |
| 4,782,832 | A | 11/1988 | Trimble et al. |
| 4,878,491 | A | 11/1989 | Mcgilvray, III |
| 4,944,310 | A | 7/1990 | Sullivan |
| 5,018,519 | A | 5/1991 | Brown |
| 5,069,222 | A | 12/1991 | Mcdonald, Jr. |
| 5,233,978 | A | 8/1993 | Callaway |
| 5,269,296 | A | 12/1993 | Landis |
| 5,438,979 | A | 8/1995 | Johnson, Jr. et al. |
| 5,538,000 | A | 7/1996 | Rudolph |
| 5,687,715 | A | 11/1997 | Landis |
| 6,021,816 | A | 2/2000 | Jeltsch et al. |
| 6,044,844 | A | 4/2000 | Kwok et al. |
| 6,478,026 | B1 | 11/2002 | Wood |
| 6,532,959 | B1 | 3/2003 | Berthon-Jones |
| 6,581,594 | B1 | 6/2003 | Drew et al. |
| 6,595,215 | B2 | 7/2003 | Wood |
| 6,679,265 | B2 | 1/2004 | Strickland et al. |
| 7,080,645 | B2 | 7/2006 | Genger et al. |
| 7,178,525 | B2 | 2/2007 | Matula, Jr. et al. |
| 7,370,652 | B2 | 5/2008 | Matula, Jr. et al. |
| 7,735,490 | B2 | 6/2010 | Rinaldi |
| 7,856,982 | B2 | 12/2010 | Matula, Jr. et al. |
| 7,866,944 | B2 | 1/2011 | Kenyon et al. |
| 7,900,628 | B2 | 3/2011 | Matula, Jr. et al. |
| 7,975,694 | B2 | 7/2011 | Ho |
| 8,025,057 | B2 | 9/2011 | Ging et al. |
| 8,297,285 | B2 | 10/2012 | Henry et al. |
| 8,636,479 | B2 | 1/2014 | Kenyon et al. |
| 8,638,014 | B2 | 1/2014 | Sears et al. |
| 8,648,259 | B2 | 2/2014 | Gniewek et al. |
| 8,667,962 | B2 | 3/2014 | Kenyon et al. |
| 8,733,349 | B2 | 5/2014 | Bath et al. |
| 8,770,230 | B2 | 7/2014 | Steinhanses et al. |
| 8,826,909 | B2 | 9/2014 | Nashed et al. |
| 8,985,115 | B2 | 3/2015 | Baecke et al. |
| 9,162,034 | B2 | 10/2015 | Veliss et al. |
| 9,365,004 | B2 | 6/2016 | Forrester |
| 9,517,319 | B2 | 12/2016 | Omura et al. |
| 9,731,090 | B2 | 8/2017 | Ovzinsky et al. |
| 9,764,107 | B2 | 9/2017 | Grashow et al. |
| 9,981,104 | B1 | 5/2018 | Groll et al. |
| 10,071,216 | B2 | 9/2018 | Rutan |
| 10,357,626 | B1 | 7/2019 | Baker |
| 10,441,738 | B2 | 10/2019 | Formica et al. |
| 10,744,291 | B2 | 8/2020 | Kwok et al. |
| 2004/0025885 | A1 | 2/2004 | Payne, Jr. |
| 2005/0092329 | A1 | 5/2005 | Sta-Maria |
| 2005/0205096 | A1 | 9/2005 | Matula, Jr. et al. |
| 2005/0284481 | A1 | 12/2005 | Meyer et al. |
| 2006/0213521 | A1 | 9/2006 | Radney |
| 2006/0231102 | A1 | 10/2006 | Bordewick et al. |
| 2007/0131229 | A1 | 6/2007 | Madaus et al. |
| 2007/0246043 | A1 | 10/2007 | Kwok et al. |
| 2008/0047560 | A1 | 2/2008 | Veliss et al. |
| 2008/0053451 | A1 | 3/2008 | Bordewick et al. |
| 2008/0060649 | A1 | 3/2008 | Veliss et al. |
| 2009/0044808 | A1 | 2/2009 | Guney et al. |
| 2009/0050156 | A1 | 2/2009 | Ng et al. |
| 2009/0065005 | A1 | 3/2009 | Ades |
| 2009/0078259 | A1 | 3/2009 | Kooij |
| 2010/0000534 | A1 | 1/2010 | Kooij et al. |
| 2010/0018534 | A1 | 1/2010 | Veliss et al. |
| 2010/0313891 | A1 | 12/2010 | Veliss et al. |
| 2011/0000492 | A1 | 1/2011 | Veliss et al. |
| 2011/0030692 | A1 | 2/2011 | Jones et al. |
| 2011/0240031 | A1 | 10/2011 | Jaffre |
| 2011/0247619 | A1 | 10/2011 | Formica et al. |
| 2011/0247628 | A1 | 10/2011 | Ho et al. |
| 2011/0253144 | A1 | 10/2011 | Groll |
| 2011/0265796 | A1 | 11/2011 | Amarasinghe et al. |
| 2012/0067349 | A1 | 3/2012 | Barlow et al. |
| 2012/0204881 | A1 | 8/2012 | Davidson et al. |
| 2012/0266890 | A1 | 10/2012 | Baecke et al. |
| 2012/0325219 | A1 | 12/2012 | Smith |
| 2013/0139822 | A1 | 6/2013 | Gibson et al. |
| 2013/0213400 | A1 | 8/2013 | Barlow et al. |
| 2013/0319408 | A1 | 12/2013 | Zwolinsky |
| 2014/0000616 | A1 | 1/2014 | Haibach |
| 2014/0090649 | A1 | 4/2014 | Groll et al. |
| 2014/0102456 | A1 | 4/2014 | Ovizinksy |
| 2014/0137870 | A1 | 5/2014 | Barlow |
| 2014/0158136 | A1 | 6/2014 | Romagnoli et al. |
| 2014/0251338 | A1 | 9/2014 | Asvadi et al. |
| 2015/0083136 | A1 | 3/2015 | Grashow et al. |
| 2015/0128949 | A1 | 5/2015 | Jablonski |
| 2015/0128954 | A1* | 5/2015 | Smith ............... A61M 16/0875 128/206.24 |
| 2015/0182719 | A1 | 7/2015 | Grashow et al. |
| 2015/0238423 | A1 | 8/2015 | Wertz et al. |
| 2015/0328423 | A1 | 11/2015 | Siew et al. |
| 2015/0352306 | A1 | 12/2015 | Scheiner et al. |
| 2016/0030696 | A1 | 2/2016 | Klenner et al. |
| 2016/0082214 | A1 | 3/2016 | Barlow et al. |
| 2016/0095996 | A1 | 4/2016 | Gusky et al. |
| 2016/0151597 | A1 | 6/2016 | Baecke et al. |
| 2016/0296720 | A1 | 10/2016 | Henry et al. |
| 2017/0049983 | A1 | 2/2017 | Ellis et al. |
| 2017/0119988 | A1* | 5/2017 | Allan ............... A61M 16/0683 |
| 2017/0224944 | A1 | 8/2017 | Gunaratnam et al. |
| 2017/0246411 | A1 | 8/2017 | Mashal et al. |
| 2017/0246412 | A1 | 8/2017 | Melidis et al. |
| 2017/0291004 | A1 | 10/2017 | Ng et al. |
| 2017/0312466 | A1 | 11/2017 | Manning |
| 2017/0312468 | A1 | 11/2017 | Formica et al. |
| 2017/0326320 | A1 | 11/2017 | Baignet et al. |
| 2017/0326321 | A1 | 11/2017 | Grashow et al. |
| 2017/0333658 | A1 | 11/2017 | Haibach |
| 2018/0043120 | A1 | 2/2018 | Hunley et al. |
| 2018/0099113 | A1 | 4/2018 | Bell et al. |
| 2018/0140795 | A1 | 5/2018 | Wells et al. |
| 2018/0177965 | A1 | 6/2018 | Patel et al. |
| 2018/0236198 | A1* | 8/2018 | Veliss ............... A61M 16/0622 |
| 2018/0264218 | A1 | 9/2018 | Chodkowski et al. |
| 2018/0272095 | A1 | 9/2018 | Eves et al. |
| 2018/0318539 | A1 | 11/2018 | Scheiner et al. |
| 2019/0009045 | A1 | 1/2019 | Bernard |
| 2019/0022343 | A1 | 1/2019 | Kooij et al. |
| 2019/0070379 | A1 | 3/2019 | Lockhart et al. |
| 2019/0091428 | A1 | 3/2019 | Chodkowski et al. |
| 2019/0091431 | A1 | 3/2019 | Formica et al. |
| 2019/0125996 | A1 | 5/2019 | Bentley et al. |
| 2019/0224343 | A1 | 7/2019 | Gazendam |
| 2019/0240436 | A1 | 8/2019 | Romagnoli et al. |
| 2019/0298958 | A1 | 10/2019 | O'Connor |
| 2020/0016358 | A1 | 1/2020 | Bornholdt et al. |
| 2021/0038848 | A1 | 2/2021 | Eves et al. |

FOREIGN PATENT DOCUMENTS

| | | | |
|---|---|---|---|
| CN | 101405046 | A | 4/2009 |
| CN | 101495170 | A | 7/2009 |
| CN | 102791314 | A | 11/2012 |
| CN | 104602745 | A | 5/2015 |

(56) References Cited

FOREIGN PATENT DOCUMENTS

| | | | | |
|---|---|---|---|---|
| CN | 109152903 A | 1/2019 | | |
| CN | 213884641 U | 8/2021 | | |
| CN | 214633323 U | 11/2021 | | |
| JP | 2017-527365 | 9/2017 | | |
| JP | 2019-502492 A | 1/2019 | | |
| JP | 2019-514542 A | 6/2019 | | |
| WO | WO 98/004310 A1 | 2/1998 | | |
| WO | WO 98/034665 A1 | 8/1998 | | |
| WO | WO 2000/078381 A1 | 12/2000 | | |
| WO | WO 2004/073778 A1 | 9/2004 | | |
| WO | WO 2005/063328 A1 | 7/2005 | | |
| WO | 2005/076874 | 8/2005 | | |
| WO | 2005/086943 | 9/2005 | | |
| WO | 2005/099801 | 10/2005 | | |
| WO | WO 2006/074513 A1 | 7/2006 | | |
| WO | WO 2006/130903 A1 | 12/2006 | | |
| WO | 2007/028877 | 3/2007 | | |
| WO | 2008/011682 | 1/2008 | | |
| WO | 2008/011683 | 1/2008 | | |
| WO | 2008/070929 | 6/2008 | | |
| WO | WO 2009/052560 A1 | 4/2009 | | |
| WO | 2009/139647 | 11/2009 | | |
| WO | 2010/131189 | 11/2010 | | |
| WO | 2010/139014 | 12/2010 | | |
| WO | WO 2010/135785 A1 | 12/2010 | | |
| WO | 2011/059346 | 5/2011 | | |
| WO | 2011/110962 | 11/2011 | | |
| WO | 2012/061783 | 5/2012 | | |
| WO | 2012/107858 | 8/2012 | | |
| WO | 2012/154064 | 11/2012 | | |
| WO | WO 2012/171072 A1 | 12/2012 | | |
| WO | WO-2013006913 A1 | * | 1/2013 | ............ A61M 16/06 |
| WO | WO 2013/020167 A1 | 2/2013 | | |
| WO | 2013/156960 | 10/2013 | | |
| WO | 2014/013371 | 1/2014 | | |
| WO | 2014/077708 | 5/2014 | | |
| WO | 2014/110626 | 7/2014 | | |
| WO | 2015/125080 | 8/2015 | | |
| WO | 2016/032343 A1 | 3/2016 | | |
| WO | 2016/108116 A1 | 7/2016 | | |
| WO | 2016/193859 | 12/2016 | | |
| WO | 2017/037638 | 3/2017 | | |
| WO | 2017/044392 | 3/2017 | | |
| WO | 2017/049361 A1 | 3/2017 | | |
| WO | 2017/124152 | 7/2017 | | |
| WO | 2017/124155 | 7/2017 | | |
| WO | 2017/185140 | 11/2017 | | |
| WO | WO-2017185140 A1 | * | 11/2017 | ........ A61M 16/0066 |
| WO | 2018/085889 A1 | 5/2018 | | |
| WO | 2018/176094 | 10/2018 | | |
| WO | WO-2019183680 A1 | * | 10/2019 | ........ A61M 16/0605 |
| WO | 2020/000033 A1 | 1/2020 | | |
| WO | 2020/009589 A1 | 10/2020 | | |

OTHER PUBLICATIONS

International Search Report dated Oct. 2, 2020 issued in International Application No. PCT/AU2020/050749 (14 pages).

Written Opinion of the International Searching Authority dated Oct. 2, 2020 issued in International Application No. PCT/AU2020/050749 (13 pages).

International Preliminary Report on Patentability dated Nov. 8, 2021 issued in International Application No. PCT/AU2020/050749 (15 pages).

Examination Report dated Jul. 10, 2023 issued in Australian Application No. 2020318577 (5 pages).

Extended European Search Report dated Jul. 10, 2023 issued in European Application No. 20843057.9 (11 pages).

Office Action dated May 29, 2023 issued in Japanese Application No. 2022-504249 with English translation (10 pages).

Office Action dated Sep. 30, 2024 issued in Japanese Application No. 2024-004506 with English translation (7 pages).

Office Action dated Nov. 29, 2024 issued in Chinese Application No. 202010713844.6 with English translation (23 pages).

* cited by examiner

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Relatively Large
Positive Curvature

Relatively Small
Positive Curvature

Zero Curvature

Relatively Small
Negative Curvature

Relatively Large
Negative Curvature

Copyright 2015 ResMed Limited

Copyright 2015 ResMed Limited

Copyright 2015 ResMed Limited

Copyright 2015 ResMed Limited

CUSHION MODULE FOR A PATIENT INTERFACE

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

1 CROSS-REFERENCE TO RELATED APPLICATIONS

This application is the U.S. national phase of International Application No. PCT/AU2020/050749 filed 22 Jul. 2020 which designated the U.S. and claims priority to Australian Patent Application No. 2019902580 filed 22 Jul. 2019, Australian Patent Application No. 2019904852 filed 20 Dec. 2019, Singaporean patent application number 10202001774V filed 27 Feb. 2020, Australian Patent Application No. 2020901769 filed 29 May 2020 and Australian Patent Application No. 2020901770 filed 29 May 2020, the entire contents of each of which are hereby incorporated by reference in their entirety.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See “Respiratory Physiology”, by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hypoventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Respiratory failure is an umbrella term for respiratory disorders in which the lungs are unable to inspire sufficient oxygen or exhale sufficient $CO_2$ to meet the patient’s needs. Respiratory failure may encompass some or all of the following disorders: Obesity Hypoventilation Syndrome (OHS), Chronic Obstructive Pulmonary Disease (COPD), Neuromuscular Disease (NMD) and chest wall disorders.

A patient with respiratory insufficiency (a form of respiratory failure) may experience abnormal shortness of breath on exercise.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fits and is comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.1.3 Pressurised Air Conduit

In one type of treatment system, a flow of pressurised air is provided to a patient interface through a conduit in an air circuit that fluidly connects to the patient interface so that, when the patient interface is positioned on the patient's face during use, the conduit extends out of the patient interface forwards away from the patient's face. This may sometimes be referred to as an "elephant trunk" style of interface.

Some patients find such interfaces to be unsightly and are consequently deterred from wearing them, reducing patient compliance. Additionally, conduits connecting to an interface at the front of a patient's face may sometimes be vulnerable to becoming tangled up in bed clothes.

2.2.3.1.4 Pressurised Air Conduit Used for Positioning/Stabilising the Seal-Forming Structure An alternative type of treatment system which seeks to address these problems comprises a patient interface in which a tube that delivers pressurised air to the patient's airways also functions as part of the headgear to position and stabilise the seal-forming portion of the patient interface to the appropriate part of the patient's face. This type of patient interface may be referred to as incorporating 'headgear tubing' or 'conduit headgear'. Such patient interfaces allow the conduit in the air circuit providing the flow of pressurised air from a respiratory pressure therapy device to connect to the patient interface in a position other than in front of the patient's face. One example of such a treatment system is disclosed in US Patent Publication No. US 2007/0246043, the contents of which are incorporated herein by reference, in which the conduit connects to a tube in the patient interface through a port positioned in use on top of the patient's head.

Patient interfaces incorporating headgear tubing may provide some advantages, for example avoiding a conduit connecting to the patient interface at the front of a patient's face, which may be unsightly and obtrusive. However, it is desirable for patient interfaces incorporating headgear tubing to be comfortable for a patient to wear over a prolonged duration when the patient is asleep while forming an effective seal with the patient's face.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition, in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers.

While a number of medical humidifiers are known, they can suffer from one or more shortcomings. Some medical humidifiers may provide inadequate humidification, some are difficult or inconvenient to use by patients.

2.2.3.4 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focused airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 $cmH_2O$ pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(* one specimen only, measured using test method specified in ISO 3744 in CPAP mode at 10 $cmH_2O$)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

One form of the present technology comprises a patient interface for delivery of a supply of pressurised breathable gas to an entrance of a patient's airways.

One aspect of the present technology comprises a patient interface having a plenum chamber pressurisable to a therapeutic pressure of at least 6 $cmH_2O$ above ambient air pressure. The plenum chamber may be at least partially formed by a chassis portion and a seal-forming structure of the patient interface.

One aspect of the present technology is a cushion module for a patient interface, the cushion module comprising a chassis portion and a seal-forming structure.

3.1 Decoupling Portions in Lateral Posterior Regions of Seal-Forming Structure One aspect of one form of the present technology is a patient interface, or a cushion module for a patient interface, comprising a chassis portion and a seal-forming structure together forming a plenum chamber. The chassis portion may comprise laterally projecting connection portions configured for connection to gas delivery tubes. The seal-forming structure may comprise a central portion configured to seal in use against an inferior periphery of the patient's nose surrounding the patient's nares. The seal-forming structure may comprise decoupling portions each configured to at least partially decouple the central portion from a respective one of the laterally projecting connection portions. The seal-forming structure may further comprise peripheral portions adjacent the decoupling portions and being stiffer and/or thicker than the decoupling portions.

One aspect of one form of the present technology is a patient interface comprising:

- a chassis portion partially forming a plenum chamber pressurisable to a therapeutic pressure of at least 6 $cmH_2O$ above ambient air pressure, the chassis portion comprising a pair of laterally projecting connection portions configured to connect to gas delivery tubes and being sized and structured to receive a flow of air at the therapeutic pressure for breathing by a patient;

a seal-forming structure provided to the chassis portion and partially forming the plenum chamber, the seal-forming structure being constructed and arranged to form a seal with a region of the patient's face surrounding an entrance to the patient's airways, the seal-forming structure having at least one hole therein such that the flow of air at the therapeutic pressure is delivered to at least an entrance to the patient's nares, the seal-forming structure constructed and arranged to maintain said therapeutic pressure in the plenum chamber throughout the patient's respiratory cycle in use;

a vent to allow a flow of gases exhaled by the patient from an interior of the plenum chamber to ambient, said vent being sized and shaped to maintain the therapeutic pressure in the plenum chamber in use;

wherein the seal forming structure comprises:

a central portion configured to seal in use against at least the patient's pronasale, nasal alae and lip superior;

a pair of lateral posterior regions provided on respective lateral posterior sides of the seal-forming structure, each lateral posterior region comprising:

a decoupling portion configured to at least partially decouple the central portion of the seal-forming structure from a respective one of the laterally projecting connection portions, the decoupling portion being located in a portion of the lateral posterior region that is configured to face away from and not contact the patient's face during use; and a peripheral portion provided adjacent the decoupling portion, at least part of the peripheral portion being located posterior to the decoupling portion, wherein the decoupling portion has a stiffness less than a stiffness of the peripheral portion.

In examples: (a) the stiffness of each peripheral portion is greater than a stiffness of the central portion of the seal-forming structure; (b) the stiffness of the decoupling portion of each lateral posterior region is greater than the stiffness of the central portion of the seal-forming structure; (c) a wall thickness of the peripheral portion of each lateral posterior region is greater than a wall thickness of the central portion of the seal-forming structure; (d) the wall thickness of the peripheral portion of each lateral posterior region is greater than a wall thickness of the decoupling portion of each lateral posterior region; (e) the wall thickness of the decoupling portion of each lateral posterior region is greater than the wall thickness of the central portion of the seal-forming structure; (f) the decoupling portion of each lateral posterior region is C-shaped when viewed from a lateral side of the seal-forming structure; (g) each of the peripheral portions partially or fully surrounds a respective decoupling portion; (h) each decoupling portion is formed by a recess in an internal surface of the seal-forming structure within the respective lateral posterior region; (i) the patient interface further comprises a positioning and stabilising structure to provide a force to hold the seal-forming structure in a therapeutically effective position on the patient's head; (j) the patient interface further comprises the gas delivery tubes, and the gas delivery tubes form part of the positioning and stabilising structure, each gas delivery tube being configured to convey the flow of air from a location atop the patient's head to the interior of the chassis portion in use; (k) the central portion of the seal-forming structure is formed from a textile material; (l) the central portion of the seal-forming structure is formed from silicone or another elastomeric material; (m) the lateral posterior regions are formed from silicone or another elastomeric material; (n) the chassis portion is formed from a flexible material; (o) the chassis portion is formed from silicone; (p) the patient interface comprises a removable cushion module, the removable cushion module comprising the chassis portion and the seal-forming structure; and/or (q) the chassis portion is formed from an elastomeric material.

One aspect of one form of the present technology is a patient interface comprising a chassis portion and a seal-forming structure together at least partially forming a plenum chamber pressurisable to a therapeutic pressure of at least 6 $cmH_2O$ above ambient air pressure. The chassis portion may comprise a pair of laterally projecting connection portions configured to connect to gas delivery tubes and being sized and structured to receive a flow of air at the therapeutic pressure for breathing by a patient. The seal-forming structure may be supported by the chassis portion and may have at least one hole therein such that the flow of air at the therapeutic pressure is delivered to at least an entrance to the patient's nares, the seal-forming structure being constructed and arranged to maintain said therapeutic pressure in the plenum chamber throughout the patient's respiratory cycle in use.

The seal forming structure may comprise a central portion configured to form a seal in use against the patient's face surrounding the patient's nares and without contacting the bridge of the patient's nose. The seal-forming structure may further comprise a pair of lateral posterior regions provided on respective lateral posterior sides of the seal-forming structure. Each lateral posterior region may comprise a decoupling portion configured to at least partially decouple the central portion of the seal-forming structure from a respective one of the laterally projecting connection portions. Each lateral posterior region may comprise a peripheral portion at least partially surrounding the respective decoupling portion. At least part of the peripheral portion may be located posterior to the respective decoupling portion. The decoupling portions may be thicker than the peripheral portions.

3.2 Rigidising Portions in Seal-Forming Structure

One aspect of one form of the present technology is a patient interface, or a cushion module for a patient interface, comprising a chassis portion and a seal-forming structure together forming a plenum chamber. The seal-forming structure may comprise a central portion configured to seal in use against an inferior periphery of the patient's nose surrounding the patient's nares. The seal-forming structure may further comprise mid-lateral portions on either side of the central portion and being configured to lie alongside the patient's nasal ala. The seal-forming structure may further comprise rigidising portions located on at least a posterior side of the seal-forming structure. The rigidising portions may be stiffer and/or thicker than the mid-lateral portions. The mid-lateral portions may be stiffer and/or thicker than the central portion.

One aspect of one form of the present technology is a patient interface comprising:

a chassis portion partially forming a plenum chamber pressurisable to a therapeutic pressure of at least 6$cmH_2O$ above ambient air pressure, the chassis portion being sized and structured to receive a flow of air at the therapeutic pressure for breathing by a patient; and a seal-forming structure provided to the chassis portion, the seal-forming structure partially forming the plenum chamber and being constructed and arranged to form a seal with a region of the patient's face surrounding an entrance to the patient's airways, the seal-forming structure having at least one hole therein such that the flow of air at the therapeutic pressure is delivered to at least an entrance to the patient's nares, the seal-forming structure constructed and arranged to maintain said therapeutic pressure in the plenum chamber throughout the patient's respiratory cycle in use;

a vent to allow a flow of gases exhaled by the patient from an interior of the plenum chamber to ambient, said vent being sized and shaped to maintain the therapeutic pressure in the plenum chamber in use;

wherein the seal forming structure comprises:

a central portion provided to a posterior side of the seal-forming structure, the central portion configured to seal in use against at least the patient's pronasale, nasal alae and lip superior;

a pair of mid-lateral portions provided on the posterior side of the seal-forming structure, each mid-lateral portion provided on a respective lateral side of the central portion and configured to lie alongside a respective nasal ala of the patient's nose in use, each mid-lateral portion having a stiffness greater than a stiffness of the central portion; and a pair of rigidising portions, each of the rigidising portions extending from the posterior side of the seal-forming structure to an anterior side of the seal-forming structure configured to face away from the patient's face during use, each rigidising portion located on a respective lateral side of the seal-forming structure, and each rigidising portion having a stiffness greater than the stiffness of the mid-lateral portions.

In examples: (a) each rigidising portion has negative curvature along a first path from the posterior side of the seal-forming structure to the anterior side of the seal-forming structure; (b) each rigidising portion has zero curvature or negative curvature along a second path that is perpendicular to the first path; (c) each rigidising portion comprises an anterior portion provided to the anterior side of the seal-forming structure and a posterior portion provided to the posterior side of the seal-forming structure, wherein the anterior portion has a stiffness greater than a stiffness of the posterior portion; (d) the anterior portion of each rigidising portion comprises a thickness greater than a thickness of the posterior portion of the rigidising portion; (e) each rigidising portion comprises a tapered increase in thickness between the posterior portion of the rigidising portion and the anterior portion of the rigidising portion; (f) the stiffness of the anterior portion of the rigidising portion is greater than a stiffness of an adjacent portion of the seal-forming structure on the anterior side thereof; (g) the thickness of the anterior portion of the rigidising portion is greater than a thickness of the adjacent portion of the seal-forming structure on the anterior side thereof; (h) the stiffness of the posterior portion of the rigidising portion is greater than a stiffness of an adjacent portion of the posterior side of the seal-forming structure; (i) the thickness of the posterior portion of the rigidising portion is greater than a thickness of the adjacent portion on the posterior side of the seal-forming structure; (j) each rigidising portion comprises a greater wall thickness than adjacent regions, the greater wall thickness being formed by extra thickness of an internal surface of the seal-forming structure; (k) each rigidising portion is located in use proximate a respective one of the patient's nasal ala; (l) the chassis portion comprises a pair of laterally projecting connection portions configured to connect to gas delivery tubes each configured to connect to and receive the flow of gas from a respective one of a pair of gas delivery tubes; (m) the patient interface comprises a positioning and stabilising structure to provide a force to hold the seal-forming structure in a therapeutically effective position on the patient's head, the positioning and stabilising structure comprising the gas delivery tubes, each gas delivery tube configured to receive the flow of air from a connection port on top of the patient's head and to deliver the flow of air to a respective one of the laterally projecting connection portions of the chassis portion; (n) each rigidising portion is located proximate a respective one of the laterally projecting connection portions; (o) the chassis portion is formed from a flexible material; (p) the chassis portion is formed from silicone or another elastomeric material; (q) the central portion of the seal-forming structure is formed from a textile material; (r) the central portion of the seal-forming structure is formed from silicone or another elastomeric material; and/or (s) the rigidising portions are formed from silicone or another elastomeric material.

One aspect of one form of the present technology is a patient interface comprising a chassis portion and a seal-forming structure together at least partially forming a plenum chamber pressurisable to a therapeutic pressure of at least 6 $cmH_2O$ above ambient air pressure. The seal-forming structure may be supported by the chassis portion and may have at least one hole therein such that the flow of air at the therapeutic pressure is delivered to at least an entrance to the patient's nares, the seal-forming structure being constructed and arranged to maintain said therapeutic pressure in the plenum chamber throughout the patient's respiratory cycle in use.

The seal forming structure may comprise a central portion on a posterior side of the seal-forming structure and configured to form a seal in use against the patient's face surrounding the patient's nares and without contacting the bridge of the patient's nose. The seal-forming structure may comprise a pair of rigidising portions, each rigidising portion located on a respective lateral side of the seal-forming structure. Each rigidising portion may have an anterior portion on non-patient contacting side of the seal-forming structure and a posterior portion on a patient-contacting side of the seal-forming structure. The anterior portion may be thicker than the posterior portion.

3.3 Mid-Lateral Posterior Support Portions in Seal-Forming Structure

One aspect of one form of the present technology is a patient interface, or a cushion module for a patient interface, comprising a chassis portion and a seal-forming structure together forming a plenum chamber. The seal-forming structure may comprise a central portion configured to seal in use against an inferior periphery of the patient's nose surrounding the patient's nares. The seal-forming structure may further comprise mid-lateral portions on either side of the central portion and configured to lie alongside the patient's nasal ala. The seal-forming structure may further comprise a pair of mid-lateral posterior support portions each located proximate a junction between the central portion and a respective mid-lateral portion. Each mid-lateral posterior support portion may have a stiffness and/or thickness greater than the stiffness of the central portion and less than the stiffness of each mid-lateral portion.

One aspect of one form of the present technology is a patient interface comprising:

a chassis portion partially forming a plenum chamber pressurisable to a therapeutic pressure of at least 6 $cmH_2O$ above ambient air pressure, the chassis portion being sized and structured to receive a flow of air at the therapeutic pressure for breathing by a patient a seal-forming structure provided to the chassis portion, the seal-forming structure partially forming the plenum chamber and being constructed and arranged to form a seal with a region of the patient's face surrounding an entrance to the patient's airways, the seal-forming structure having at least one hole therein such that the flow of air at the therapeutic pressure is delivered to at least an entrance to the patient's nares, the seal-forming structure constructed and arranged to maintain said therapeutic pressure in the plenum chamber throughout the patient's respiratory cycle in use;

a vent to allow a flow of gases exhaled by the patient from an interior of the plenum chamber to ambient, said vent being sized and shaped to maintain the therapeutic pressure in the plenum chamber in use;

wherein the seal forming structure comprises:

a central portion provided to a posterior side of the seal-forming structure, the central portion configured to seal in use against at least the patient's pronasale, nasal alae and lip superior;

a pair of mid-lateral portions provided to the posterior side of the seal-forming structure, each mid-lateral portion provided on a respective lateral side of the central portion, each mid-lateral portion having a stiffness greater than a stiffness of the central portion;

a pair of mid-lateral posterior support portions provided to the posterior side of the seal-forming structure, each provided proximate a junction between the central portion and a respective mid-lateral portion and being configured to lie proximate a respective lateral posterior corner of the base of the patient's nose in use, each mid-lateral posterior support portion having a stiffness greater than the stiffness of the central portion and less than the stiffness of each mid-lateral portion.

In examples: (a) the seal-forming structure comprises a pair of posterior corner portions configured to engage with the patient's face proximate the patient's nasolabial sulci in use, the stiffness of each mid-lateral posterior support portion being less than a stiffness of each posterior corner portions; (b) the stiffness of each posterior corner portion is greater than the stiffness of each mid-lateral portion; (c) each mid-lateral portion comprises a thickness greater than a thickness of the central portion; (d) the thickness of each mid-lateral posterior support portion is greater than the thickness of the central portion; (e) the thickness of each mid-lateral posterior support portion is less than the thickness of each mid-lateral portion; (f) the thickness of each mid-lateral posterior support portion is less than a thickness of each posterior corner portion; (g) the thickness of each posterior corner portion is greater than the thickness of the mid-lateral portions; (h) the thickness of each mid-lateral posterior support portion is tapered and increases towards the respective adjacent mid-lateral portion; (i) the tapered thickness of each mid-lateral posterior support portion increases to the thickness of the respective adjacent mid-lateral portion; (j) the thickness of each mid-lateral support portion may be in the range of 0.3-0.7 mm; and/or (k) the thickness of each mid-lateral support portion may be in the range of 0.4-0.6 mm.

In further examples: (a) the chassis portion comprises a pair of laterally projecting connection portions each configured to connect to and receive the flow of gas from a respective one of a pair of gas delivery tubes; (b) wherein the patient interface comprises a positioning and stabilising structure to provide a force to hold the seal-forming structure in a therapeutically effective position on the patient's head, the positioning and stabilising structure comprising the gas delivery tubes, each gas delivery tube configured to receive the flow of air from a connection port on top of the patient's head and to deliver the flow of air to a respective one of the laterally projecting connection portions of the chassis portion; (c) the central portion of the seal-forming structure is formed from a textile material; (d) the central portion of the seal-forming structure is formed from silicone or another elastomeric material; (e) the laterally posterior regions are formed from silicone or another elastomeric material; (f) the chassis portion is flexible; and/or (g) the chassis portion is formed from silicone or another elastomeric material.

3.4 Chassis Portion Formed from Flexible Material with Rigidiser

One aspect of one form of the present technology is a patient interface, or a cushion module for a patient interface, comprising a chassis portion and a seal-forming structure together forming a plenum chamber. The chassis portion may comprise laterally projecting connection portions configured for connection to gas delivery tubes. The seal-forming structure may comprise a central portion configured to seal in use against an inferior periphery of the patient's nose surrounding the patient's nares. The chassis portion may be formed from a flexible material and may be stiffened by a rigidiser. The rigidiser may comprise a vent module.

One aspect of one form of the present technology is a patient interface comprising:

a chassis portion partially forming a plenum chamber pressurisable to a therapeutic pressure of at least 6 $cmH_2O$ above ambient air pressure, the chassis portion comprising a pair of laterally projecting connection portions sized and structured to receive a flow of air at the therapeutic pressure for breathing by a patient;

a seal-forming structure provided to the chassis portion, the seal-forming structure partially forming the plenum chamber and being constructed and arranged to form a seal with a region of the patient's face surrounding an entrance to the patient's airways, the seal-forming structure having at least one hole therein such that the flow of air at the therapeutic pressure is delivered to at least an entrance to the patient's nares, the seal-forming structure constructed and arranged to maintain said therapeutic pressure in the plenum chamber throughout the patient's respiratory cycle in use;

a positioning and stabilising structure to provide a force to hold the seal-forming structure in a therapeutically effective position on the patient's head, the positioning and stabilising structure comprising a pair of gas delivery tubes, each gas delivery tube configured to receive the flow of air from a connection port on top of the patient's head and to deliver the flow of air to a respective one of the laterally projecting connection portions of the chassis portion;

a vent to allow a flow of gases exhaled by the patient from an interior of the plenum chamber to ambient, said vent being sized and shaped to maintain the therapeutic pressure in the plenum chamber in use;

wherein the chassis portion and the seal-forming structure are formed from a flexible material, and wherein the patient interface further comprises a rigidiser provided to the chassis portion, the rigidiser configured to resist deformation of the chassis portion.

In examples: (a) the rigidiser is provided to an anterior side of the chassis portion; (b) the chassis portion comprises an anterior hole configured to receive the rigidiser; (c) the rigidiser comprises a vent module comprising the vent; (d) the vent comprises a plurality of vent holes through which the continuous flow of gases exhaled by the patient passes from the interior of the plenum chamber to ambient; (e) the plurality of vent holes comprises upstream vent holes and downstream vent holes; (f) the plurality of downstream vent holes comprises one or more superior vent holes and one or more inferior vent holes; (g) the one or more superior vent holes are configured to direct exhaust gas in a direction at an angle towards the superior with respect to an axis normal to an anterior face of the vent module; (h) the one or more inferior vent holes are configured to direct exhaust gas in a direction at an angle towards the inferior with respect to the axis normal to the anterior face of the vent module; (i) the angle towards the superior is greater than the angle towards the inferior; (j) a sum of the angle towards the superior and the angle towards the inferior is within the range of 60-100 degrees; (k) the sum of the angle towards the superior and the angle towards the inferior is within the range of 70-90 degrees; (l) the sum of the angle towards the superior and the angle towards the inferior is substantially 80 degrees; (m) the plurality of downstream vent holes comprises a pair of superior vent holes; (n) the plurality of downstream vent holes comprises a pair of inferior vent holes; (o) the vent module is configured to support a diffuser through which the continuous flow of gases exhaled by the patient is able to pass when flowing to ambient; (p) the vent module is configured to allow the continuous flow of gases exhaled by the patient from the interior of the plenum chamber to ambient to pass into and out of the diffuser after passing through the upstream vent holes; (q) the vent module is configured to allow the continuous flow of gases exhaled by the patient from the interior of the plenum chamber to ambient to pass into and out of the diffuser before passing through the downstream vent holes; and/or (r) the vent module is configured to allow the continuous flow of gases exhaled by the patient from the interior of the plenum chamber to ambient to pass by the diffuser without flowing through the diffuser.

In further examples: (a) the vent module comprises a peripheral channel configured to receive a portion of the chassis portion of the plenum chamber; (b) the chassis portion comprises a lip configured to be received within the peripheral channel of the vent module; (c) the lip defines the anterior hole of the plenum chamber; (d) the lip is thicker than adjacent portions of the chassis portion of the plenum chamber; (e) the lip is the thickest portion of the chassis portion; (f) the lip comprises a thickness in the range of 3-5 mm; and/or (g) the thickness of the lip is within the range of 3.5-4.5 mm; (h) thickness of the lip is substantially 4 mm.

In further examples: (a) the chassis portion is formed from an elastomeric material; (b) the chassis portion is formed from silicone; (c) the seal-forming structure is formed at least partially from silicone; (d) the seal-forming structure is formed at least partially from a textile material; and/or (e) the rigidiser is formed at least partially from a substantially rigid material.

In further examples: (a) the seal-forming structure comprises a central portion on a posterior side of the seal-forming structure, the central portion being configured to seal in use against at least the patient's pronasale, nasal alae and lip superior; (b) the seal-forming structure does not enter the patient's nares; (c) the patient interface is configured to leave the patient's mouth uncovered.

One aspect of one form of the present technology is a patient interface comprising a chassis portion and a seal-forming structure together at least partially forming a plenum chamber pressurisable to a therapeutic pressure of at least 6 $cmH_2O$ above ambient air pressure. The chassis portion may comprise a pair of laterally projecting connection portions configured to connect to gas delivery tubes and being sized and structured to receive a flow of air at the therapeutic pressure for breathing by a patient. The seal-forming structure may be supported by the chassis portion and may have at least one hole therein such that the flow of air at the therapeutic pressure is delivered to at least an entrance to the patient's nares, the seal-forming structure being constructed and arranged to maintain said therapeutic pressure in the plenum chamber throughout the patient's respiratory cycle in use.

The patient interface may comprise a vent to allow a flow of gases exhaled by the patient from an interior of the plenum chamber to ambient, said vent being sized and shaped to maintain the therapeutic pressure in the plenum chamber in use. The vent may comprise a plurality of vent holes through which the flow of gases exhaled by the patient passes from the interior of the plenum chamber to ambient, including one or more superior vent holes and one or more inferior vent holes. The one or more superior vent holes may be configured to direct exhaust gas in a direction at an angle towards the superior with respect to an axis normal to an anterior face of the vent module and the one or more inferior vent holes are configured to direct exhaust gas in a direction at an angle towards the inferior with respect to the axis normal to the anterior face of the vent module. The angle towards the superior may be greater than the angle towards the inferior.

3.5 Superior/Inferior Portions of Central Anterior Portion of Seal-Forming Structure Another aspect of one form of the present technology is a patient interface comprising:

a chassis portion partially forming a plenum chamber pressurisable to a therapeutic pressure of at least 6 $cmH_2O$ above ambient air pressure, the chassis portion being sized and structured to receive a flow of air at the therapeutic pressure for breathing by a patient;

a seal-forming structure provided to the chassis portion and partially forming the plenum chamber, the seal-forming structure being constructed and arranged to form a seal with a region of the patient's face surrounding an entrance to the patient's airways, the seal-forming structure having at least one hole therein such that the flow of air at the therapeutic pressure is delivered to at least an entrance to the patient's nares, the seal-forming structure constructed and arranged to maintain said therapeutic pressure in the plenum chamber throughout the patient's respiratory cycle in use;

a vent to allow a flow of gases exhaled by the patient from an interior of the plenum chamber to ambient, said vent being sized and shaped to maintain the therapeutic pressure in the plenum chamber in use;

wherein the seal-forming structure comprises:

a central portion on a posterior side of the seal-forming structure, the central portion being configured to seal in use against at least the patient's pronasale, nasal alae and lip superior; and a central anterior portion on an anterior side of the seal-forming structure and located in use proximate and inferior to the patient's pronasale, the central anterior portion comprising a superior portion and an inferior portion, the inferior portion having a stiffness greater than a stiffness of the superior portion.

In examples: (a) the inferior portion of the central anterior portion has a wall thickness greater than a wall thickness of the superior portion of the central anterior portion; (b) the superior portion of the central anterior portion has substantially the same wall thickness as the central portion of the seal-forming structure; (c) the seal-forming structure comprises a pair of mid-lateral portions on the posterior side of the seal-forming structure, each mid-lateral portion provided on a respective lateral side of the central portion, each mid-lateral portion having a stiffness greater than a stiffness of the central portion; (d) the mid-lateral portions have a wall thickness greater than the superior portion of the central anterior portion; (e) the seal-forming structure comprises a pair of mid-lateral anterior portions on the anterior side of the seal-forming structure and located on respective lateral sides of the central anterior portion, each of the pair or mid-lateral anterior portions having a wall thickness greater than a wall thickness of the central anterior portion; (f) the chassis portion comprises a pair of laterally projecting connection portions each configured to connect to and receive the flow of gas from a respective one of a pair of gas delivery tubes; and/or (g) the patient interface comprises a positioning and stabilising structure to provide a force to hold the seal-forming structure in a therapeutically effective position on the patient's head, the positioning and stabilising structure comprising the gas delivery tubes, each gas delivery tube configured to receive the flow of air from a connection port on top of the patient's head and to deliver the flow of air to a respective one of the laterally projecting connection portions of the chassis portion.

In further examples: (a) the chassis portion is formed from an elastomeric material; (b) the chassis portion is formed from silicone; (c) the seal-forming structure is formed at least partially from silicone; and/or (d) the seal-forming structure is formed at least partially from a textile material.

One aspect of one form of the present technology is a patient interface comprising a chassis portion and a seal-forming structure together at least partially forming a plenum chamber pressurisable to a therapeutic pressure of at least 6 $cmH_2O$ above ambient air pressure. The seal-forming structure may be supported by the chassis portion and may have at least one hole therein such that the flow of air at the therapeutic pressure is delivered to at least an entrance to the patient's nares, the seal-forming structure being constructed and arranged to maintain said therapeutic pressure in the plenum chamber throughout the patient's respiratory cycle in use.

The seal forming structure may comprise a central portion on a posterior side of the seal-forming structure and configured to form a seal in use against the patient's face surrounding the patient's nares and without contacting the bridge of the patient's nose. The seal-forming structure may comprise a central anterior portion on a non-patient contacting side of the seal-forming and a pair of mid-lateral anterior portions provided on either lateral side of the central anterior portion. The central anterior portion may comprise a superior portion and an inferior portion, the inferior portion of the central anterior portion being thicker than the superior portion of the central anterior portion. The mid-lateral anterior portions may each have a superior portion and an inferior portion, the inferior portion of each mid-lateral anterior portion being thicker than the superior portion of each mid-lateral anterior portion.

3.6 Superior/Inferior Portions of Mid-Lateral Anterior Portions of Seal-Forming Structure Another aspect of one form of the present technology is a patient interface comprising:

a chassis portion partially forming a plenum chamber pressurisable to a therapeutic pressure of at least 6 $cmH_2O$ above ambient air pressure, the chassis portion being sized and structured to receive a flow of air at the therapeutic pressure for breathing by a patient;

a seal-forming structure provided to the chassis portion and partially forming the plenum chamber, the seal-forming structure being constructed and arranged to form a seal with a region of the patient's face surrounding an entrance to the patient's airways, the seal-forming structure having at least one hole therein such that the flow of air at the therapeutic pressure is delivered to at least an entrance to the patient's nares, the seal-forming structure constructed and arranged to maintain said therapeutic pressure in the plenum chamber throughout the patient's respiratory cycle in use;

a vent to allow a flow of gases exhaled by the patient from an interior of the plenum chamber to ambient, said vent being sized and shaped to maintain the therapeutic pressure in the plenum chamber in use;

wherein the seal-forming structure comprises:

a central portion on a posterior side of the seal-forming structure, the central portion being configured to seal in use against at least the patient's pronasale, nasal alae and lip superior;

a central anterior portion on an anterior side of the seal-forming structure and located in use proximate and inferior to the patient's pronasale; and a pair of mid-lateral anterior portions on the anterior side of the seal-forming structure and each located on a respective lateral side of the central anterior portion, each mid-lateral anterior portion comprising a superior portion and an inferior portion, the inferior portion having a stiffness greater than a stiffness of the superior portion.

In examples: (a) the inferior portion of each mid-lateral anterior portion has a wall thickness greater than a wall thickness of the respective superior portion of the mid-lateral anterior portion; (b) the wall thickness of the inferior portion of each mid-lateral anterior portion is greater than a wall thickness of the central anterior portion of the seal-forming structure; (c) the wall thickness of the inferior portion of each mid-lateral anterior portion is greater than a wall thickness of the central portion of the posterior side of the seal-forming structure; (d) the superior portion of each mid-lateral anterior portion has a wall thickness greater than a wall thickness of the central anterior portion of the seal-forming structure; (e) the wall thickness of the superior portion of each mid-lateral anterior portion is greater than a wall thickness of the central portion of the posterior side of the seal-forming structure; (f) the seal-forming structure comprises a pair of mid-lateral portions on the posterior side of the seal-forming structure, each mid-lateral portion provided on a respective lateral side of the central portion, each mid-lateral portion having a wall thickness greater than a wall thickness of the central portion; (g) the inferior portion of each mid-lateral anterior portion has a greater wall thickness than a wall thickness of the mid-lateral portions of the posterior side of the seal-forming structure; (h) the superior portion of each mid-lateral anterior portion has a greater wall thickness than the wall thickness of the mid-lateral portions of the posterior side of the seal-forming structure; (i) the chassis portion comprises a pair of laterally projecting connection portions each configured to connect to and receive the flow of gas from a respective one of a pair of gas delivery tubes; and/or (j) the patient interface comprises a positioning and stabilising structure to provide a force to hold the seal-forming structure in a therapeutically effective position on the patient's head, the positioning and stabilising structure comprising the gas delivery tubes, each gas delivery tube configured to receive the flow of air from a connection port on top of the patient's head and to deliver the flow of air to a respective one of the laterally projecting connection portions of the chassis portion.

In further examples: (a) the chassis portion is formed from an elastomeric material; (b) the chassis portion is formed from silicone; (c) the seal-forming structure is formed at least partially from silicone; and/or (d) the seal-forming structure is formed at least partially from a textile material.

One aspect of one form of the present technology is a patient interface comprising a chassis portion and a seal-forming structure together at least partially forming a plenum chamber pressurisable to a therapeutic pressure of at least 6 $cmH_2O$ above ambient air pressure. The seal-forming structure may be supported by the chassis portion and may have at least one hole therein such that the flow of air at the therapeutic pressure is delivered to at least an entrance to the patient's nares, the seal-forming structure being constructed and arranged to maintain said therapeutic pressure in the plenum chamber throughout the patient's respiratory cycle in use.

The seal forming structure may comprise a central portion on a posterior side of the seal-forming structure and configured to form a seal in use against the patient's face surrounding the patient's nares and without contacting the bridge of the patient's nose. The seal-forming structure may comprise a central anterior portion on a non-patient contacting side of the seal-forming and a pair of mid-lateral anterior portions provided on either lateral side of the central anterior portion. The mid-lateral anterior portions each having a superior portion and an inferior portion, the inferior portion of each mid-lateral anterior portion being thicker than the superior portion of each mid-lateral anterior portion. The seal-forming structure may further comprise a pair of mid-lateral portions on the posterior side of the seal-forming structure, each provided on a respective lateral side of the central portion and having a wall thickness greater than a wall thickness of the central portion.

3.7 Chassis Superior Reinforcing Portions

Another aspect of one form of the present technology is a patient interface comprising:

- a chassis portion formed from a flexible material and partially forming a plenum chamber pressurisable to a therapeutic pressure of at least 6 $cmH_2O$ above ambient air pressure, the chassis portion comprising a pair of laterally projecting connection portions sized and structured to receive a flow of air at the therapeutic pressure for breathing by a patient;
- a seal-forming structure provided to the chassis portion and partially forming the plenum chamber, the seal-forming structure being constructed and arranged to form a seal with a region of the patient's face surrounding an entrance to the patient's airways, the seal-forming structure having at least one hole therein such that the flow of air at the therapeutic pressure is delivered to at least an entrance to the patient's nares, the seal-forming structure constructed and arranged to maintain said therapeutic pressure in the plenum chamber throughout the patient's respiratory cycle in use;
- a vent to allow a flow of gases exhaled by the patient from an interior of the plenum chamber to ambient, said vent being sized and shaped to maintain the therapeutic pressure in the plenum chamber in use;
- a positioning and stabilising structure to provide a force to hold the seal-forming structure in a therapeutically effective position on the patient's head, the positioning and stabilising structure comprising a pair of gas delivery tubes, each gas delivery tube configured to receive the flow of air from a connection port on top of the patient's head and to deliver the flow of air to a respective one of the laterally projecting connection portions of the chassis portion;
- wherein the seal-forming structure comprises a central portion on a posterior side of the seal-forming structure, the central portion being configured to seal in use against at least the patient's pronasale, nasal alae and lip superior;
- wherein the chassis portion comprises a pair of chassis superior reinforcing portions each provided to a respective lateral and anterior side of the chassis portion, the chassis superior reinforcing portions each having a greater stiffness than one or more adjacent portions of the chassis portions.

In examples: (a) the chassis superior reinforcing portions are located adjacent the seal-forming structure; (b) each chassis superior reinforcing portion is located at a respective superior corner of an anterior hole of the chassis portion; (c) the seal-forming structure comprises: a central anterior portion on an anterior side of the seal-forming structure and located in use proximate and inferior to the patient's pronasale; and a pair of mid-lateral anterior portions on the anterior side of the seal-forming structure each located on a respective lateral side of the central anterior portion, wherein each of the chassis superior reinforcing portions is located adjacent a respective one of the mid-lateral anterior portions of the seal-forming structure; (d) each one of the mid-lateral anterior portions of the seal-forming structure comprises a superior portion and an inferior portion, the chassis superior reinforcing portions each being located adjacent a respective one of the inferior portions; (e) the chassis superior reinforcing portions has a wall thickness that is the same as the wall thickness of the inferior portions of the mid-lateral anterior portions; (f) the chassis superior reinforcing portions have a wall thickness of between 1 mm and 3 mm; (g) the chassis superior reinforcing portions have a wall thickness of between 1.5 mm and 2 mm; (h) the chassis superior reinforcing portions have a wall thickness of 1.7 mm; (i) the seal-forming structure is formed from the flexible material; (j) the seal-forming structure does not enter the patient's nares; (k) the patient interface is configured to leave the patient's mouth uncovered; and/or (l) the chassis superior reinforcing portions have a wall thickness greater than the one or more adjacent portions of the chassis portion.

In further examples: (a) the chassis portion is formed from an elastomeric material; (b) the chassis portion is formed from silicone; (c) the seal-forming structure is formed at least partially from silicone; and/or (d) the seal-forming structure is formed at least partially from a textile material.

One aspect of one form of the present technology is a patient interface comprising a chassis portion and a seal-forming structure together at least partially forming a plenum chamber pressurisable to a therapeutic pressure of at least 6 $cmH_2O$ above ambient air pressure. The seal-forming structure may be supported by the chassis portion and may have at least one hole therein such that the flow of air at the therapeutic pressure is delivered to at least an entrance to the patient's nares, the seal-forming structure being constructed and arranged to maintain said therapeutic pressure in the plenum chamber throughout the patient's respiratory cycle in use. The chassis portion may be formed from a flexible material and may comprise a pair of chassis superior reinforcing portions each provided to a respective lateral and anterior side of the chassis portion. The chassis superior reinforcing portions may each have a greater stiffness than one or more adjacent portions of the chassis portions.

3.8 Anterior/Posterior Portions of Lip Superior Portion of Seal-Forming Structure Another aspect of one form of the present technology is a patient interface comprising:

- a chassis portion formed from a flexible material and partially forming a plenum chamber pressurisable to a therapeutic pressure of at least 6 $cmH_2O$ above ambient air pressure, the chassis portion comprising a pair of laterally projecting connection portions sized and structured to receive a flow of air at the therapeutic pressure for breathing by a patient;
- a seal-forming structure provided to the chassis portion and partially forming the plenum chamber, the seal-forming structure formed from the flexible material, the seal-forming structure being constructed and arranged to form a seal with a region of the patient's face surrounding an entrance to the patient's airways, the seal-forming structure having at least one hole therein such that the flow of air at the therapeutic pressure is delivered to at least an entrance to the patient's nares, the seal-forming structure constructed and arranged to maintain said therapeutic pressure in the plenum chamber throughout the patient's respiratory cycle in use;
- a vent to allow a flow of gases exhaled by the patient from an interior of the plenum chamber to ambient, said vent being sized and shaped to maintain the therapeutic pressure in the plenum chamber in use;
- a positioning and stabilising structure to provide a force to hold the seal-forming structure in a therapeutically effective position on the patient's head, the positioning and stabilising structure comprising a pair of gas delivery tubes, each gas delivery tube configured to receive the flow of air from a connection port on top of the patient's head and to deliver the flow of air to a respective one of the laterally projecting connection portions of the chassis portion;
- wherein the seal-forming structure and at least a majority of the chassis portion are formed together from a single homogenous piece of the flexible material;
- wherein the seal-forming structure comprises:
  - a central portion on a posterior side of the seal-forming structure, the central portion being configured to seal in use against at least the patient's pronasale, nasal alae and lip superior;
  - a lip superior portion comprising a posterior portion configured to seal in use against the patient's lip superior and an anterior portion adjacent the chassis portion having a stiffness greater than a stiffness of the posterior portion of the lip superior portion.

In examples: (a) the anterior portion of the lip superior portion has a thickness greater than a thickness of the posterior portion of the lip superior portion; (b) the thickness of the posterior portion of the lip superior portion is the same as a thickness of a portion of the central portion of the seal-forming structure adjacent to the lip superior portion; (c) the thickness of the posterior portion of the lip superior portion is in the range of 0.1 mm to 0.5 mm; (d) the thickness of the posterior portion of the lip superior portion is in the range of 0.2 mm to 0.3 mm; (e) the thickness of the posterior portion of the lip superior portion is 0.25 mm; (f) the thickness of the anterior portion of the lip superior portion is in the range of 1.2 mm to 1.8 mm; (g) the thickness of the anterior portion of the lip superior portion is in the range of 1.4 to 1.6 mm; (h) the thickness of the anterior portion of the lip superior portion is 1.5 mm; (i) the seal-forming structure comprises a pair of lateral posterior regions on respective lateral posterior sides of the lip superior portion, the thickness of the posterior portion of the lip superior portion is less than a thickness of the lateral posterior regions; and/or (j) the thickness of the anterior portion of the lip superior portion is the same as the thickness of the lateral posterior regions.

In further examples: (a) the chassis portion is formed from an elastomeric material; (b) the chassis portion is formed from silicone; (c) the seal-forming structure is formed at least partially from silicone; and/or (d) the seal-forming structure is formed at least partially from a textile material.

One aspect of one form of the present technology is a patient interface comprising a chassis portion and a seal-forming structure together at least partially forming a plenum chamber pressurisable to a therapeutic pressure of at least 6 $cmH_2O$ above ambient air pressure. The seal-forming structure may be supported by the chassis portion and may have at least one hole therein such that the flow of air at the therapeutic pressure is delivered to at least an entrance to the patient's nares, the seal-forming structure being constructed and arranged to maintain said therapeutic pressure in the plenum chamber throughout the patient's respiratory cycle in use. The seal-forming structure may comprise a central portion on the posterior side of the seal-forming structure configured to seal against the patient's face surrounding the patient's airways, the central portion comprising a lip superior portion configured to seal against the patient's lip superior, the lip superior portion comprising an anterior portion adjacent the chassis portion and a posterior portion configured to contact the patient's lip superior, the anterior portion being thicker than the posterior portion. The chassis portion may be formed from a flexible material.

3.9 Cushion Module Connectors

Another aspect of one form of the present technology is a patient interface comprising:

- a cushion module comprising:
  - a chassis portion partially forming a plenum chamber pressurisable to a therapeutic pressure of at least 6 $cmH_2O$ above ambient air pressure, the chassis portion comprising a pair of laterally projecting connection portions sized and structured to receive a flow of air at the therapeutic pressure for breathing by a patient; and a seal-forming structure provided to the chassis portion and partially forming the plenum chamber, the seal-forming structure being constructed and arranged to form a seal with a region of the patient's face surrounding an entrance to the patient's airways, the seal-forming structure having at least one hole therein such that the flow of air at the therapeutic pressure is delivered to at least an entrance to the patient's nares, the seal-forming structure constructed and arranged to maintain said therapeutic pressure in the plenum chamber throughout the patient's respiratory cycle in use, a positioning and stabilising structure to provide a force to hold the seal-forming structure in a therapeutically effective position on the patient's head, the positioning and stabilising structure comprising a pair of gas delivery tubes, each gas delivery tube configured to receive the flow of air from a connection port on top of the patient's head and to deliver the flow of air to a respective one of the laterally projecting connection portions of the chassis portion; and a vent to allow a flow of gases exhaled by the patient from an interior of the plenum chamber to ambient, said vent being sized and shaped to maintain the therapeutic pressure in the plenum chamber in use, wherein each gas delivery tube of the positioning and stabilising structure comprises a tube end connector proximate a tube end of the gas delivery tube, each tube end connector having at least one clip projection; and wherein the cushion module comprises a pair of connectors, each connector configured to fluidly connect a respective one of the laterally projecting connection portions of the chassis portion to a respective one of the gas delivery tubes, each connector comprising:

a chassis connection portion connected to said respective one of the laterally projecting connection portions of the chassis portion; and a projecting connector portion projecting away from the chassis connection portion along a length of the connector, the projecting connector portion comprising:

a clip base portion adjacent the chassis connection portion; and at least one clip arm projecting away from the clip base portion, the at least one clip arm comprising a recess configured to receive the clip projection of the tube end connector of the respective gas delivery tube to form a snap-fit connection with the tube end connector, wherein a length of the clip base portion along the length of the connector is equal to or greater than a length of the clip arm between the clip base portion and the recess along the length of the connector.

In examples: (a) the length of the clip base portion is greater than the length of the clip arm between the clip base portion and the recess; (b) a ratio of the length of the clip base portion to the length of the clip arm between the clip base portion and the recess is equal to or greater than 1.5:1; (c) the ratio is equal to or greater than 1.7:1; (d) the ratio is equal to or greater than 1.9:1; (e) the ratio is equal to or greater than 2:1; (f) a force required to disconnect each connector of the cushion module from the tube end connector of the respective gas delivery tube is greater than 12N; (g) the force required is greater than 20N; (h) the force required is greater than 25N; (i) the force required is greater than 30N; (j) the force required is in the range of 12N-50N; the force required is in the range of 20N-40N; (k) the force required is in the range 25N-35N; (l) the connector of the cushion module comprises a pair of clip arms projecting away from the clip base portion; (m) each one of the pair of clip arms comprises a respective recess configured to receive a respective clip projection; and/or (n) the chassis portion of the cushion module is formed from a flexible material.

3.10 Medial/Lateral Portions of Mid-Lateral Anterior Portions of Seal-Forming Structure Another aspect of one form of the present technology comprises a patient interface comprising:

a chassis portion formed from a flexible material and partially forming a plenum chamber pressurisable to a therapeutic pressure of at least 6 $cmH_2O$ above ambient air pressure, the chassis portion being sized and structured to receive a flow of air at the therapeutic pressure for breathing by a patient;

a seal-forming structure provided to the chassis portion and partially forming the plenum chamber, the seal-forming structure being constructed and arranged to form a seal with a region of the patient's face surrounding an entrance to the patient's airways, the seal-forming structure having at least one hole therein such that the flow of air at the therapeutic pressure is delivered to at least an entrance to the patient's nares, the seal-forming structure constructed and arranged to maintain said therapeutic pressure in the plenum chamber throughout the patient's respiratory cycle in use;

a vent to allow a flow of gases exhaled by the patient from an interior of the plenum chamber to ambient, said vent being sized and shaped to maintain the therapeutic pressure in the plenum chamber in use;

wherein the seal-forming structure comprises:

a central portion on a posterior side of the seal-forming structure, the central portion being configured to seal in use against at least the patient's pronasale, nasal alae and lip superior;

a central anterior portion on an anterior side of the seal-forming structure and located in use proximate and inferior to the patient's pronasale;

a pair of mid-lateral anterior portions on the anterior side of the seal-forming structure each located on a respective lateral side of the central anterior portion, each mid-lateral portion comprising a medial portion located adjacent the central anterior portion and a lateral portion located laterally of the medial portion, the medial portion of each mid-lateral anterior portion having a stiffness greater than a stiffness of the lateral portion of the mid-lateral anterior portion.

In examples: (a) the stiffness of each of the medial portions of the mid-lateral anterior portions is greater than a stiffness of the central anterior portion; (b) each of the medial portions of the mid-lateral anterior portions comprises a wall thickness greater than a wall thickness of the central anterior portion; (c) each of the lateral portions of the mid-lateral anterior portions comprises a superior portion and an inferior portion, the inferior portion having a stiffness greater than a stiffness of the superior portion; (d) the inferior portion of the lateral portion of each mid-lateral anterior portion has a wall thickness greater than a wall thickness of the superior portion; (e) the wall thickness of the medial portion of the mid-lateral anterior portion is greater than a wall thickness of the superior portion of the lateral portion of each mid-lateral anterior portion; (f) the wall thickness of the medial portion of the mid-lateral anterior portion is less than a wall thickness of the inferior portion of each mid-lateral anterior portion; (g) the chassis portion comprises a pair of chassis superior reinforcing portions each provided to a respective lateral and anterior side of the chassis portion, the chassis superior reinforcing portions each having a greater stiffness than one or more adjacent portions of the chassis portion; (h) the chassis superior reinforcing portions are located adjacent the seal-forming structure; (i) each chassis superior reinforcing portion is located adjacent a respective one of the mid-lateral anterior portions; (j) each chassis superior reinforcing portion is located adjacent a respective one of the inferior portions of the mid-lateral anterior portions; (k) each chassis superior reinforcing portion comprises a greater wall thickness than a wall thickness of the mid-lateral anterior portions; and/or (l) each chassis superior reinforcing portion comprises a greater wall thickness than the wall thickness of the medial portion of the mid-lateral anterior portions.

In further examples: (a) the chassis portion comprises a pair of laterally projecting connection portions each configured to connect to and receive the flow of gas from a respective one of a pair of gas delivery tubes; (b) the patient interface comprises a positioning and stabilising structure to provide a force to hold the seal-forming structure in a therapeutically effective position on the patient's head, the positioning and stabilising structure comprising the gas delivery tubes, each gas delivery tube configured to receive the flow of air from a connection port on top of the patient's head and to deliver the flow of air to a respective one of the laterally projecting connection portions of the chassis portion; (c) the chassis portion is formed from an elastomeric material; (d) the chassis portion is formed from silicone; (e) the seal-forming structure is formed at least partially from silicone; and/or (f) the seal-forming structure is formed at least partially from a textile material.

3.11 Superior/Inferior Portions of Anterior Portion of Lateral Posterior Regions of Seal-Forming Structure Another aspect of one form of the present technology is a patient interface comprising:

- a chassis portion formed from a flexible material and partially forming a plenum chamber pressurisable to a therapeutic pressure of at least 6 $cmH_2O$ above ambient air pressure, the chassis portion being sized and structured to receive a flow of air at the therapeutic pressure for breathing by a patient;
- a seal-forming structure provided to the chassis portion and partially forming the plenum chamber, the seal-forming structure being constructed and arranged to form a seal with a region of the patient's face surrounding an entrance to the patient's airways, the seal-forming structure having at least one hole therein such that the flow of air at the therapeutic pressure is delivered to at least an entrance to the patient's nares, the seal-forming structure constructed and arranged to maintain said therapeutic pressure in the plenum chamber throughout the patient's respiratory cycle in use;
- a vent to allow a flow of gases exhaled by the patient from an interior of the plenum chamber to ambient, said vent being sized and shaped to maintain the therapeutic pressure in the plenum chamber in use;

wherein the seal-forming structure comprises:

- a central portion on a posterior side of the seal-forming structure, the central portion being configured to seal in use against at least the patient's pronasale, nasal alae and lip superior;
- a pair of lateral posterior regions provided on respective lateral posterior sides of an anterior side of the seal-forming structure, each lateral posterior region comprising an anterior portion and a posterior portion, the anterior portion comprising a superior portion and an inferior portion, the superior portion having a greater stiffness than the inferior portion.

In examples: (a) the superior portion of the anterior portion of each lateral posterior region has a wall thickness greater than a wall thickness of the posterior portion; (b) the superior portion of the anterior portion of each lateral posterior region has a wall thickness greater than a wall thickness of the inferior portion of the anterior portion of each lateral posterior region; (c) the seal-forming structure comprises a pair of mid-lateral anterior portions on the anterior side of the seal-forming structure each located on a respective lateral side of the seal-forming structure, the mid-lateral anterior portions having a stiffness greater than a stiffness of the central portion; (d) each of the anterior portions of the lateral posterior regions has a wall thickness greater than a wall thickness of each of the mid-lateral anterior portions; (e) the superior portion of the anterior portion of each lateral posterior region has a wall thickness greater than the wall thickness of each mid-lateral anterior portion; (f) each mid-lateral anterior portion comprises a superior portion and an inferior portion, the inferior portion being stiffer than the superior portion; (g) the inferior portion of each mid-lateral anterior portion has a wall thickness greater than a wall thickness of the superior portion of the mid-lateral anterior portion; and/or (h) a boundary between the superior portion and the inferior portion of the anterior portion of each lateral posterior region is located at a longest portion of the lateral posterior region in an anterior-posterior direction.

In further examples: (a) the chassis portion comprises a pair of laterally projecting connection portions each configured to connect to and receive the flow of gas from a respective one of a pair of gas delivery tubes; (b) the patient interface comprises a positioning and stabilising structure to provide a force to hold the seal-forming structure in a therapeutically effective position on the patient's head, the positioning and stabilising structure comprising the gas delivery tubes, each gas delivery tube configured to receive the flow of air from a connection port on top of the patient's head and to deliver the flow of air to a respective one of the laterally projecting connection portions of the chassis portion; (c) the chassis portion is formed from an elastomeric material; (d) the chassis portion is formed from silicone; (e) the seal-forming structure is formed at least partially from silicone; and/or (f) the seal-forming structure is formed at least partially from a textile material.

3.12 Anterior/Posterior Portions of Mid-Lateral Inferior Portions of Seal-Forming Structure Another aspect of one form of the present technology is a patient interface comprising:

- a chassis portion formed from a flexible material and partially forming a plenum chamber pressurisable to a therapeutic pressure of at least 6 $cmH_2O$ above ambient air pressure, the chassis portion being sized and structured to receive a flow of air at the therapeutic pressure for breathing by a patient;

a seal-forming structure provided to the chassis portion and partially forming the plenum chamber, the seal-forming structure being constructed and arranged to form a seal with a region of the patient's face surrounding an entrance to the patient's airways, the seal-forming structure having at least one hole therein such that the flow of air at the therapeutic pressure is delivered to at least an entrance to the patient's nares, the seal-forming structure constructed and arranged to maintain said therapeutic pressure in the plenum chamber throughout the patient's respiratory cycle in use;

a vent to allow a flow of gases exhaled by the patient from an interior of the plenum chamber to ambient, said vent being sized and shaped to maintain the therapeutic pressure in the plenum chamber in use;

wherein the seal-forming structure comprises:

a central portion on a posterior side of the seal-forming structure, the central portion being configured to seal in use against at least the patient's pronasale, nasal alae and lip superior, the central portion comprising a lip superior portion configured to seal in use against the patient's lip superior;

a pair of mid-lateral inferior portions located on either lateral side of the lip superior portion, each mid-lateral inferior portion having an anterior portion adjacent the chassis portion and a posterior portion, the anterior portions of the mid-lateral inferior portions being stiffer than the posterior portions of the mid-lateral inferior portions.

In examples: (a) the lip superior portion comprises an anterior portion adjacent the chassis portion and a posterior portion configured to seal in use against the patient's lip superior; (b) the anterior portion of the lip superior portion is stiffer than the posterior portion of the lip superior portion; (c) the anterior portions of the mid-lateral inferior portions are stiffer than the anterior portion of the lip superior portion; (d) the anterior portions of the mid-lateral inferior portions are stiffer than the posterior portion of the lip superior portion; (e) the posterior portions of the mid-lateral inferior portions are stiffer than the posterior portion of the lip superior portion; (f) the anterior portions of the mid-lateral inferior portions each have a thickness that is greater than a thickness of the posterior portions of the mid-lateral inferior portions; (g) the anterior portion of the lip superior portion has a thickness greater than a thickness of the posterior portion of the lip superior portion; (h) the thickness of the anterior portions of the mid-lateral inferior portions is greater than the thickness of the anterior portion of the lip superior portion; (i) the thickness of the anterior portions of the mid-lateral inferior portions is greater than the thickness of the posterior portion of the lip superior portion; (j) the thickness of the posterior portions of the mid-lateral inferior portions is substantially the same as the thickness of the anterior portion of the lip superior portion; (k) the thickness of the posterior portions of the mid-lateral inferior portions is greater than the posterior portion of the lip superior portion; (l) the chassis portion comprises a pair of chassis inferior reinforcing portions each located adjacent a respective one of the mid-lateral inferior portions, the chassis inferior reinforcing portions each having a greater stiffness than an adjacent portion of the chassis portion; and/or (m) the chassis inferior reinforcing portions each have a thickness greater than a thickness of the adjacent portion of the chassis portion.

In further examples: (a) the chassis portion comprises a pair of laterally projecting connection portions each configured to connect to and receive the flow of gas from a respective one of a pair of gas delivery tubes; (b) the patient interface comprises a positioning and stabilising structure to provide a force to hold the seal-forming structure in a therapeutically effective position on the patient's head, the positioning and stabilising structure comprising the gas delivery tubes, each gas delivery tube configured to receive the flow of air from a connection port on top of the patient's head and to deliver the flow of air to a respective one of the laterally projecting connection portions of the chassis portion; (c) the chassis portion is formed from an elastomeric material; (d) the chassis portion is formed from silicone; (e) the seal-forming structure is formed at least partially from silicone; and/or (f) the seal-forming structure is formed at least partially from a textile material.

3.13 Chassis Inferior Reinforcing Portions

Another aspect of one form of the present technology is a patient interface comprising:

a chassis portion formed from a flexible material and partially forming a plenum chamber pressurisable to a therapeutic pressure of at least 6 $cmH_2O$ above ambient air pressure, the chassis portion comprising a pair of laterally projecting connection portions sized and structured to receive a flow of air at the therapeutic pressure for breathing by a patient;

a seal-forming structure provided to the chassis portion and partially forming the plenum chamber, the seal-forming structure being constructed and arranged to form a seal with a region of the patient's face surrounding an entrance to the patient's airways, the seal-forming structure having at least one hole therein such that the flow of air at the therapeutic pressure is delivered to at least an entrance to the patient's nares, the seal-forming structure constructed and arranged to maintain said therapeutic pressure in the plenum chamber throughout the patient's respiratory cycle in use;

a vent to allow a flow of gases exhaled by the patient from an interior of the plenum chamber to ambient, said vent being sized and shaped to maintain the therapeutic pressure in the plenum chamber in use;

a positioning and stabilising structure to provide a force to hold the seal-forming structure in a therapeutically effective position on the patient's head, the positioning and stabilising structure comprising a pair of gas delivery tubes, each gas delivery tube configured to receive the flow of air from a connection port on top of the patient's head and to deliver the flow of air to a respective one of the laterally projecting connection portions of the chassis portion;

wherein the seal-forming structure comprises a central portion on a posterior side of the seal-forming structure, the central portion being configured to seal in use against at least the patient's pronasale, nasal alae and lip superior;

wherein the chassis portion comprises a pair of chassis inferior reinforcing portions each provided to a respective lateral and inferior side of the chassis portion, the chassis inferior reinforcing portions each having a greater stiffness than one or more adjacent portions of the chassis portions.

In examples: (a) the chassis inferior reinforcing portions each have a thickness greater than a thickness of the adjacent portion of the chassis portion; (b) the chassis inferior reinforcing portions are provided adjacent the seal-forming structure; (c) the chassis inferior reinforcing portions may have spaced apart medial boundaries; (d) the chassis inferior reinforcing portions may each have a medial boundary proximate a central region on the inferior side of the chassis portion; (e) the chassis inferior reinforcing portions may each have a lateral boundary proximate a respective lateral posterior region of the seal-forming structure; (f) the chassis inferior reinforcing portions are shaped to follow a boundary between the chassis portion and the seal-forming structure; and/or (g) the central portion comprising a lip superior portion configured to seal in use against the patient's lip superior and a pair of mid-lateral inferior portions located on either lateral side of the lip superior portion and having a greater stiffness than the lip superior portion, the chassis inferior reinforcing portions each located adjacent a respective one of the mid-lateral inferior portions.

In further examples: (a) the chassis portion comprises a pair of laterally projecting connection portions each configured to connect to and receive the flow of gas from a respective one of a pair of gas delivery tubes; (b) the patient interface comprises a positioning and stabilising structure to provide a force to hold the seal-forming structure in a therapeutically effective position on the patient's head, the positioning and stabilising structure comprising the gas delivery tubes, each gas delivery tube configured to receive the flow of air from a connection port on top of the patient's head and to deliver the flow of air to a respective one of the laterally projecting connection portions of the chassis portion; (c) the chassis portion is formed from an elastomeric material; (d) the chassis portion is formed from silicone; (e) the seal-forming structure is formed at least partially from silicone; and/or (f) the seal-forming structure is formed at least partially from a textile material.

3.14 Decoupling Portions of Chassis Portion

Another aspect of one form of the present technology is a patient interface comprising:

- a chassis portion partially forming a plenum chamber pressurisable to a therapeutic pressure of at least 6 $cmH_2O$ above ambient air pressure, the chassis portion being sized and structured to receive a flow of air at the therapeutic pressure for breathing by a patient, and the chassis portion comprising a pair of laterally projecting connection portions configured to connect to gas delivery tubes;
- a seal-forming structure provided to the chassis portion and partially forming the plenum chamber, the seal-forming structure being constructed and arranged to form a seal with a region of the patient's face surrounding an entrance to the patient's airways, the seal-forming structure having at least one hole therein such that the flow of air at the therapeutic pressure is delivered to at least an entrance to the patient's nares, the seal-forming structure constructed and arranged to maintain said therapeutic pressure in the plenum chamber throughout the patient's respiratory cycle in use;
- a vent to allow a flow of gases exhaled by the patient from an interior of the plenum chamber to ambient, said vent being sized and shaped to maintain the therapeutic pressure in the plenum chamber in use;
- a positioning and stabilising structure to provide a force to hold the seal-forming structure in a therapeutically effective position on the patient's head, the positioning and stabilising structure comprising a pair of gas delivery tubes, each gas delivery tube configured to receive the flow of air from a connection port on top of the patient's head and to deliver the flow of air to a respective one of the laterally projecting connection portions of the chassis portion;
- wherein the seal-forming structure comprises a central portion on a posterior side of the seal-forming structure, the central portion being configured to seal in use against at least the patient's pronasale, nasal alae and lip superior;
- wherein the chassis portion comprises a pair of decoupling portions each provided to a respective lateral side of the chassis portion and each having a lesser stiffness than one or more adjacent portions of the chassis portion, the decoupling portions configured to at least partially decouple the central portion from forces applied to the chassis portion.

In examples: (a) each decoupling portion has a lesser thickness than one or more adjacent portions of the chassis portion; (b) each decoupling portion has a thickness of 0.5 mm; (c) the chassis portion has a thickness of 0.9 mm; (d) each decoupling portion is provided to an anterior side of the chassis portion; and/or (e) each decoupling portion extends from a superior side of the chassis portion to an inferior side of the chassis portion.

In further examples: (a) each decoupling portion is at least partially surrounded by a peripheral portion of the chassis portion having a greater stiffness than both the decoupling portion and an adjacent portion of the chassis portion to the peripheral portion; (b) each peripheral portion has a greater thickness than both the decoupling portion and an adjacent portion of the chassis portion to the peripheral portion; (c) each peripheral portion has a thickness within the range of 1.5 mm to 2 mm; and/or (d) each peripheral portion has a thickness of 1.75 mm.

In further examples: (a) the chassis portion comprises two decoupling portions on each lateral side of the chassis portion; (b) on each lateral side of the chassis portion, the chassis portion comprises a medial decoupling portion and a lateral decoupling portion, the lateral decoupling portion located laterally of the medial decoupling portion; (c) the lateral decoupling portions are configured to at least partially decouple the seal-forming structure from forces applied to the laterally projecting connection portions; (d) the medial decoupling portions are configured to at least partially decouple the seal-forming structure from forces applied to a central region of the anterior side of the chassis portion; (e) the cushion module comprises a vent module comprising the vent, the vent module located in the central region of the anterior side of the chassis portion, the medial decoupling portions being configured to at least partially decouple the seal-forming structure from forces applied to the vent module.

In further examples: (a) the lateral decoupling portions are D-shaped; (b) the medial decoupling portions are crescent shaped; (c) each lateral decoupling portion has a lateral side proximate a distal end of the respective laterally projecting connection portion and a medial side opposite the lateral side, the medial side having greater curvature than the lateral side; (d) the lateral side of each lateral decoupling portion is shaped to match a shape of the respective distal end of the laterally projecting connection portion; (e) each medial decoupling portion has a medial side proximate the vent module and a lateral side opposite the medial side, the lateral side having a greater curvature than the medial side; (f) the medial side of each medial decoupling portion is curved to follow a curvature of the vent module; (g) each decoupling portion is at least partially surrounded by a peripheral portion of the chassis portion having a greater thickness than both the decoupling portion and an adjacent portion of the chassis portion to the peripheral portion; (h) on each lateral side of the chassis portion, the chassis portion comprises a first peripheral portion located medially adjacent to the lateral decoupling portion and a second peripheral portion located laterally adjacent to the medial decoupling portion; (i) on each lateral side of the chassis portion, the first peripheral portion is curved to follow the curvature of the medial side of the lateral decoupling portion; (j) on each lateral side of the chassis portion, the second peripheral portion is curved to follow the curvature of the lateral side of the medial decoupling portion; and/or (k) on each lateral side of the chassis portion, the first peripheral portion and the second peripheral portion are closest at a midpoint of the anterior side of the chassis portion and are spaced further apart at superior and/or inferior sides of the chassis portion.

3.15 Further Aspects

Another aspect of certain forms of the present technology is a system for treating a respiratory disorder comprising a patient interface according to any one or more of the other aspects of the present technology, an air circuit and a source of air at positive pressure.

Another aspect of one form of the present technology is a patient interface that is moulded or otherwise constructed with a perimeter shape which is complementary to that of an intended wearer.

Another aspect of certain forms of the present technology is a patient interface that is configured to allow the patient to breath from ambient through their mouth in the absence of a flow of pressurised air through the plenum chamber inlet port.

Another aspect of certain forms of the present technology is a patient interface comprising a seal-forming structure configured to leave the patient's mouth uncovered in use.

Another aspect of certain forms of the present technology is a patient interface comprising a seal-forming structure configured so that no part of the seal-forming structure enters the mouth in use.

Another aspect of certain forms of the present technology is a patient interface comprising a seal-forming structure configured so that the seal-forming structure does not extend internally of the patient's airways.

Another aspect of certain forms of the present technology is a patient interface comprising a seal-forming structure configured so that the seal-forming structure does not extend below a mental protuberance region in use.

Another aspect of certain forms of the present technology is a patient interface constructed and arranged to leave a patient's eyes uncovered in use.

Another aspect of certain forms of the present technology is a patient interface constructed and arranged to allow a patient to breathe ambient air in the event of a power failure.

Another aspect of certain forms of the present technology is a patient interface comprising a seal forming structure configured to form a seal on an underside of a patient's nose without contacting a nasal bridge region of the patient's nose.

Another aspect of certain forms of the present technology is a patient interface comprising a vent and a plenum chamber, wherein the patient interface is constructed and arranged so that gases from an interior of the plenum chamber may pass to ambient via the vent.

Another aspect of certain forms of the present technology is a patient interface comprising a vent to allow a flow of gases exhaled by the patient from an interior of the plenum chamber to ambient, said vent being sized and shaped to maintain the therapeutic pressure in the plenum chamber in use. Another aspect of certain forms of a present technology is a patient interface comprising a vent to allow a continuous flow of gases exhaled by the patient from an interior of the plenum chamber to ambient, said vent being sized and shaped to maintain the therapeutic pressure in the plenum chamber in use.

Another aspect of certain forms of the present technology is a patient interface constructed and arranged so that a patient may lie comfortably in a side or lateral sleeping position, in use of the patient interface.

Another aspect of certain forms of the present technology is a patient interface constructed and arranged so that a patient may lie comfortably in a supine sleeping position, in use of the patient interface.

Another aspect of certain forms of the present technology is a patient interface constructed and arranged so that a patient may lie comfortably in a prone sleeping position, in use of the patient interface.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a patient interface that may be washed in a home of a patient, e.g., in soapy water, without requiring specialised cleaning equipment.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE DRAWINGS

The present technology is illustrated by way of example, and not by way of limitation, in the figures of the accompanying drawings, in which like reference numerals refer to similar elements including.

4.1 Treatment Systems

4.2 Respiratory System and Facial Anatomy

Figure 2A:
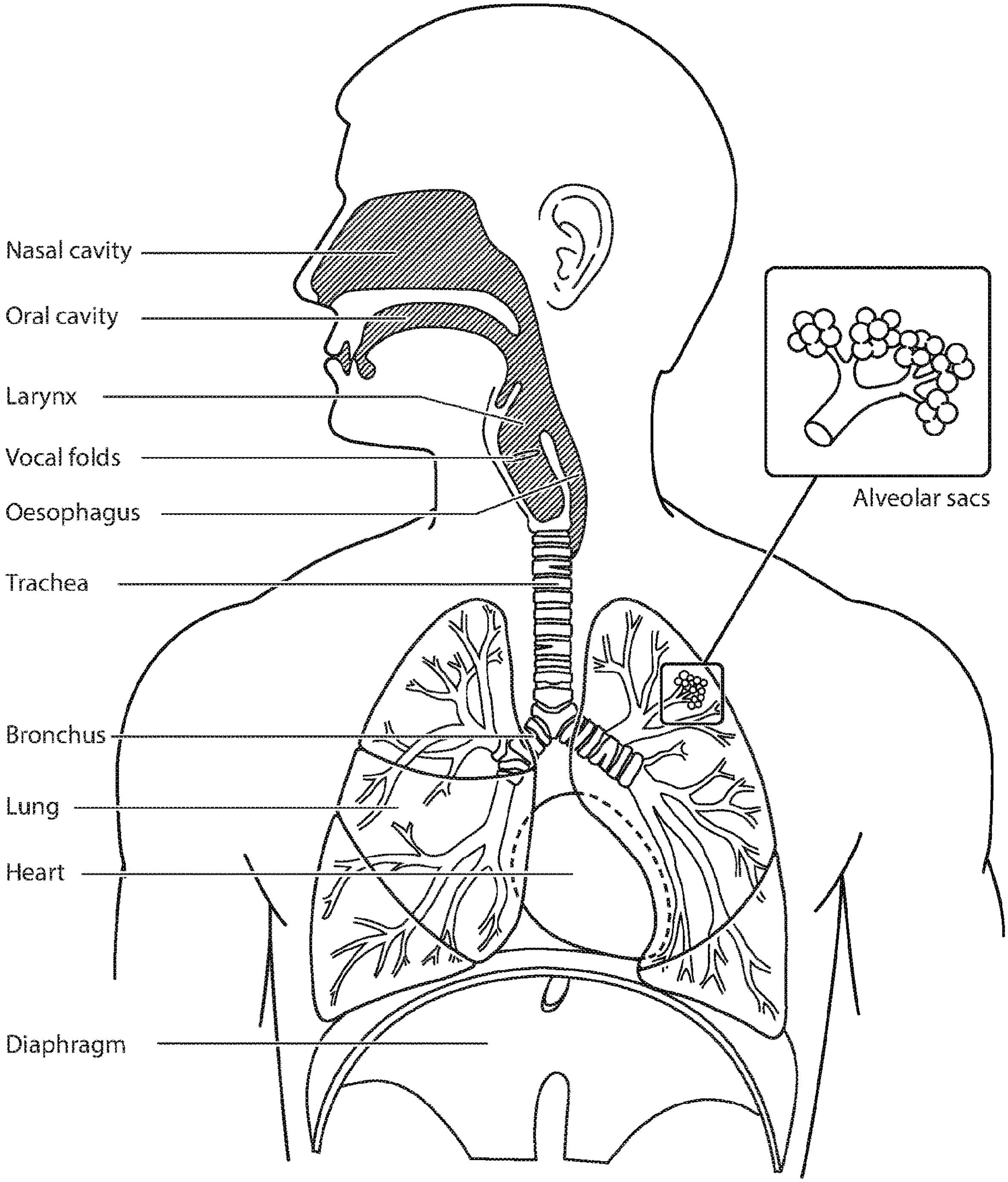

FIG. 2A shows an overview of a human respiratory system including the nasal and oral cavities, the larynx, vocal folds, oesophagus, trachea, bronchus, lung, alveolar sacs, heart and diaphragm.

Figure 2B:
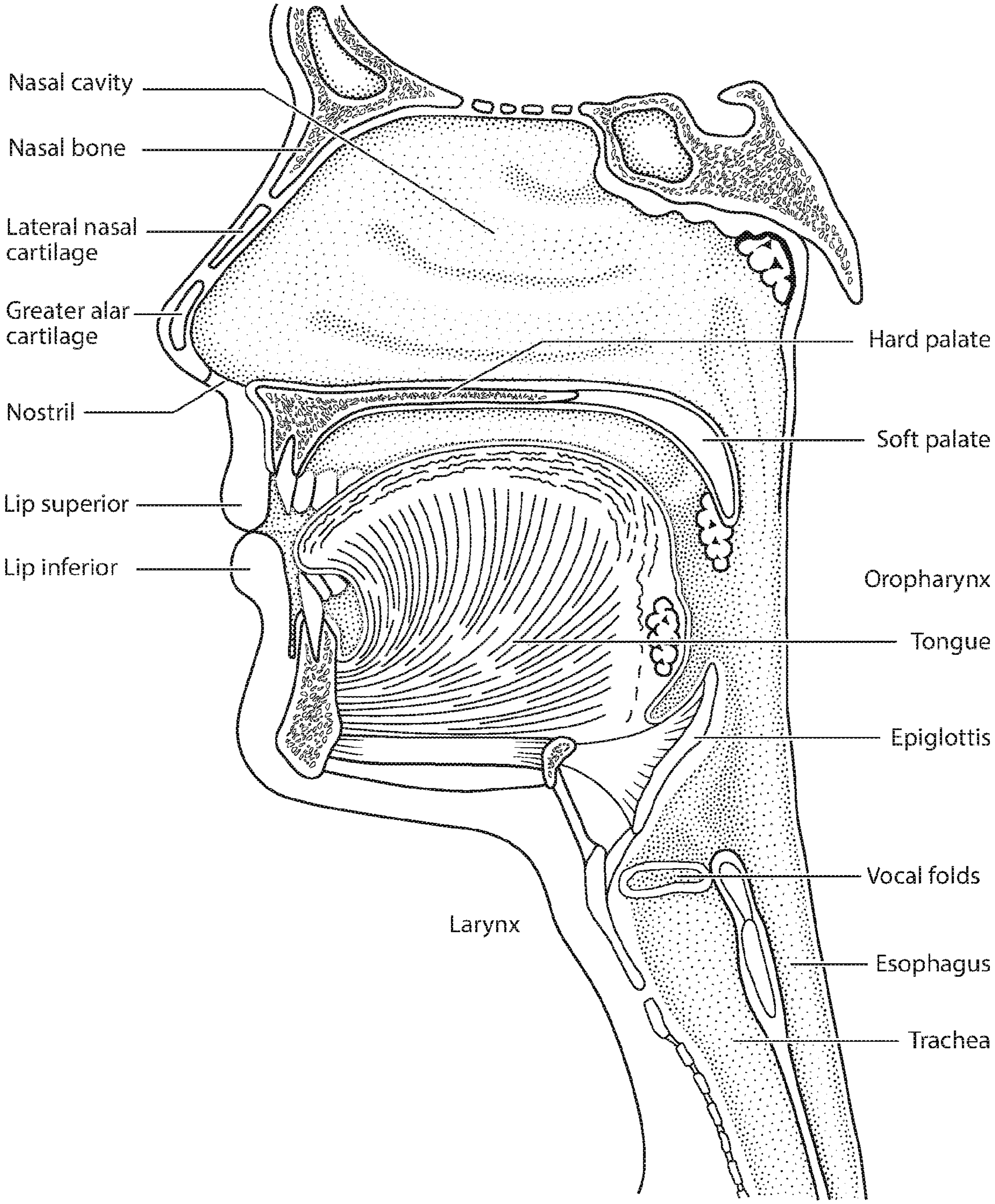

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Figure 2C:
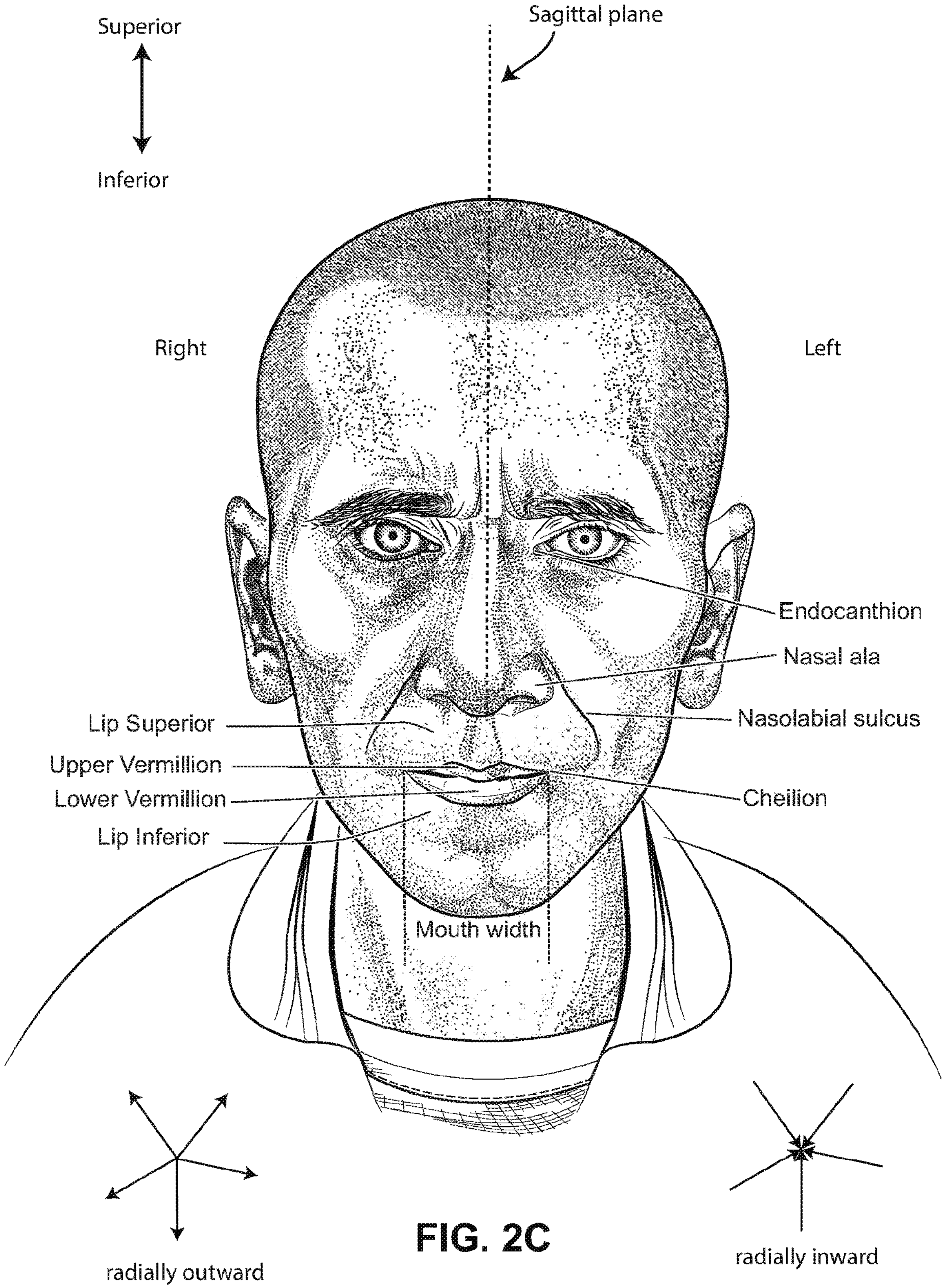

FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.

Figure 2D:
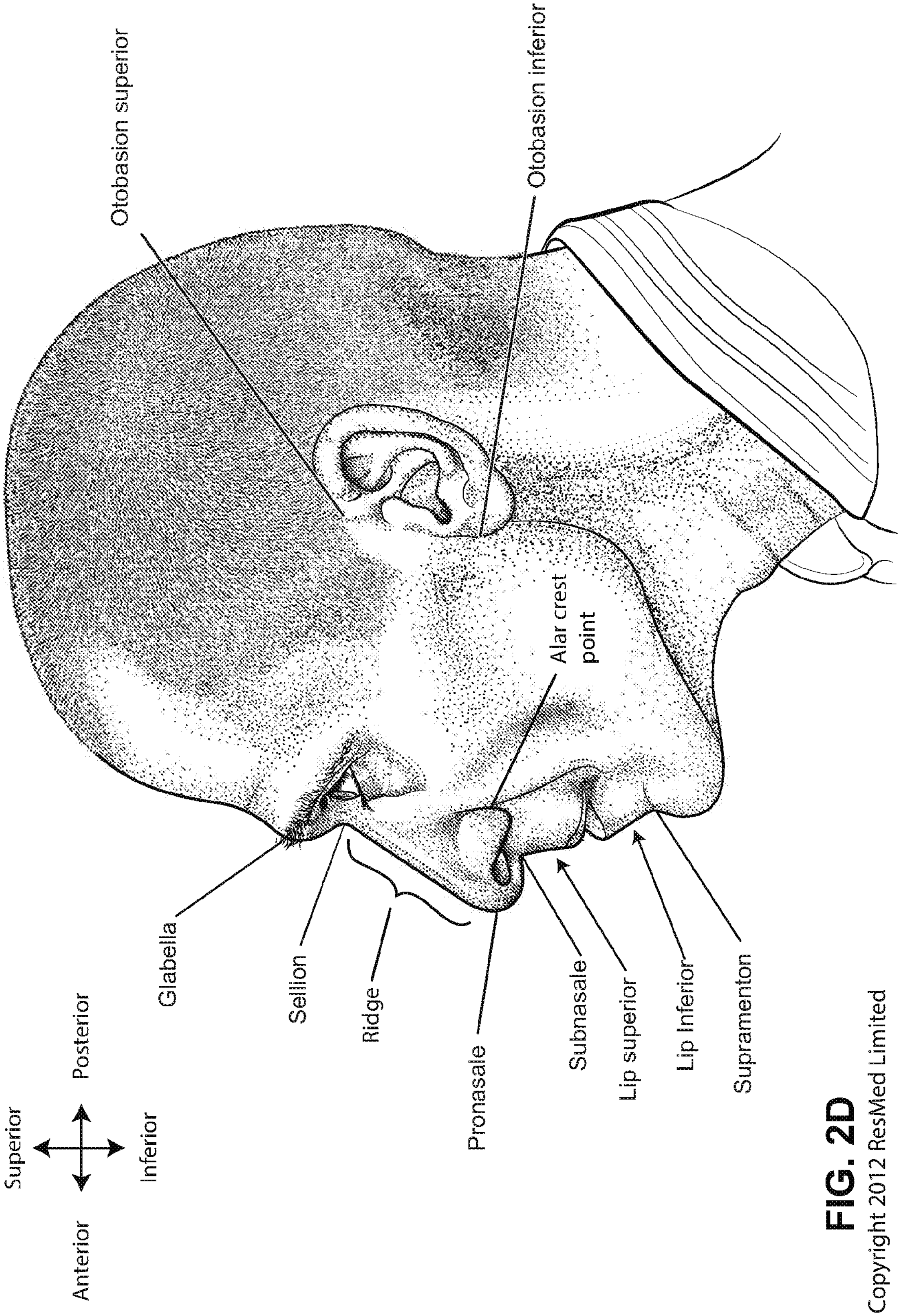

FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.

Figure 2E:
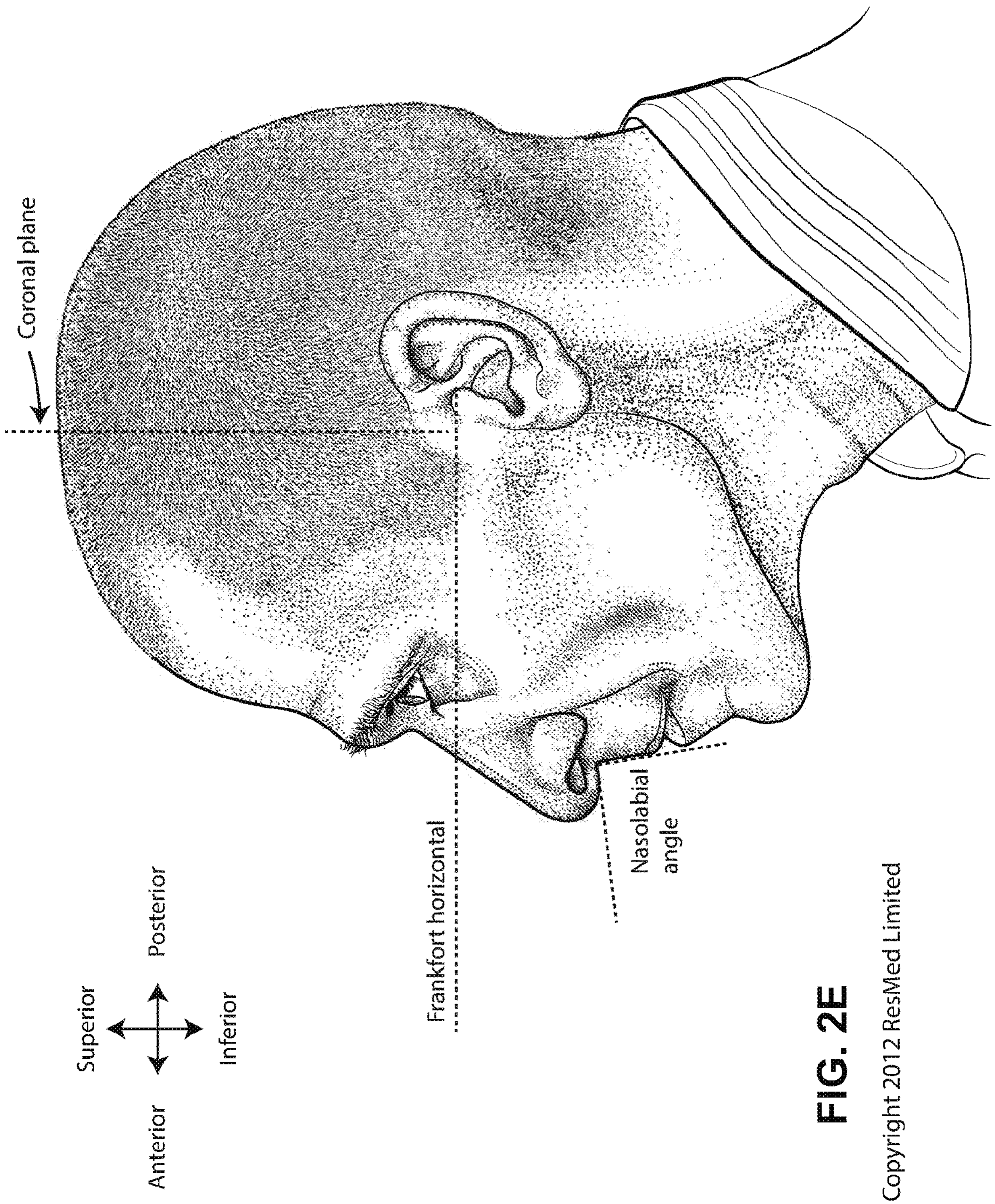

FIG. 2E is a further side view of a head. The approximate locations of the Frankfort horizontal and nasolabial angle are indicated. The coronal plane is also indicated.

Figure 2F:
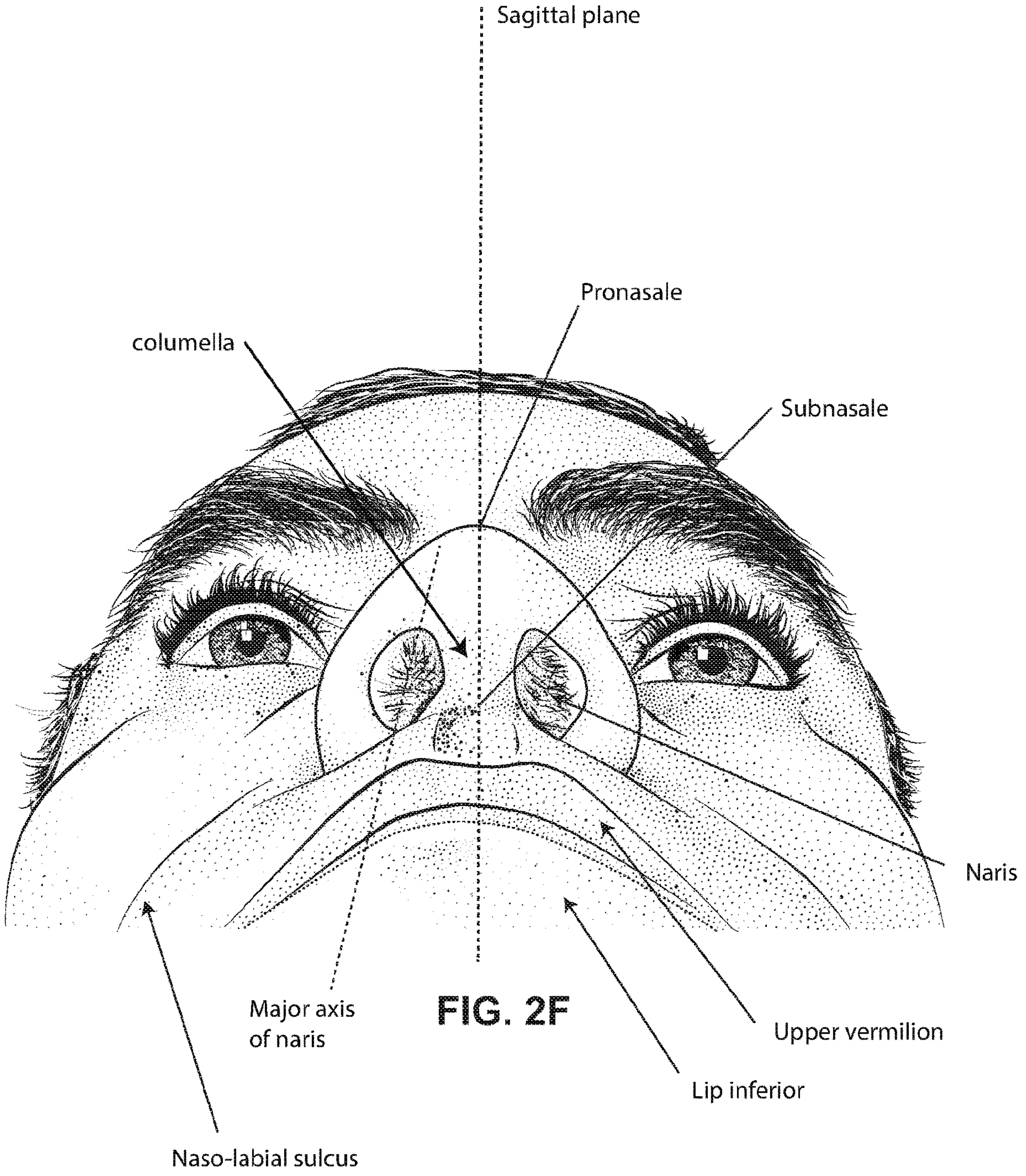

FIG. 2F shows a base view of a nose with several features identified including naso-labial sulcus, lip inferior, upper Vermilion, naris, subnasale, columella, pronasale, the major axis of a naris and the midsagittal plane.

Figure 2G:

FIG. 2G shows a side view of the superficial features of a nose.

Figure 2H:
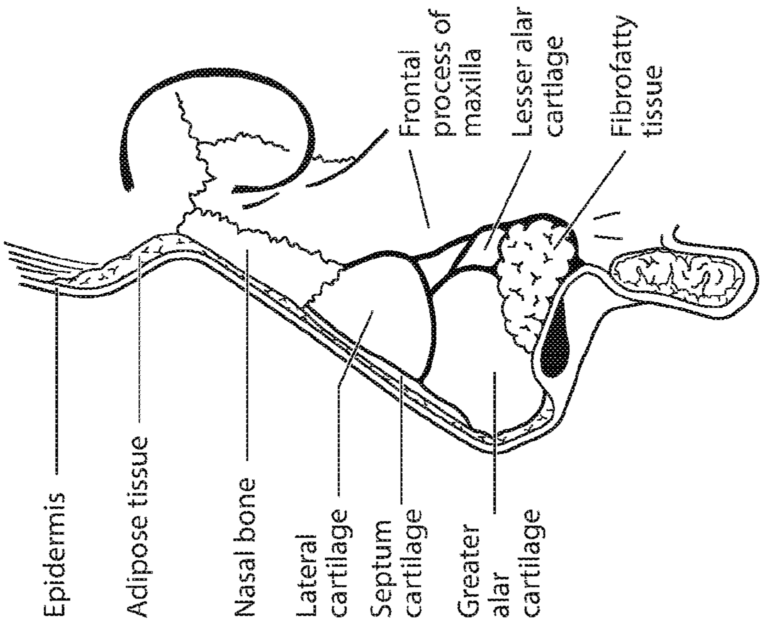
Figure 2I:
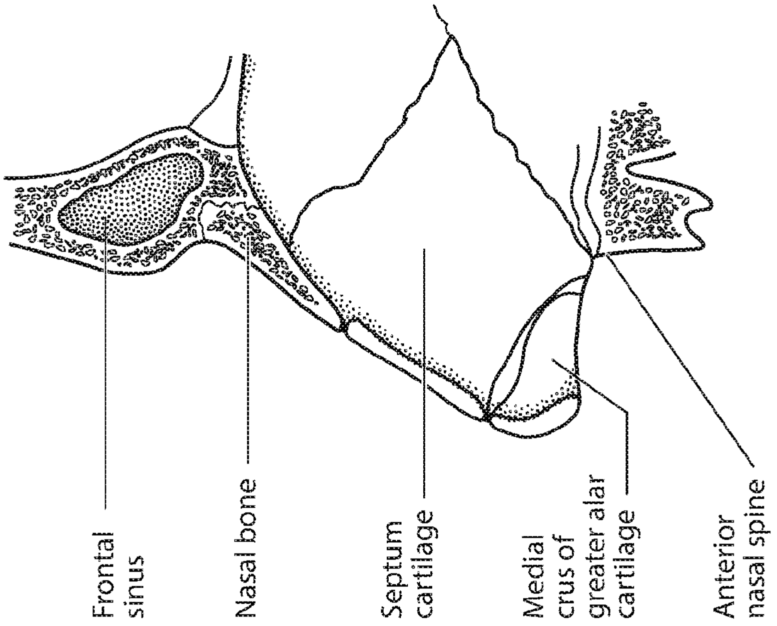

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2 shows a medial dissection of a nose, approximately several millimeters from the midsagittal plane, amongst other things showing the septum cartilage and medial crus of greater alar cartilage.

Figure 2K:
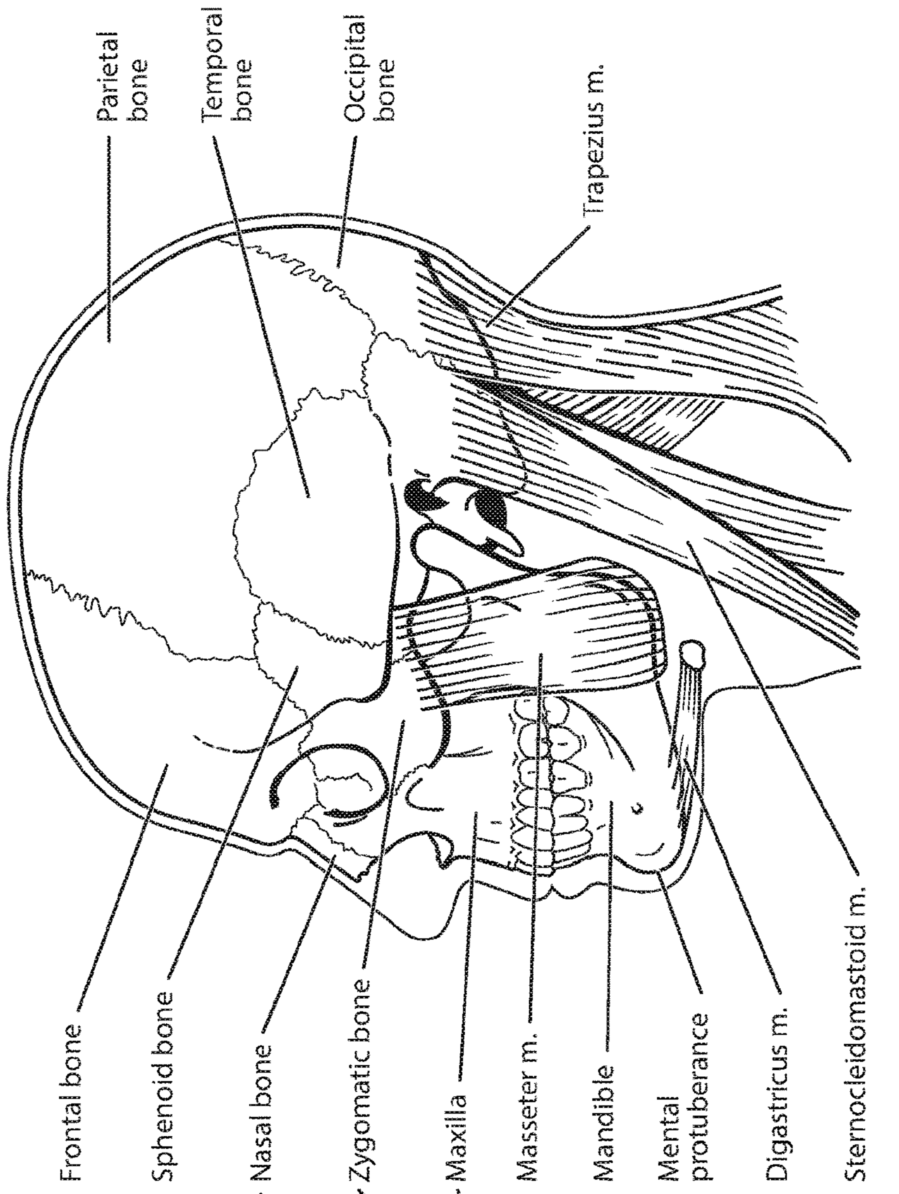
Figure 2J:
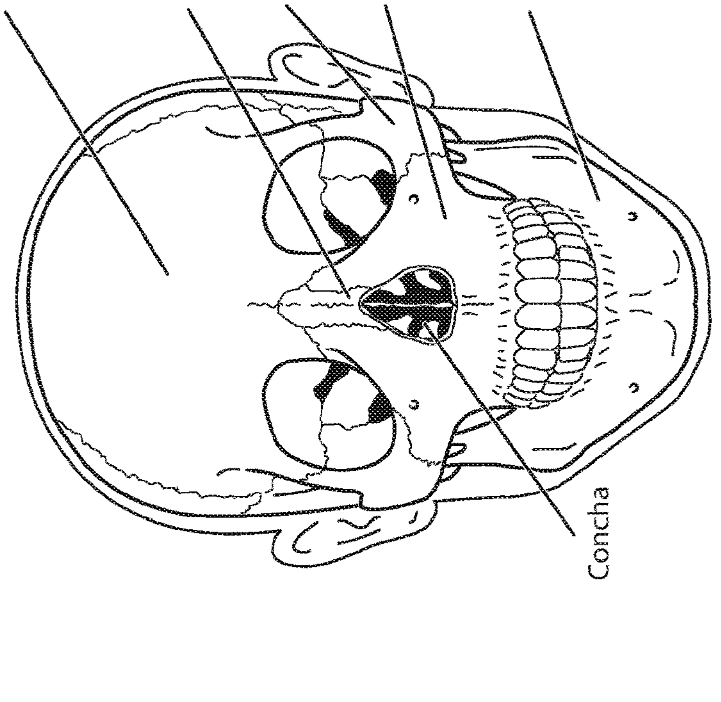

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
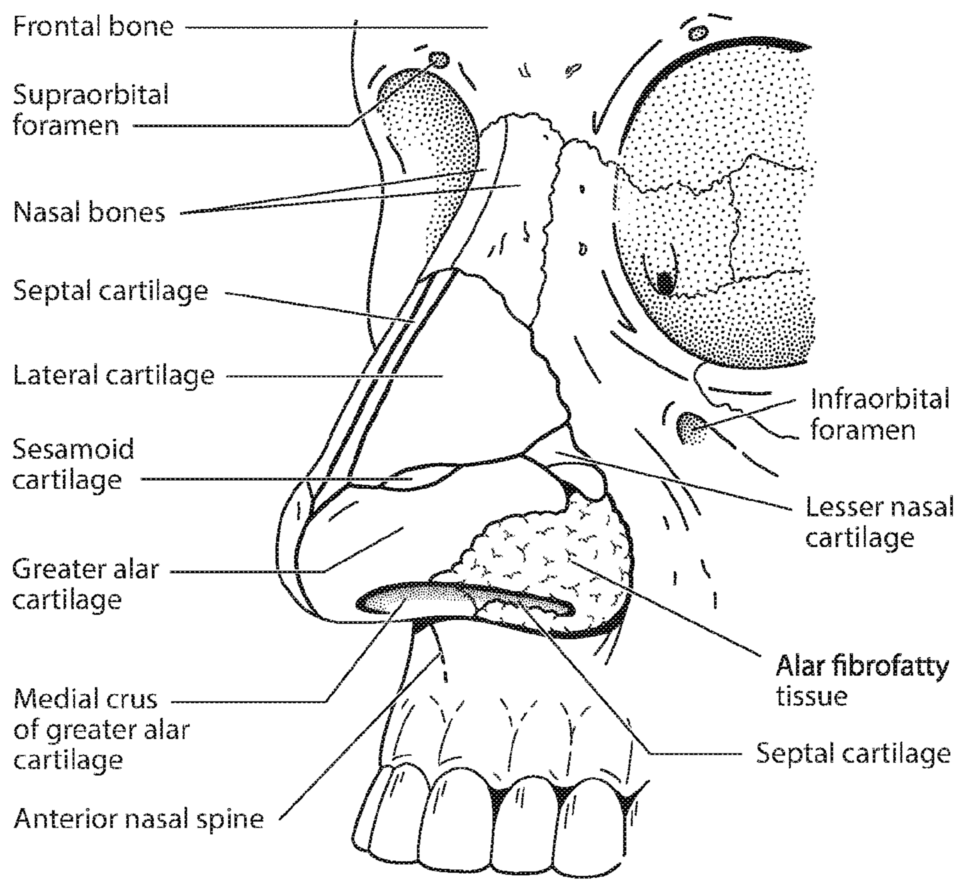

FIG. 2L shows an anterolateral view of a nose.

4.3 Patient Interface

Figure 3A:
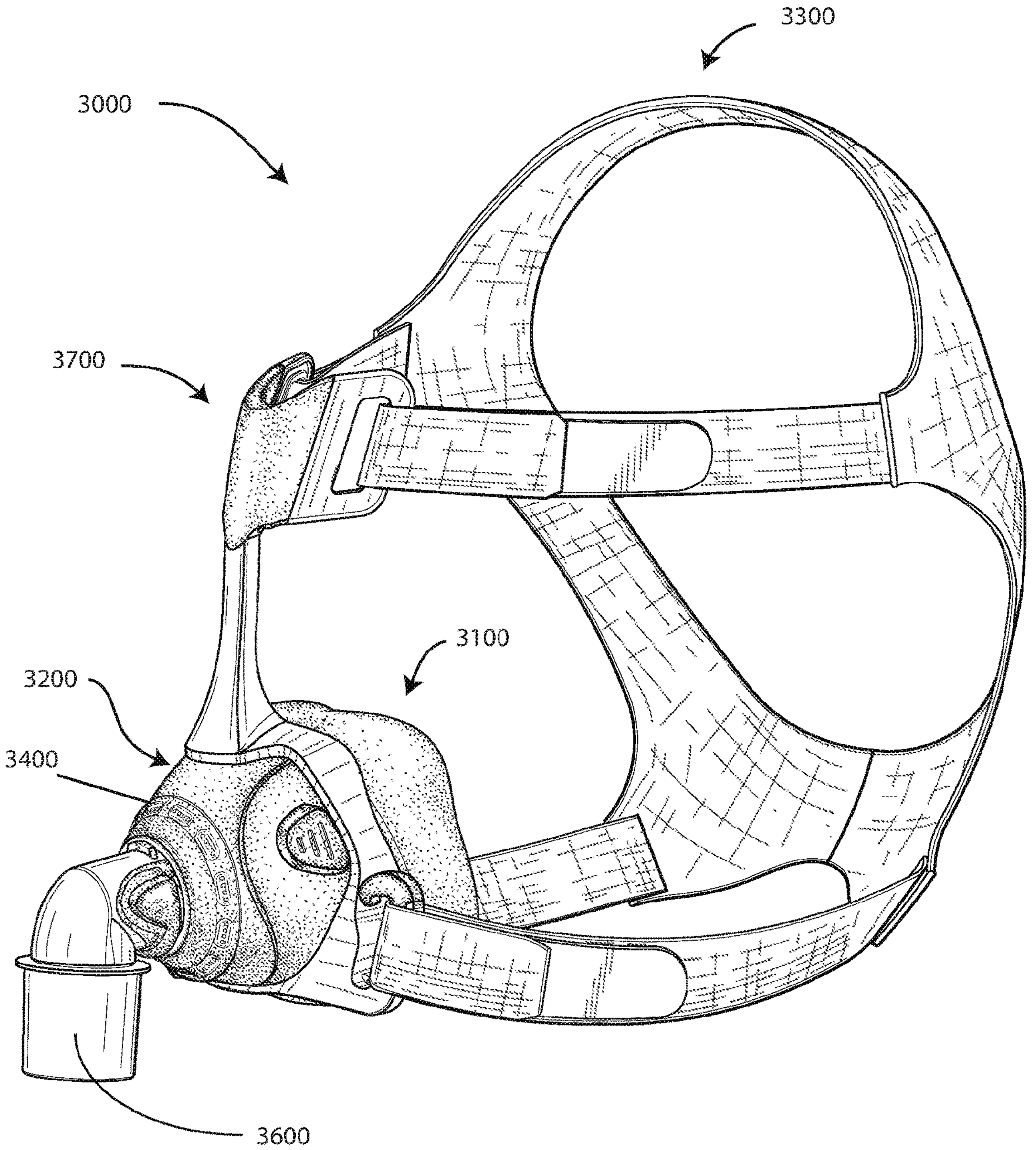

FIG. 3A shows a patient interface in the form of a nasal mask in accordance with one form of the present technology.

Figure 3B:
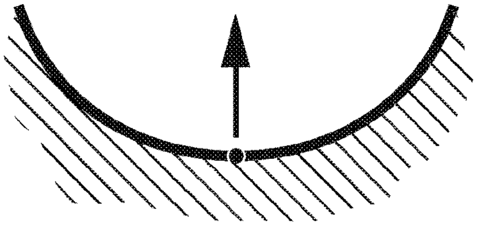

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
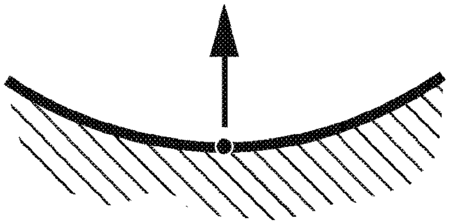

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
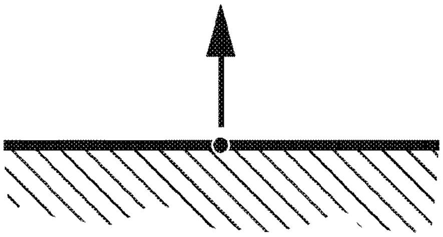

FIG. 3D shows a schematic of a cross-section through a structure at a point. An outward normal at the point is indicated. The curvature at the point has a value of zero.

Figure 3E:
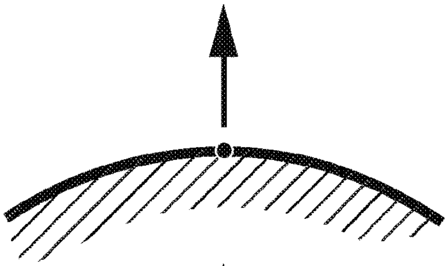

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
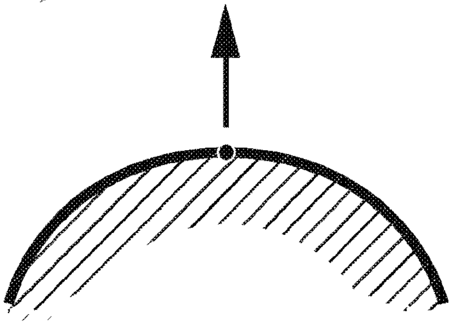

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3G:
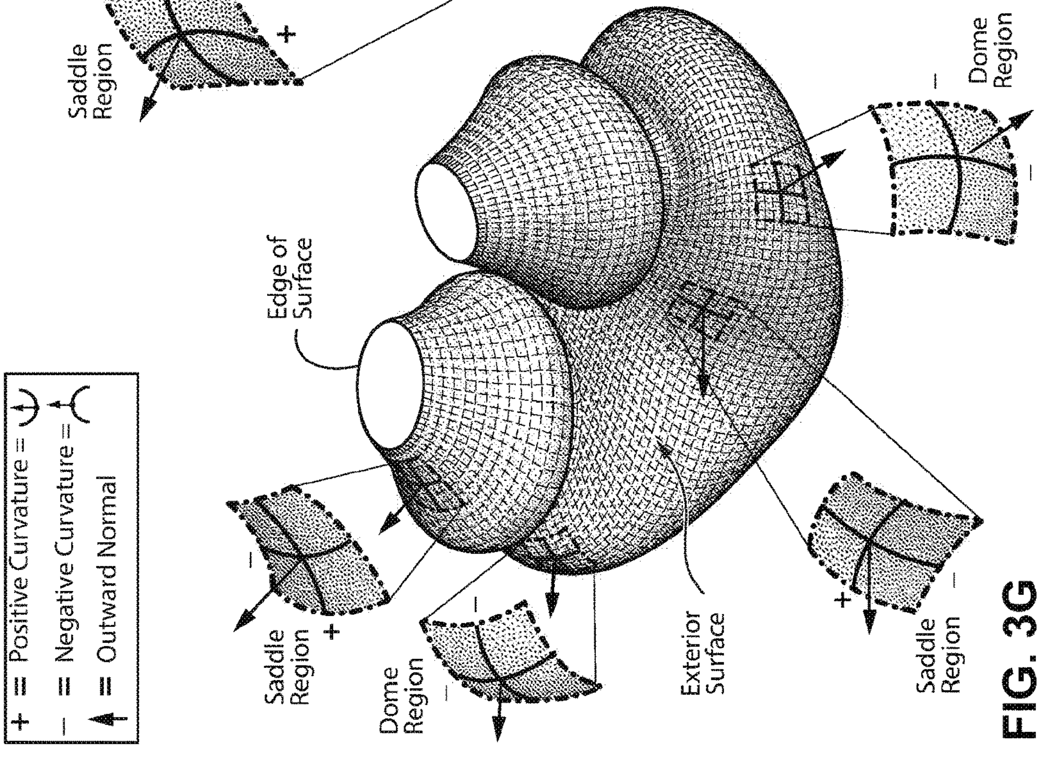

FIG. 3G shows a cushion for a mask that includes two pillows. An exterior surface of the cushion is indicated. An edge of the surface is indicated. Dome and saddle regions are indicated.

Figure 3H:
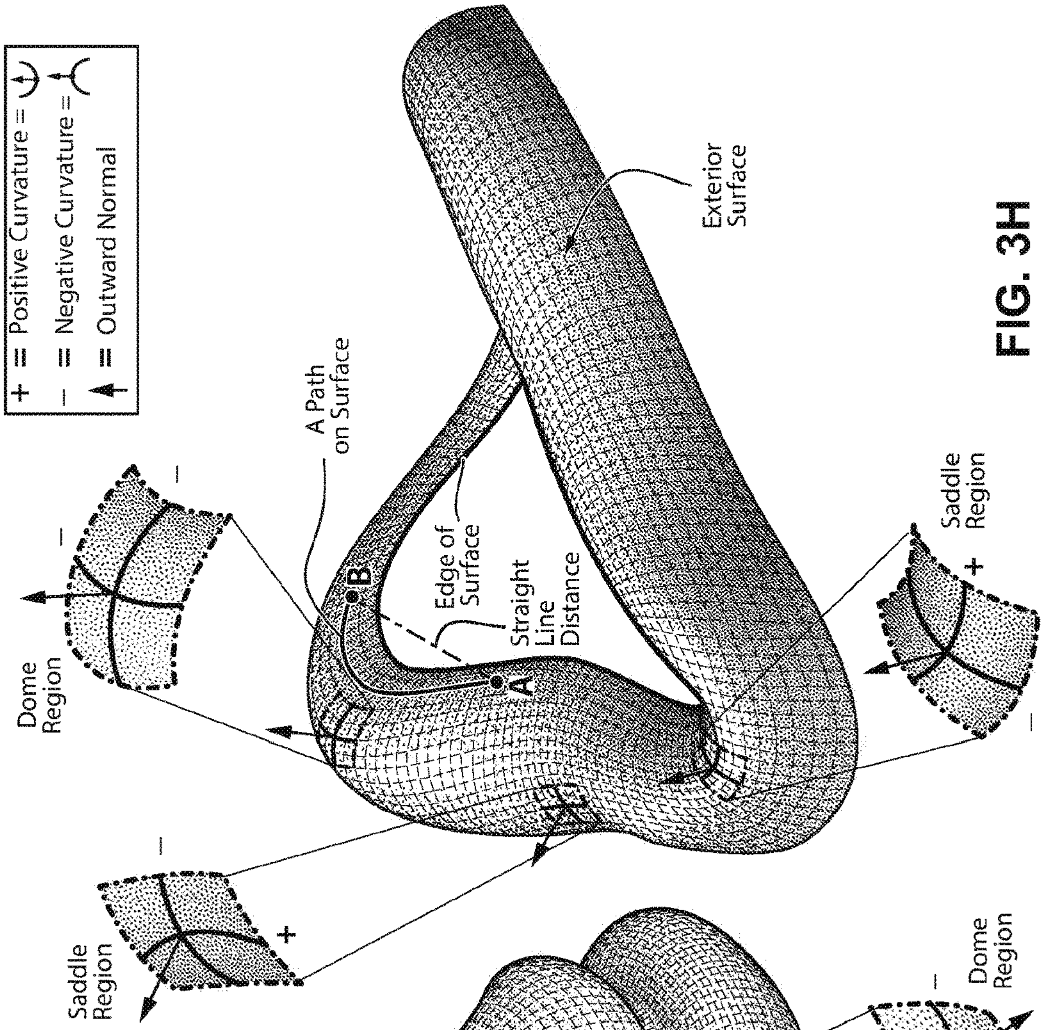

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
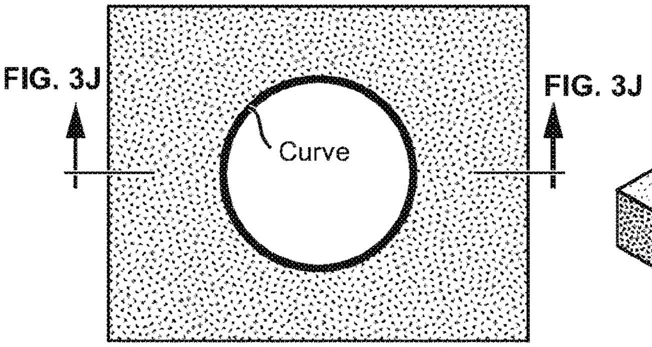

FIG. 3I shows the surface of a structure, with a one dimensional hole in the surface. The illustrated plane curve forms the boundary of a one dimensional hole.

Figure 3K:
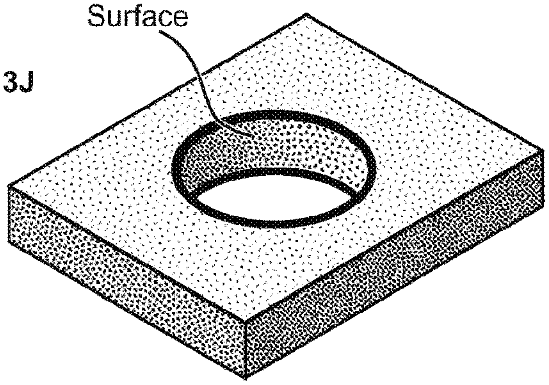
Figure 3J:
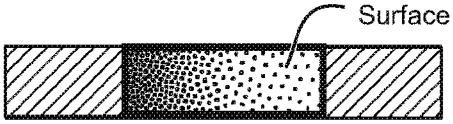

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

Figure 3L:
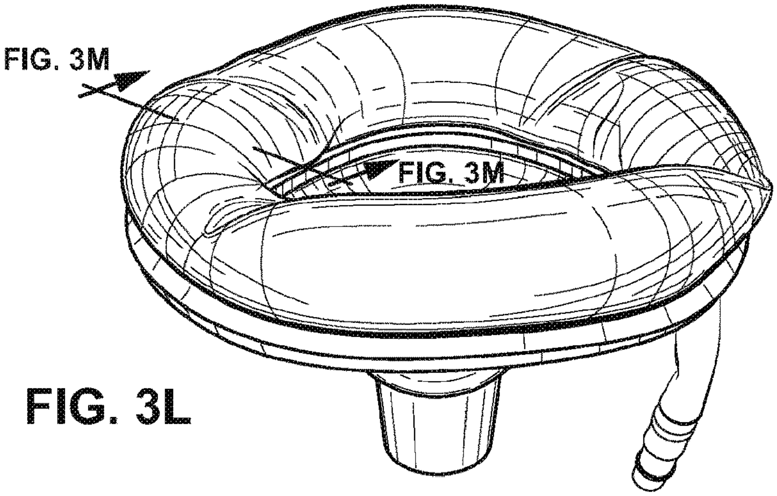

FIG. 3L shows a mask having an inflatable bladder as a cushion.

Figure 3M:
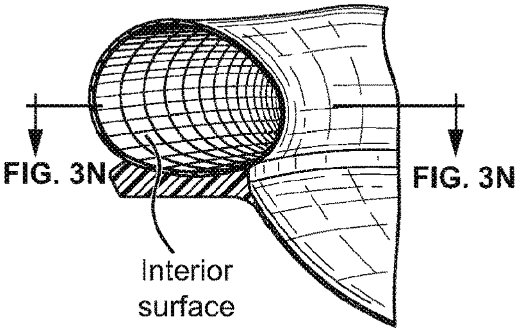

FIG. 3M shows a cross-section through the mask of FIG. 3L, and shows the interior surface of the bladder. The interior surface bounds the two dimensional hole in the mask.

Figure 3N:
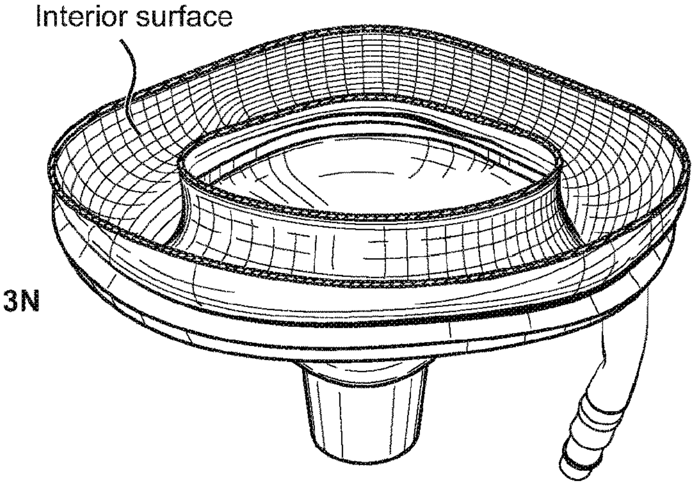

FIG. 3N shows a further cross-section through the mask of FIG. 3L. The interior surface is also indicated.

Figure 3O:
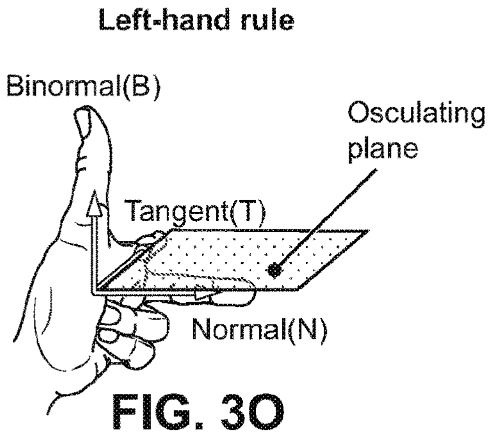

FIG. 3O illustrates a left-hand rule.

Figure 3P:
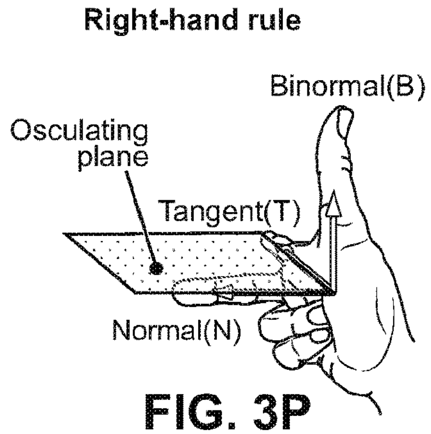

FIG. 3P illustrates a right-hand rule.

Figure 3Q:
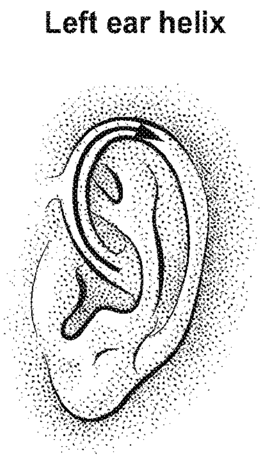

FIG. 3Q shows a left ear, including the left ear helix.

Figure 3S:
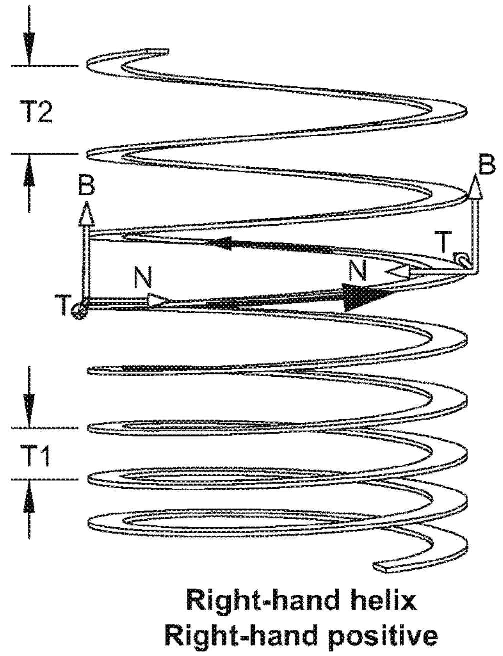
Figure 3R:
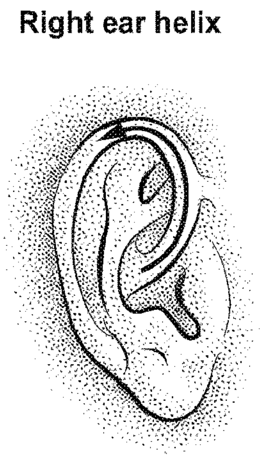

FIG. 3R shows a right ear, including the right ear helix.

FIG. 3S shows a right-hand helix.

Figure 3T:
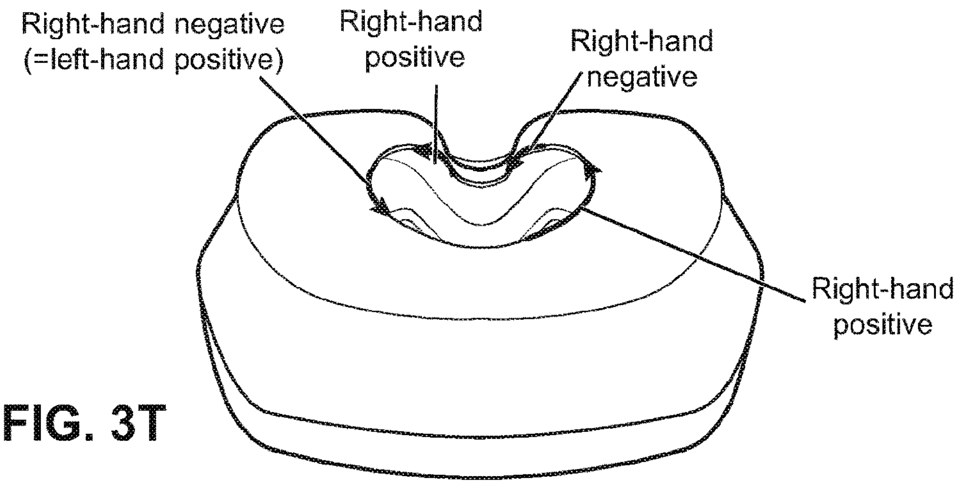

FIG. 3T shows a view of a mask, including the sign of the torsion of the space curve defined by the edge of the sealing membrane in different regions of the mask.

Figure 3U:
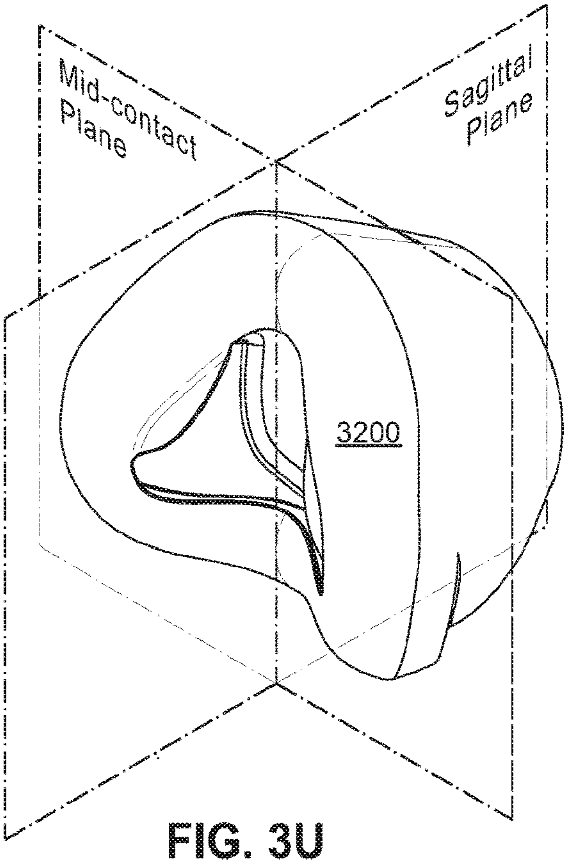

FIG. 3U shows a view of a plenum chamber 3200 showing a sagittal plane and a mid-contact plane.

Figure 3V:
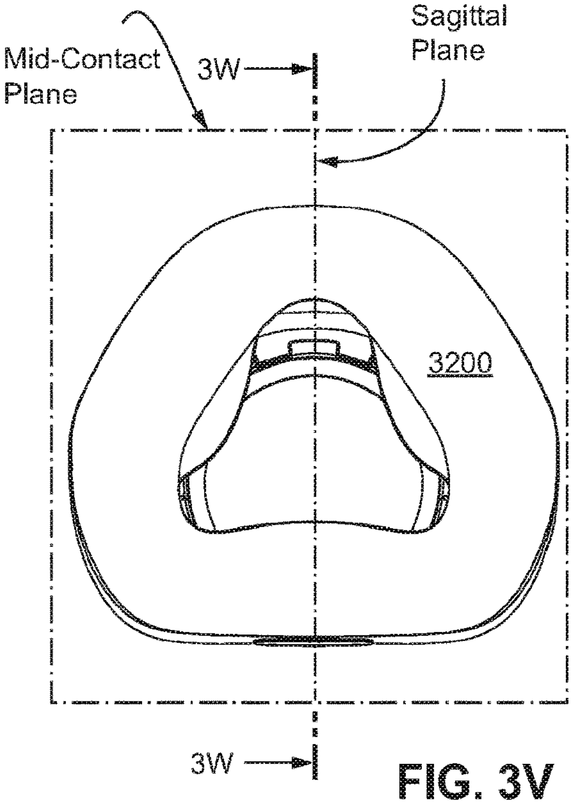

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

Figure 3W:
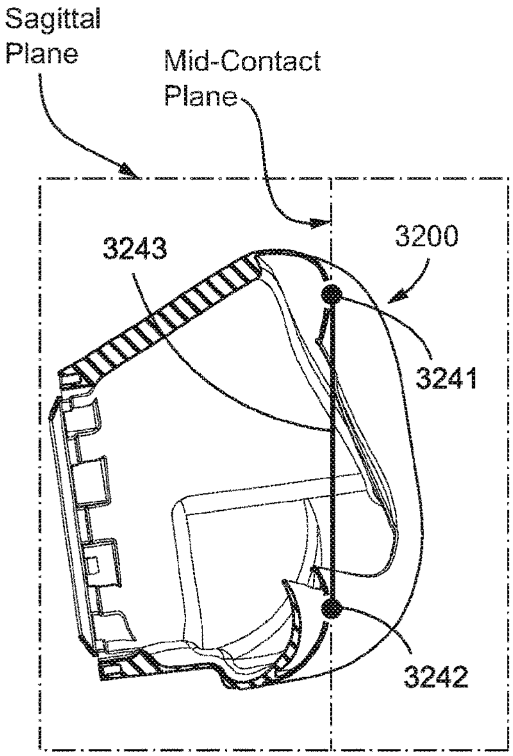

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3243 which lies on the sagittal plane and just touches the cushion of the plenum chamber at two points on the sagittal plane: a superior point 3241 and an inferior point 3242. Depending on the geometry of the cushion in this region, the mid-contact plane may be a tangent at both the superior and inferior points.

Figure 3X:
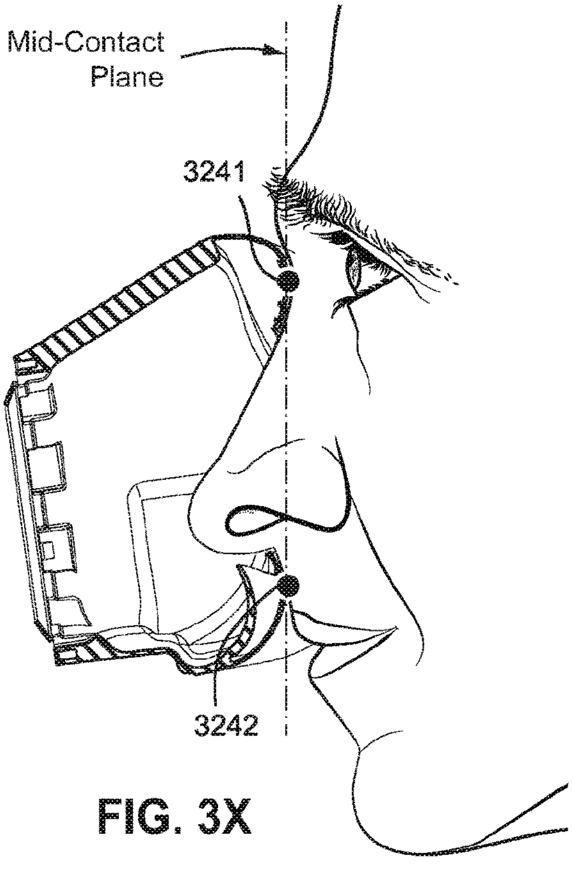

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3241 sits approximately on the sellion, while the inferior point 3242 sits on the lip superior.

4.4 RPT Device

Figure 4A:
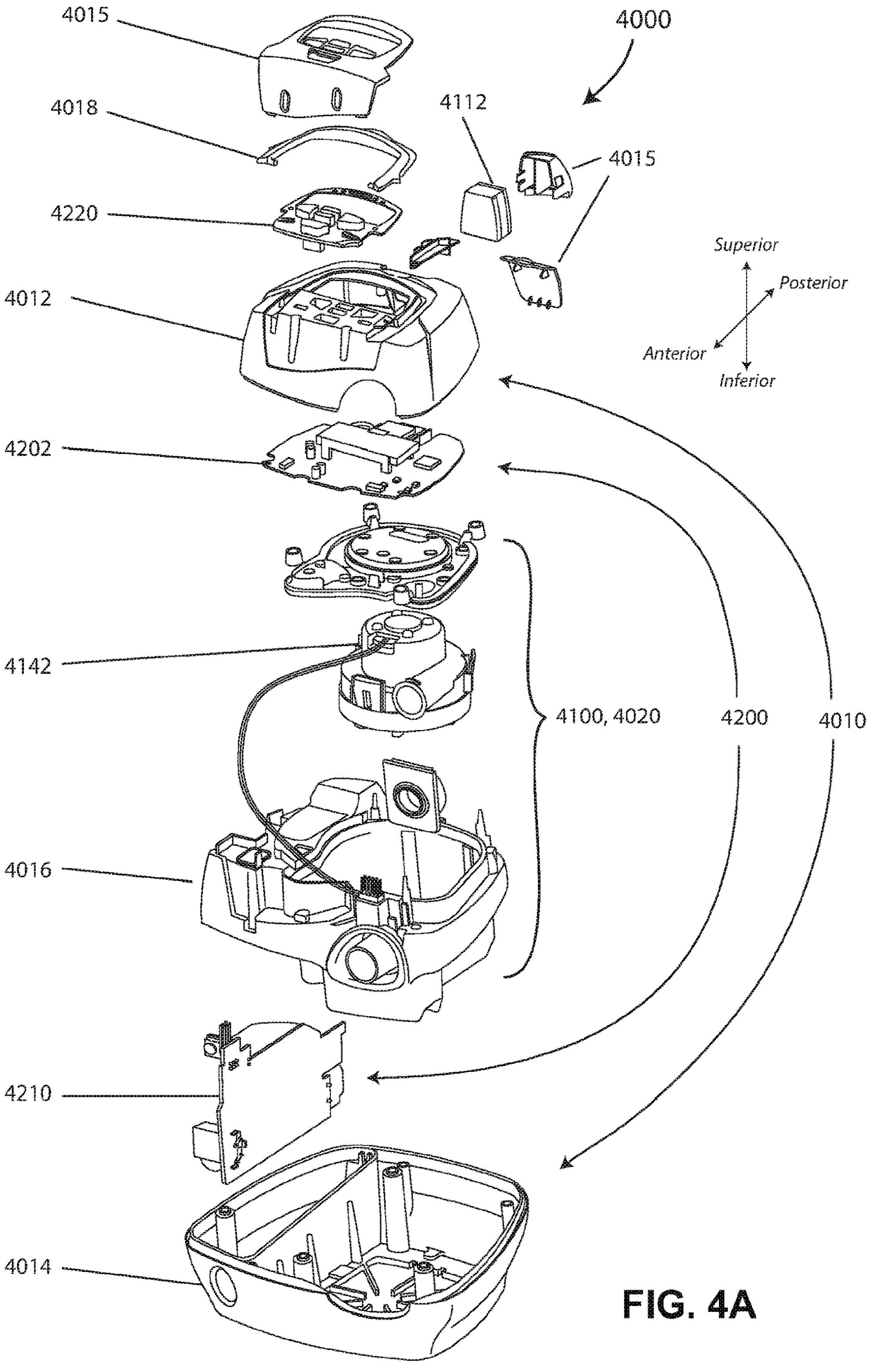

FIG. 4A shows an RPT device in accordance with one form of the present technology.

Figure 4B:
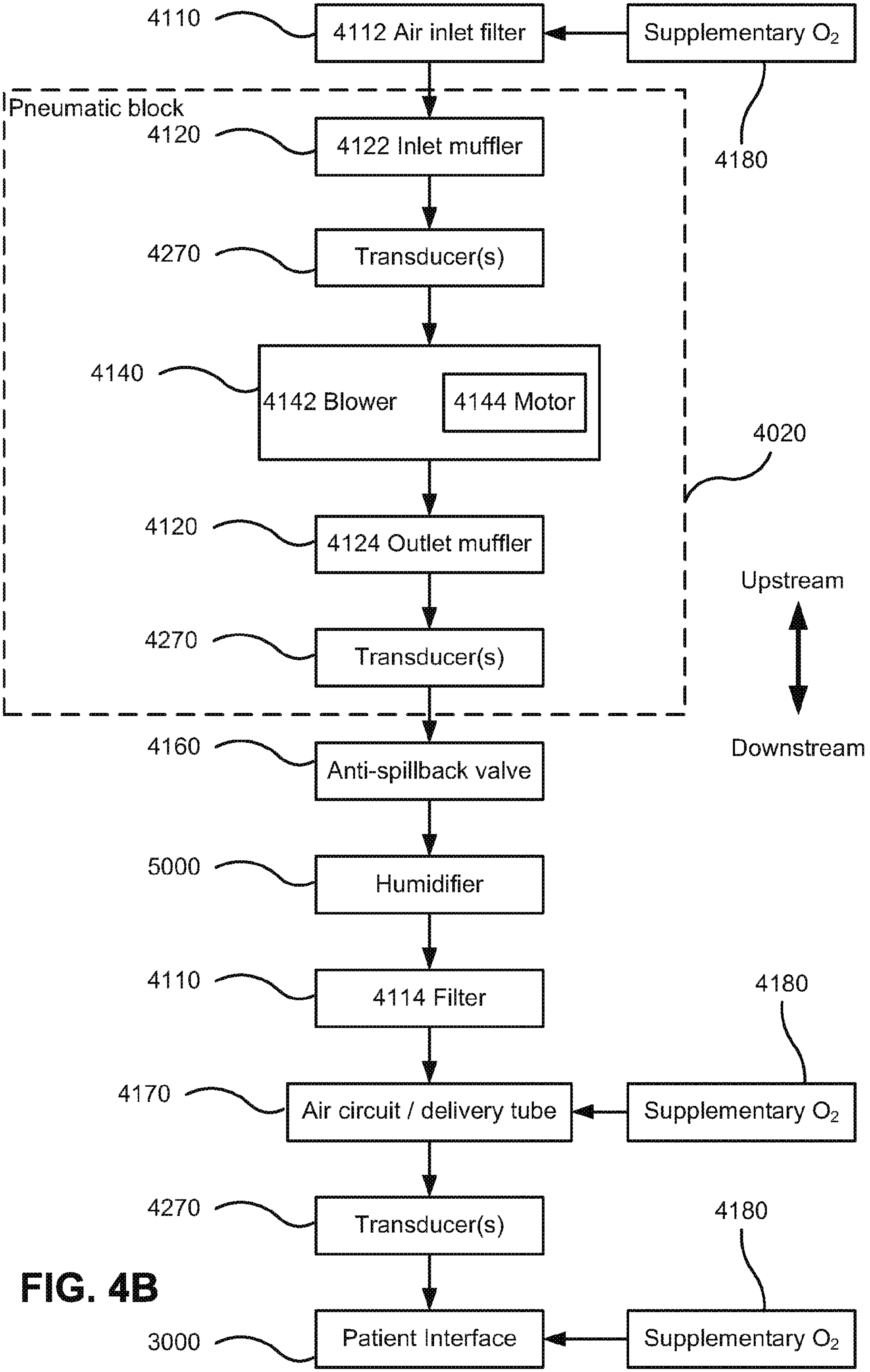

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.5 Humidifier

Figure 5A:
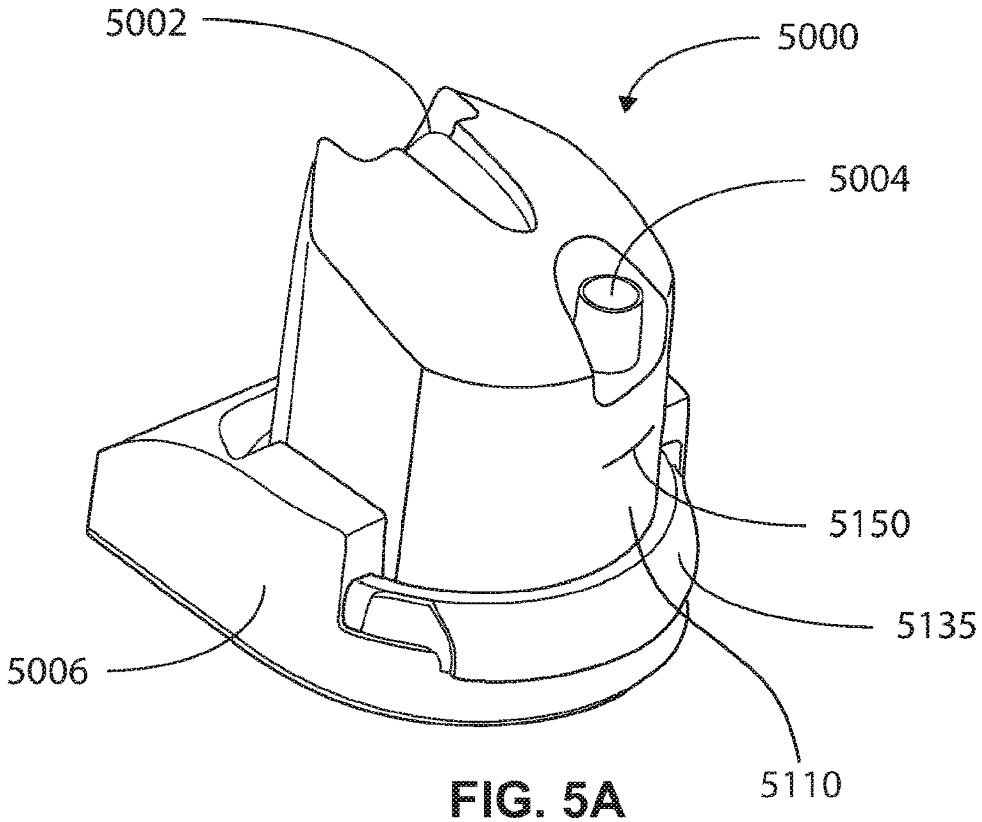

FIG. 5A shows an isometric view of a humidifier in accordance with one form of the present technology.

Figure 5B:
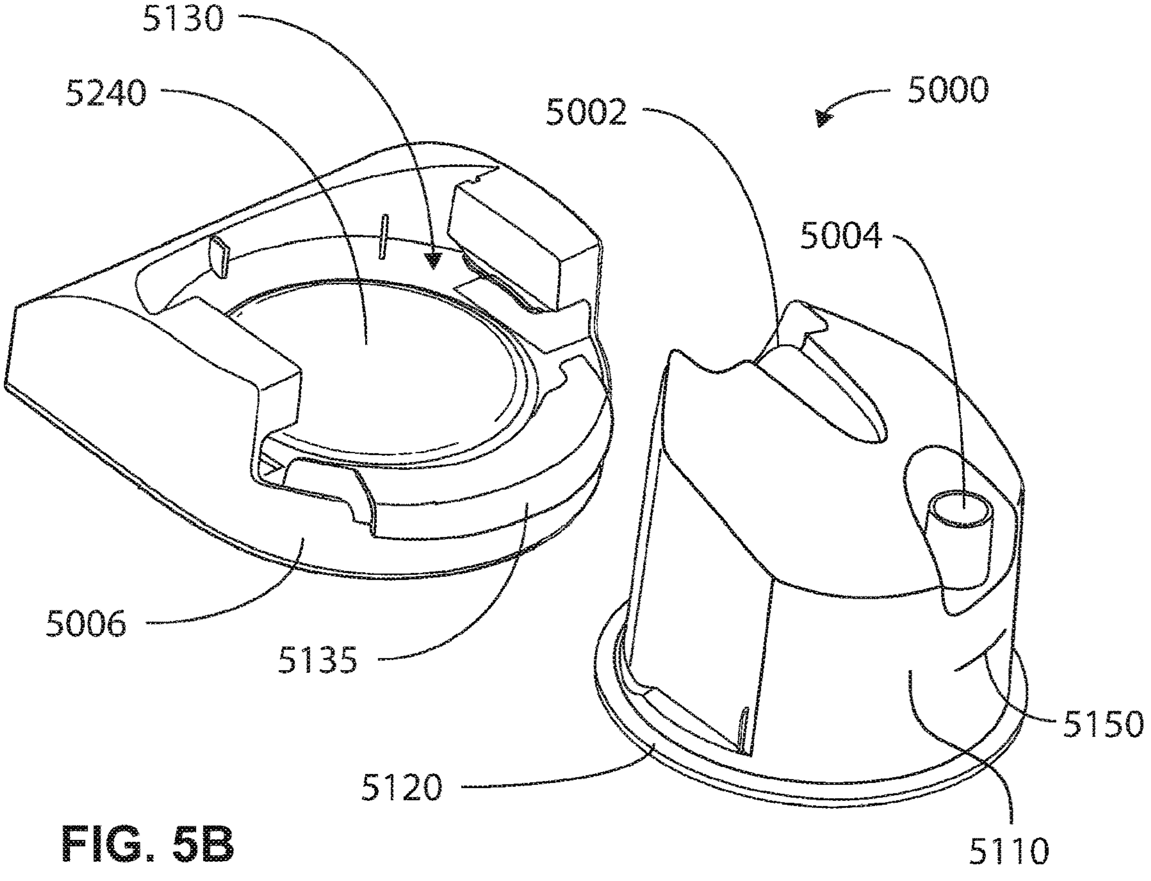

FIG. 5B shows an isometric view of a humidifier in accordance with one form of the present technology, showing a humidifier reservoir 5110 removed from the humidifier reservoir dock 5130.

4.6 Breathing Waveforms

Figure 6:
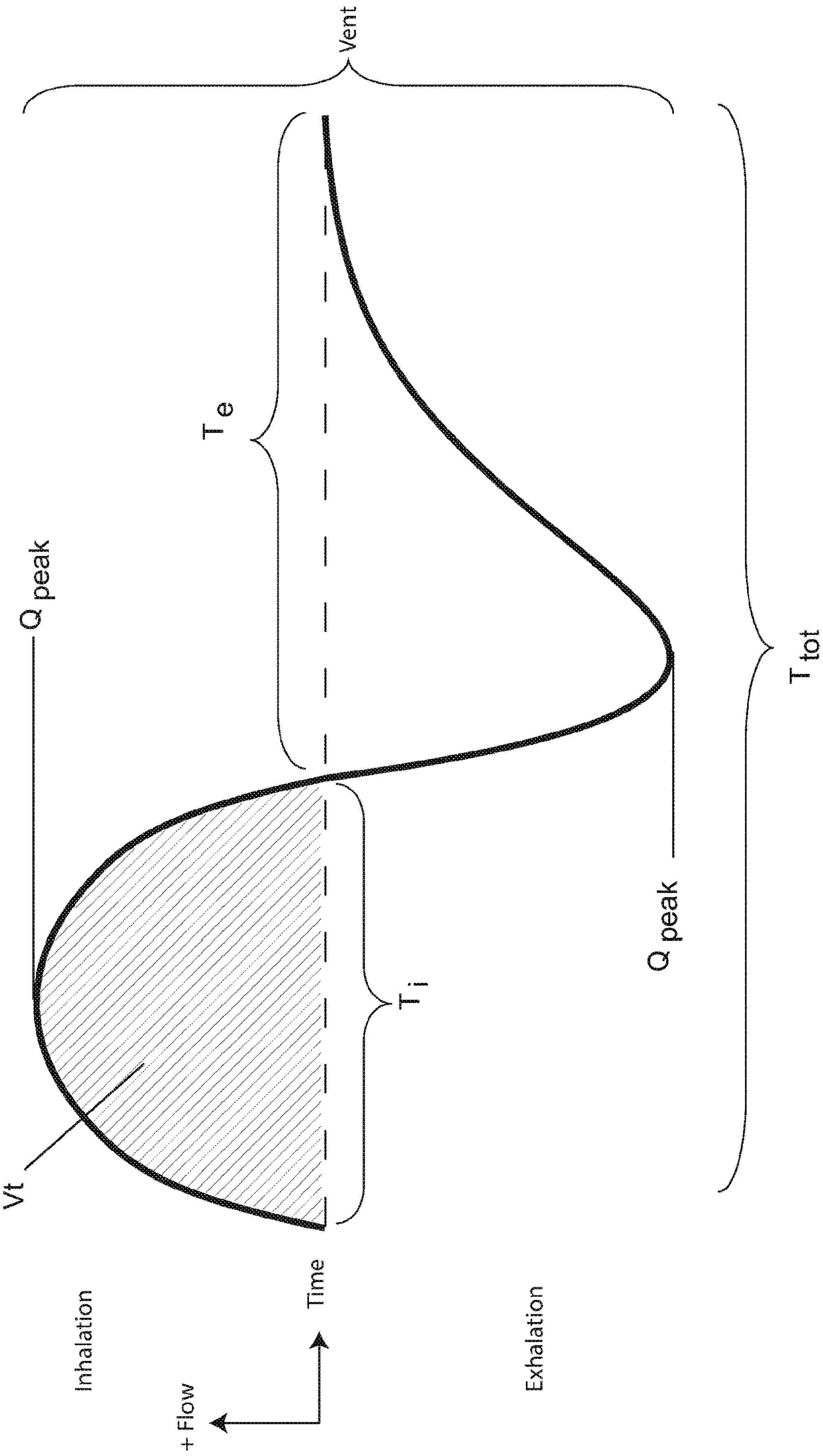

FIG. 6 shows a model typical breath waveform of a person while sleeping.

4.7 Particular Examples of the Present Technology

Figure 7A:
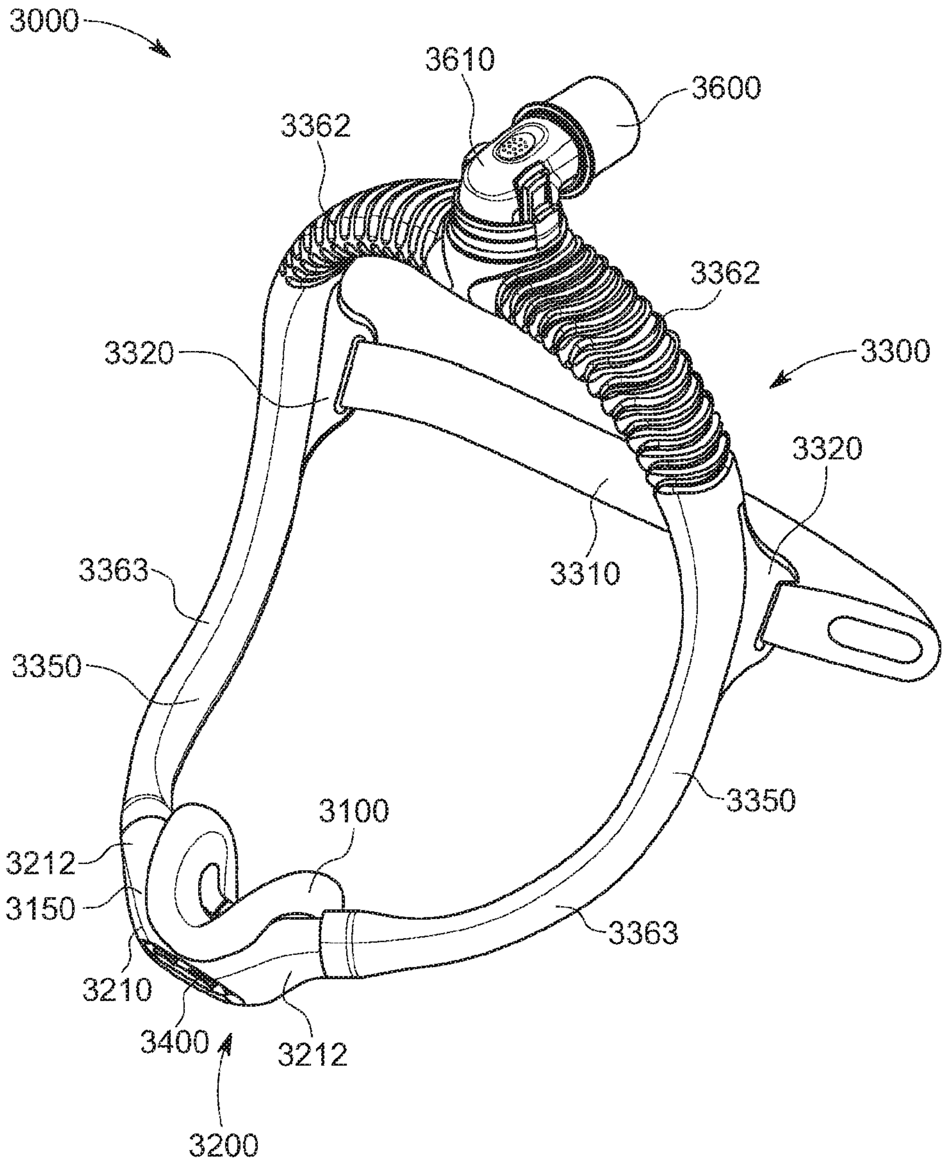

FIG. 7A is a superior anterolateral perspective view illustration of a patient interface 3000 according to one example of the present technology.

Figure 7B:
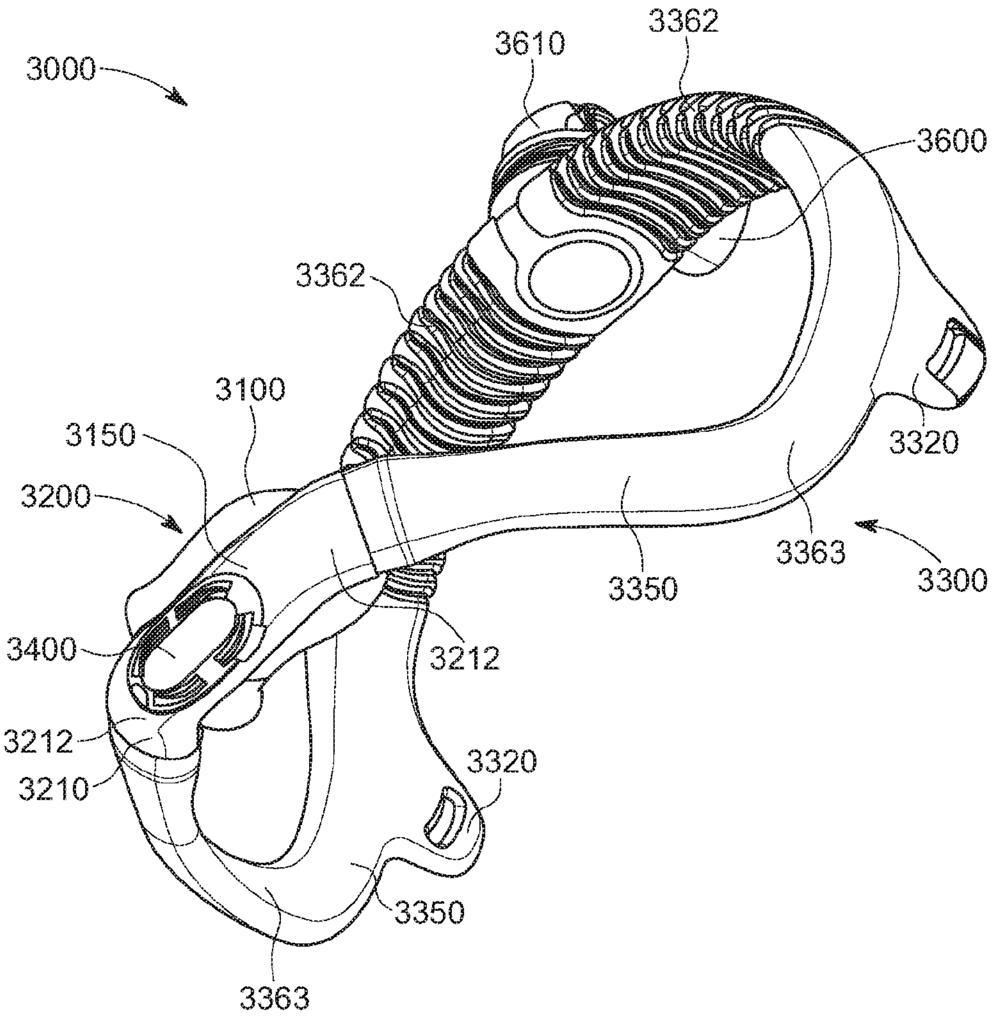

FIG. 7B is an inferior anterolateral view illustration of the patient interface 3000 shown in FIG. 7A.

Figure 7C:
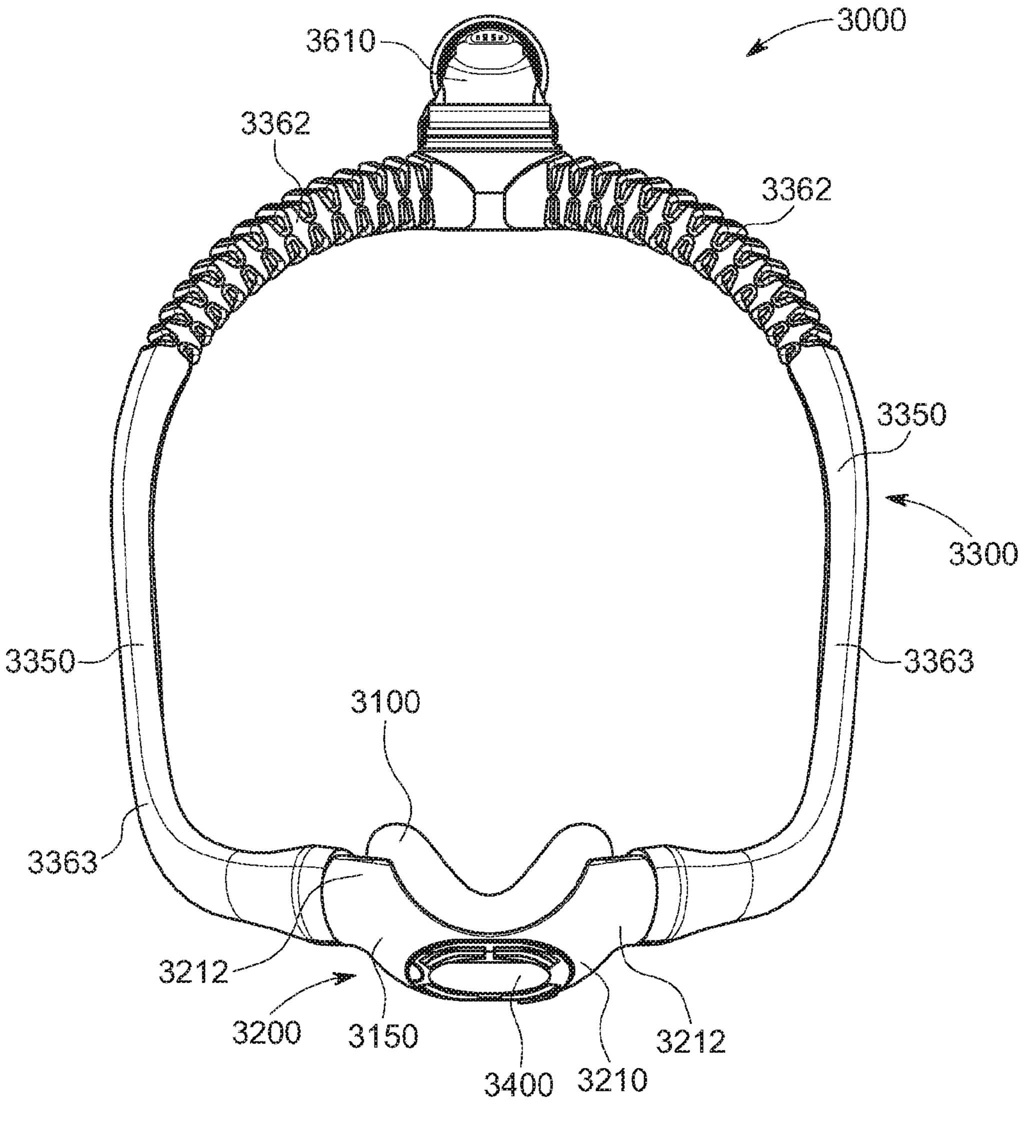

FIG. 7C is an anterior view illustration of the patient interface 3000 shown in FIG. 7A.

Figure 7D:
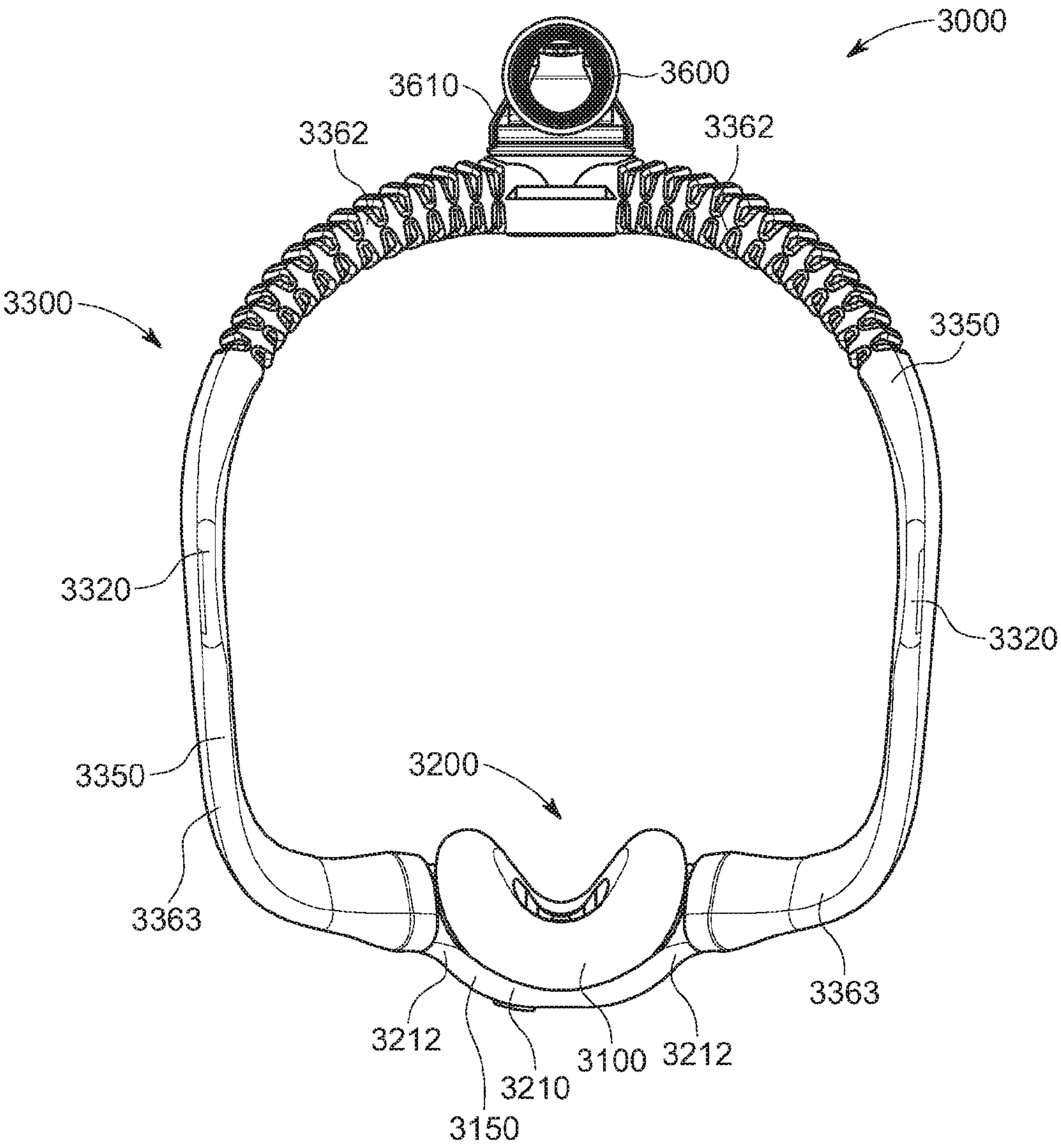

FIG. 7D is a posterior view illustration of the patient interface 3000 shown in FIG. 7A.

Figure 7E:
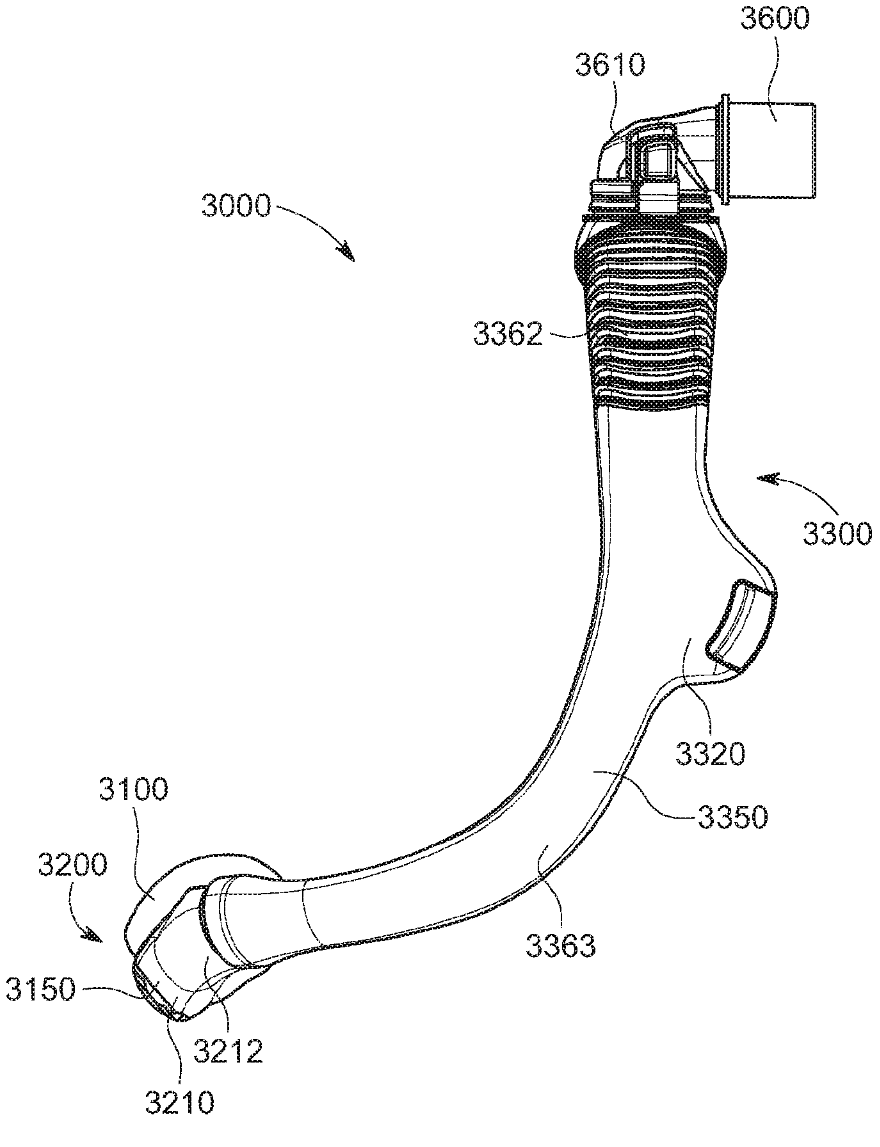

FIG. 7E is a lateral view illustration of the patient interface 3000 shown in FIG. 7A.

Figure 7F:
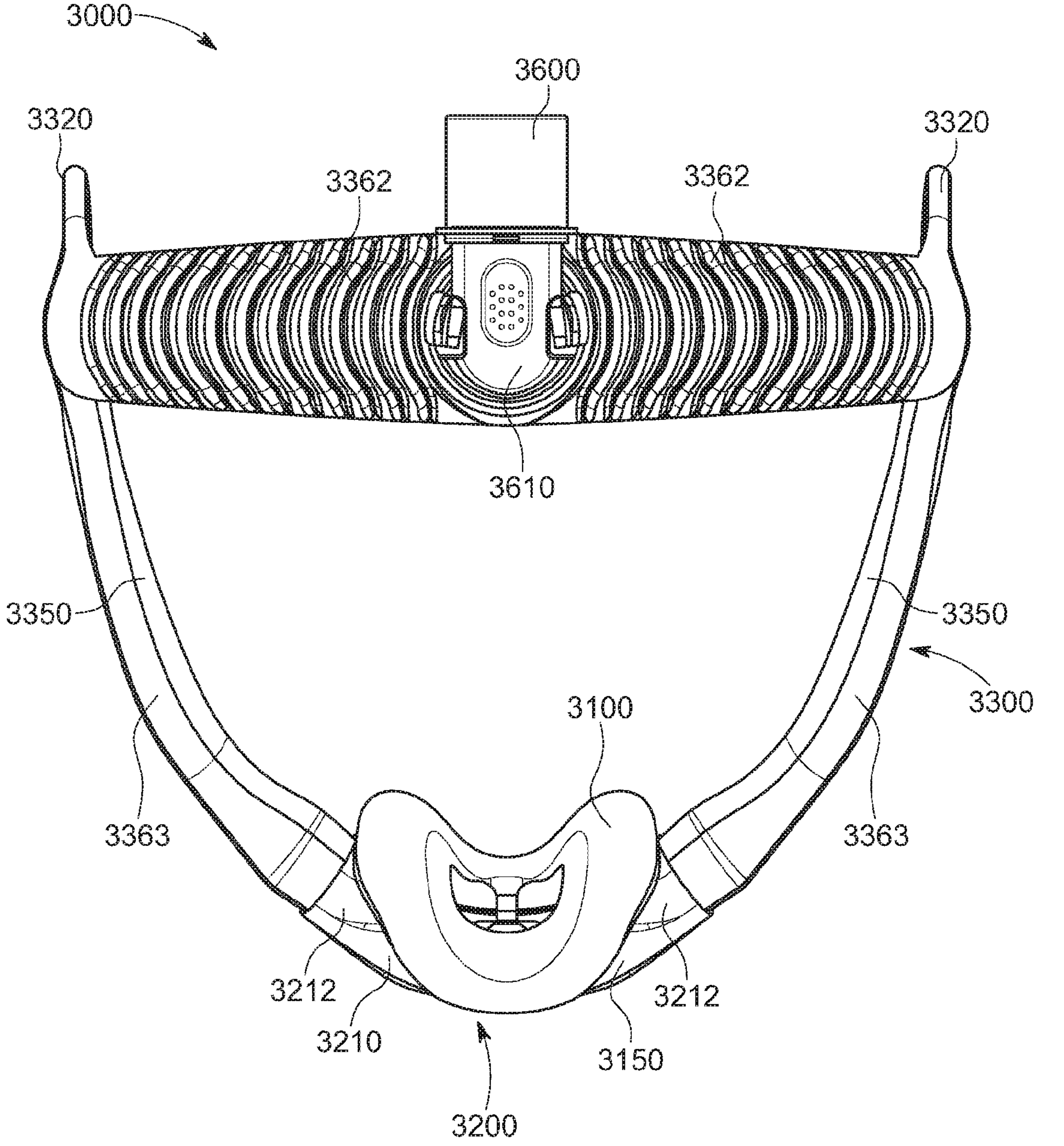

FIG. 7F is a superior view illustration of the patient interface 3000 shown in FIG. 7A.

Figure 7G:
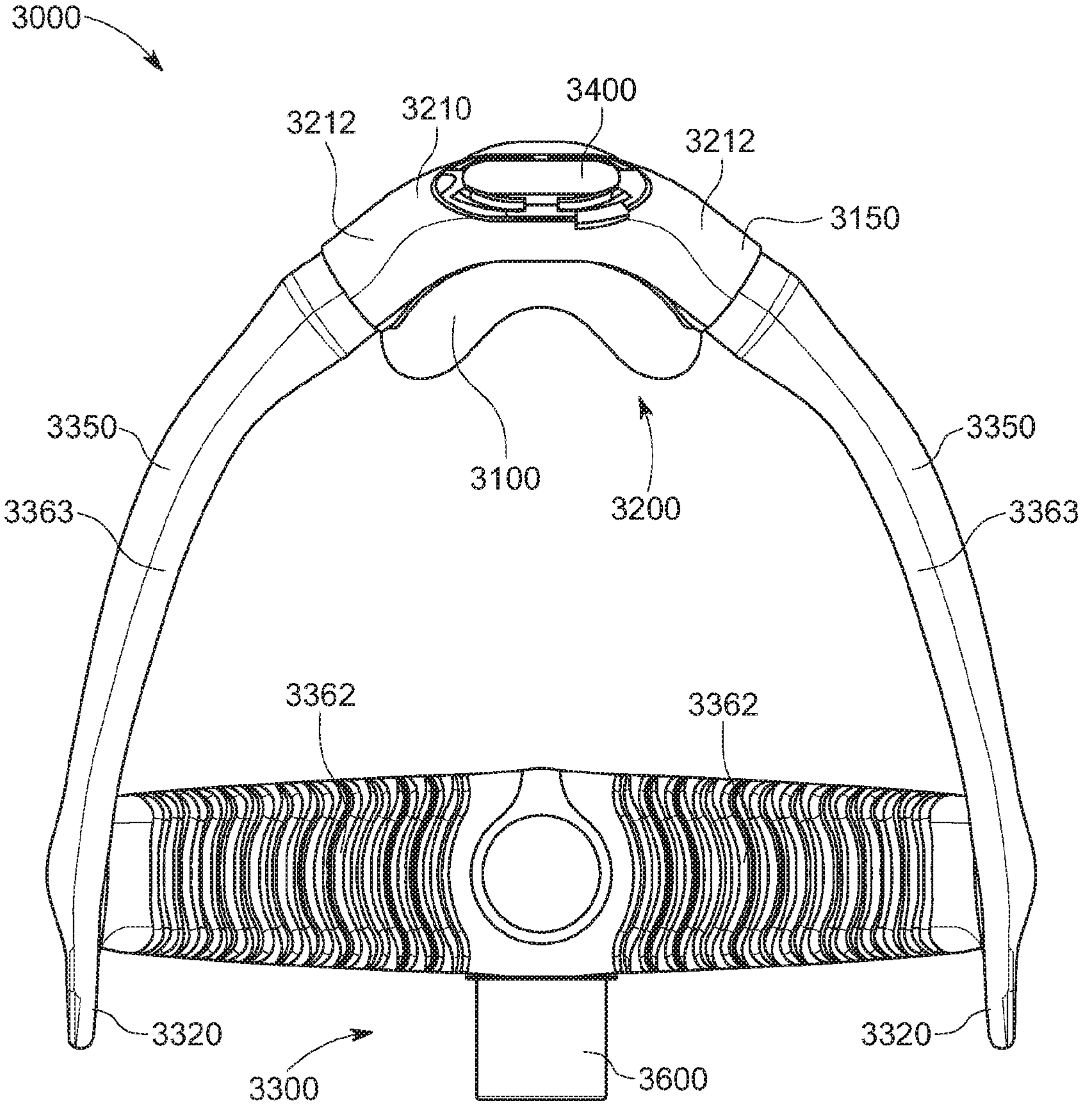

FIG. 7G is an inferior view illustration of the patient interface 3000 shown in FIG. 7A.

Figure 7H:
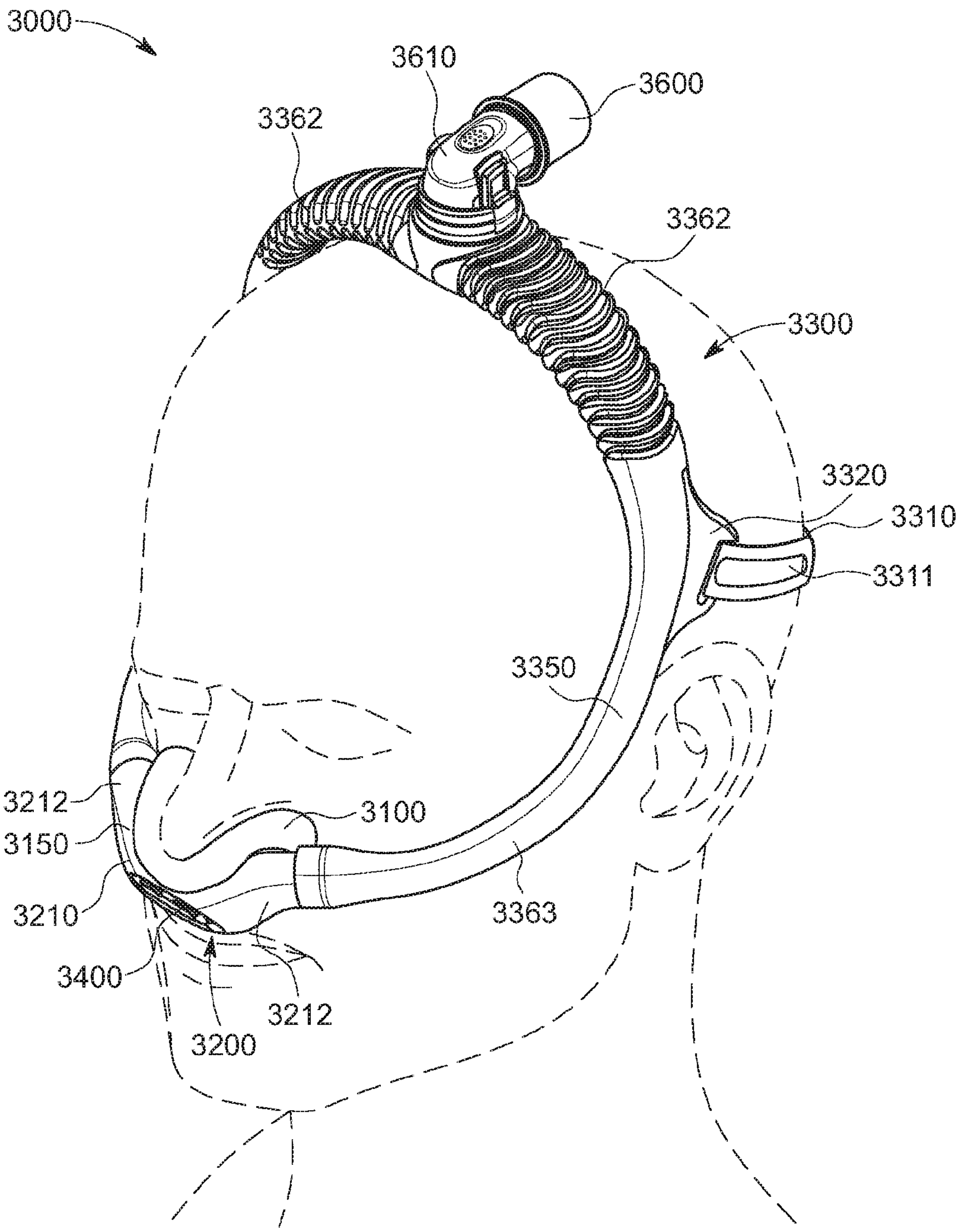

FIG. 7H is a perspective view illustration of the patient interface 3000 shown in FIG. 7A while donned by a patient.

Figure 8A:
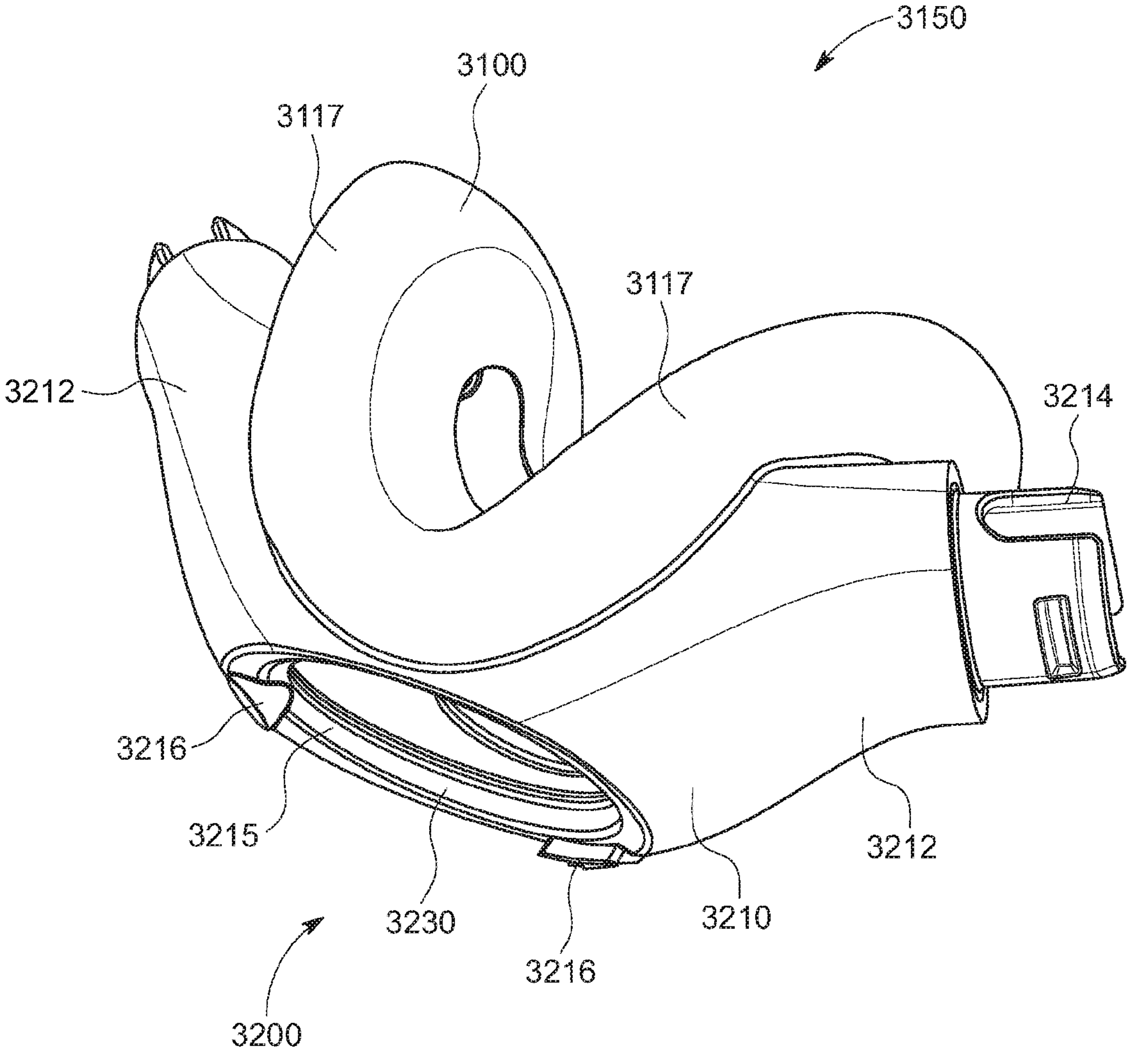

FIG. 8A is an anterolateral view illustration of the cushion module 3150 of the patient interface 3000 shown in FIG. 7A.

Figure 8B:
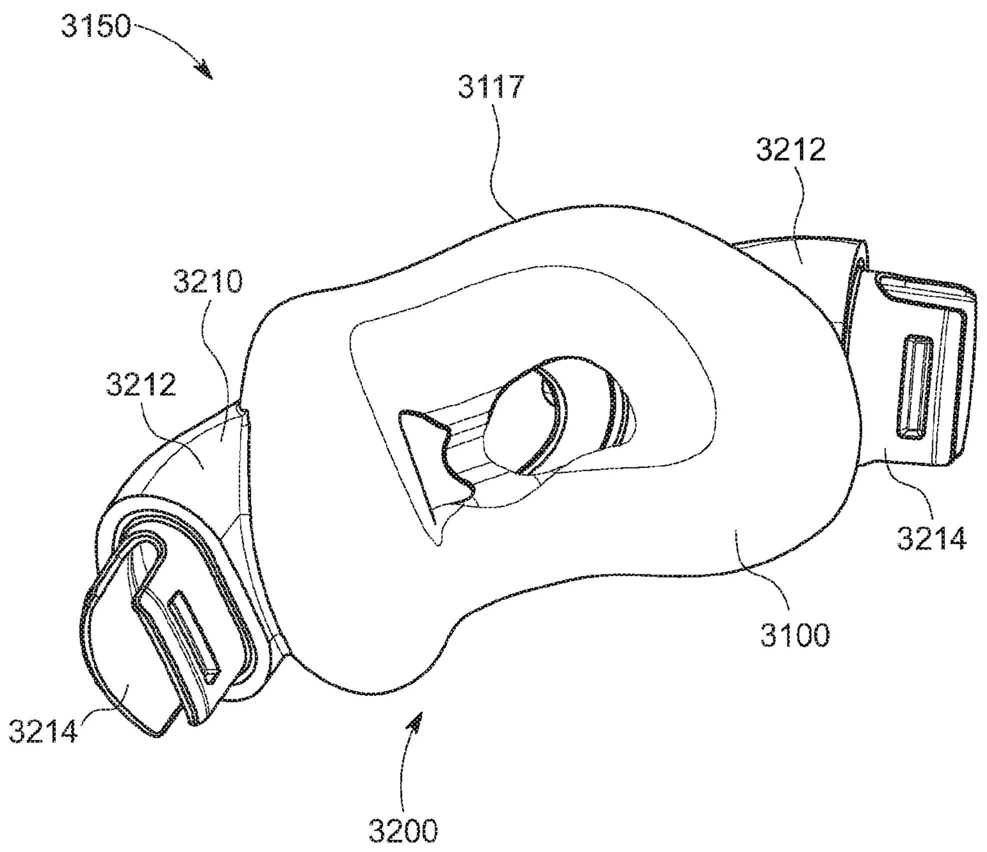

FIG. 8B is a posterolateral view illustration of the cushion module 3150 shown in FIG. 8A.

Figure 8C:
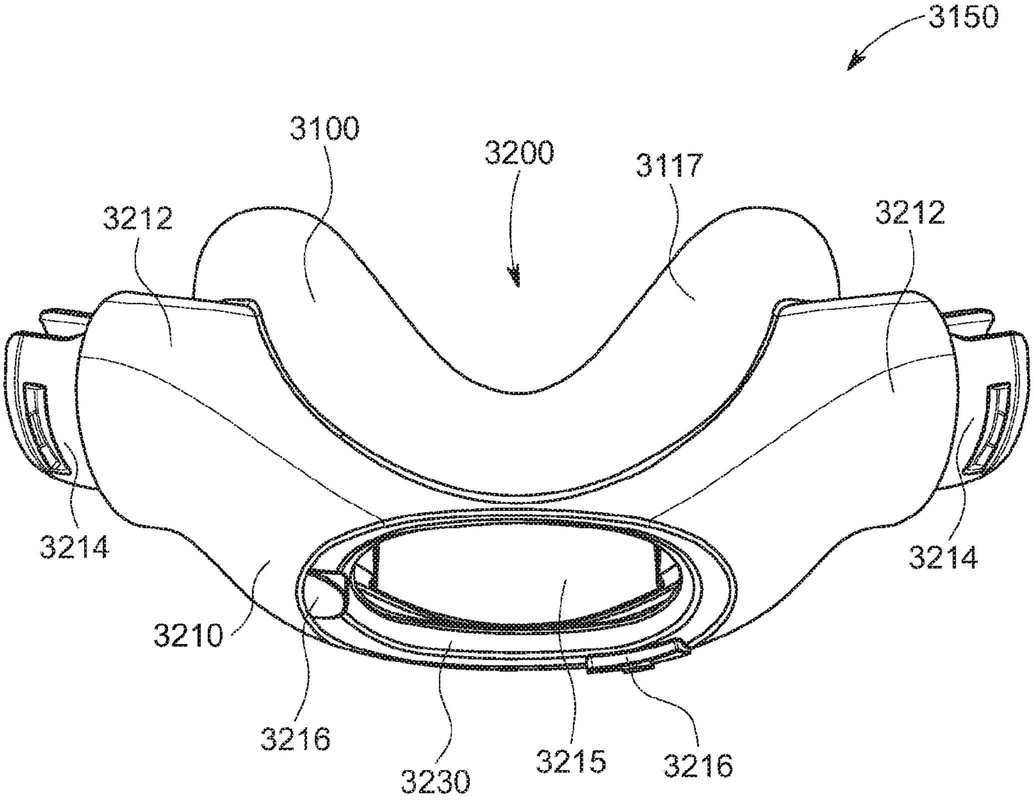

FIG. 8C is an anterior view illustration of the cushion module 3150 shown in FIG. 8A.

Figure 8D:
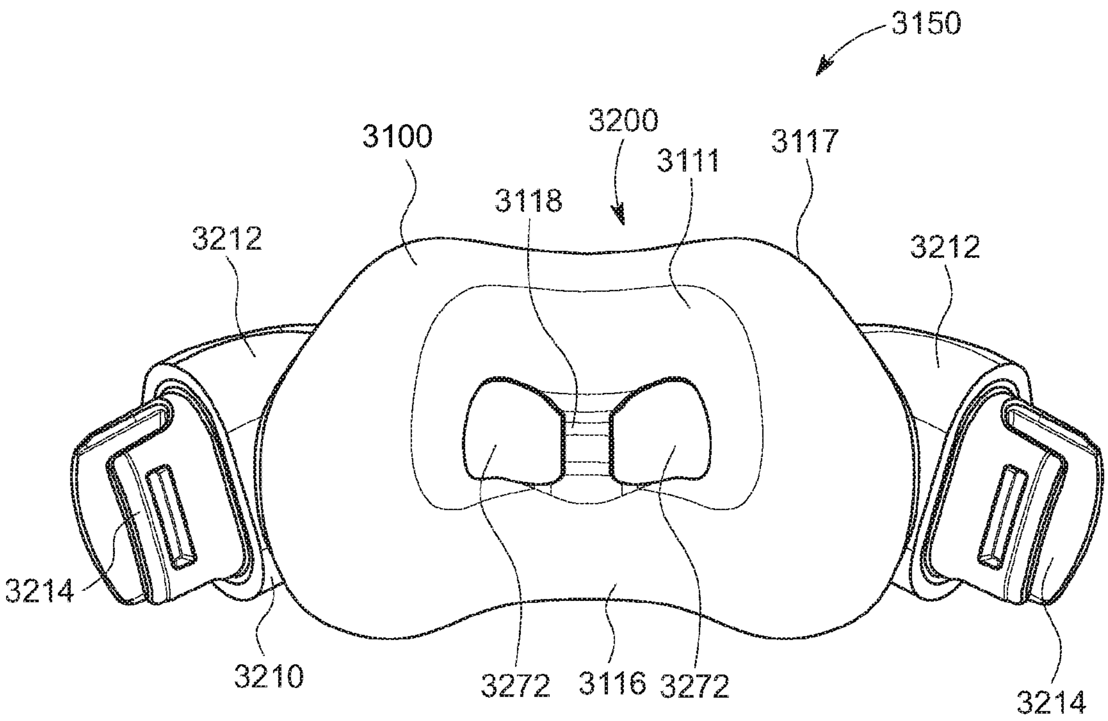

FIG. 8D is a posterior view illustration of the cushion module 3150 shown in FIG. 8A.

Figure 8E:
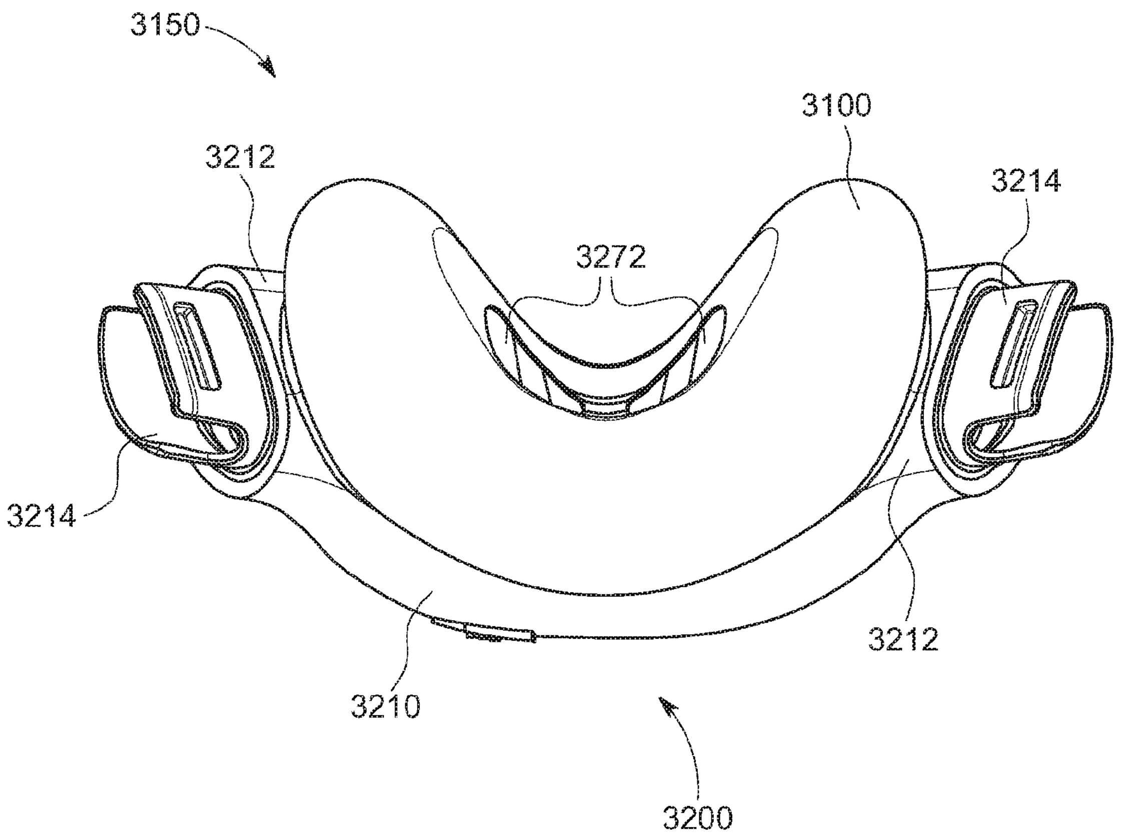

FIG. 8E is a posteroinferior view illustration of the cushion module 3150 shown in FIG. 8A.

Figure 8F:
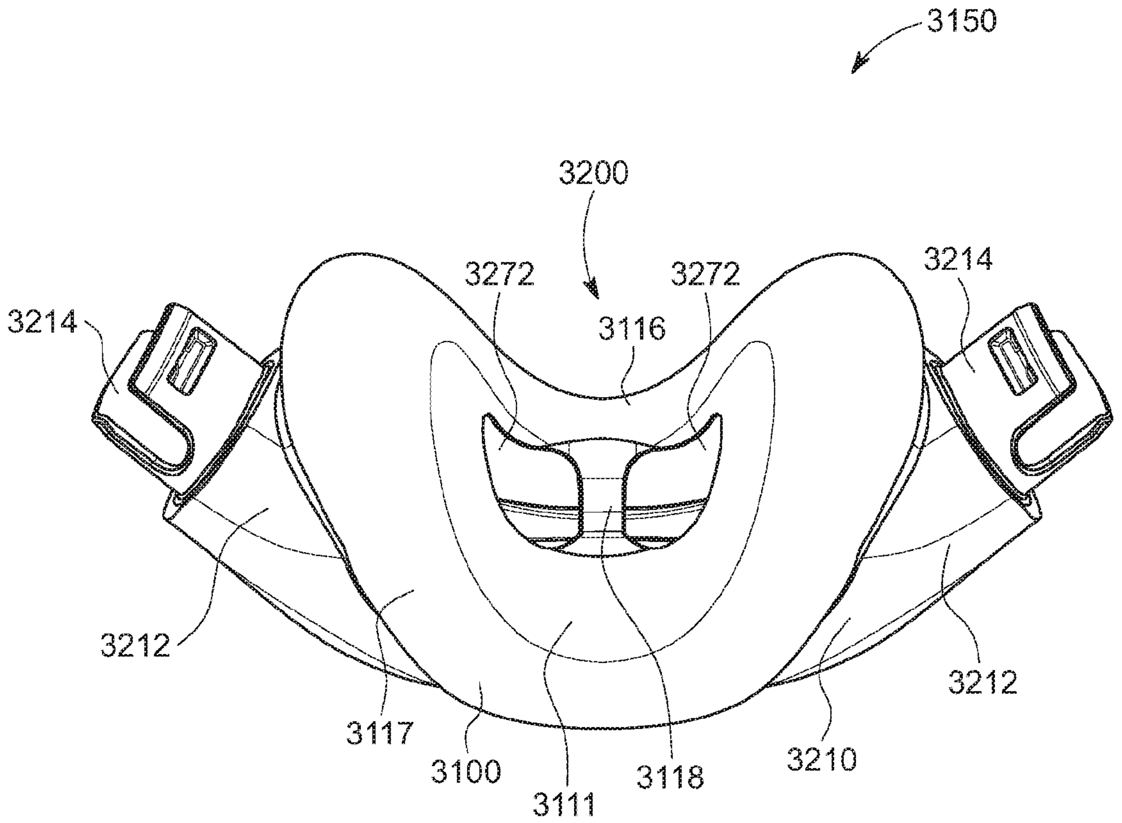

FIG. 8F is a superior view illustration of the cushion module 3150 shown in FIG. 8A.

Figure 8G:
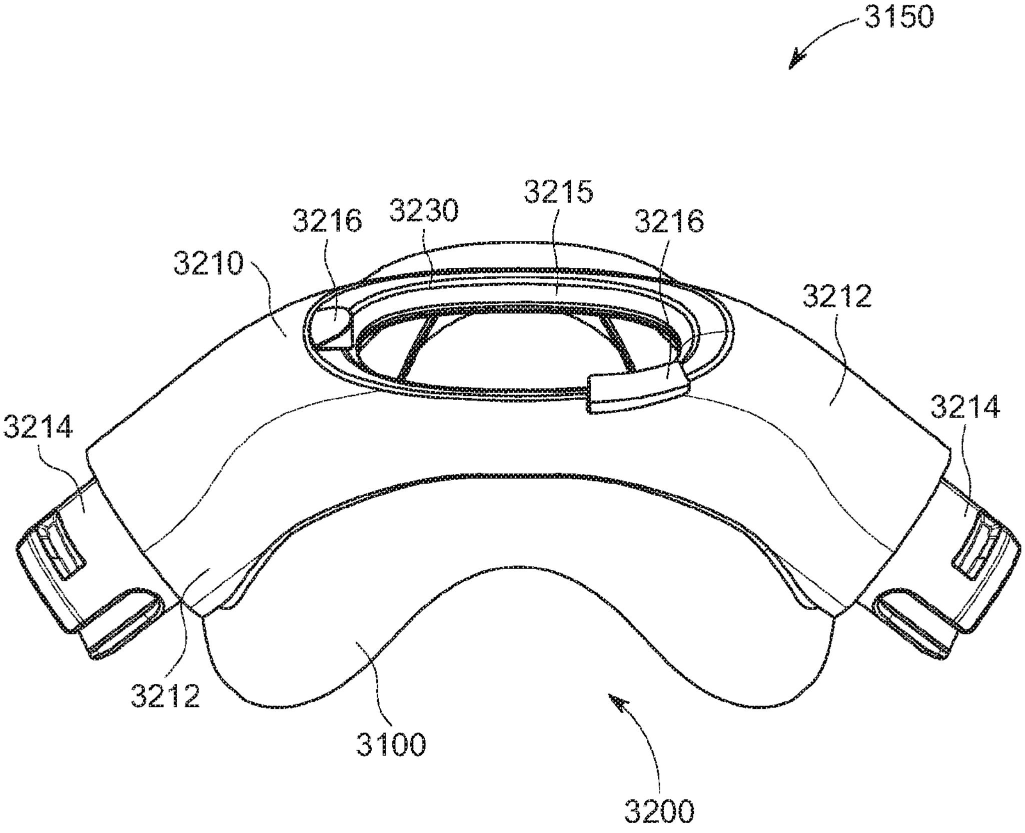

FIG. 8G is an anteroinferior view illustration of the cushion module 3150 shown in FIG. 8A.

Figure 8H:
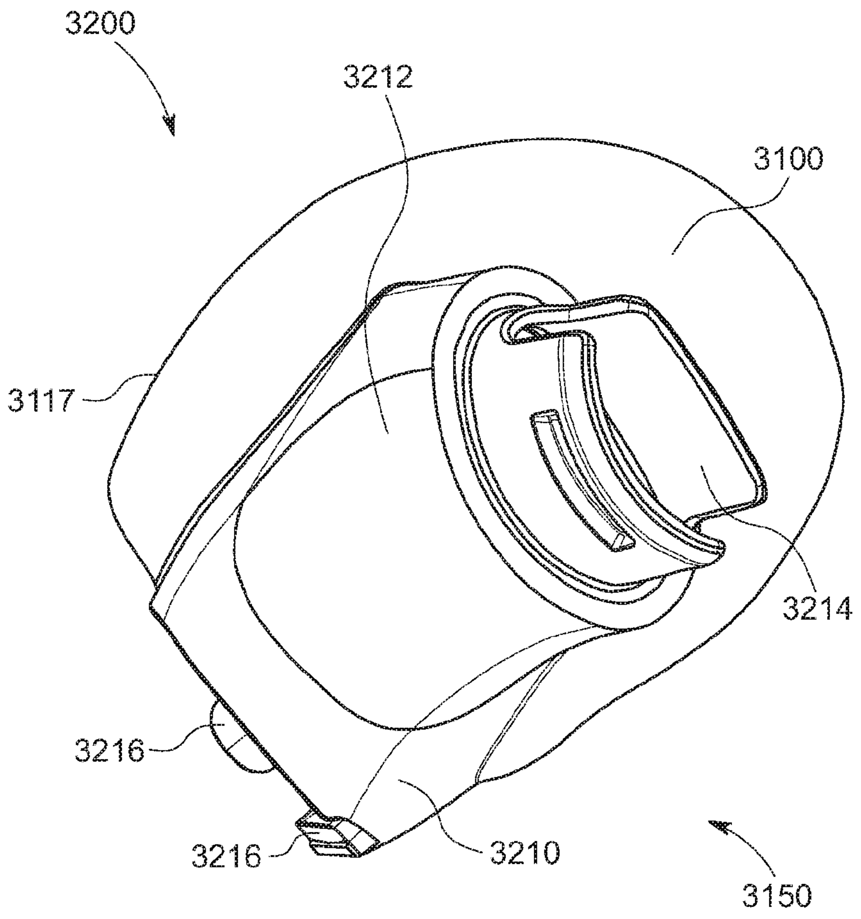

FIG. 8H is a lateral view illustration of the cushion module 3150 shown in FIG. 8A.

Figure 9A:
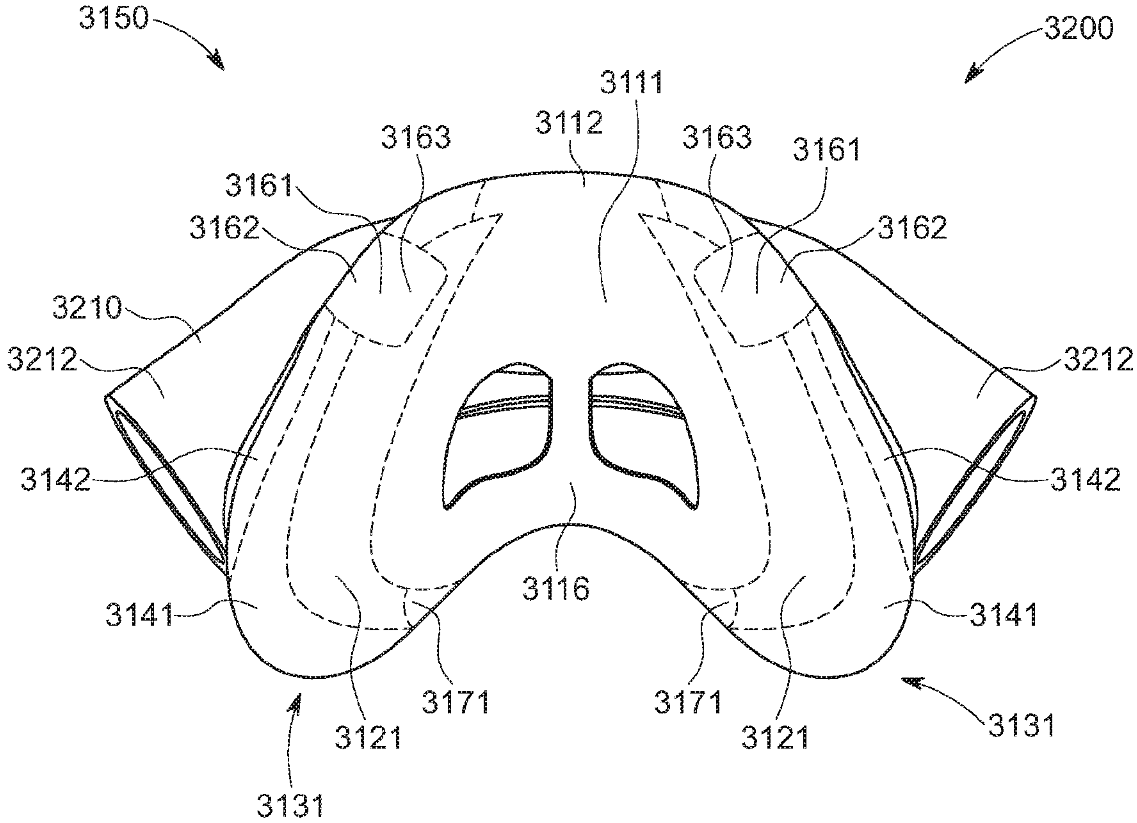

FIG. 9A is a posterosuperior view illustration of the cushion module 3150 shown in FIG. 8A with various portions identified.

Figure 9B:
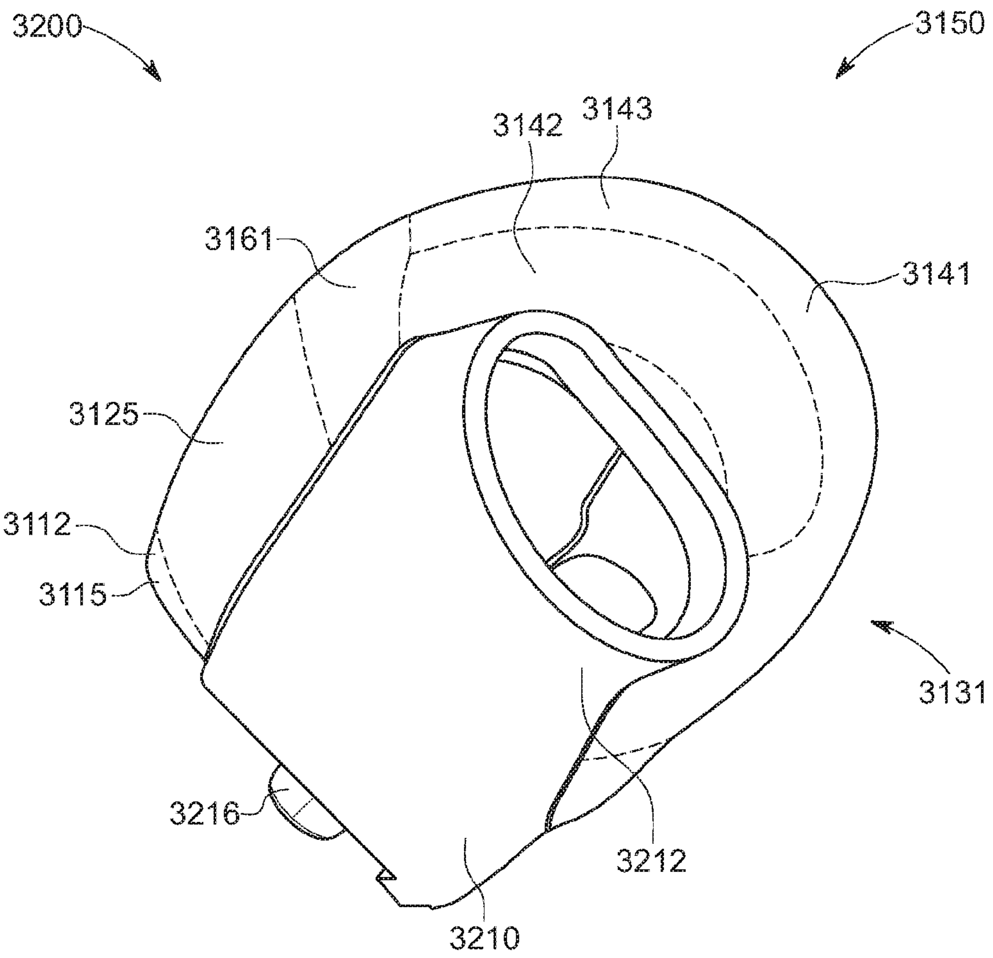

FIG. 9B is a lateral view illustration of the cushion module 3150 shown in FIG. 8A with various portions identified.

Figure 9C:
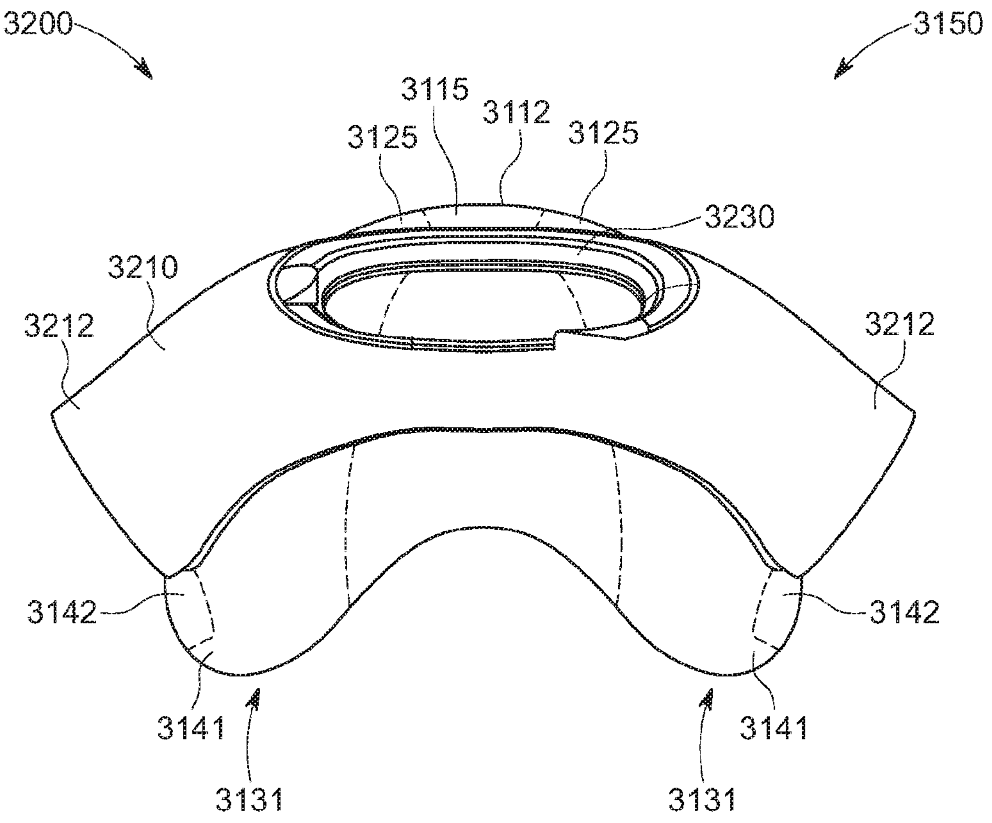

FIG. 9C is an inferior view illustration of the cushion module 3150 shown in FIG. 8A with various portions identified.

Figure 9D:
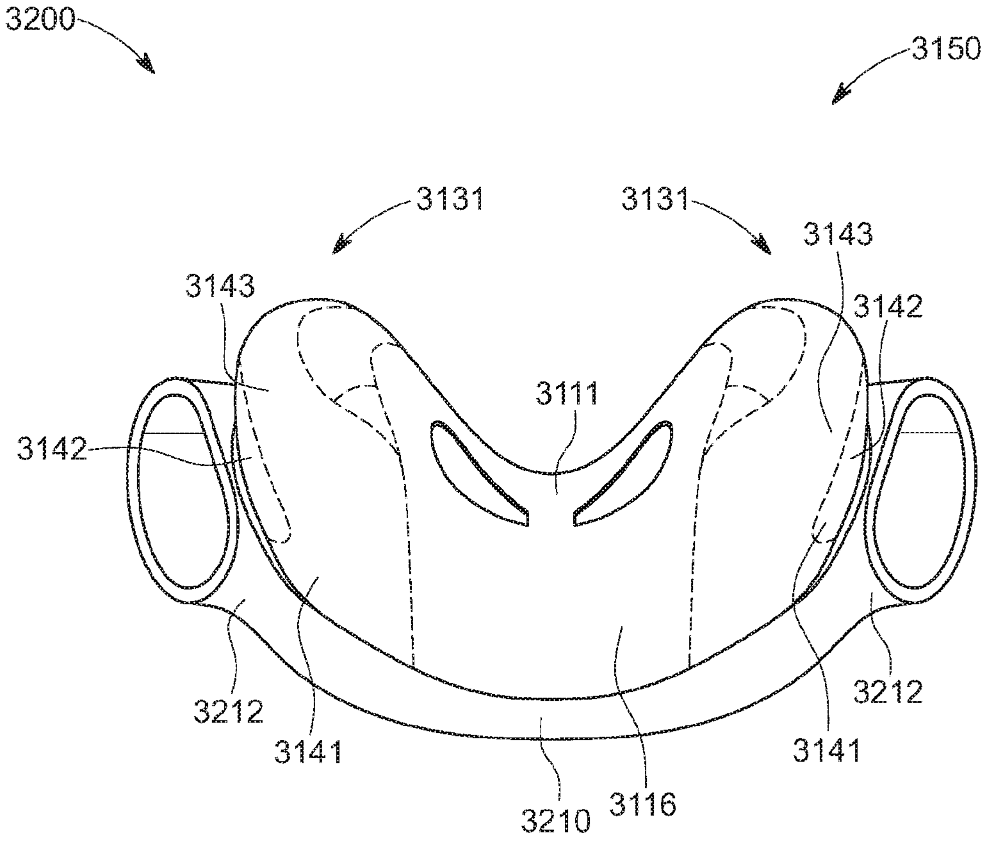

FIG. 9D is a posterior view illustration of the cushion module 3150 shown in FIG. 8A with various portions identified.

Figure 9E:
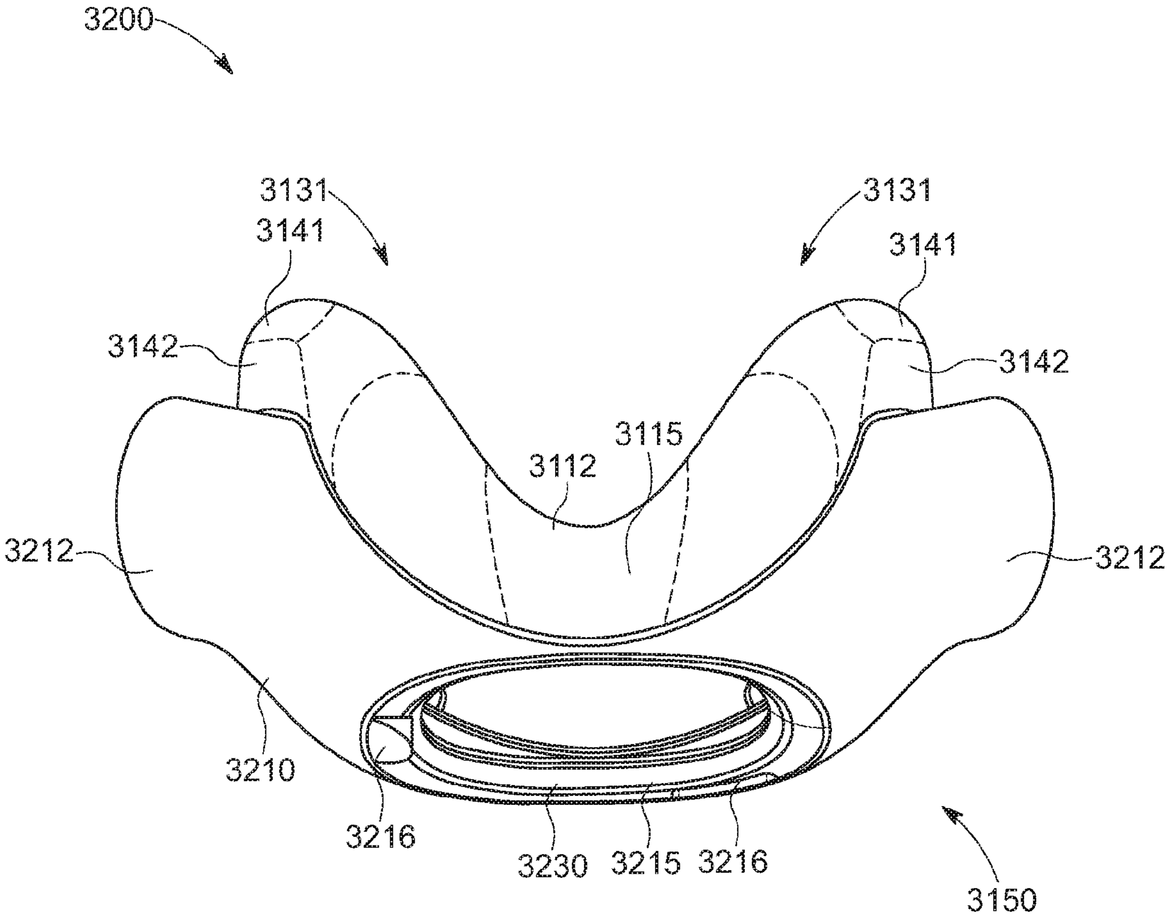

FIG. 9E is a superior view illustration of the cushion module 3150 shown in FIG. 8A with various portions identified.

Figure 9F:
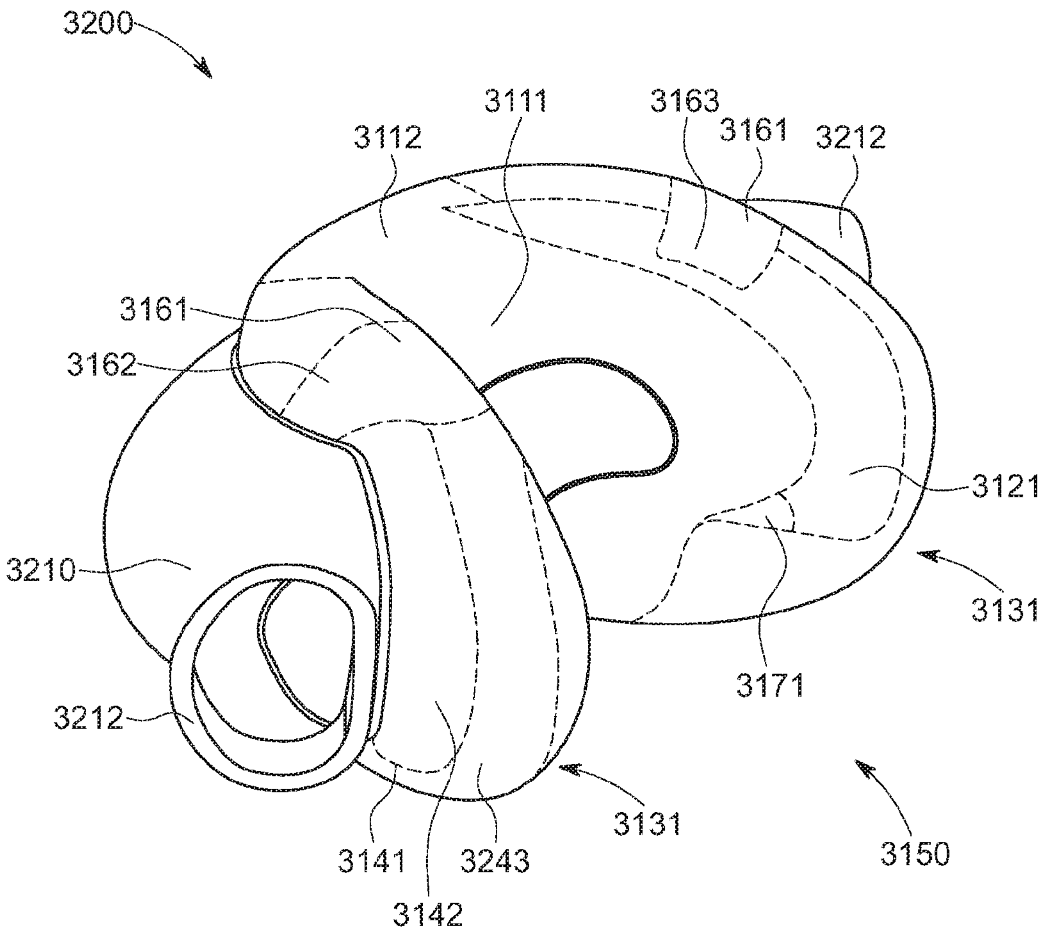

FIG. 9F is a posterolateral view illustration of the cushion module 3150 shown in FIG. 8A with various portions identified.

Figure 9G:
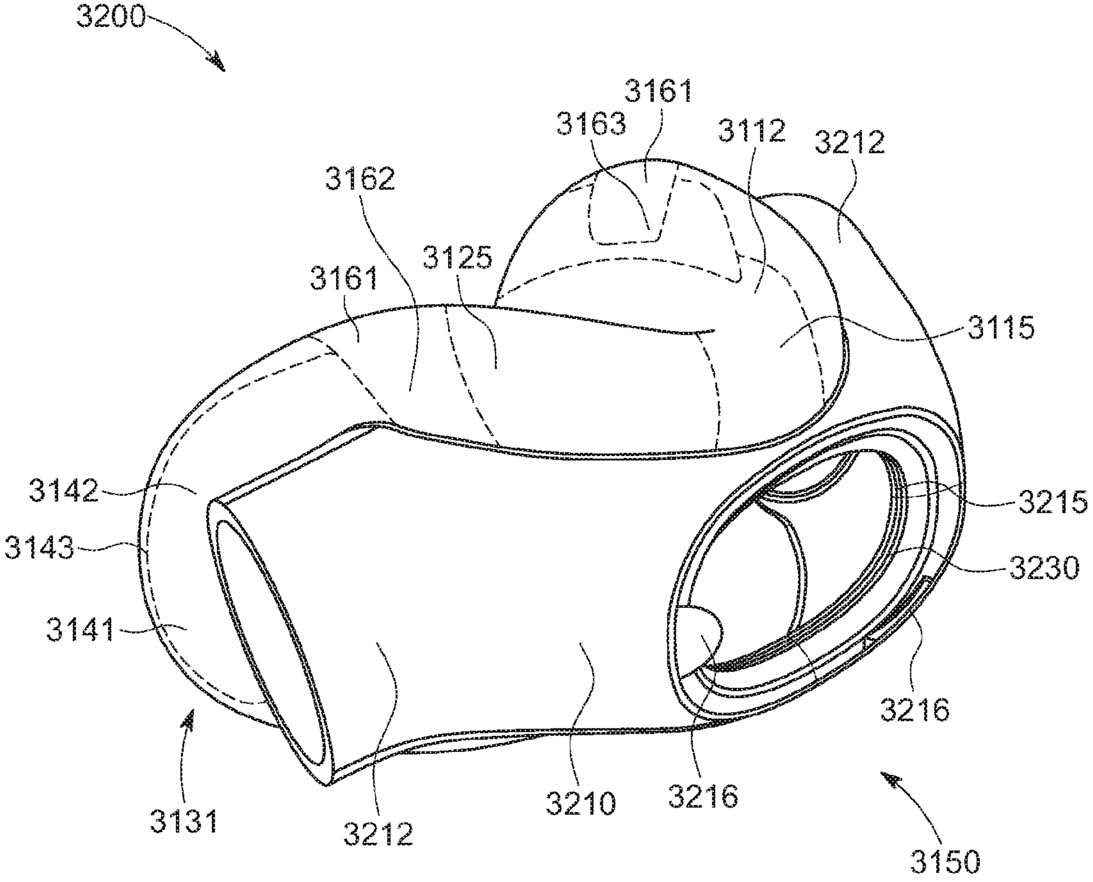

FIG. 9G is an anterolateral view illustration of the cushion module 3150 shown in FIG. 8A with various portions identified.

Figure 9H:
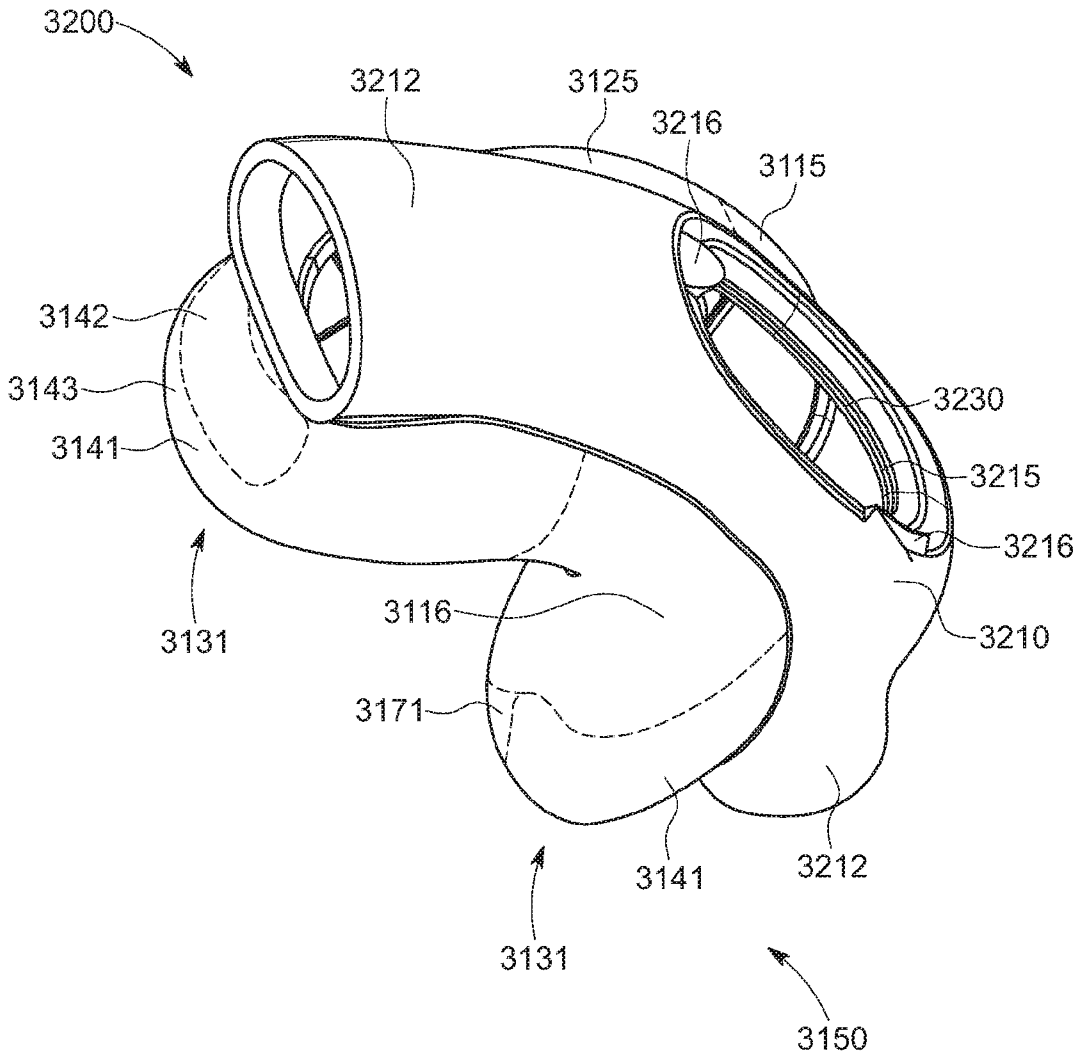

FIG. 9H is an inferior anterolateral view illustration of the cushion module 3150 shown in FIG. 8A with various portions identified.

Figure 10:
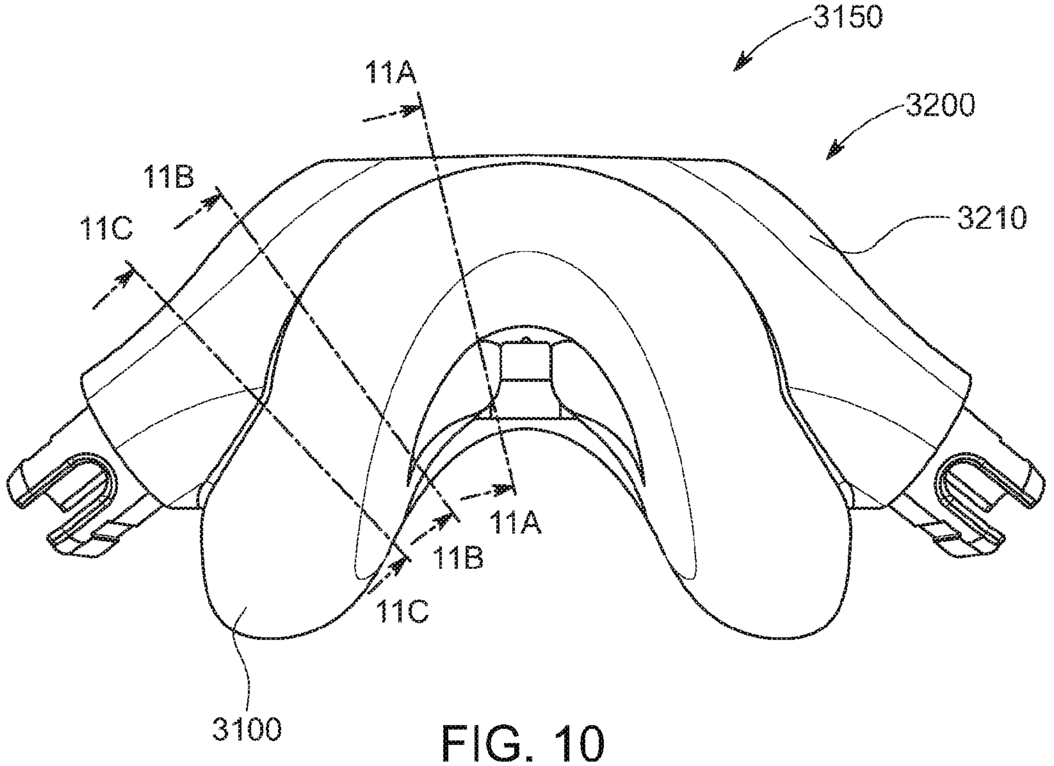

FIG. 10 is a superior view illustration of the cushion module 3150 shown in FIG. 8A.

Figure 11A:
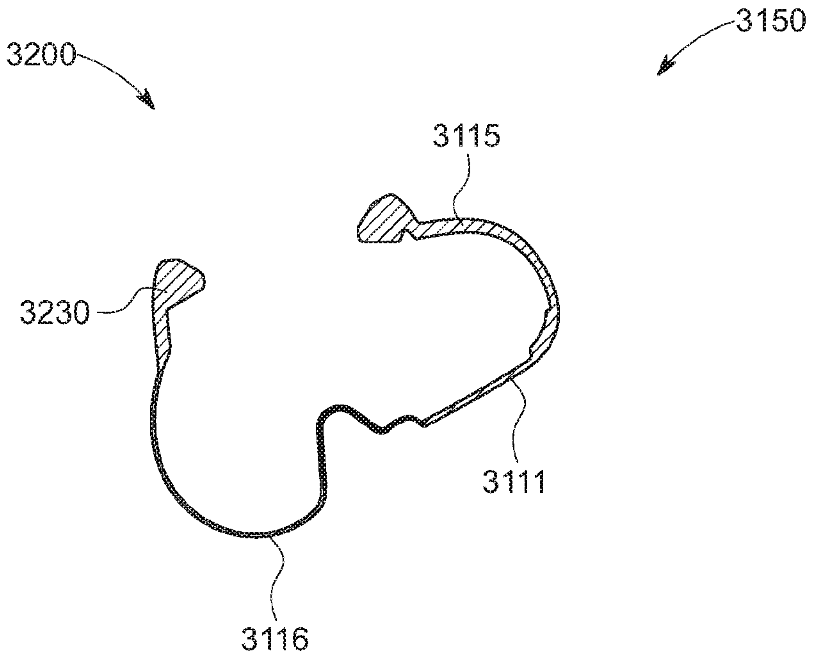

FIG. 11A is a cross section view illustration of the cushion module 3150 through line 11A-11A indicated in FIG. 10.

Figure 11B:
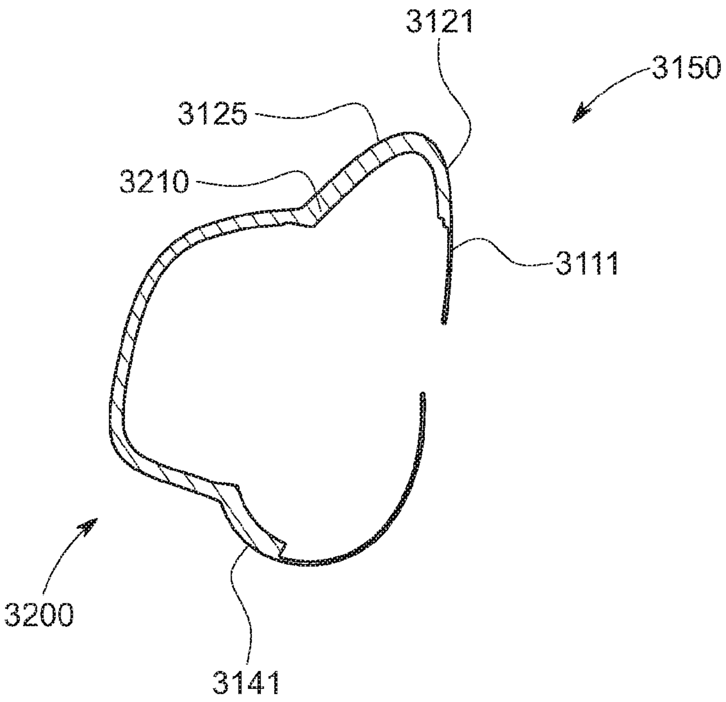

FIG. 11B is a cross section view illustration of the cushion module 3150 through line 11B-11B indicated in FIG. 10.

Figure 11C:
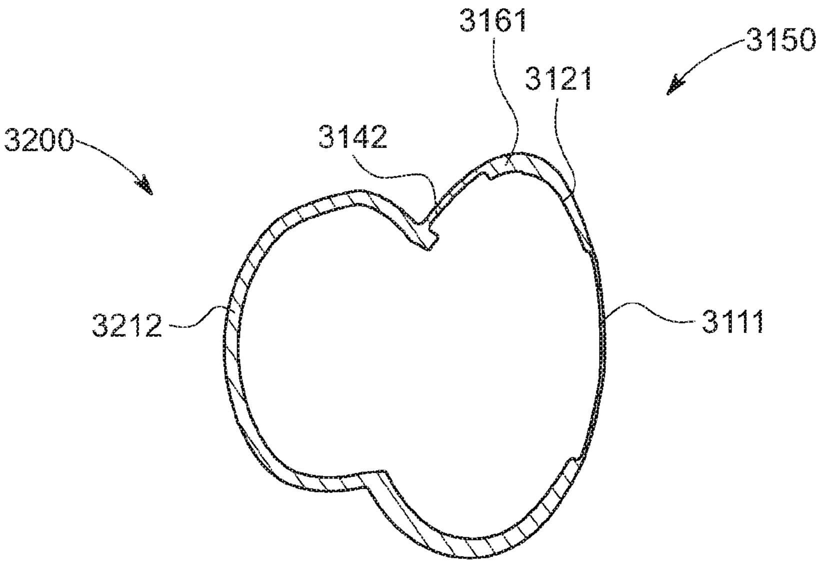

FIG. 11C is a cross section view illustration of the cushion module 3150 through line 11C-11C indicated in FIG. 10.

Figure 12:
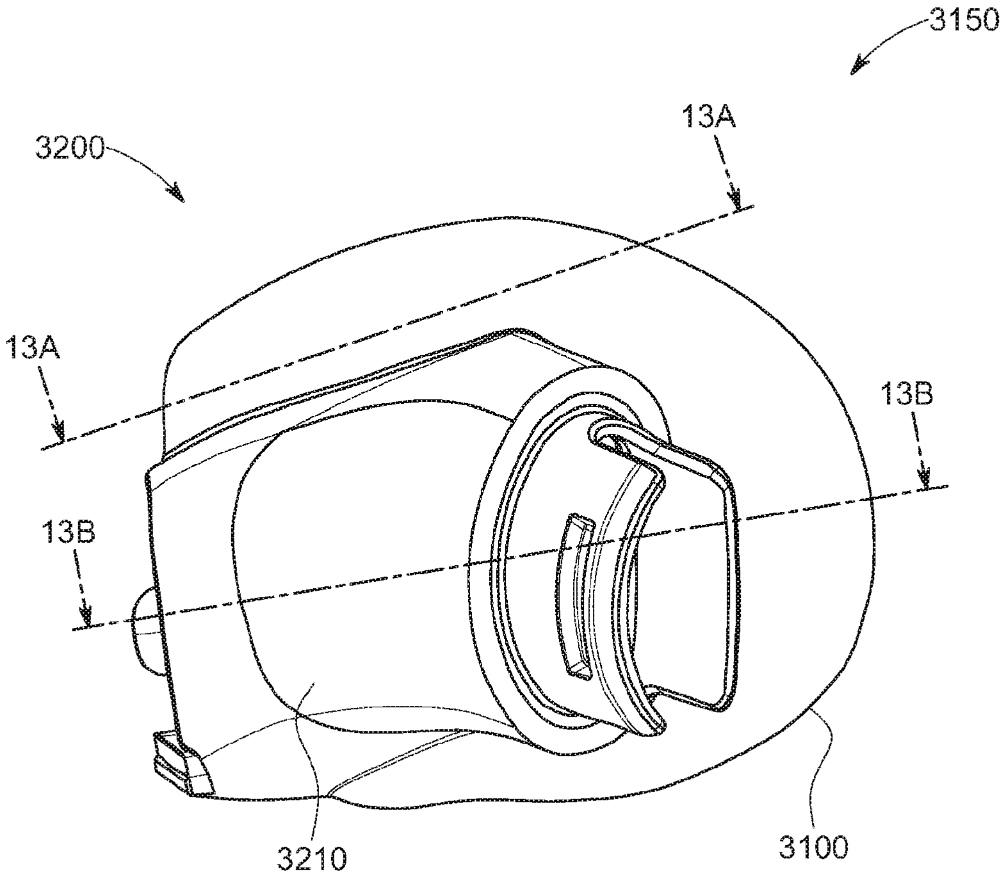

FIG. 12 is a lateral view illustration of the cushion module 3150 shown in FIG. 8A.

Figure 13A:
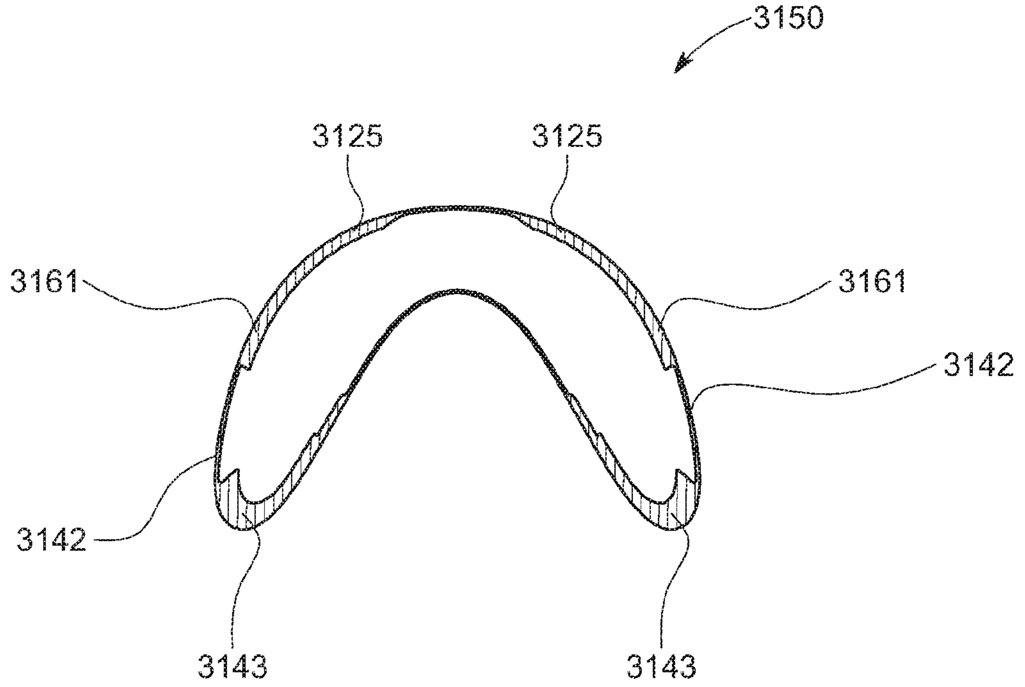

FIG. 13A is a cross section view illustration of the cushion module 3150 through line 13A-13A indicated in FIG. 12.

Figure 13B:
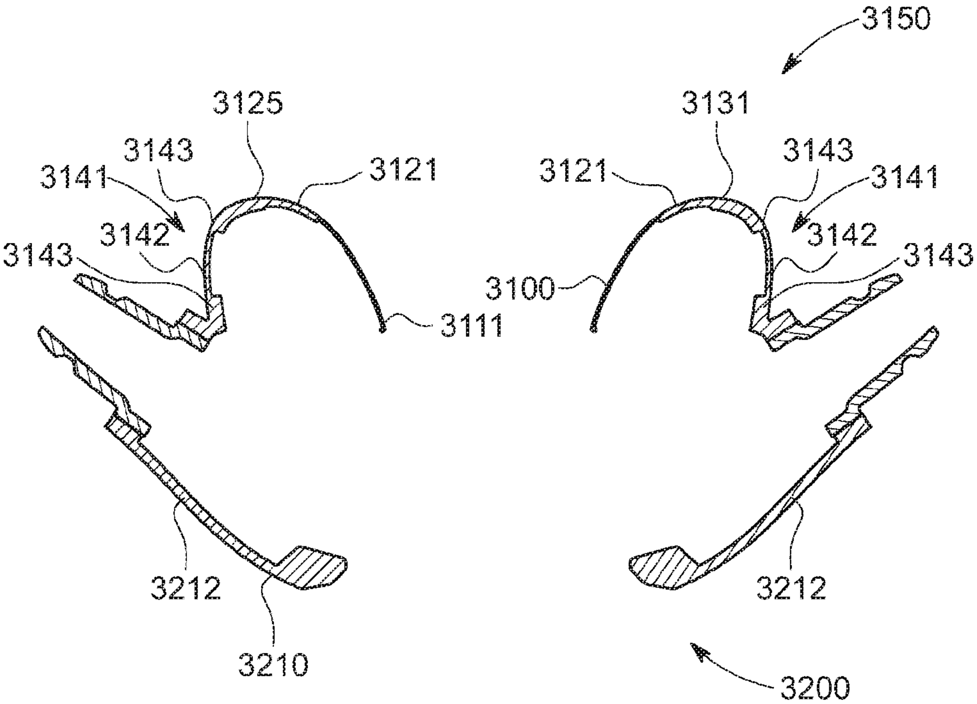

FIG. 13B is a cross section view illustration of the cushion module 3150 through line 13B-13B indicated in FIG. 12.

Figure 14A:
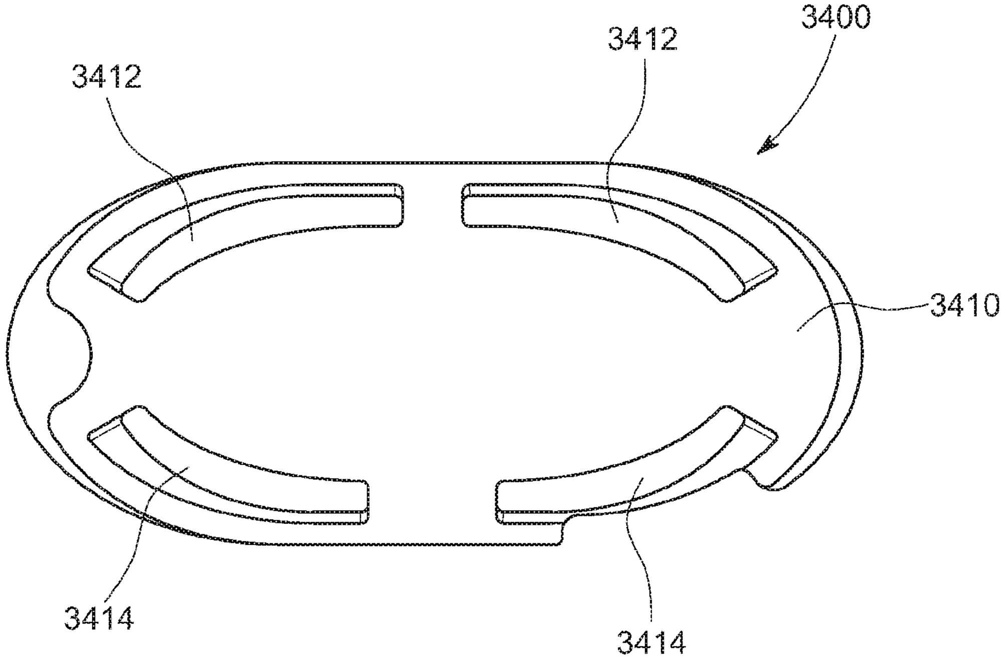

FIG. 14A is a front view illustration of a vent module 3410 of the patient interface 3000 shown in FIG. 7A.

Figure 14B:
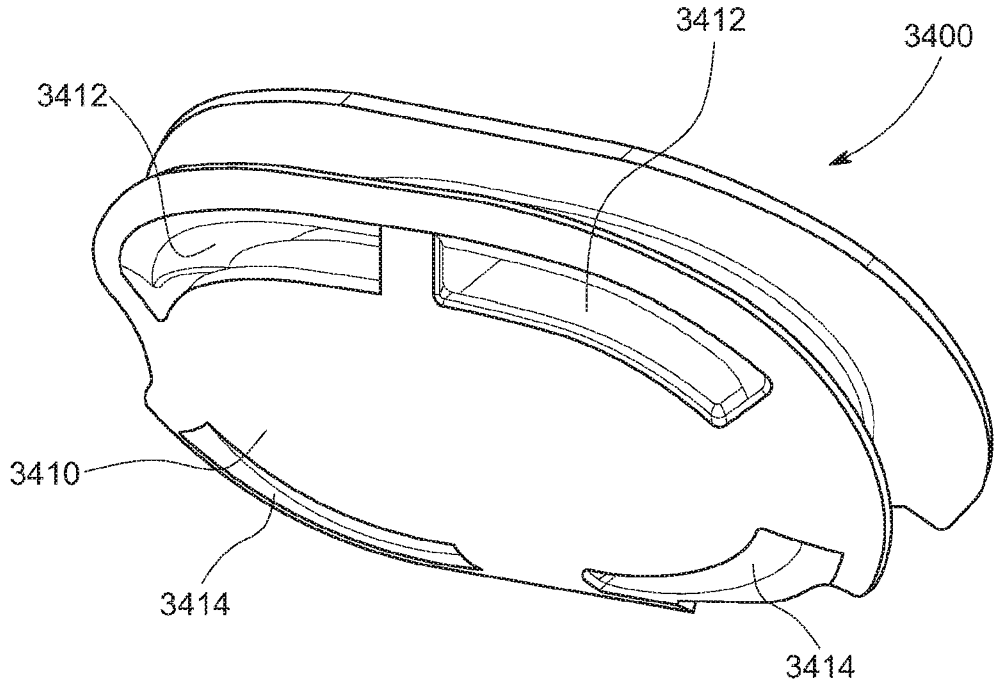

FIG. 14B is a front perspective view illustration of the vent module 3410 shown in FIG. 14A.

Figure 14C:
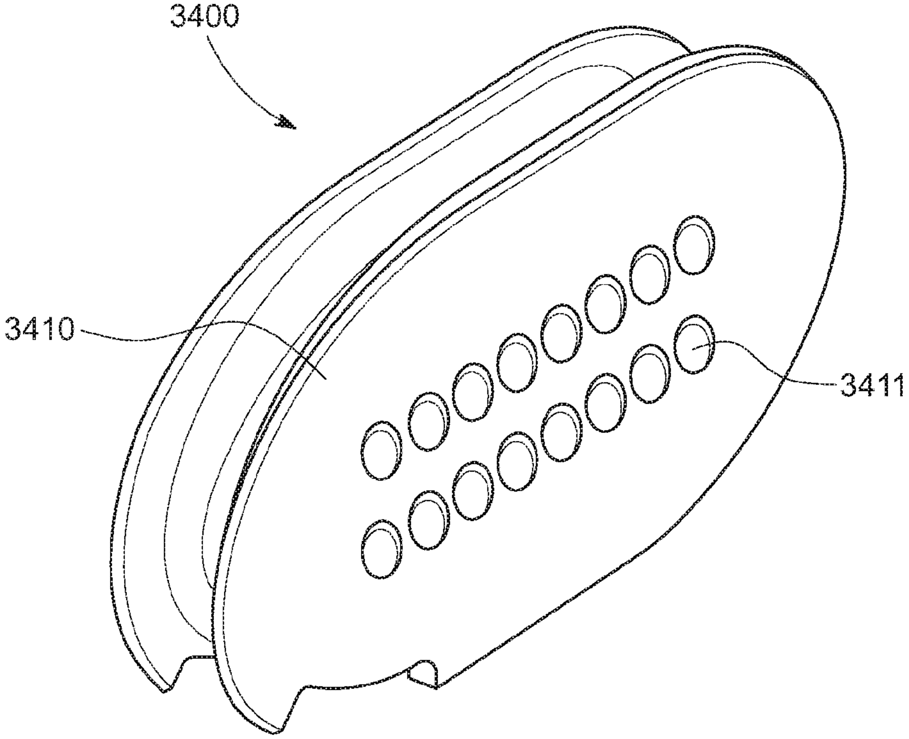

FIG. 14C is a rear perspective view illustration of the vent module 3410 shown in FIG. 14A.

Figure 14D:
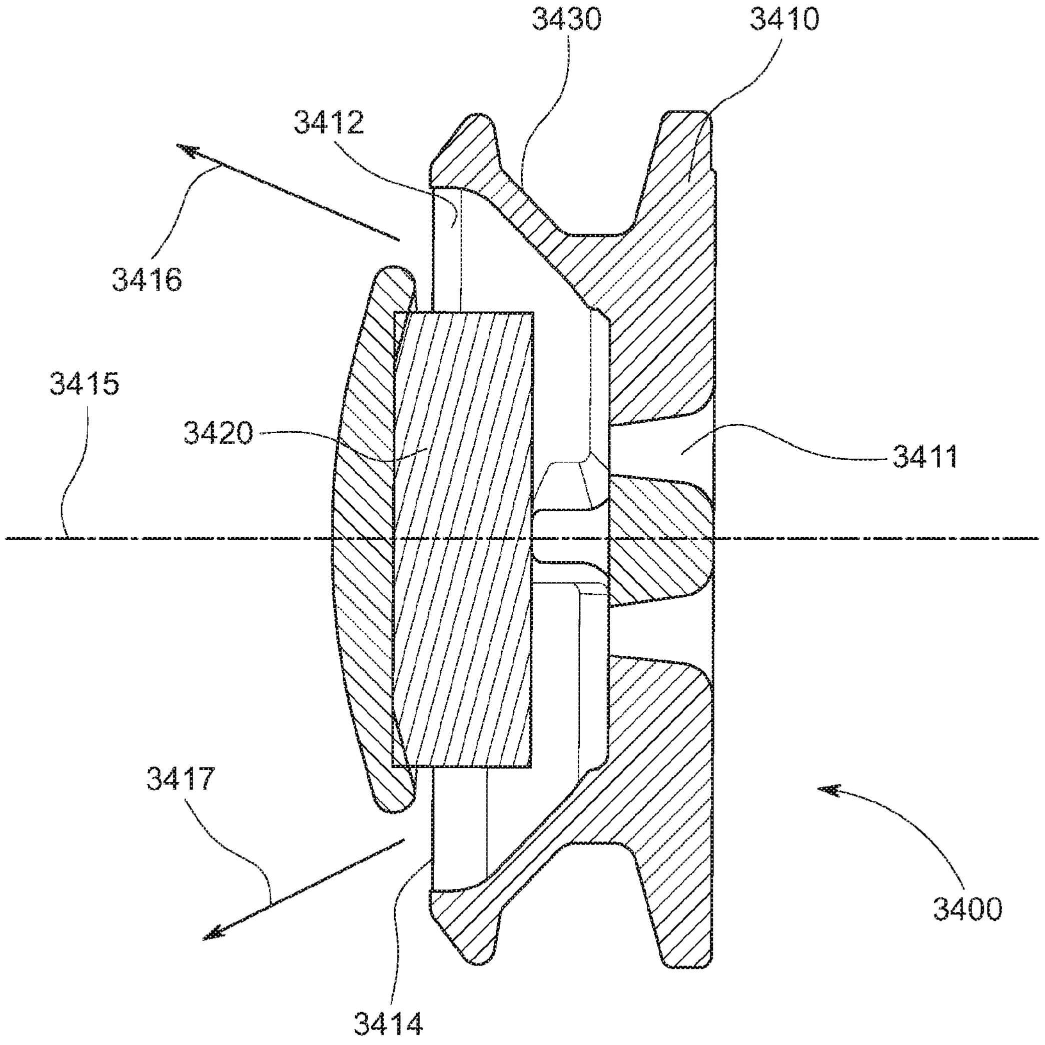

FIG. 14D is a cross section view illustration of the vent module 3410 shown in FIG. 14A.

Figure 15A:
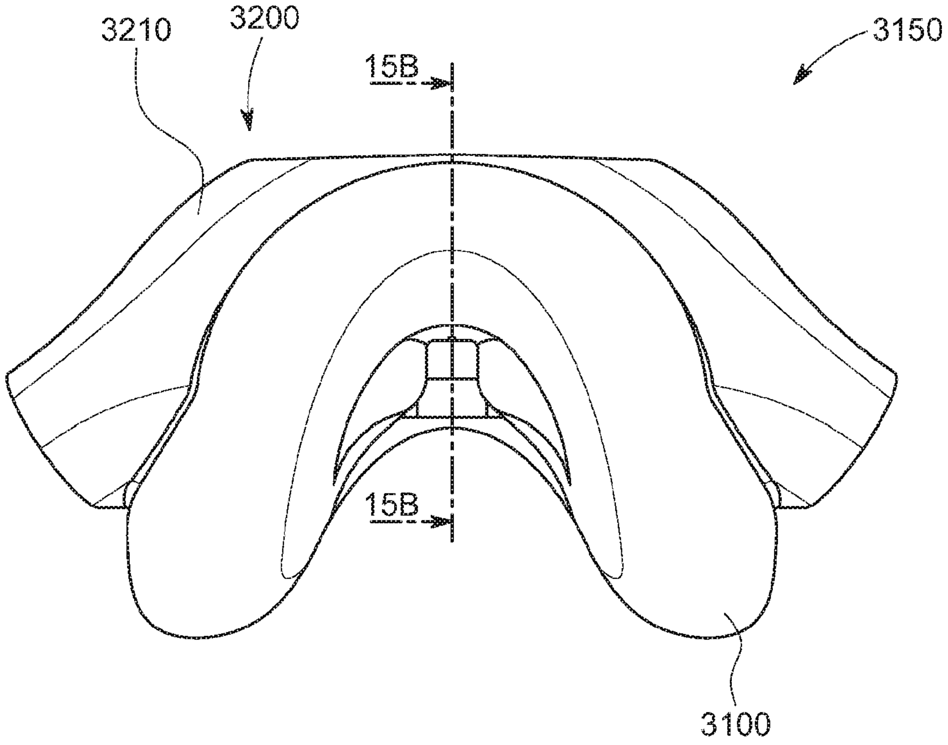

FIG. 15A is a superior view illustration of the cushion module 3150 shown in FIG. 8A with vent module 3410 removed.

Figure 15B:
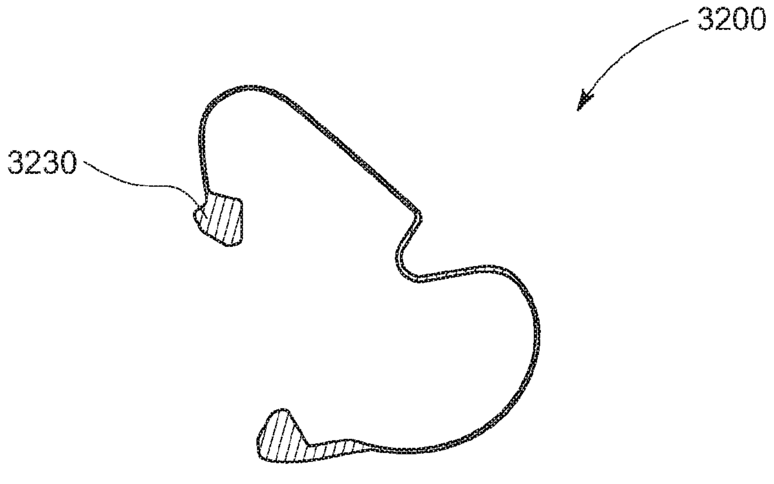

FIG. 15B is a cross section view illustration of the cushion module 3150 through line 15B-15B indicated in FIG. 15A.

Figure 15C:
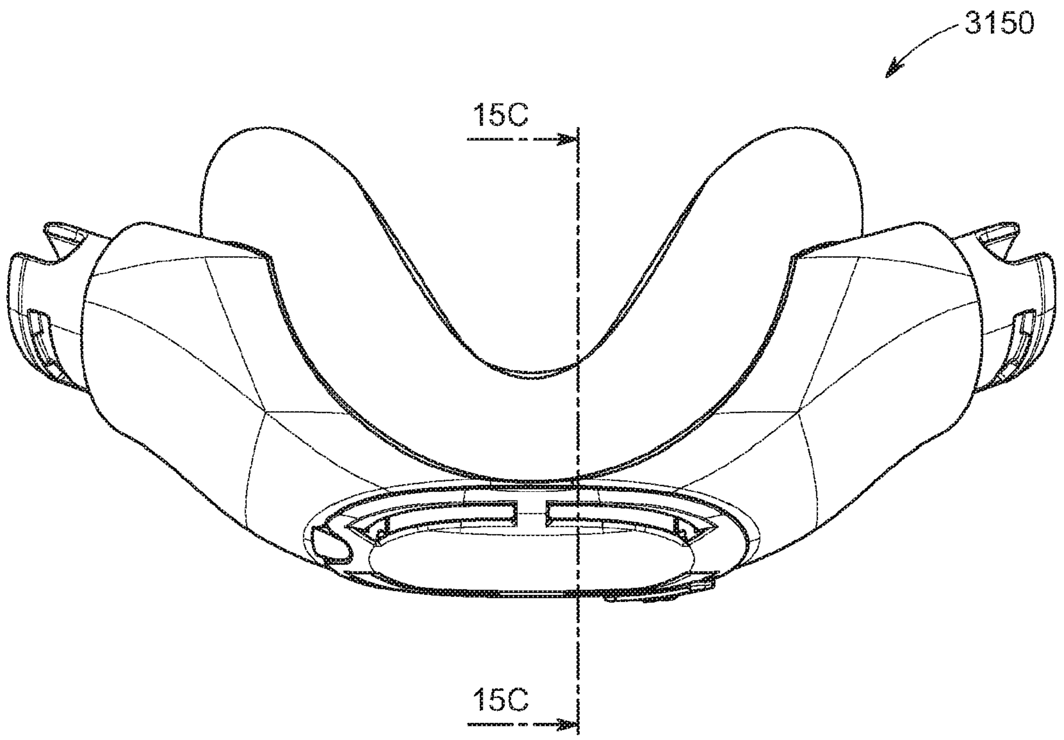

FIG. 15C is a superior view illustration of the cushion module 3150 shown in FIG. 8A with vent module 3410 included.

Figure 15D:
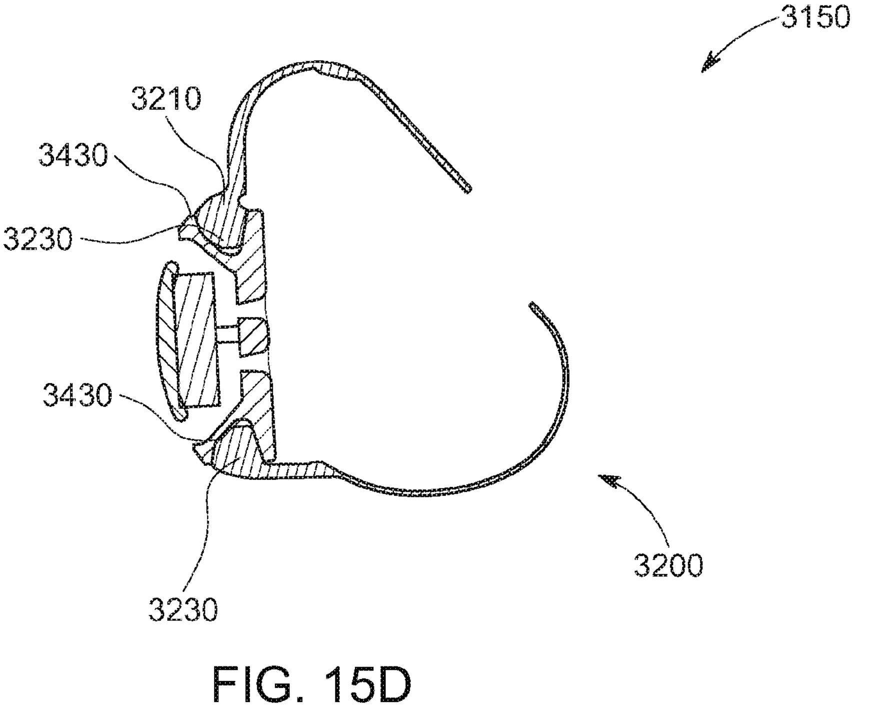

FIG. 15D is a cross section view illustration of the cushion module 3150 through line 15D-15D indicated in FIG. 15C.

Figure 16A:
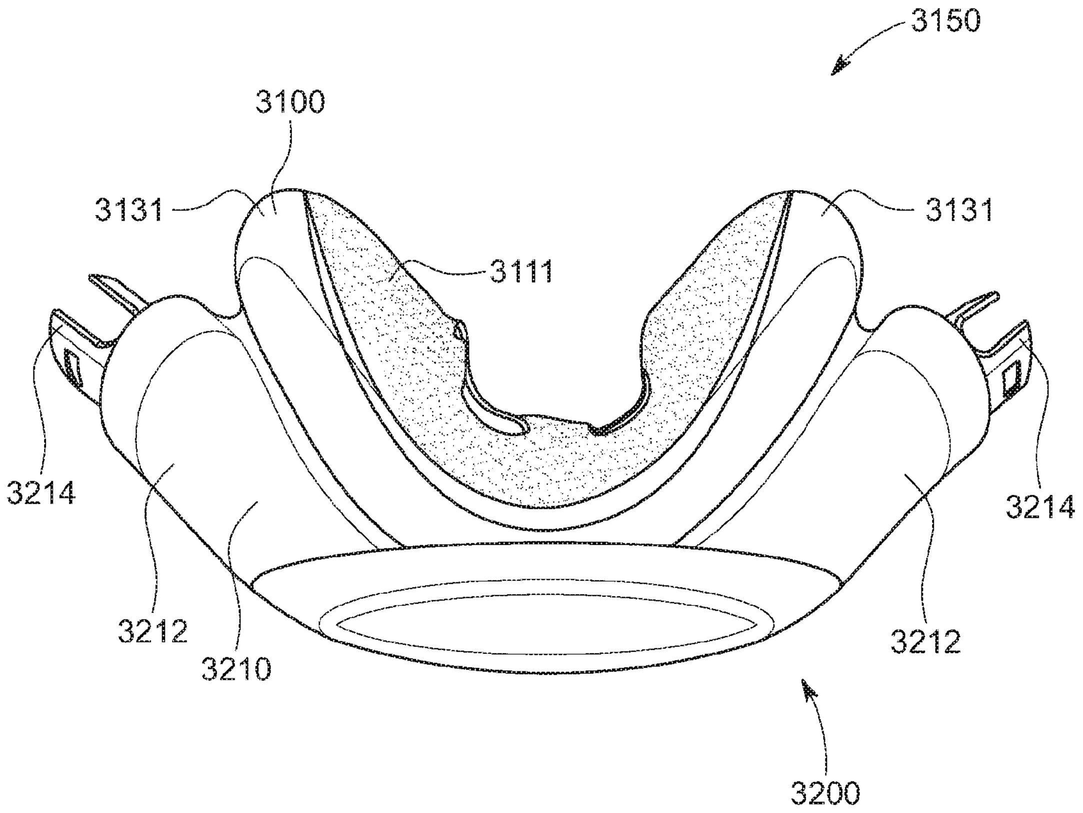

FIG. 16A is a superior view illustration of a cushion module 3150 according to another example of the present technology.

Figure 16B:
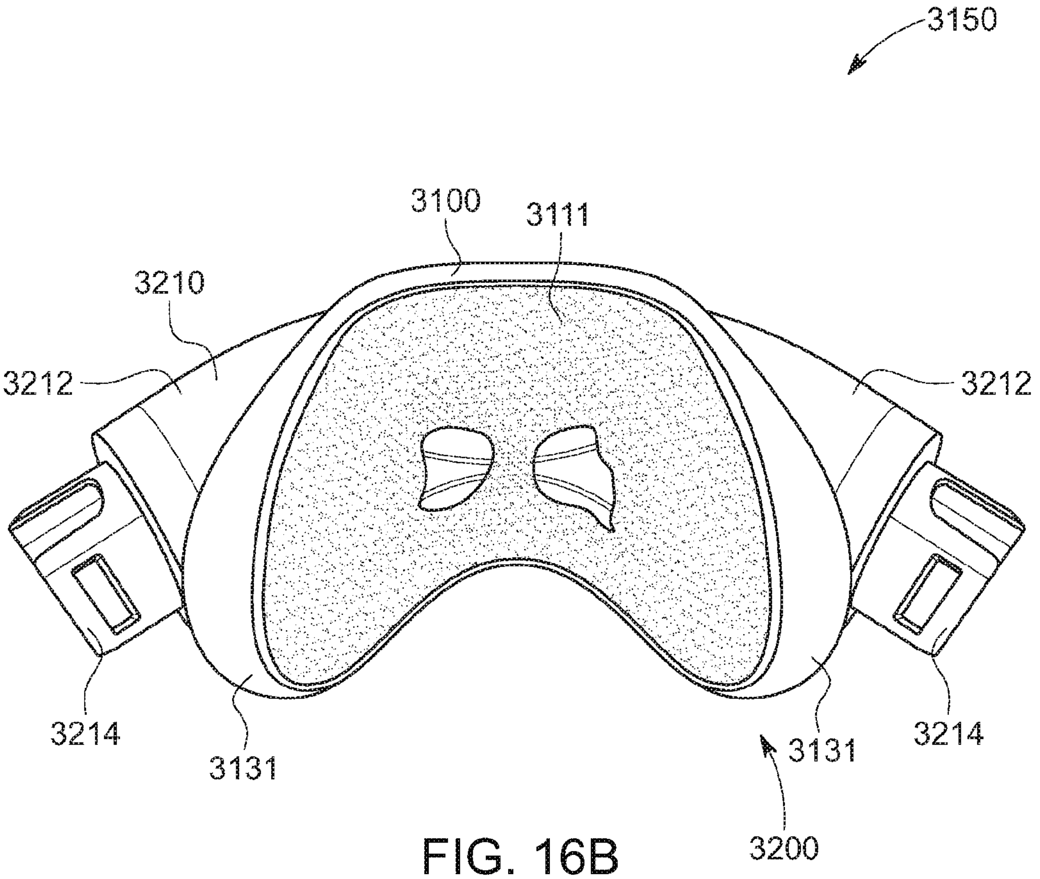

FIG. 16B is posterior view illustration of the cushion module 3150 shown in FIG. 16A.

Figure 16C:
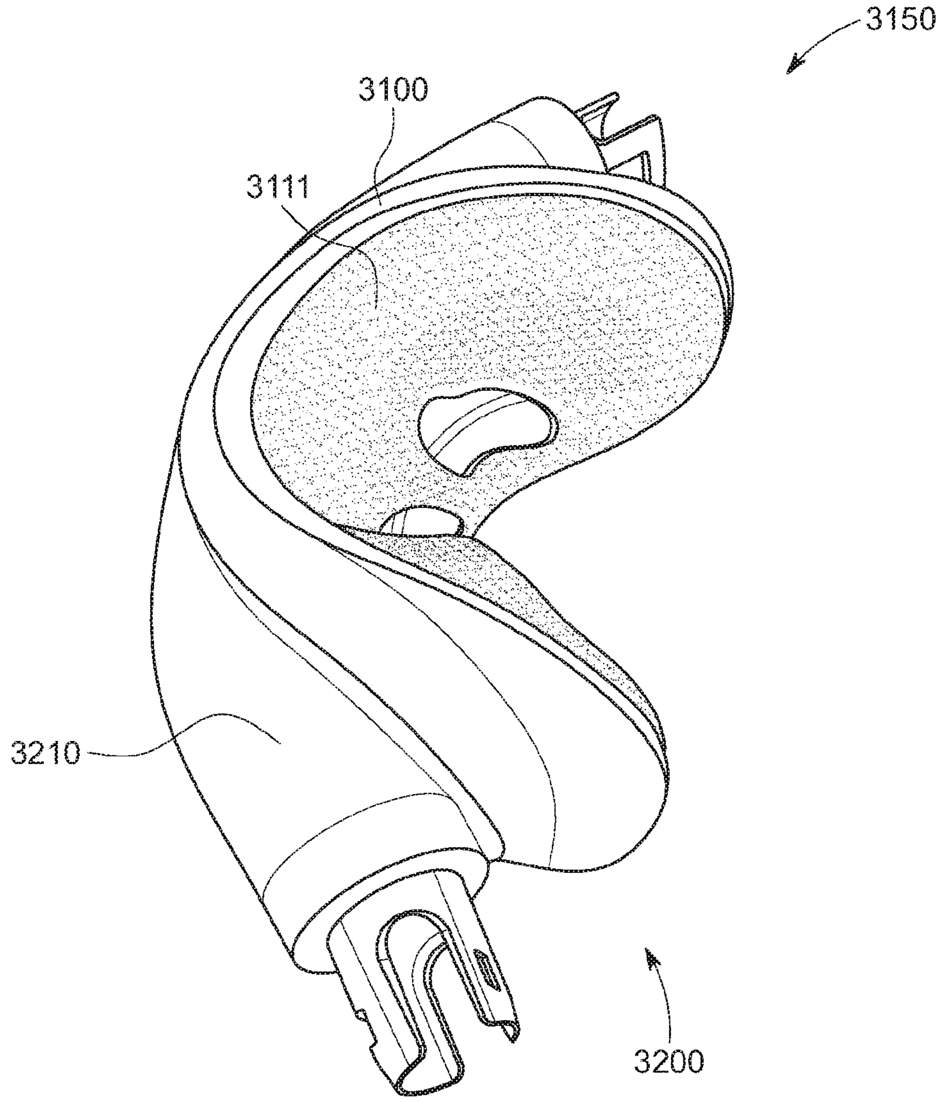

FIG. 16C is a lateral superior view illustration of the cushion module 3150 shown in FIG. 16A.

Figure 16D:
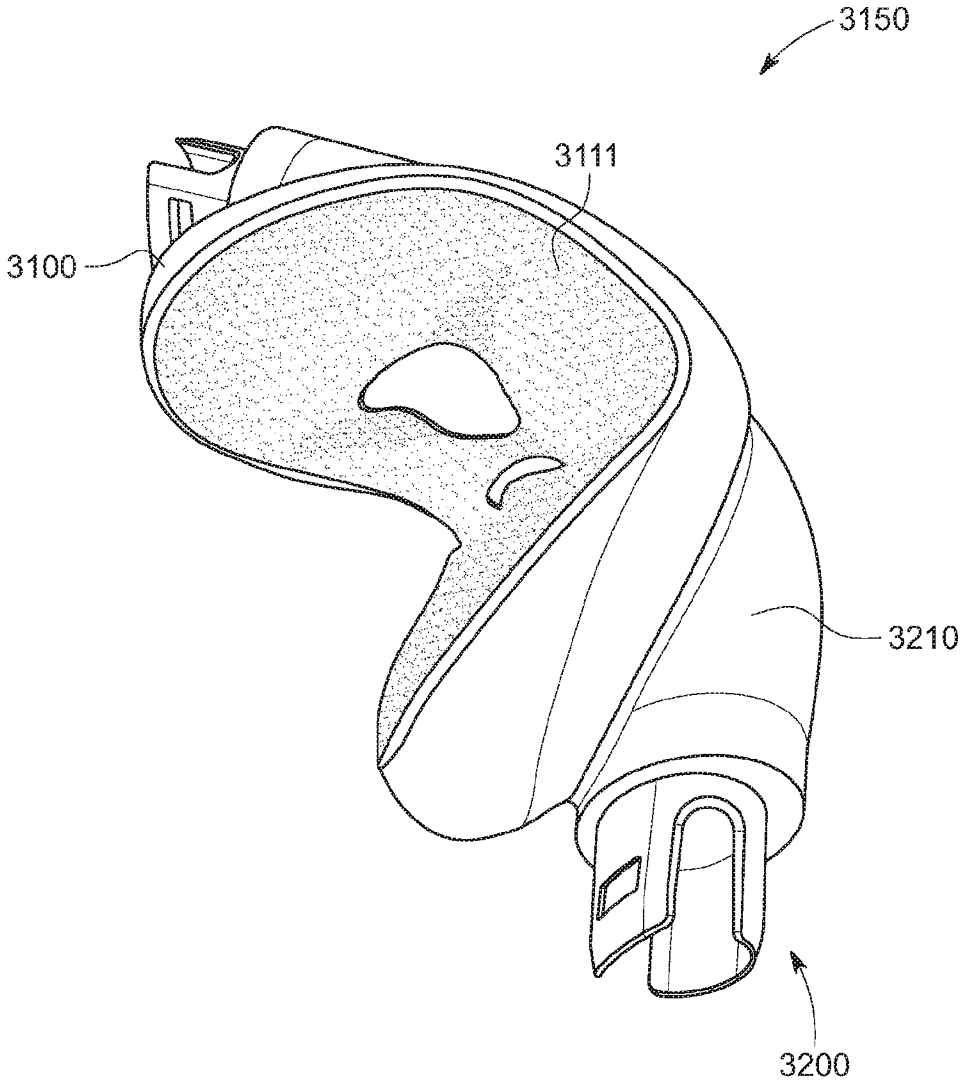

FIG. 16D is another lateral superior view illustration of the cushion module 3150 shown in FIG. 16A.

Figure 17A:
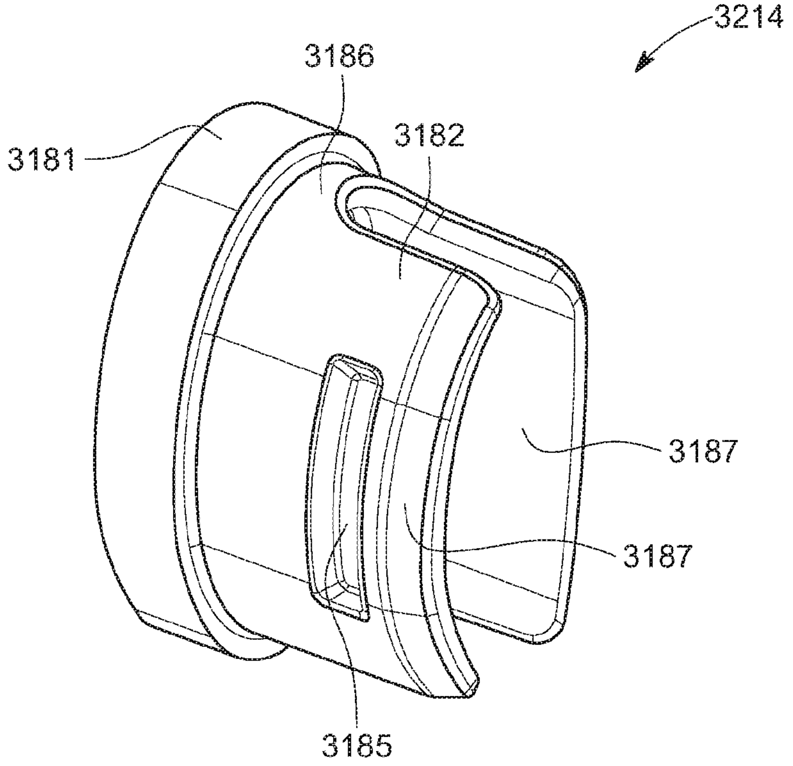

FIG. 17A is a perspective view illustration of a connector 3214 of the cushion module 3150 shown in FIG. 8A.

Figure 17B:
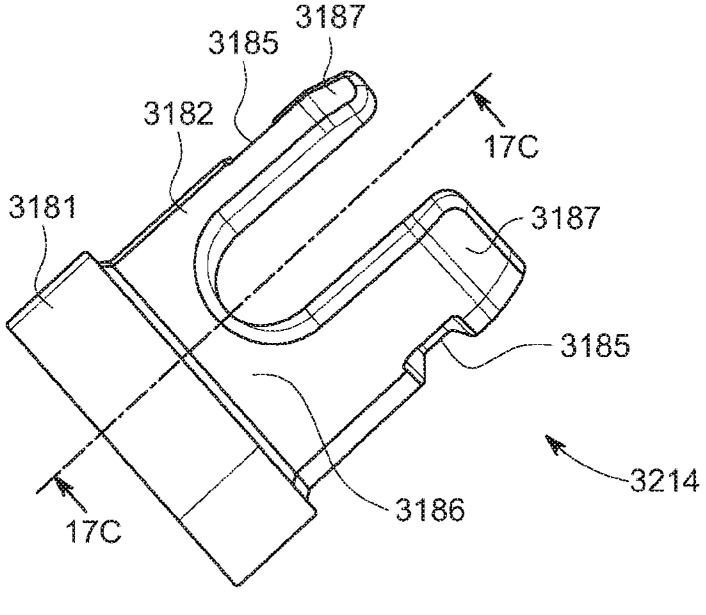

FIG. 17B is a top view illustration of the connector 3214 shown in FIG. 17A.

Figure 17C:
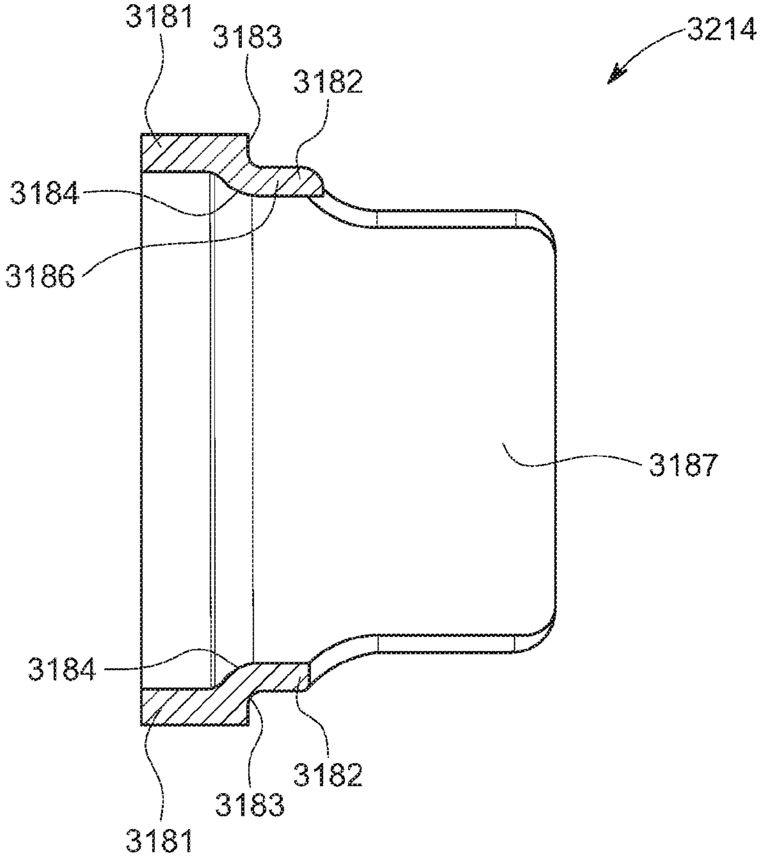

FIG. 17C is a cross section view illustration of the connector 3214 shown in FIG. 17B through line 17C-17C.

Figure 17D:
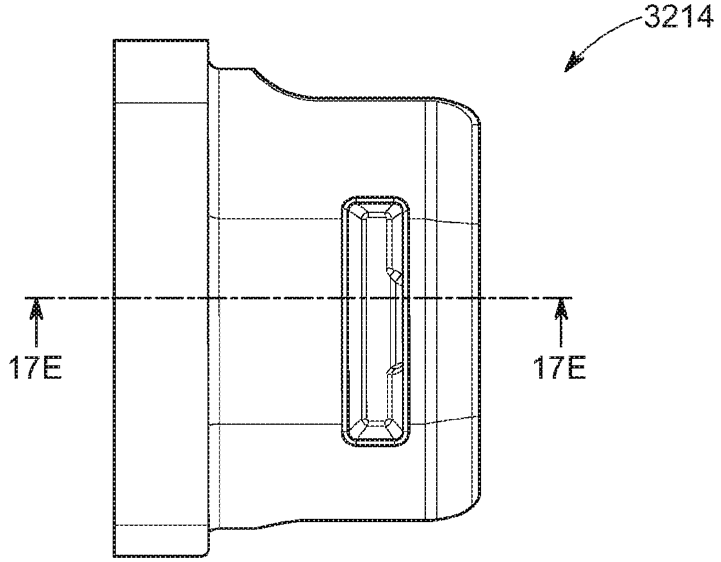

FIG. 17D is a side view illustration of the connector 3214 shown in FIG. 17A.

Figure 17E:
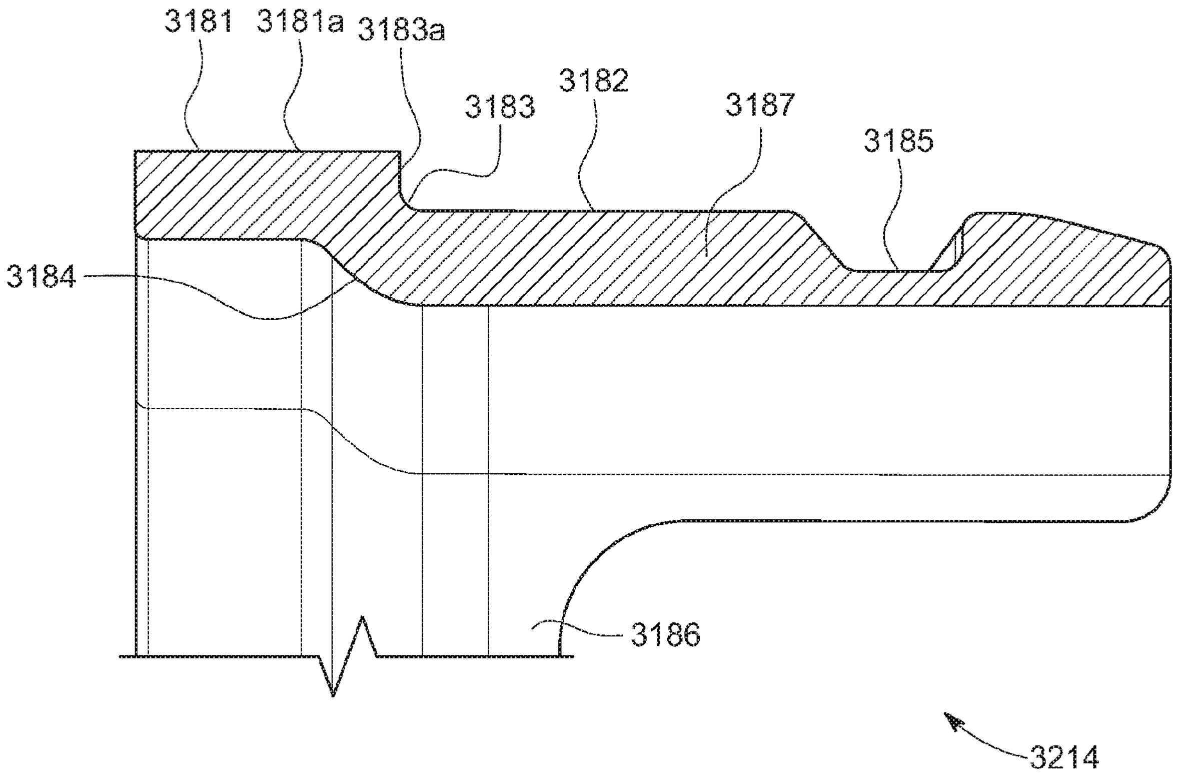

FIG. 17E is a cross section view illustration of the connector 3214 shown in FIG. 17D through line 17E-17E.

Figure 18:
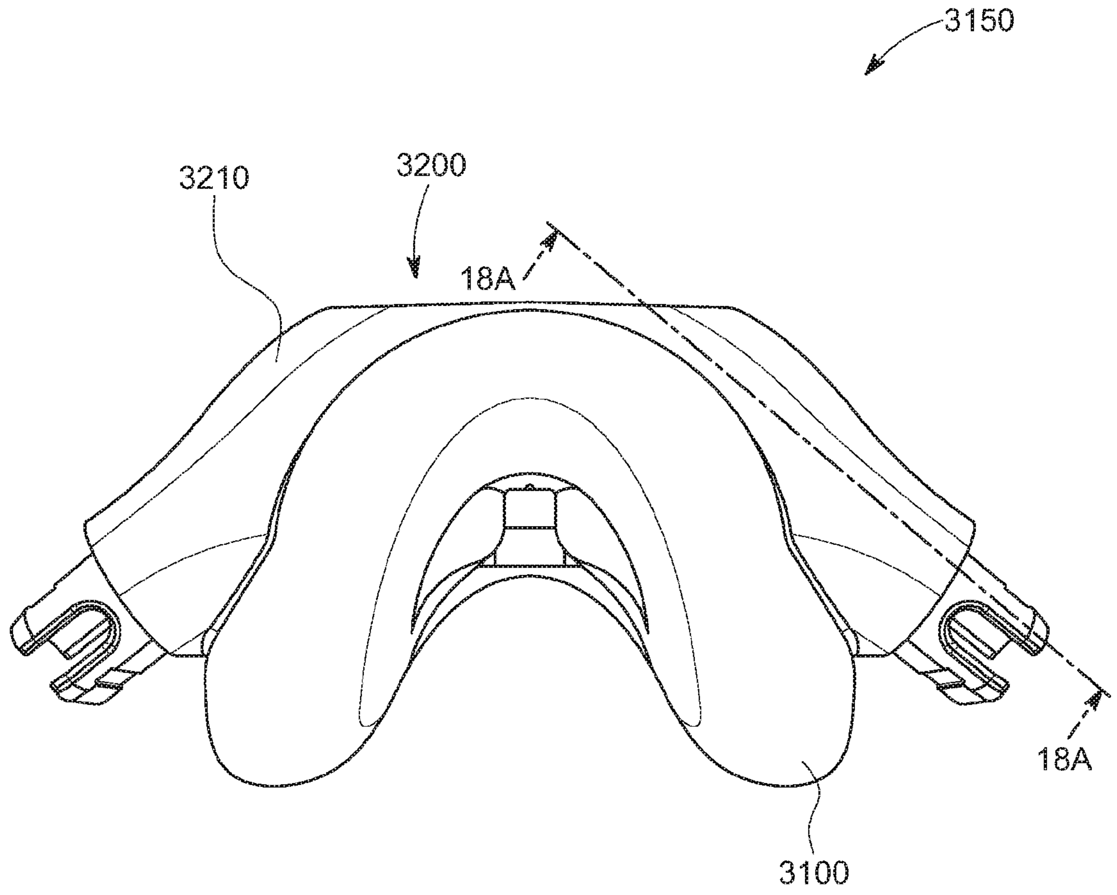

FIG. 18 is a superior view illustration of the cushion module 3150 shown in FIG. 8A.

Figure 18A:
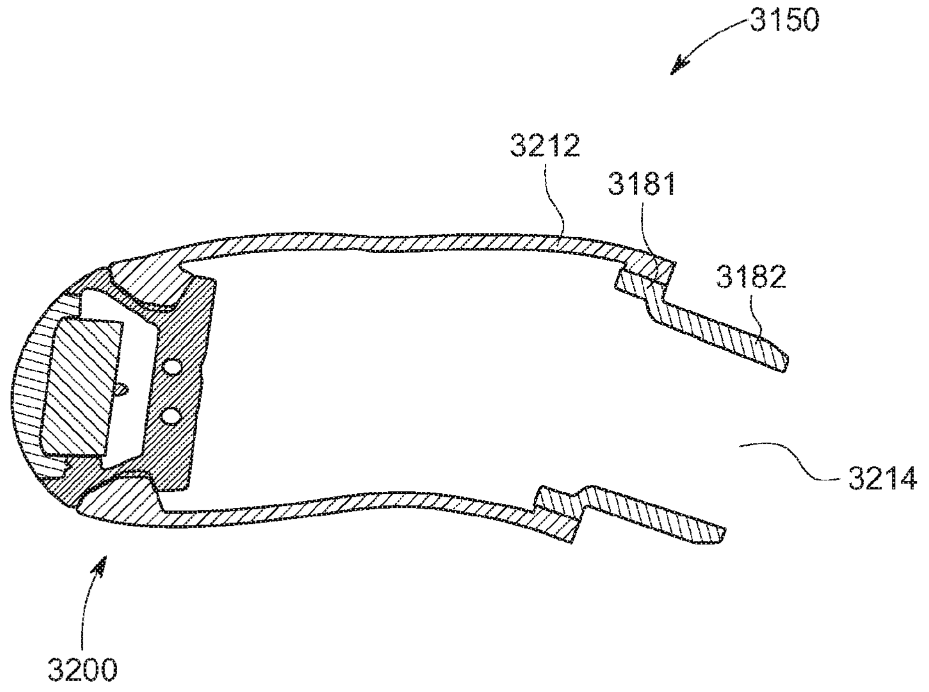

FIG. 18A is a cross section view illustration of the cushion module 3150 shown in FIG. 18 through line 18A-18A.

Figure 19A:
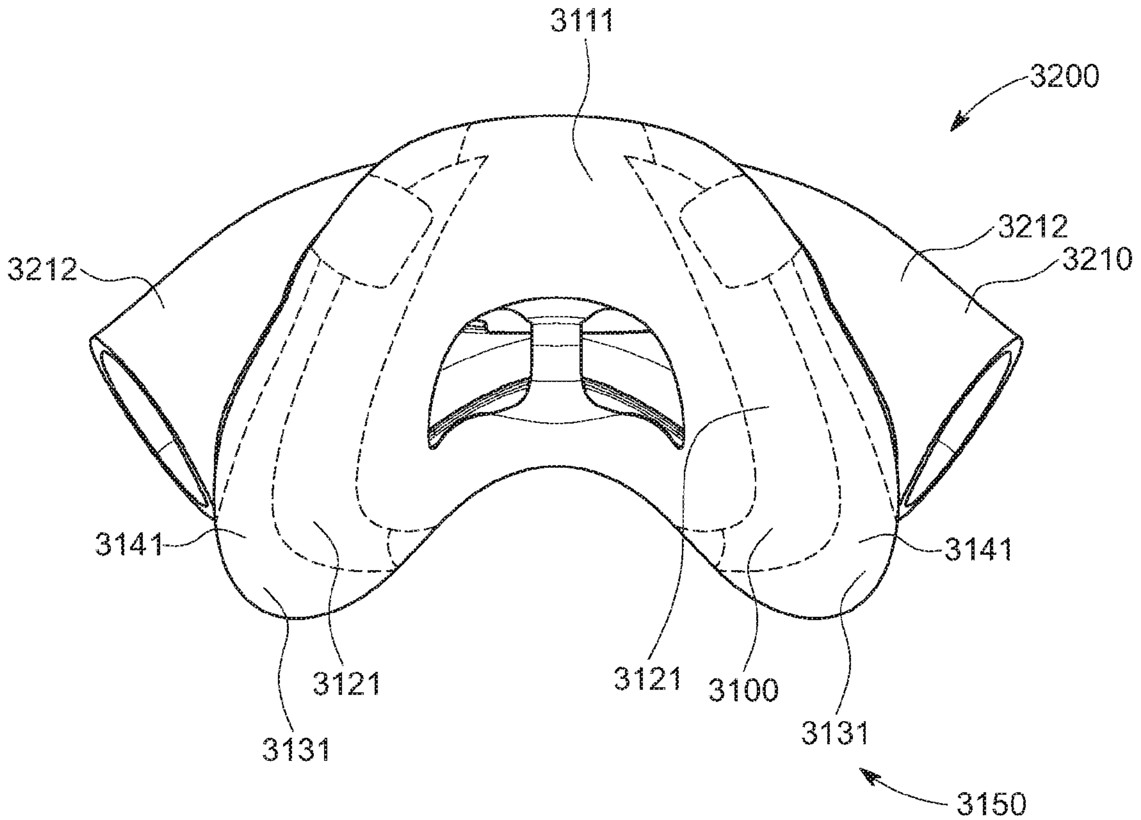

FIG. 19A is a superior view illustration of a cushion module 3150 according another example of the present technology.

Figure 19B:
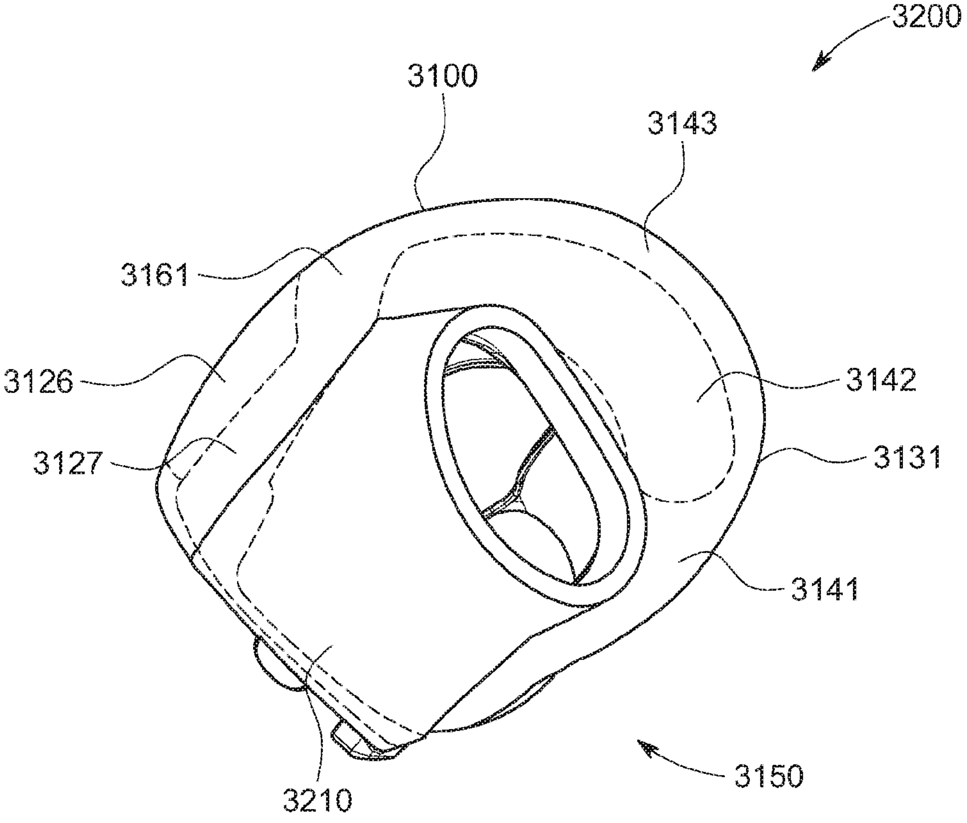

FIG. 19B is a lateral view illustration of the cushion module 3150 shown in FIG. 19A.

Figure 19C:
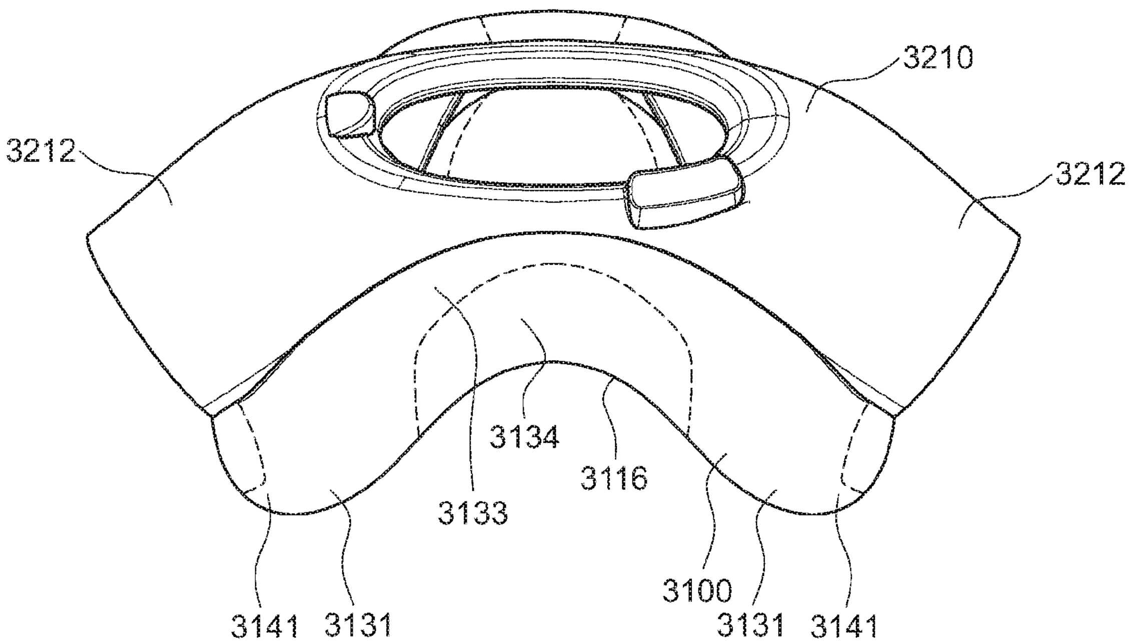

FIG. 19C is an anteroinferior view illustration of the cushion module 3150 shown in FIG. 19A.

Figure 19D:
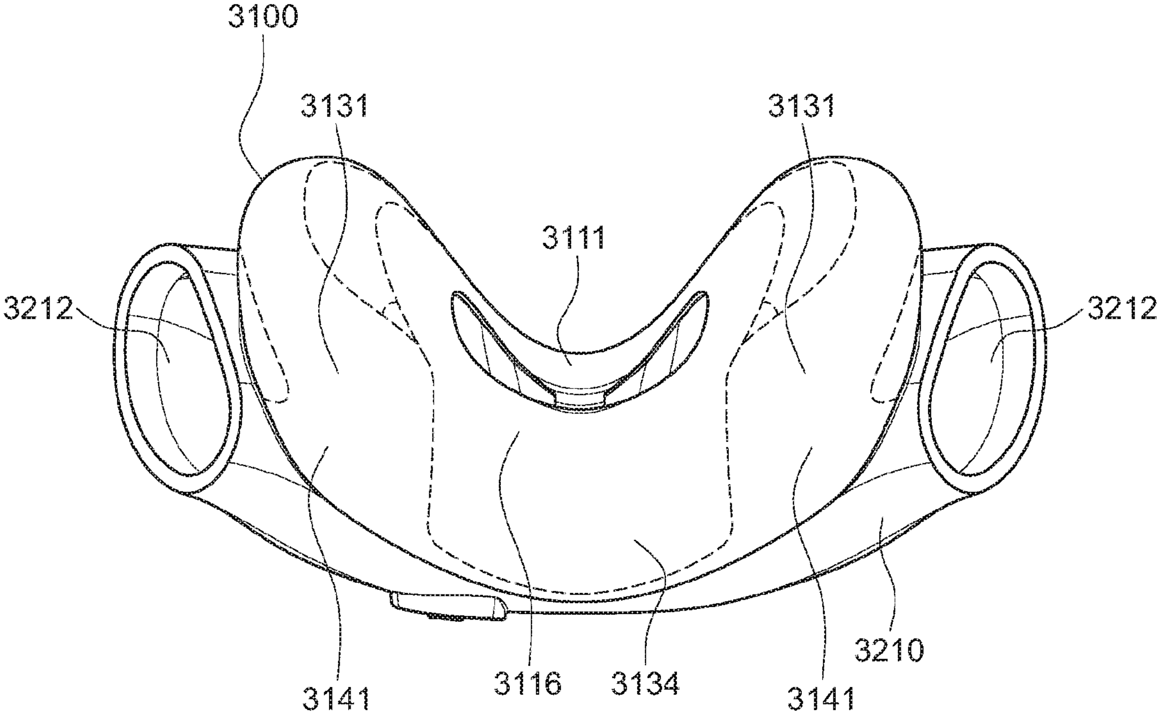

FIG. 19D is a posteroinferior view illustration of the cushion module 3150 shown in FIG. 19A.

Figure 19E:
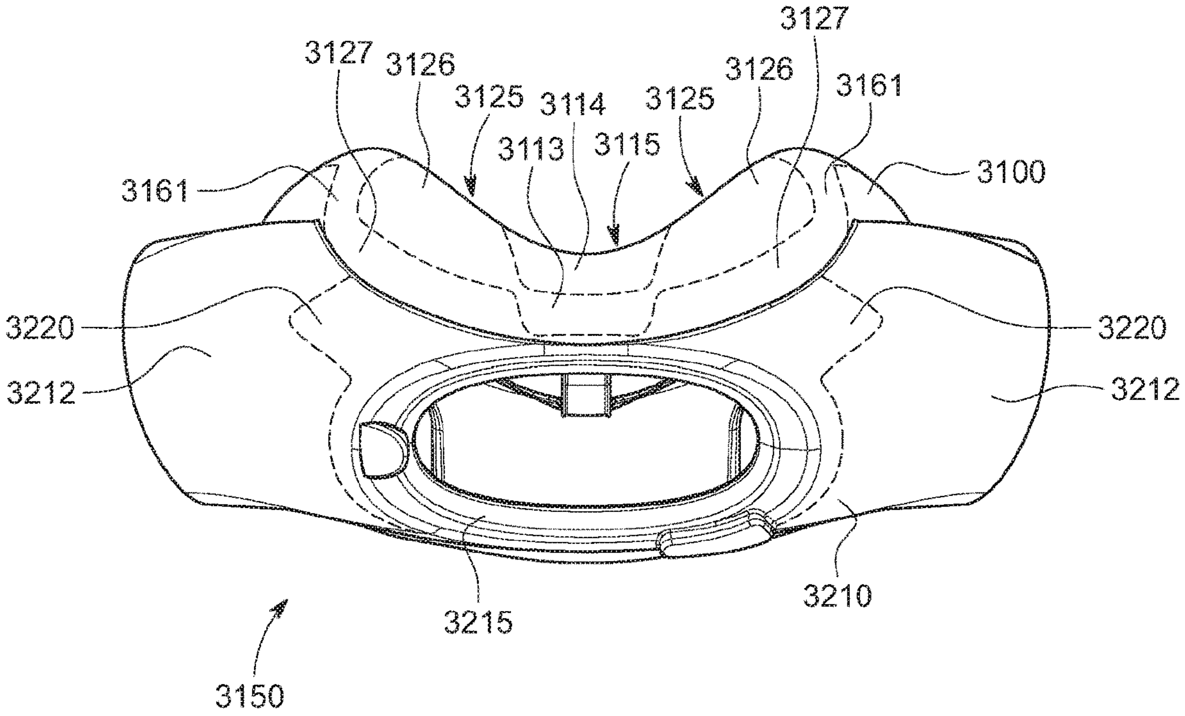

FIG. 19E is an anterior view illustration of the cushion module 3150 shown in FIG. 19A.

Figure 19F:
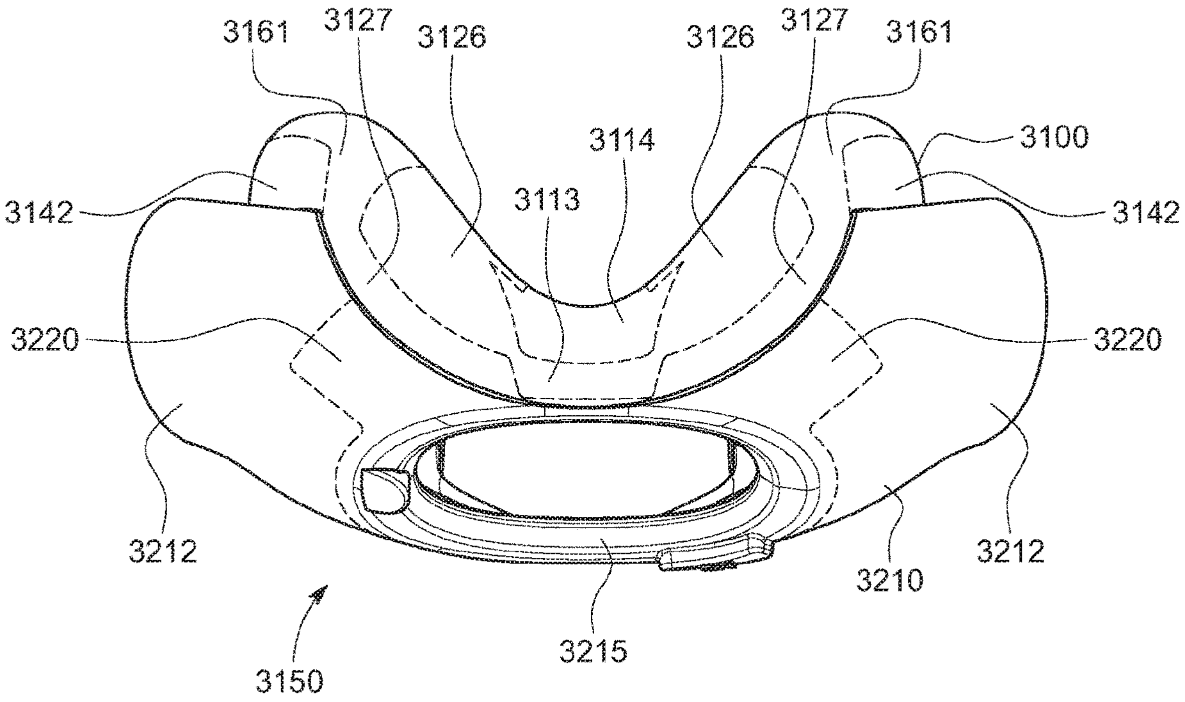

FIG. 19F is an anterosuperior view illustration of the cushion module 3150 shown in FIG. 19A.

Figure 20:
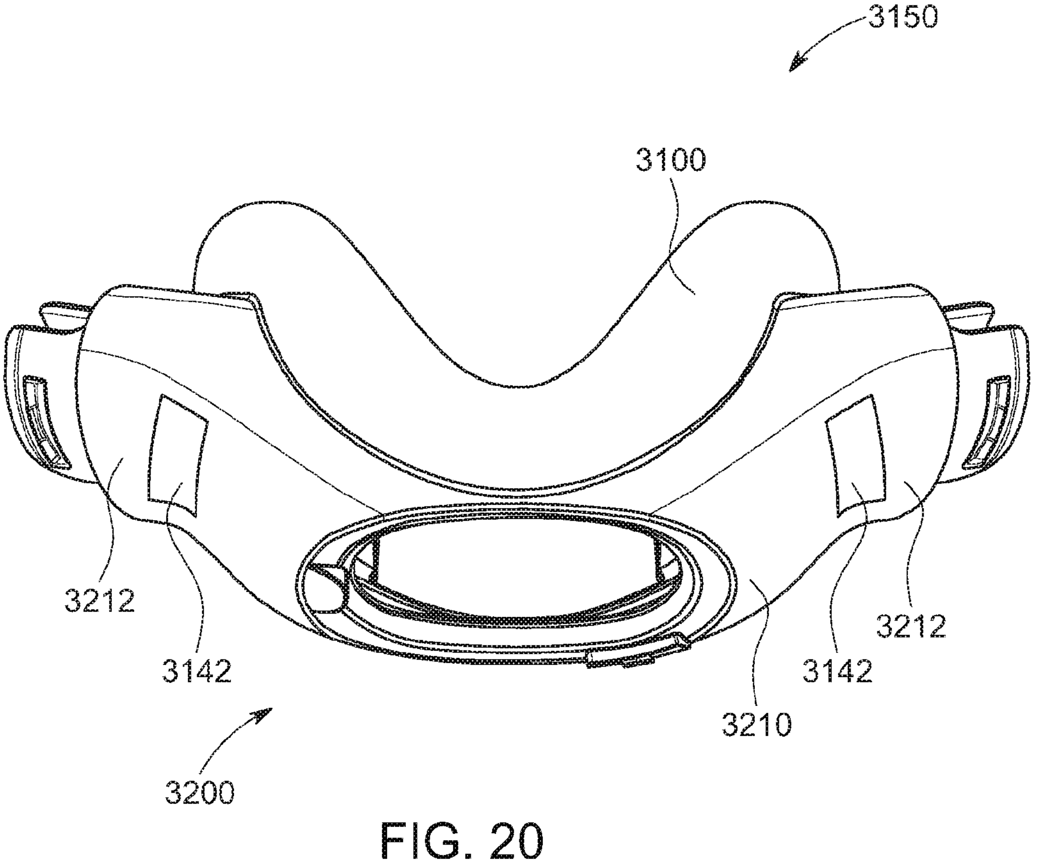

FIG. 20 is an anterior view illustration of a cushion module 3150 according to another example of the present technology.

Figure 21:
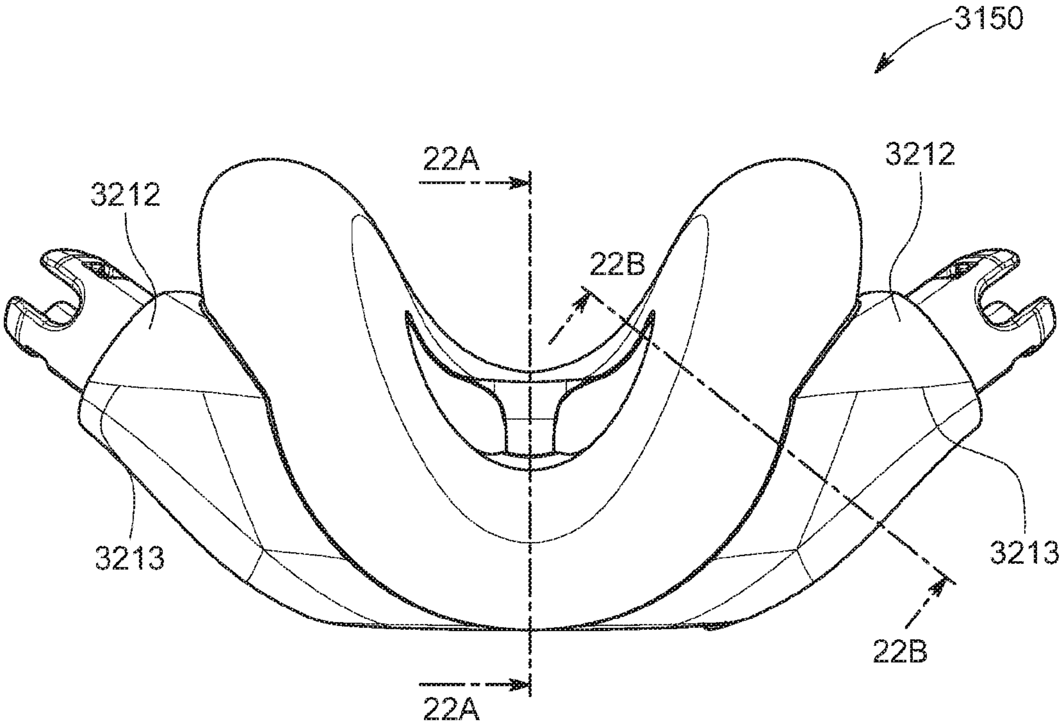

FIG. 21 is a superior view illustration of the cushion module 3150 shown in FIG. 19A.

Figure 22A:
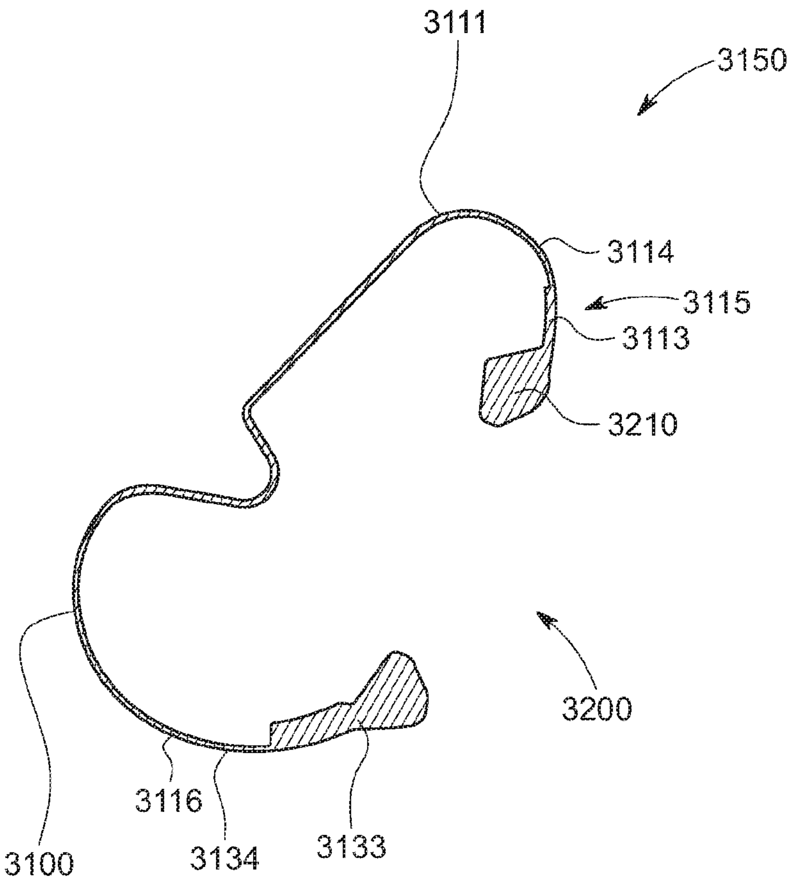

FIG. 22A is a cross section view illustration of the cushion module 3150 shown in FIG. 21 through line 22A-22A.

Figure 22B:
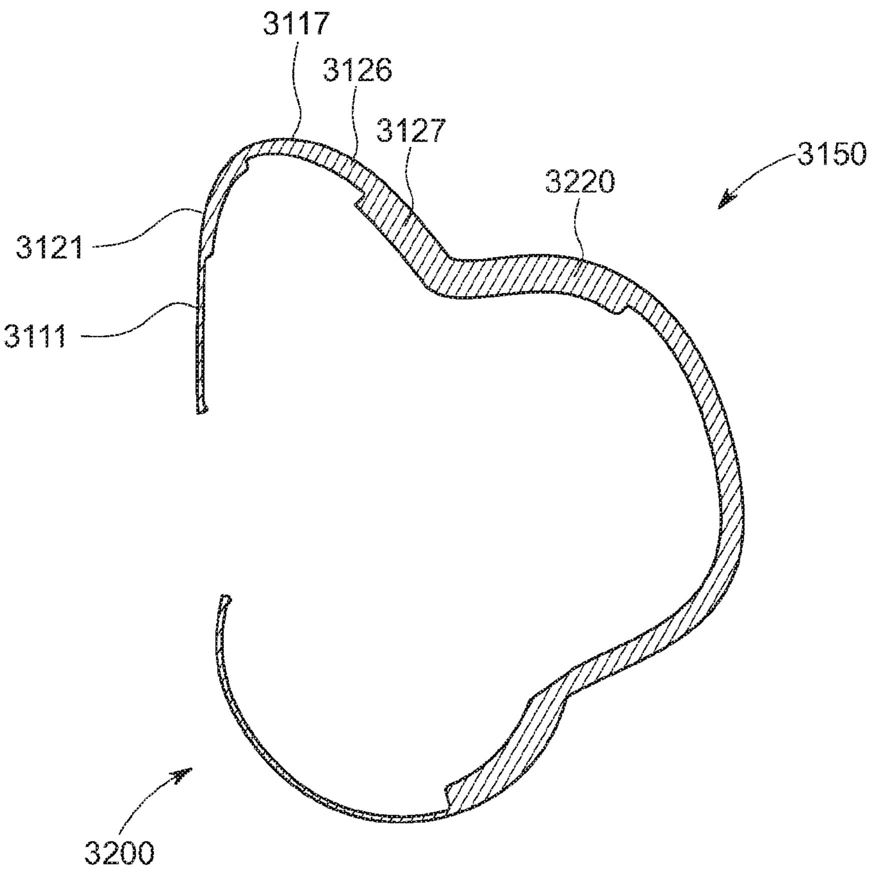

FIG. 22B is a cross section view illustration of the cushion module 3150 shown in FIG. 21 through line 22B-22B.

Figure 23:
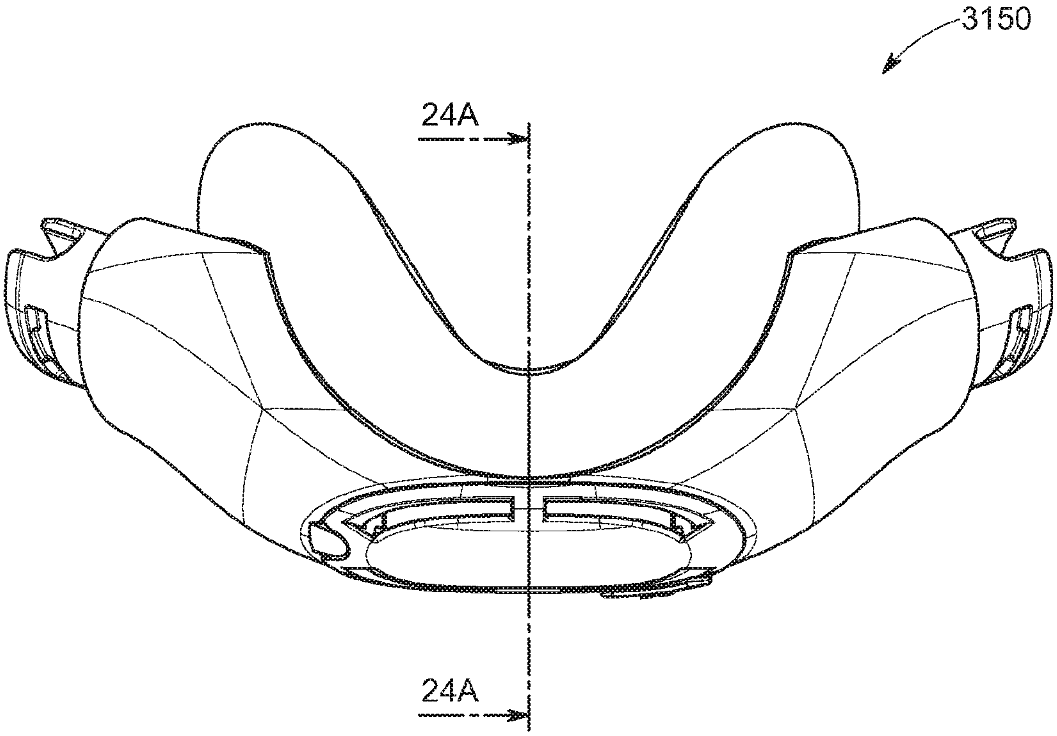

FIG. 23 is an anterior view illustration of the cushion module 3150 shown in FIG. 19A.

Figure 24A:
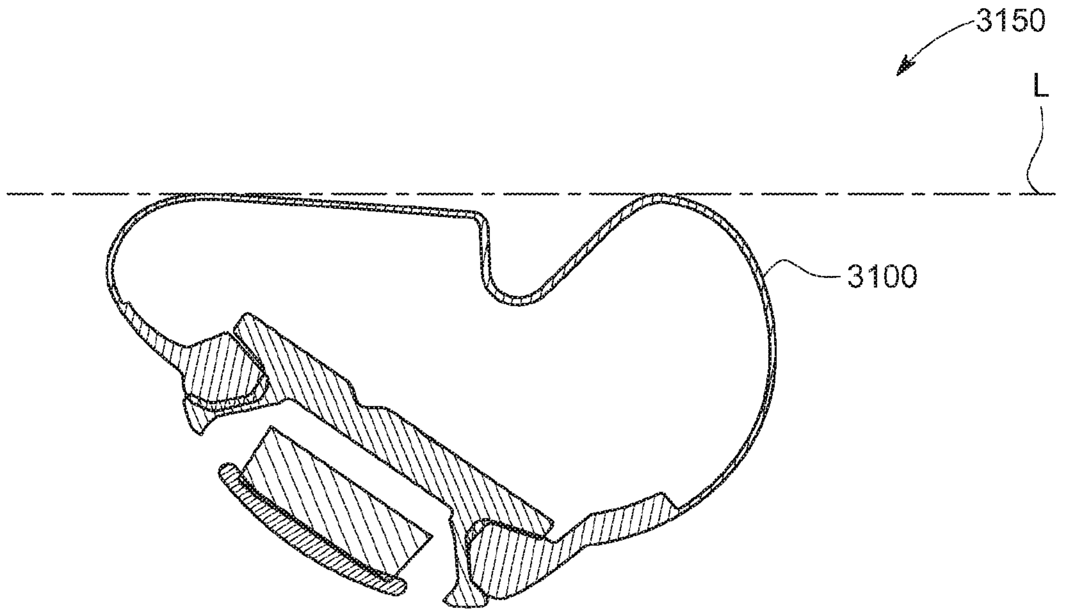

FIG. 24A is a cross section view illustration of the cushion module 3150 shown in FIG. 23 through line 24A-24A.

Figure 24B:
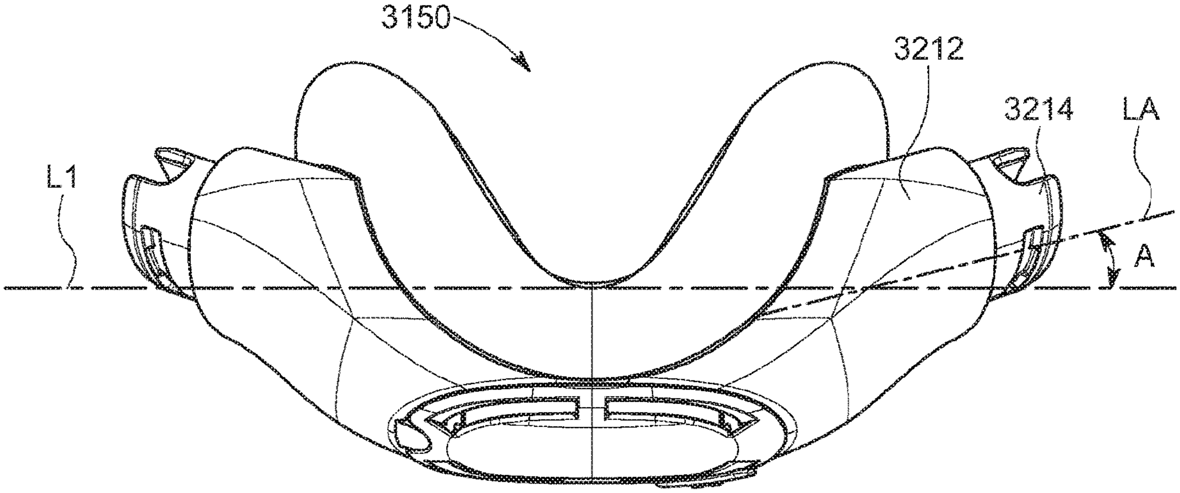

FIG. 24B is another anterior view illustration of the cushion module 3150 shown in FIG. 23.

Figure 24C:
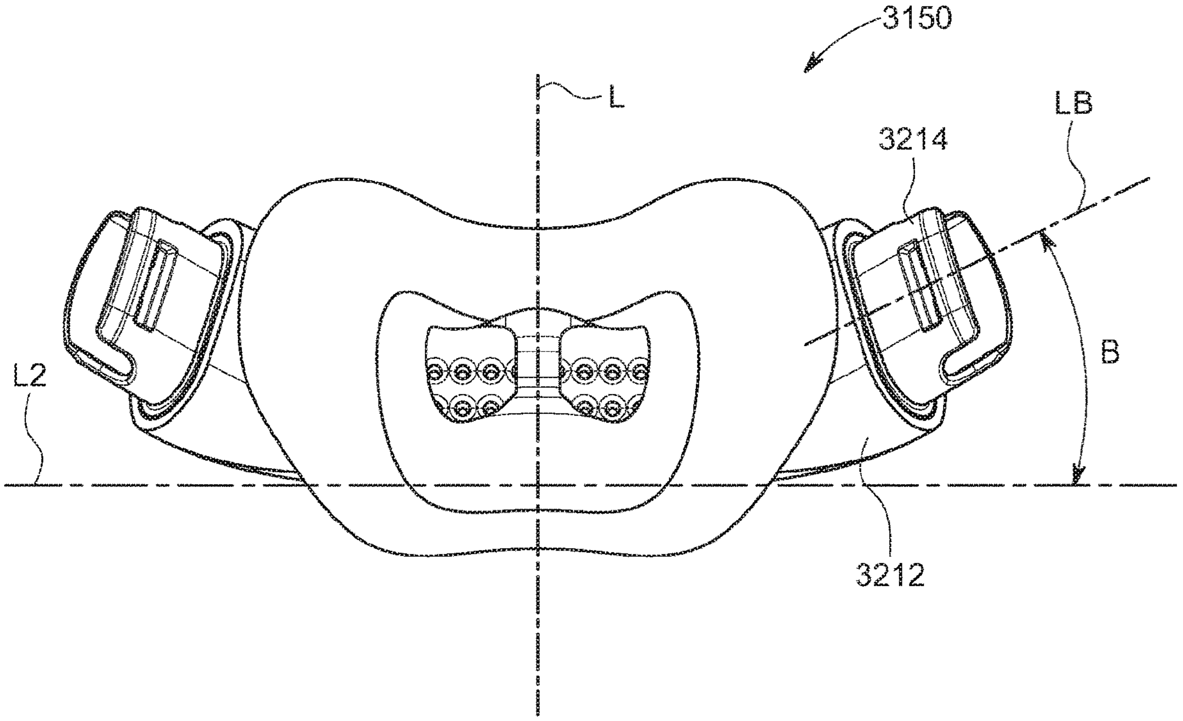

FIG. 24C is a superior view illustration of the cushion module 3150 shown in FIG. 23.

Figure 25A:
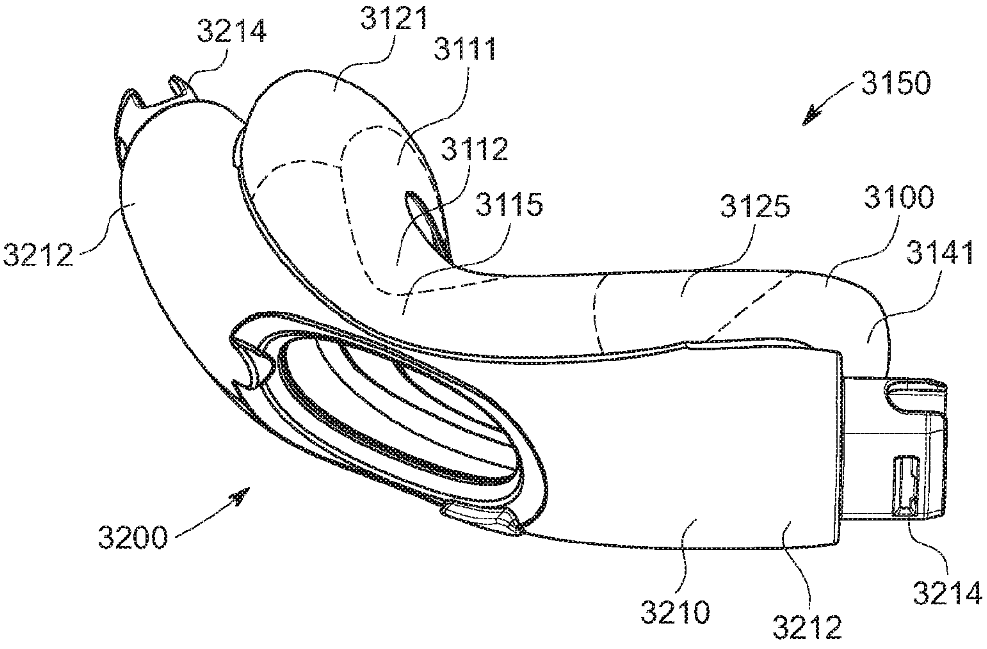

FIG. 25A is an anterolateral perspective view illustration of a cushion module 3150 according to another example of the present technology, having various portions identified.

Figure 25B:
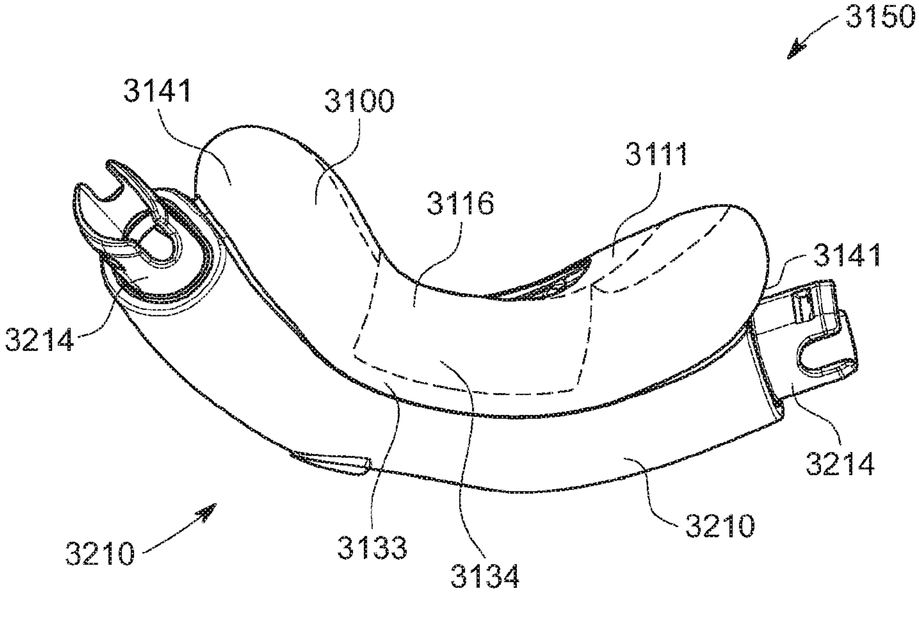

FIG. 25B is an inferior posterolateral perspective view illustration of the cushion module 3150 shown in FIG. 25A, having various portions identified.

Figure 25C:
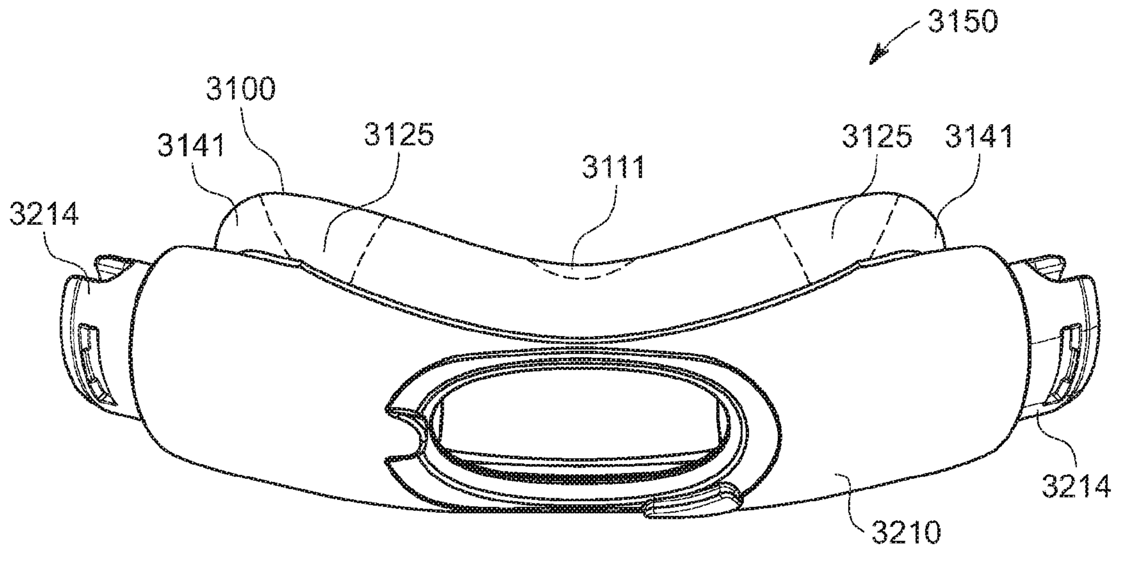

FIG. 25C is an anterior view illustration of the cushion module 3150 shown in FIG. 25A, having various portions identified.

Figure 25D:
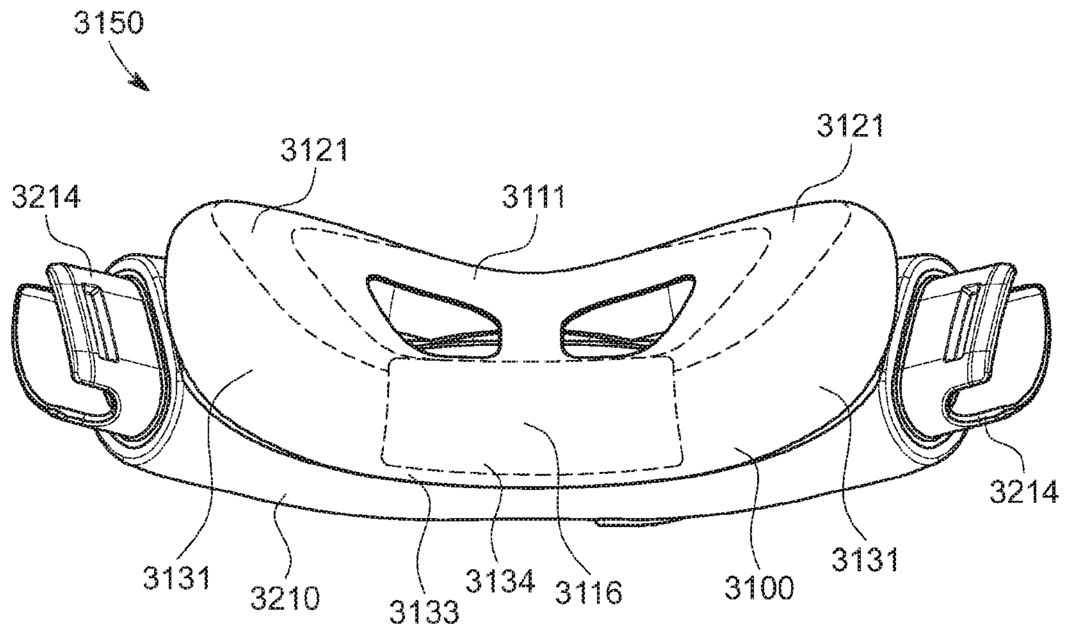

FIG. 25D is a posterior view illustration of the cushion module 3150 shown in FIG. 25A, having various portions identified.

Figure 25E:
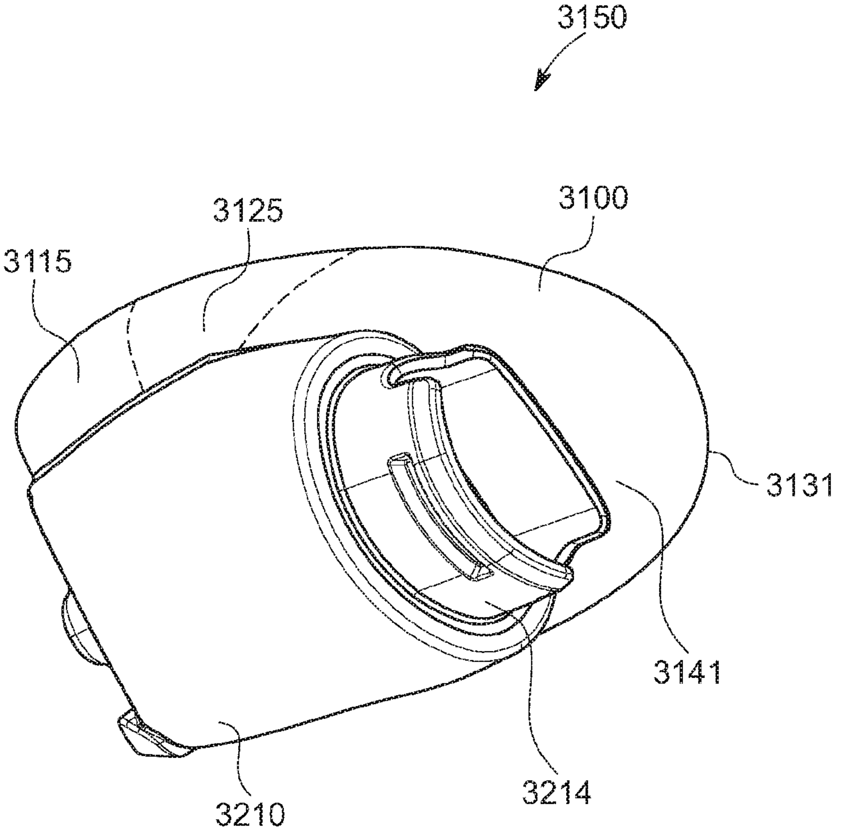

FIG. 25E is a lateral view illustration of the cushion module 3150 shown in FIG. 25A, having various portions identified.

Figure 25F:
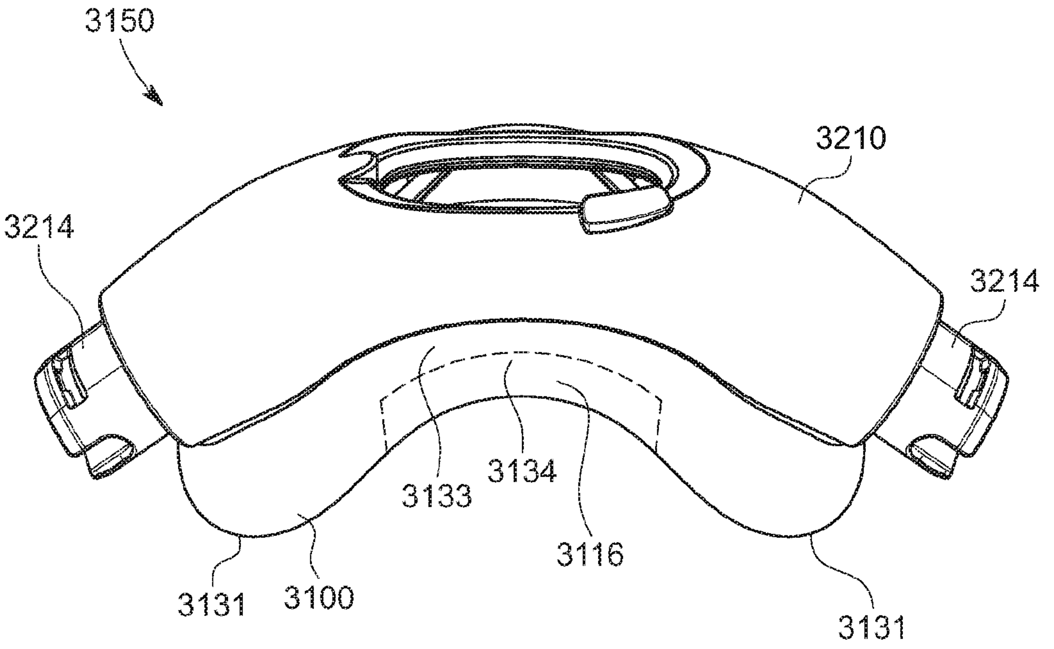

FIG. 25F is an inferior view illustration of the cushion module 3150 shown in FIG. 25A, having various portions identified.

Figure 25G:
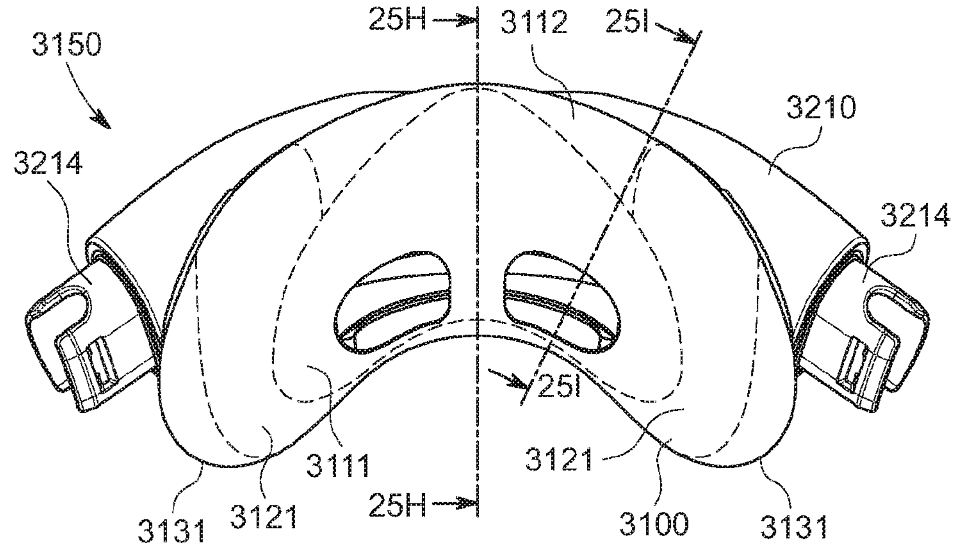

FIG. 25G is a superior view illustration of the cushion module 3150 shown in FIG. 25A, having various portions identified.

Figure 25H:
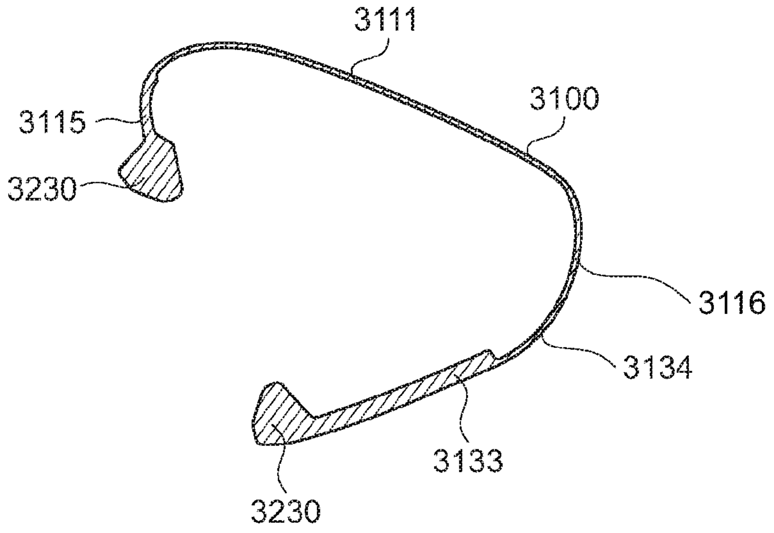

FIG. 25H is a cross section view illustration of the cushion module 3150 shown in FIG. 25A, through the line 25H-25H indicated in FIG. 25G.

Figure 25I:
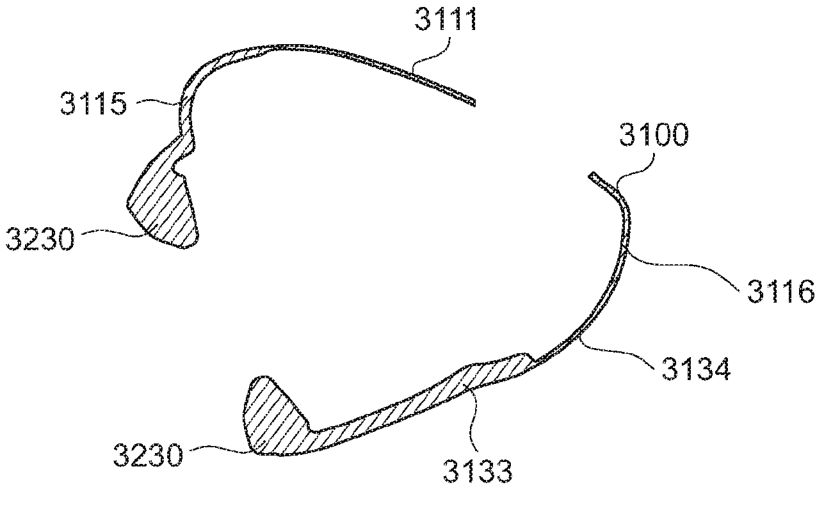

FIG. 25I is a cross section view illustration of the cushion module 3150 shown in FIG. 25A, through the line 25I-25I indicated in FIG. 25G.

Figure 26A:
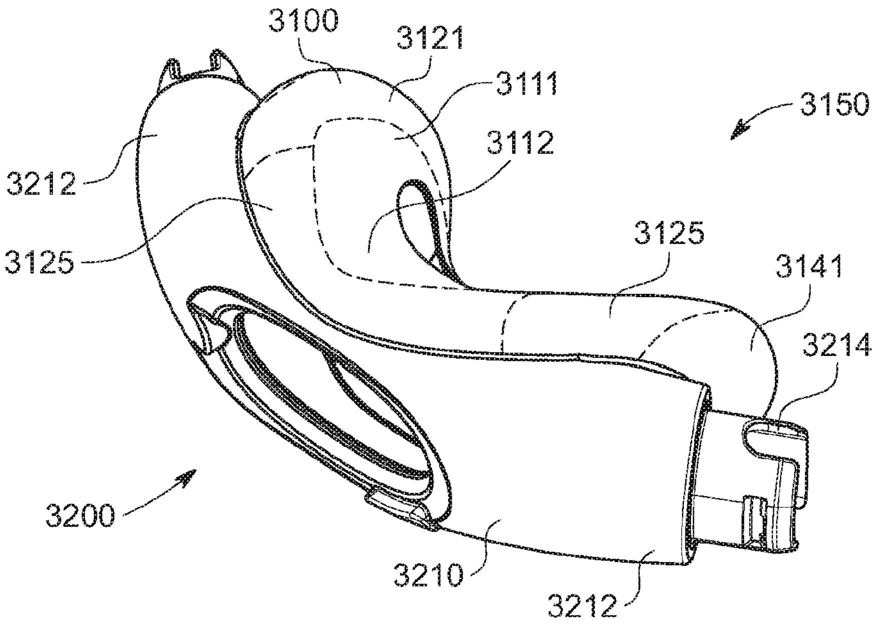

FIG. 26A is an anterolateral perspective view illustration of a cushion module 3150 according to another example of the present technology, having various portions identified.

Figure 26B:
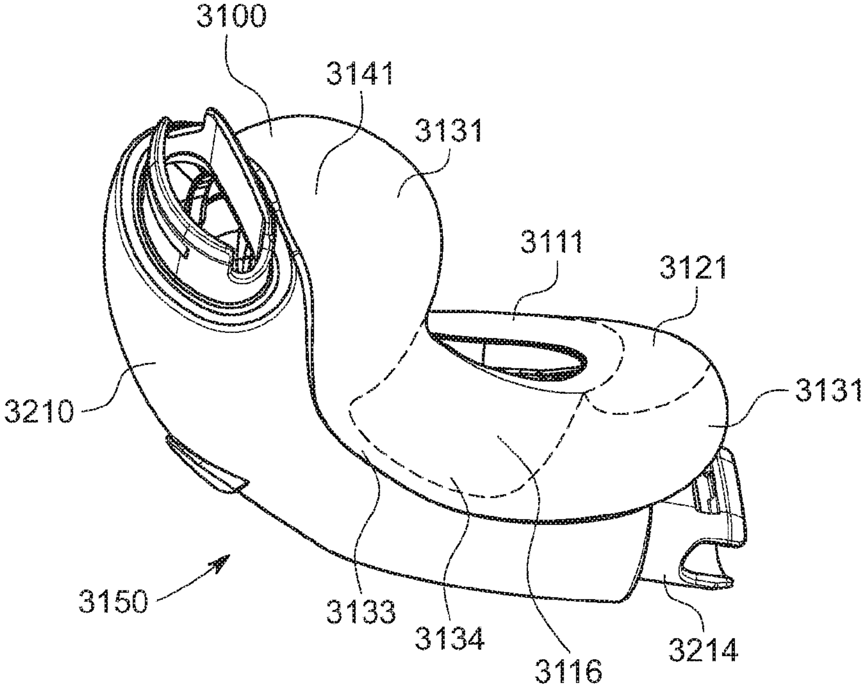

FIG. 26B is an inferior posterolateral perspective view illustration of the cushion module 3150 shown in FIG. 26A, having various portions identified.

Figure 26C:
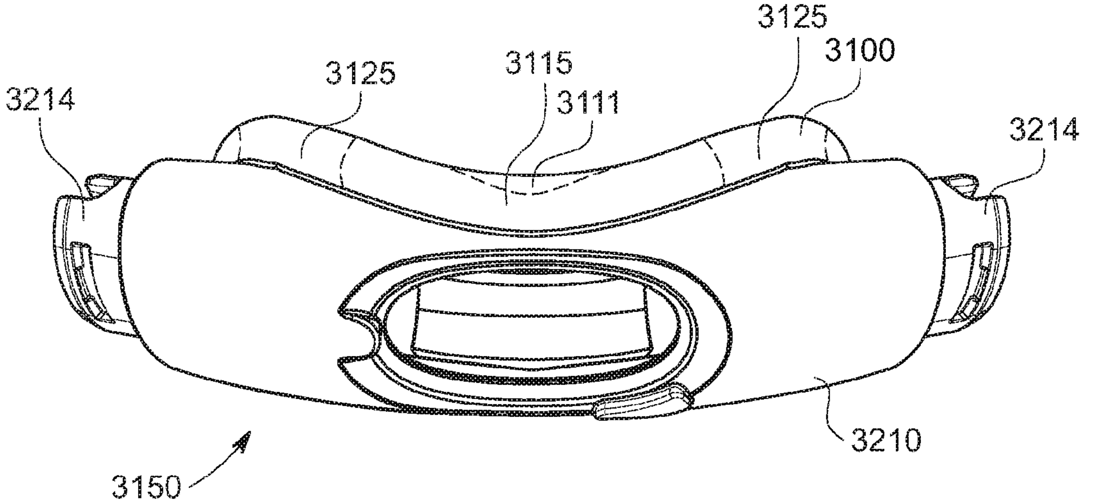

FIG. 26C is an anterior view illustration of the cushion module 3150 shown in FIG. 26A, having various portions identified.

Figure 26D:
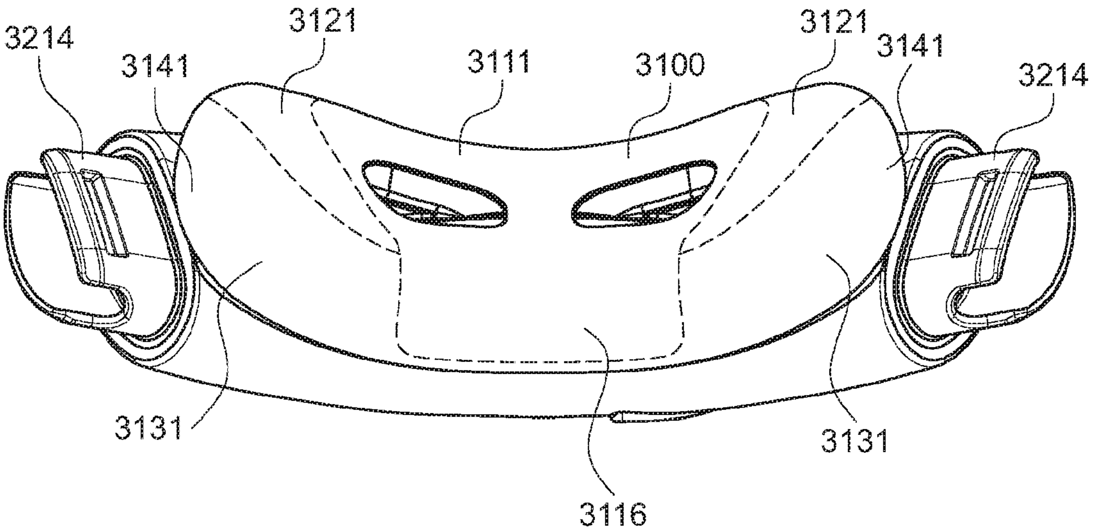

FIG. 26D is a posterior view illustration of the cushion module 3150 shown in FIG. 26A, having various portions identified.

Figure 26E:
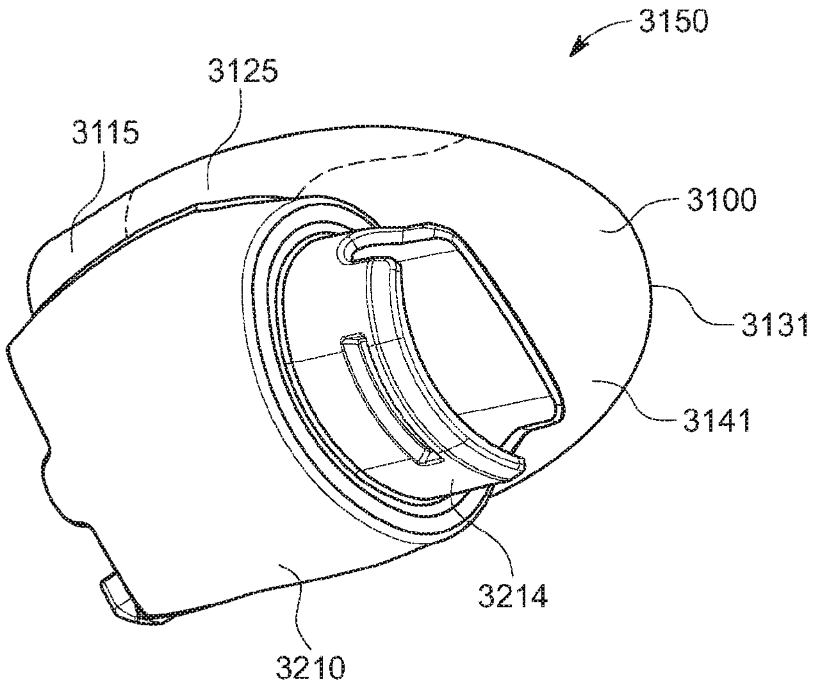

FIG. 26E is a lateral view illustration of the cushion module 3150 shown in FIG. 26A, having various portions identified.

Figure 26F:
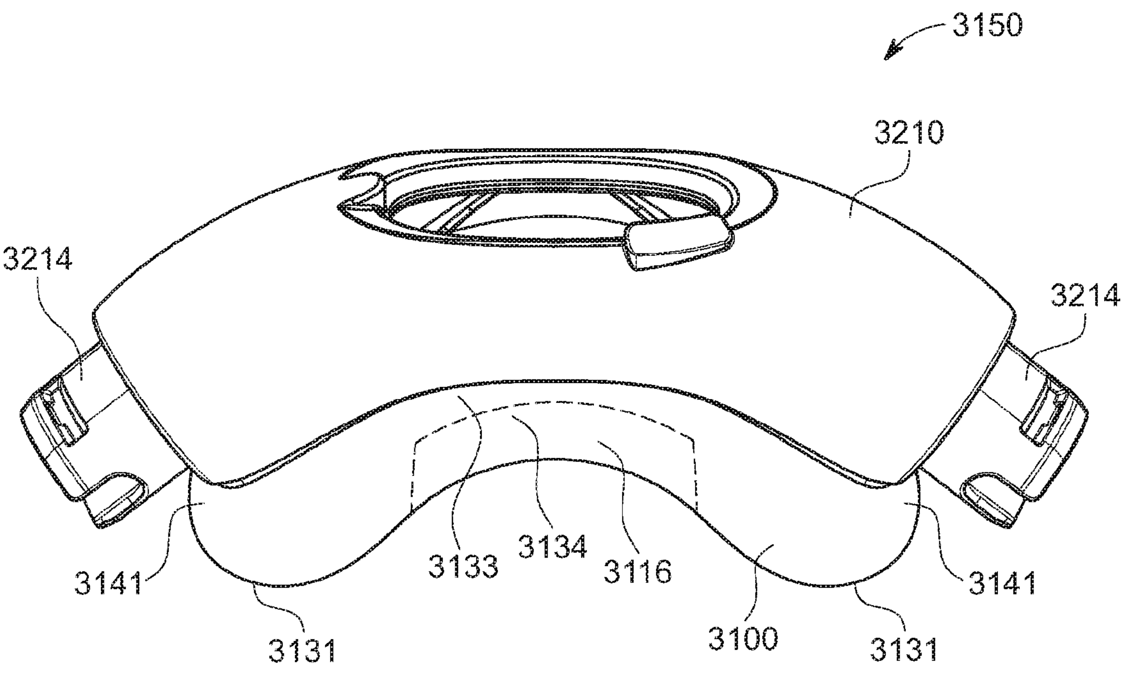

FIG. 26F is an inferior view illustration of the cushion module 3150 shown in FIG. 26A, having various portions identified.

Figure 26G:
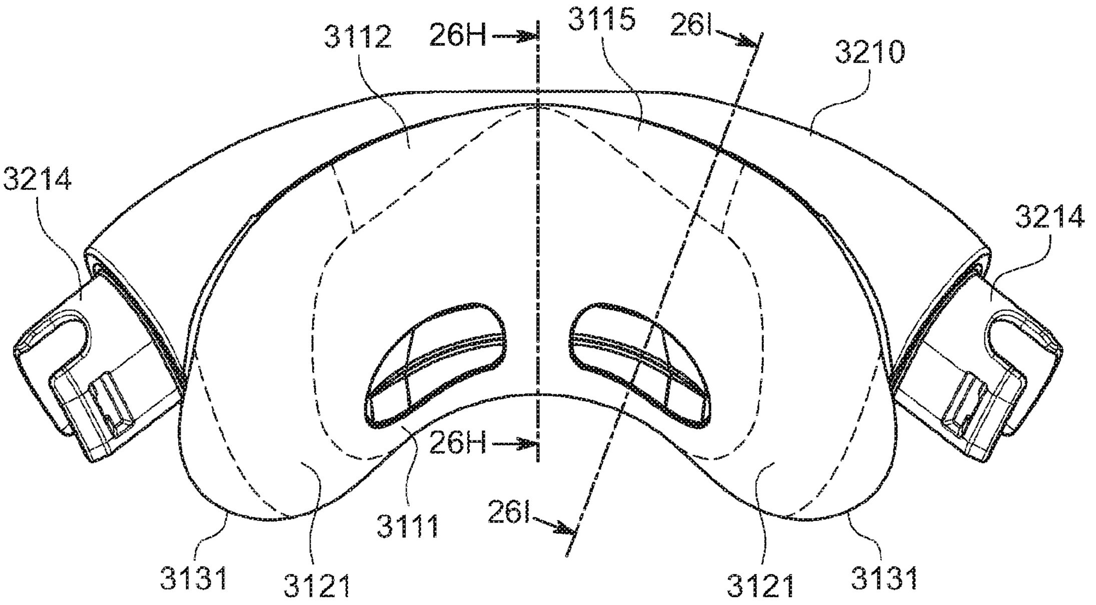

FIG. 26G is a superior view illustration of the cushion module 3150 shown in FIG. 26A, having various portions identified.

Figure 26H:
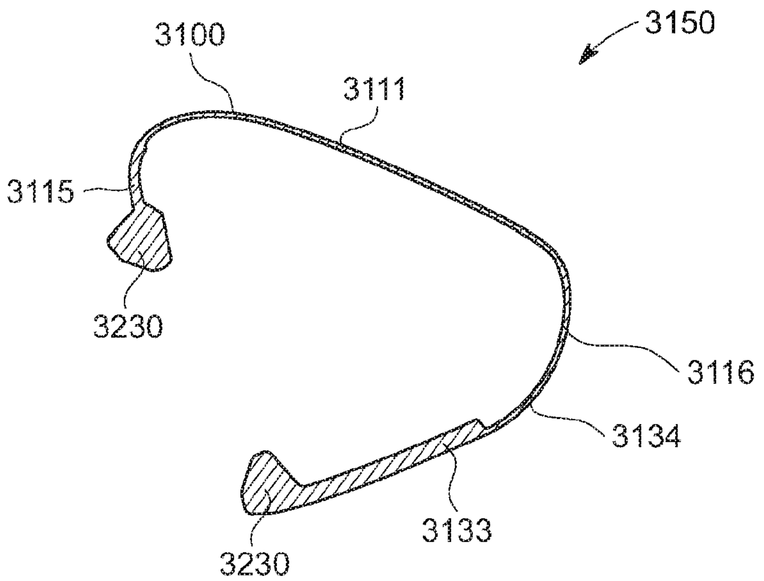

FIG. 26H is a cross section view illustration of the cushion module 3150 shown in FIG. 26A, through line 26H-26H indicated in FIG. 26G.

Figure 26I:
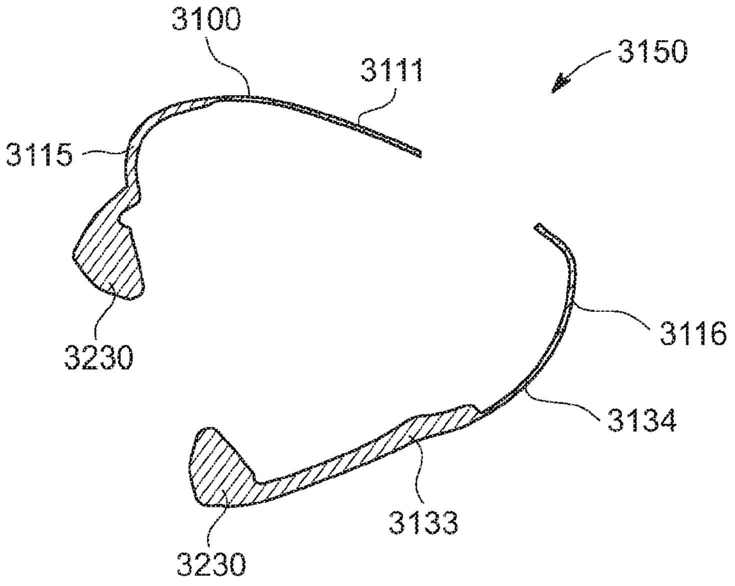

FIG. 26I is a cross section view illustration of the cushion module 3150 in FIG. 26A, through line 26I-26I indicated in FIG. 26G.

Figure 27A:
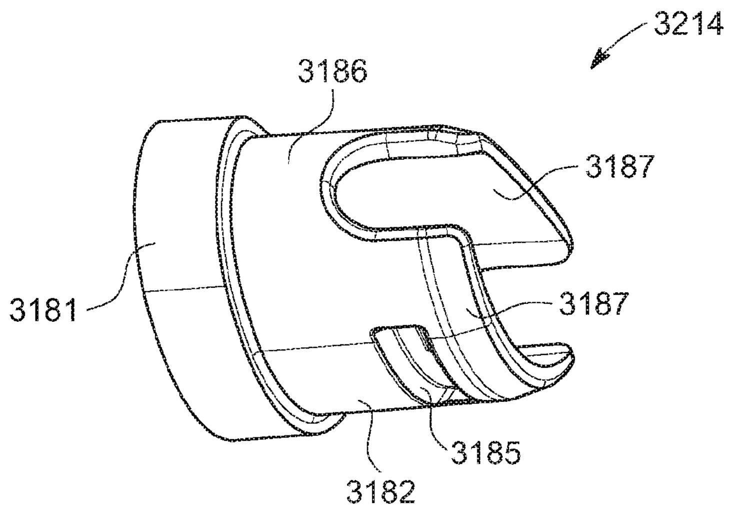

FIG. 27A is a perspective view illustration of a connector 3214 of the cushion module shown in FIG. 26A.

Figure 27B:
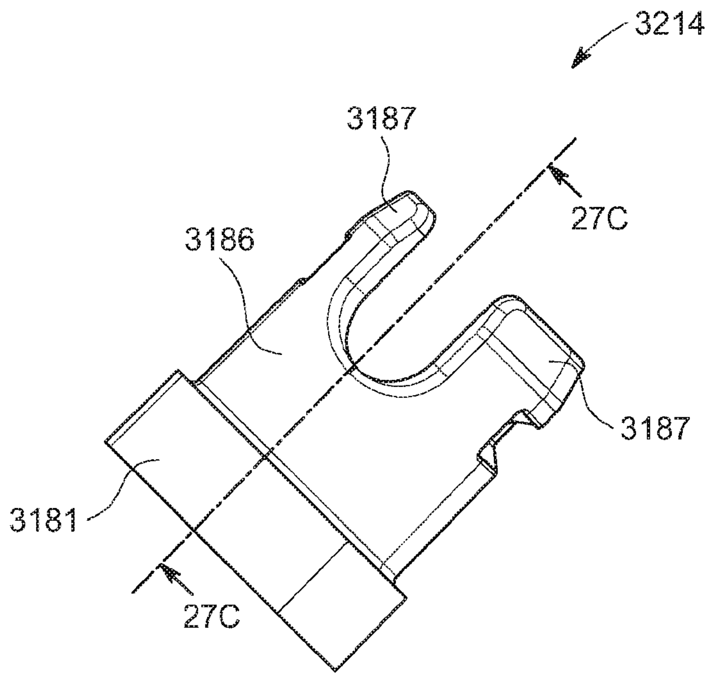

FIG. 27B is a superior view illustration of the connector 3214 shown in FIG. 27A.

Figure 27C:
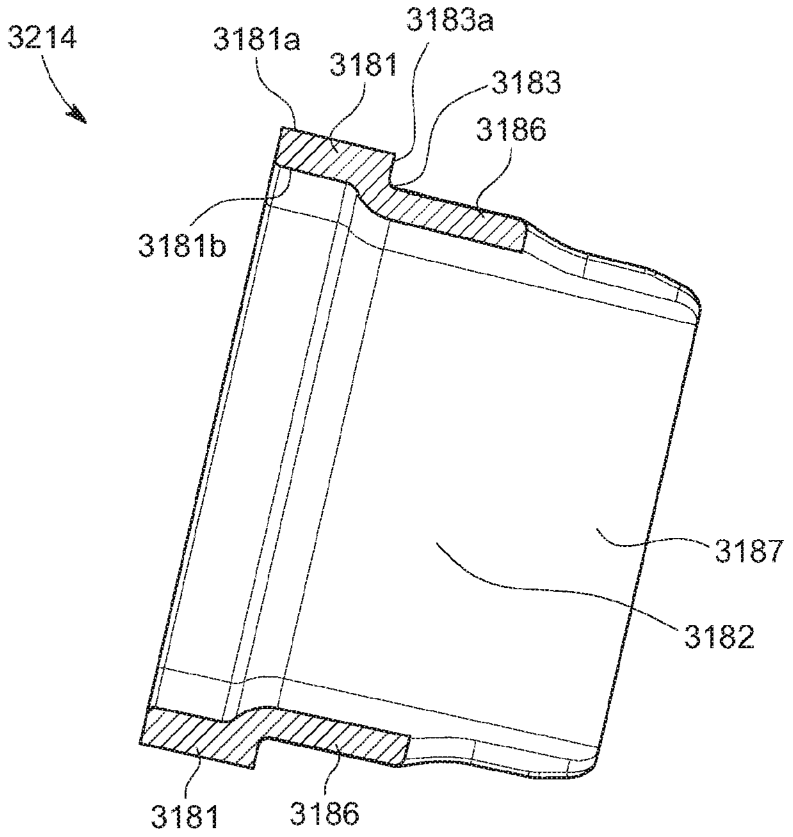

FIG. 27C is a cross section view illustration of the connector 3214 shown in FIG. 27A, through line 27C-27C indicated in FIG. 27B.

Figure 28A:
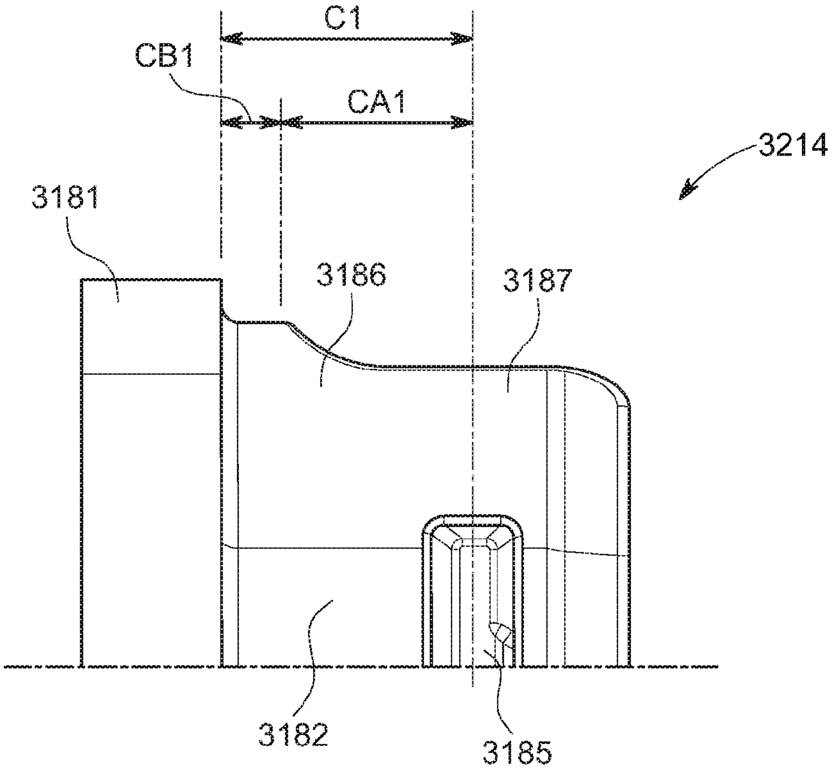

FIG. 28A is a partial side view illustration of the connector 3214 shown in FIG. 17A with certain dimensions labelled.

Figure 28B:
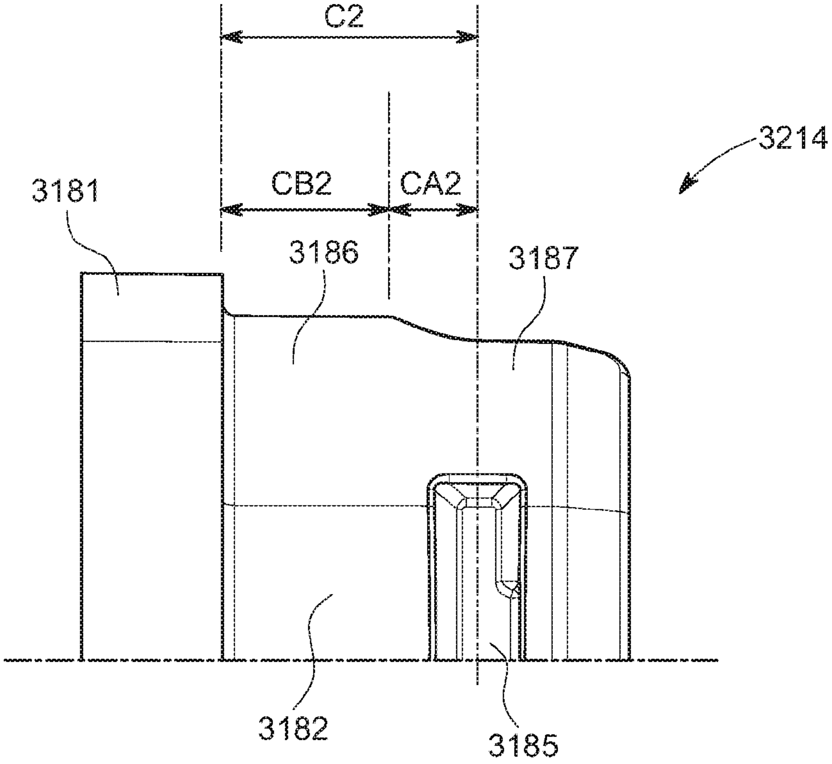

FIG. 28B is a partial side view illustration of the connector 3214 shown in FIG. 27A with certain dimensions labelled.

Figure 29:
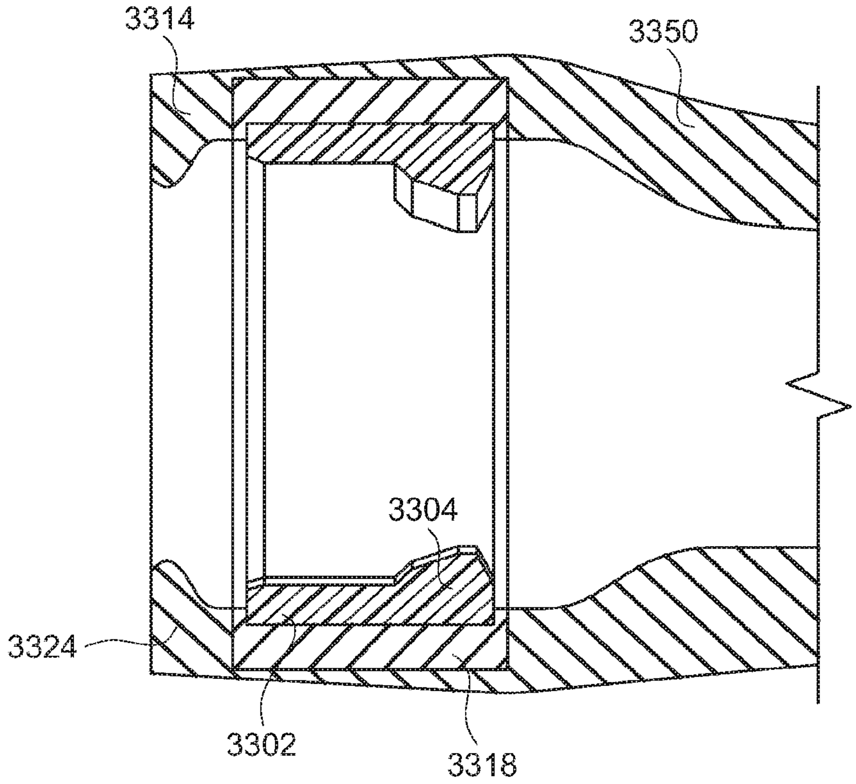

FIG. 29 is a cross section view illustration of a tube end 3314 of a gas delivery tube 3350 of the patient interface 3000 shown in FIG. 7A.

Figure 30A:
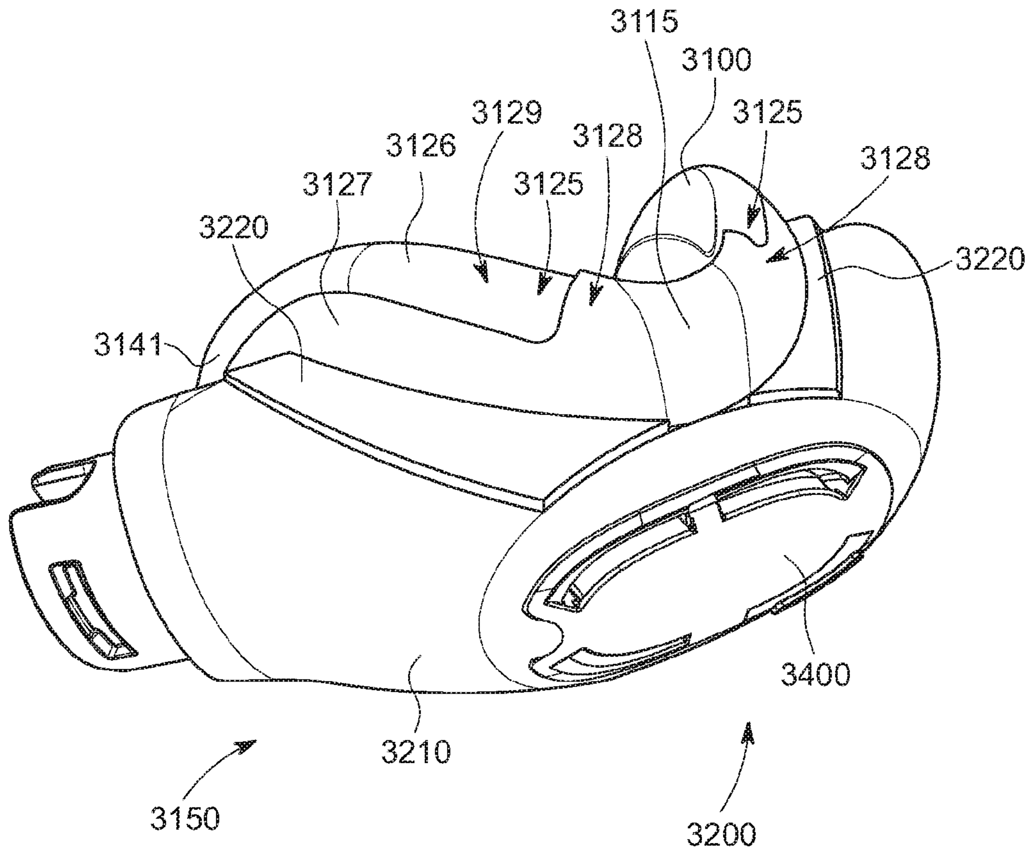

FIG. 30A is an anterior perspective view illustration of a cushion module 3150 according to another example of the present technology.

Figure 30B:
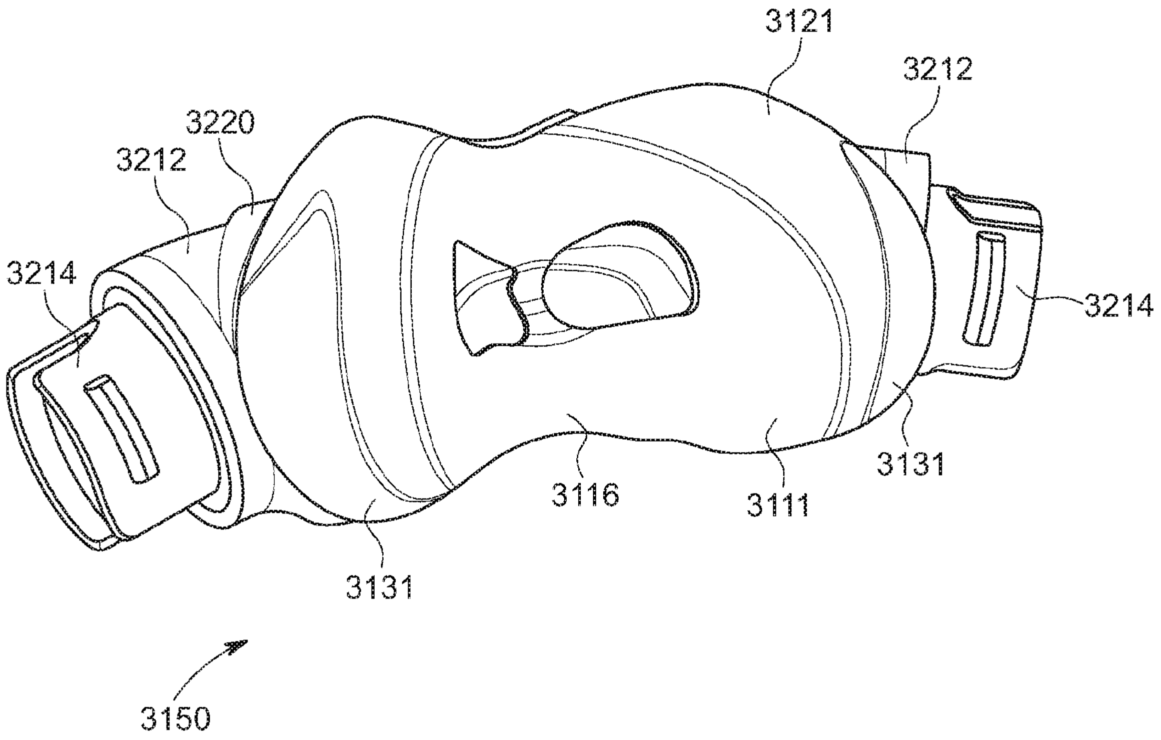

FIG. 30B is a posterior perspective view illustration of the cushion module 3150 of FIG. 30A.

Figure 30C:
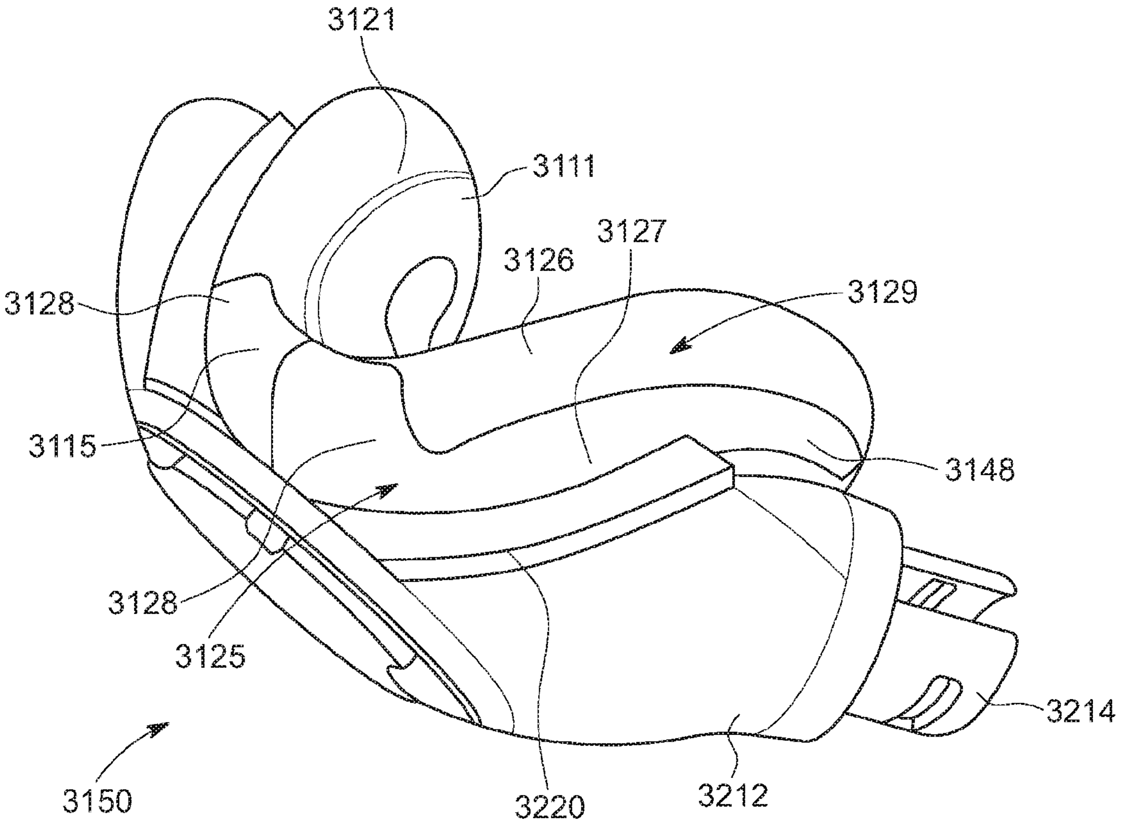

FIG. 30C is an anterolateral perspective view illustration of the cushion module 3150 of FIG. 30A.

Figure 30D:
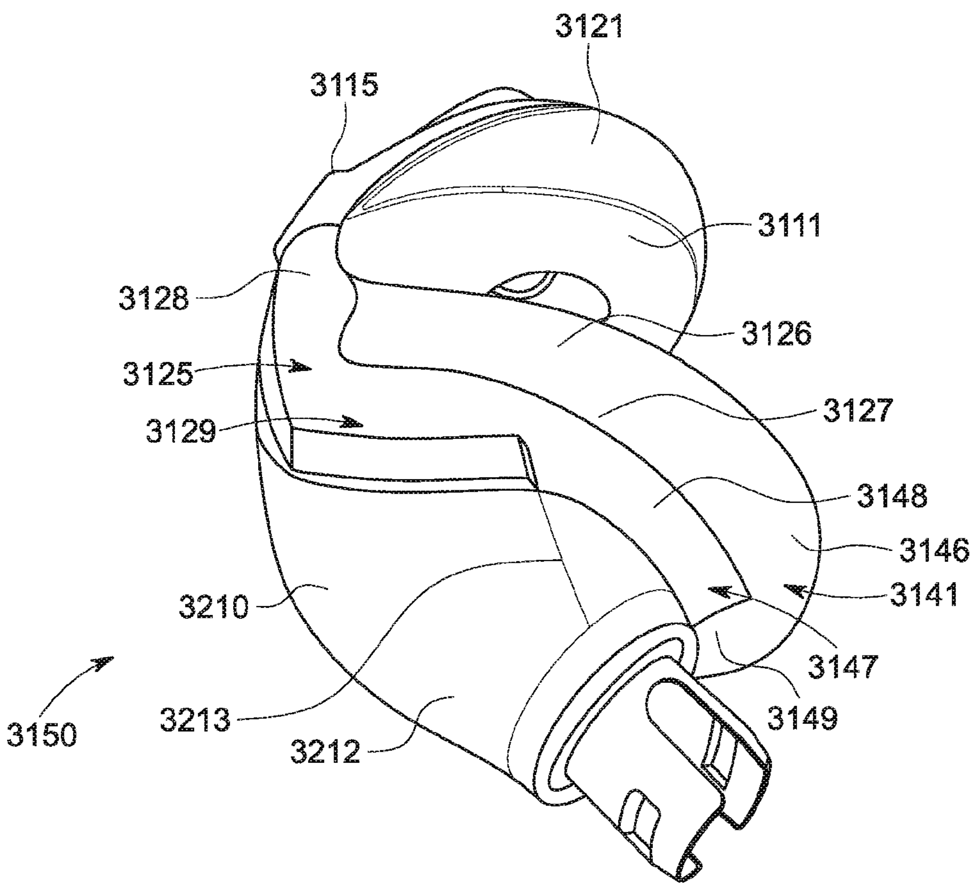

FIG. 30D is a lateral perspective view illustration of the cushion module 3150 of FIG. 30A.

Figure 30E:
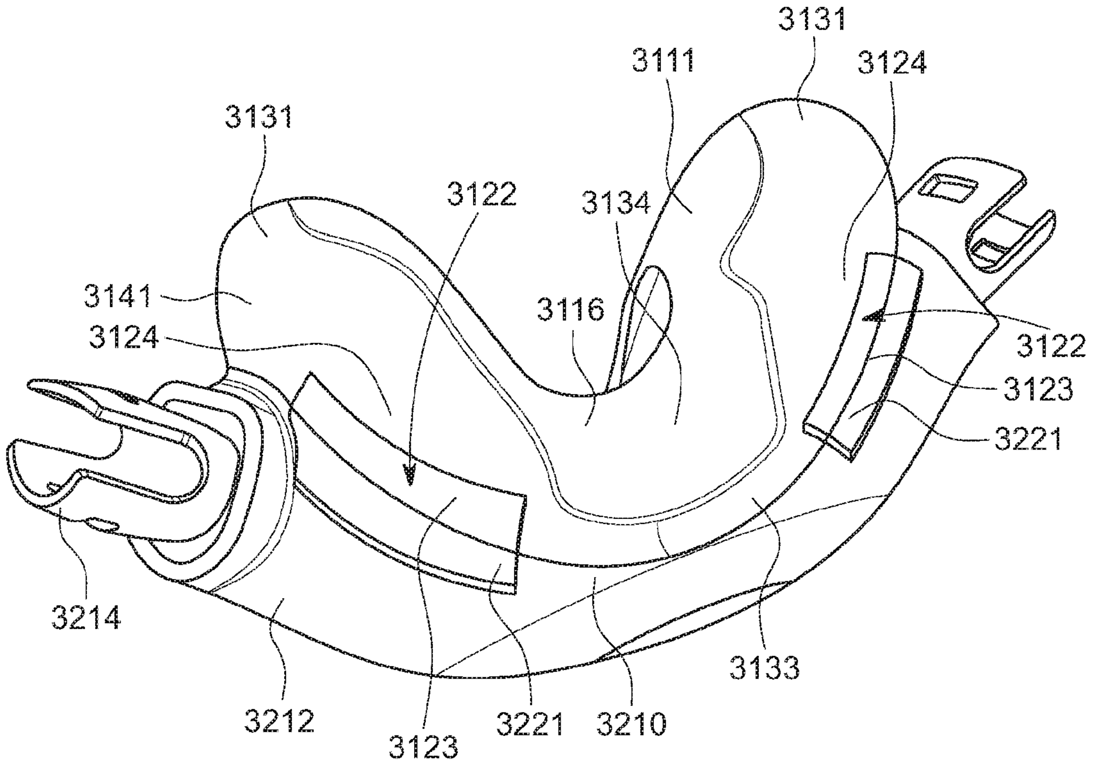

FIG. 30E is an inferior perspective view illustration of the cushion module 3150 of FIG. 30A.

Figure 31A:
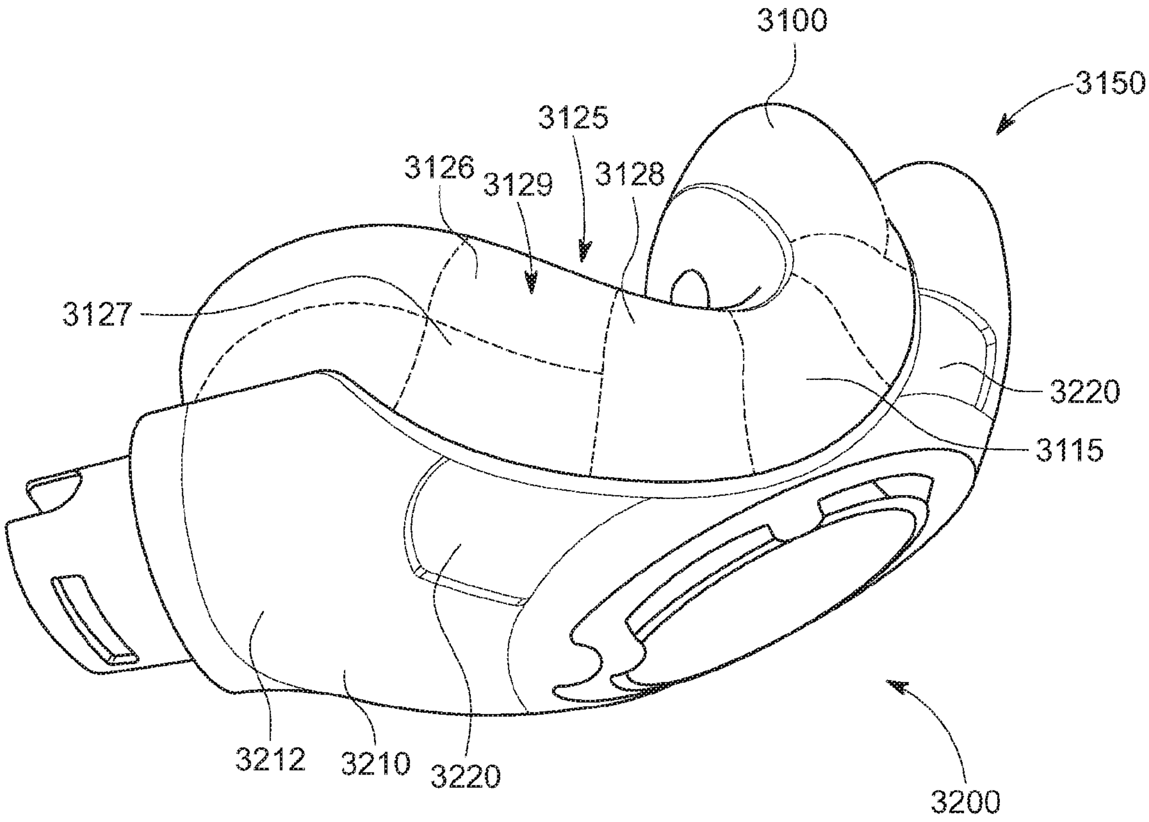

FIG. 31A is an anterior perspective view illustration of a cushion module 3150 according to another example of the present technology.

Figure 31B:
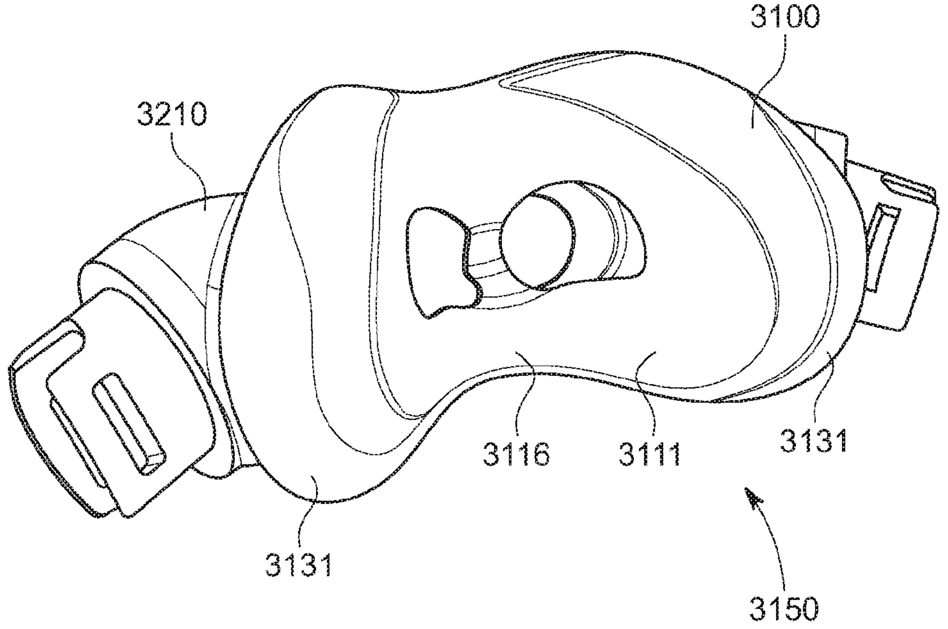

FIG. 31B is a posterior perspective view illustration of the cushion module 3150 of FIG. 31A.

Figure 31C:
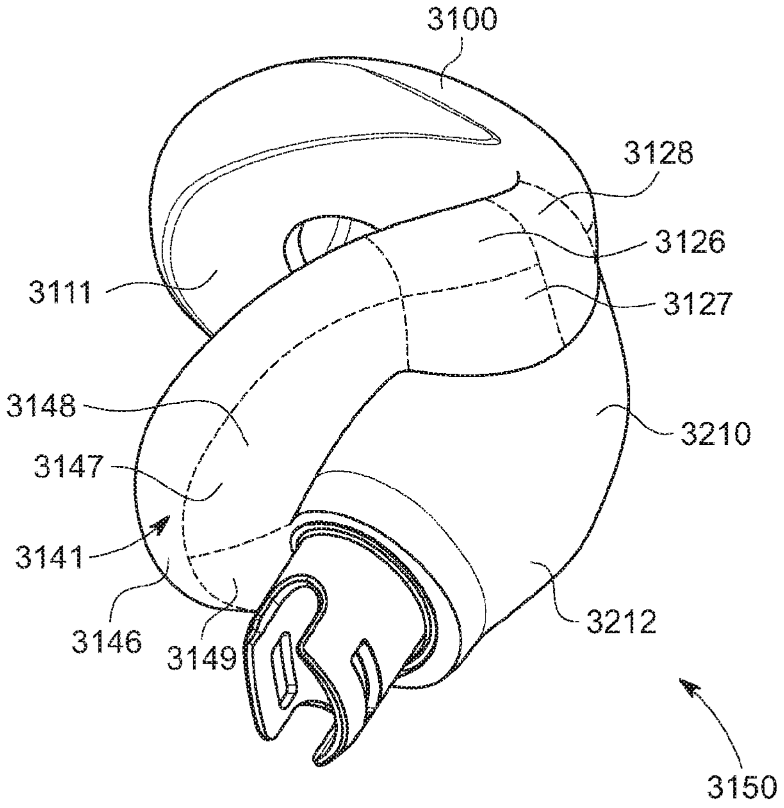

FIG. 31C is a lateral perspective view illustration of the cushion module 3150 of FIG. 31A.

Figure 31D:
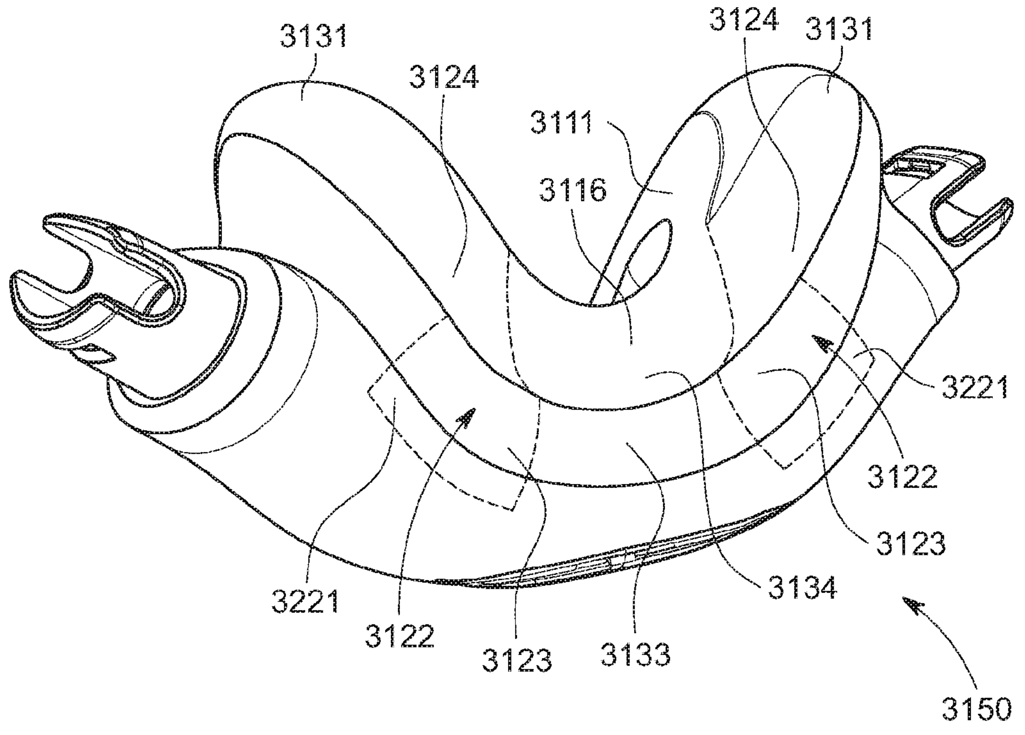

FIG. 31D is an inferior view illustration of the cushion module 3150 of FIG. 31A.

Figure 32A:
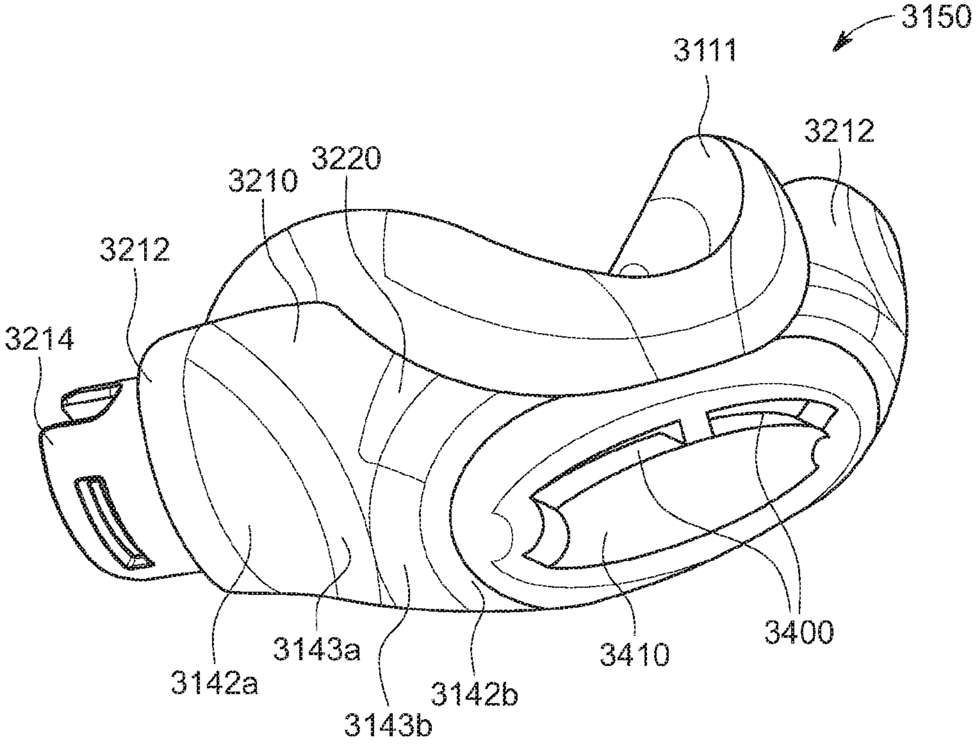

FIG. 32A is an anterior view illustration of a cushion module 3150 according to another example of the present technology.

Figure 32B:
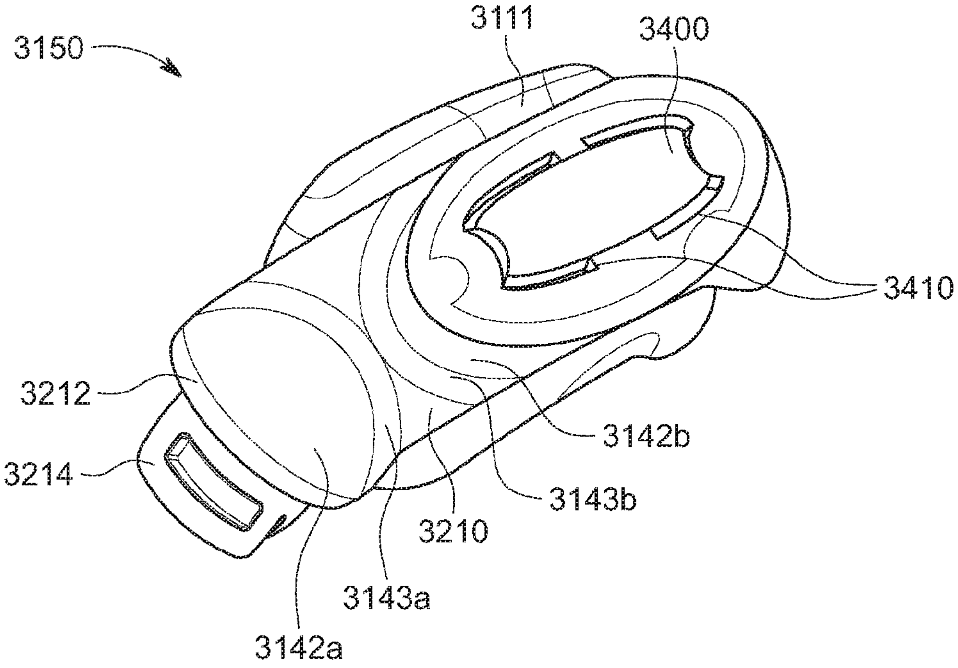

FIG. 32B is an anteroinferior view illustration of the cushion module 3150 of FIG. 32A.

Figure 32C:
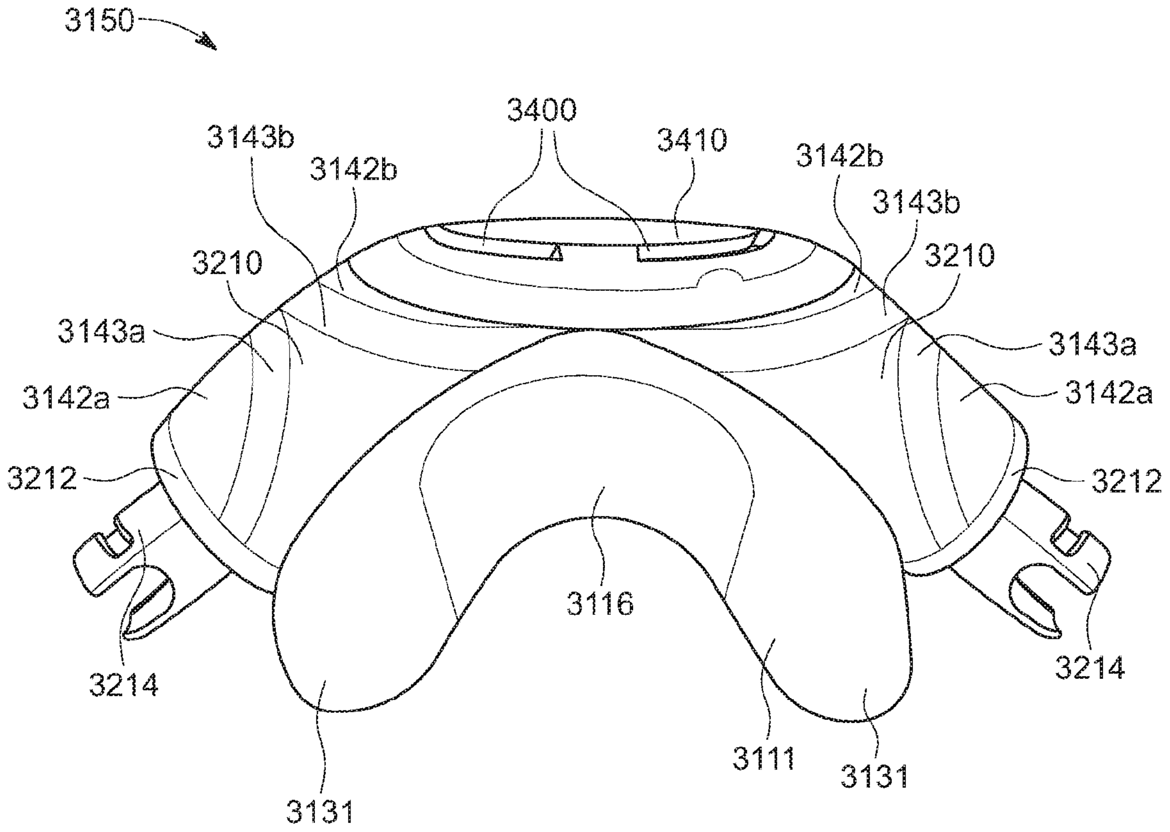

FIG. 32C is an inferior view illustration of the cushion module 3150 of FIG. 32A in an undeformed state.

Figure 32D:
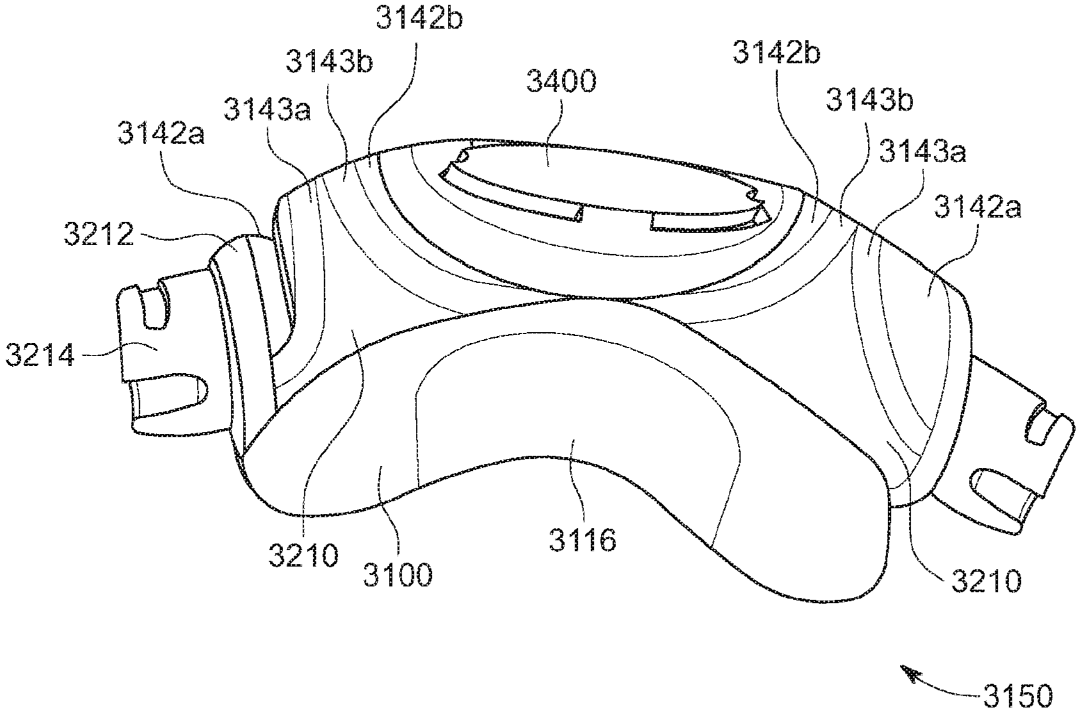

FIG. 32D is an inferior view illustration of the cushion module 3150 of FIG. 32A in a deformed state.

Figure 33A:
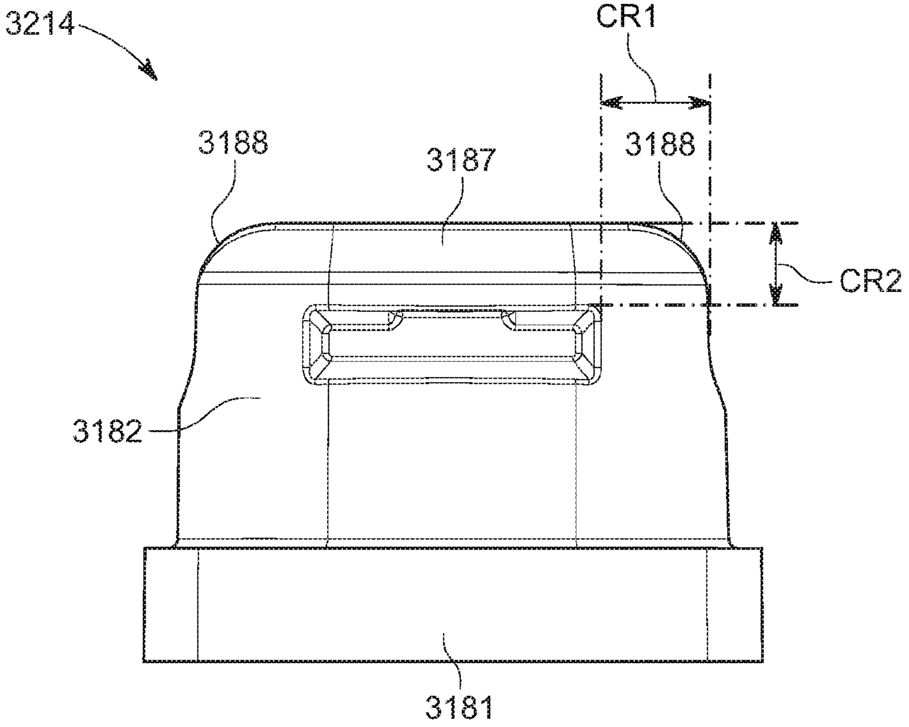

FIG. 33A is an anterior view illustration of a connector 3214 according to another example of the present technology.

Figure 33B:
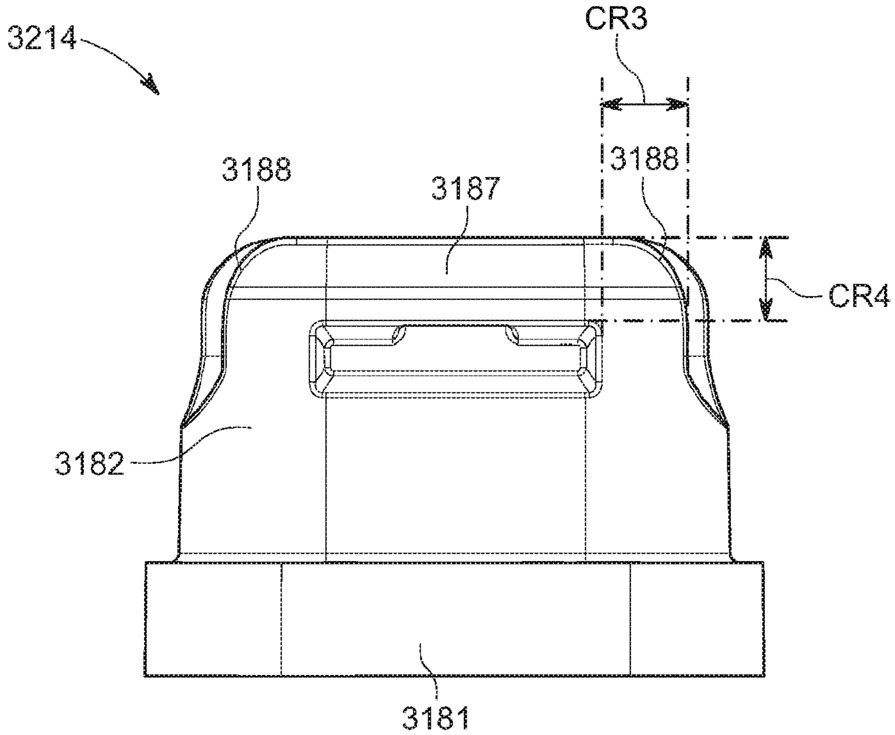

FIG. 33B is a posterior view illustration of the connector 3214 shown in FIG. 33A.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

Figure 1A:
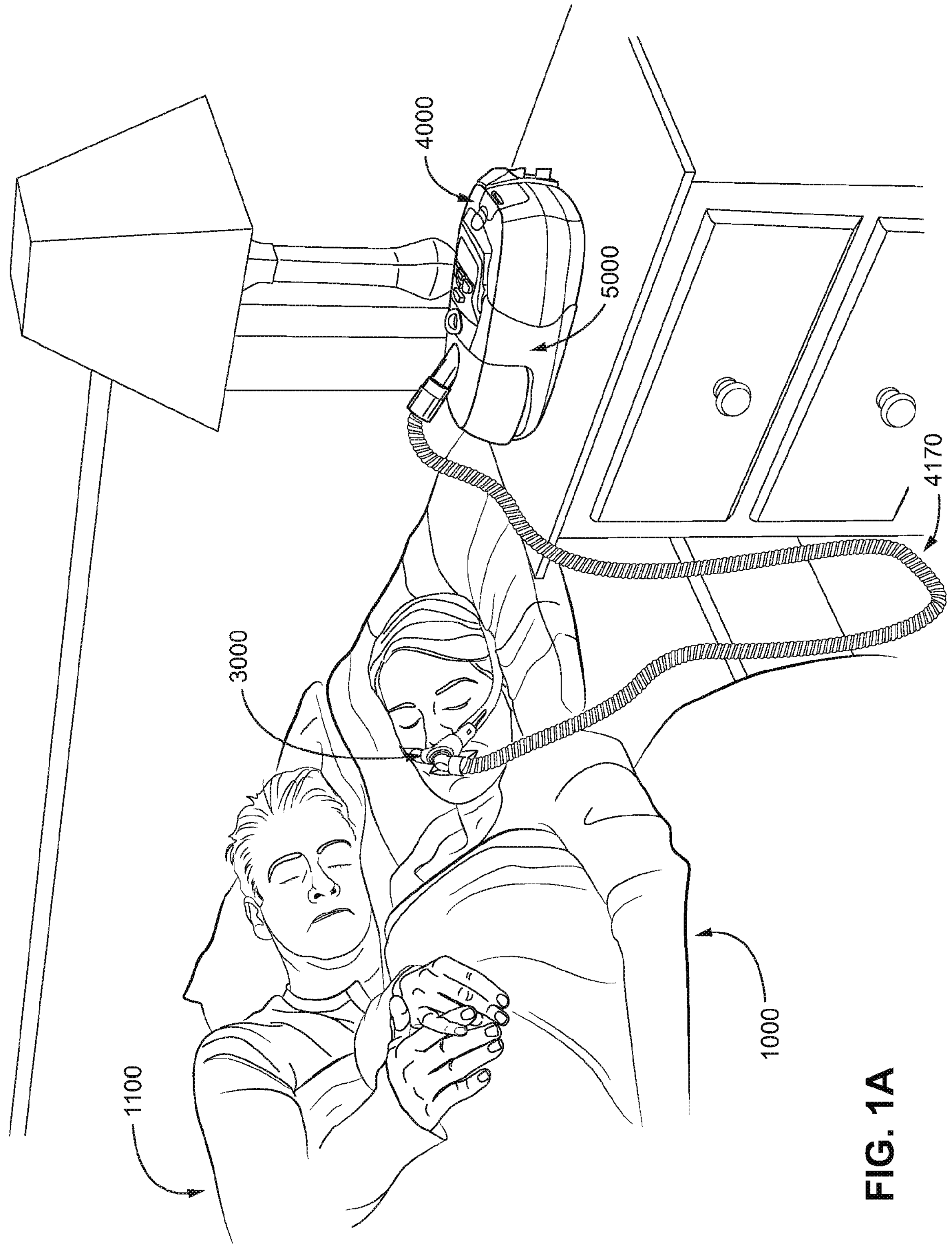
FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

In one form as shown in FIG. 1A, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

Figure 1B:
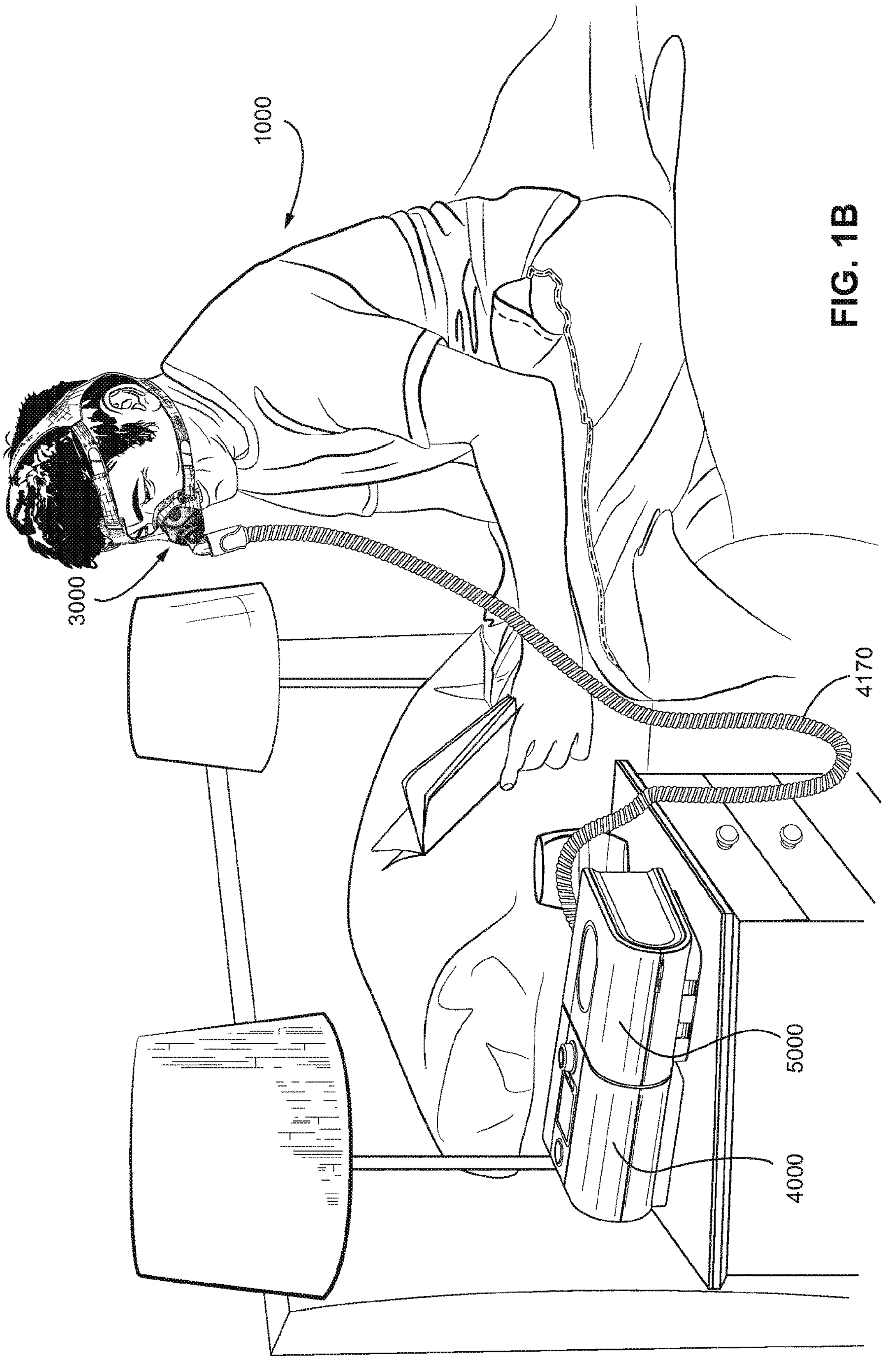
FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.
Figure 1C:
FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

In one form, the present technology comprises an apparatus or device for treating a respiratory disorder. The apparatus or device may comprise an RPT device 4000 for supplying pressurised air to the patient 1000 via an air circuit 4170 to a patient interface 3000. FIGS. 1A, 1B and 1C illustrate treatment systems that utilise patent interfaces 3000 with RPT devices 4000 and humidifiers 5000.

5.3 Patient Interface

With reference to FIG. 3A, a non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

As shown in FIGS. 7A-7G, a non-invasive patient interface 3000 in accordance with one aspect of the present technology comprises the following functional aspects: a seal-forming structure 3100, a plenum chamber 3200, a positioning and stabilising structure 3300, a vent 3400 and one form of connection port 3600 for connection to an air circuit (e.g. the air circuit 4170 shown in FIGS. 1A-1C). In this form of the present technology, the plenum chamber 3200 and seal-forming structure 3100 functional aspects are provided by one physical component. In the example illustrated in FIGS. 7A-7G, the patient interface 3000 comprises a cushion module 3150. In this example, the cushion module 3150 provides both the plenum chamber 3200 and the seal-forming structure 3100 functional aspects of the patient interface 3000. The cushion module 3150 of the patient interface 3000 of FIGS. 7A-7G is shown in FIGS. 8A-8G in isolation. The seal-forming structure 3100 and other wall portions of the cushion module 3150 form the plenum chamber 3200 in this example. In this form of the present technology, the positioning and stabilising structure 3300 is provided by and comprises a plurality of physical components.

The cushion module 3150 may be modular in the sense that it can be replaced in the patient interface 3000 with another cushion module 3150. In some examples a first cushion module 3150 of the patient interface may be able to be replaced by a second cushion module 3150, the second cushion module 3150 being a different type of cushion module from the first cushion module 3150. For example, the second cushion module 3150 may have a different size, shape and/or structure from the first cushion module. In particular examples, a patient interface 3000 having the cushion module 3150 shown in FIGS. 8A-8H may be disassembled and reassembled such that the patient interface includes one of the cushion modules 3150 shown in FIG. 19A-19F, 25A-25I, 26A-26I, 30A-30E, 31A-31D or 32A-32D, for example.

In other forms of the present technology, the plenum chamber 3200 and seal-forming structure 3100 may be inseparable from components of the positioning and stabilising structure 3300. For example, a cushion module 3150 fully or partially forming the plenum chamber 3200 may permanently connected to one or more other components of the patient interface 3000. The cushion module 3150 in such an example of the present technology may be modular in the sense that is a sub-part of a larger assembly.

In some examples of the present technology the component(s) forming the plenum chamber 3200 and/or seal-forming structure 3100 may be permanently attached to one or more headgear conduits. In some examples, the patient interface 3000 may comprise a non-removable cushion module 3150 located proximate an entrance of the patient's airways in use forming the plenum chamber 3200 and comprising a seal-forming structure 3100. The cushion module 3150 may be permanently attached to one or more gas delivery tubes configured to lie against the patient's head in use and convey a flow of air from a location on top of the patient's head to the plenum chamber 3200 for breathing by the patient. A non-removable cushion module 3150 may have a similar shape and size to the removable cushion module 3150 shown in FIGS. 8A-8H (or FIG. 19A-19F, 25A-25I, 26A-26I, 30A-30E, 31A-31D or 32A-32D) and described herein but may be permanently connected to one or more gas delivery tubes.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 $cmH_2O$ with respect to ambient.

The patient interface 3000 in accordance with one form of the present technology is constructed and arranged to be able to provide a supply of air at a positive pressure of at least 10 $cmH_2O$ with respect to ambient.

The patient interface 3000 in accordance with one form of the present technology is constructed and arranged to be able to provide a supply of air at a positive pressure of at least 20 $cmH_2O$ with respect to ambient.

5.3.1 Plenum Chamber

A patient interface 3000 according to some examples of the present technology comprises a plenum chamber 3200 pressurisable to a therapeutic pressure of at least 6 $cmH_2O$ above ambient air pressure. The plenum chamber 3200 may receive a flow of air at the therapeutic pressure for breathing by a patient.

The plenum chamber 3200 in some forms of the present technology is at least partially provided by a cushion module 3150 of the patient interface 3000. The cushion module 3150 according to some examples (such as those shown in FIGS. 7A-7G, 8A-8H, 16A-16D, 25A-25I, 26A-26I, 30A-30E, 31A-31D, 32A-32D) may comprise a chassis portion 3210 and a seal-forming structure 3100. The plenum chamber 3200 may be at least partially formed by both the chassis portion 3210 and the seal-forming structure 3100. The chassis portion 3210 may support the seal-forming structure 3100 in position against the patient's face in use. Walls of the chassis portion 3210 and seal-forming structure 3100 may together partially enclose a volume of space which in use has air therein pressurised above atmospheric pressure, forming the plenum chamber 3200.

In particular, the chassis portion 3210 may at least partially form a plenum chamber 3200 pressurisable to a therapeutic pressure of at least 6 $cmH_2O$ above ambient air pressure. The chassis portion 3210 may comprise one or more laterally projecting connection portions 3212 configured to connect to gas delivery tubes 3350 and being sized and structured to receive a flow of air at the therapeutic pressure for breathing by a patient. The laterally projecting connection portions 3212 may also partially form the plenum chamber 3200 along with other portions of the cushion module 3150. The seal-forming structure 3100 may be provided to the chassis portion 3210 and may at least partially form the plenum chamber 3200. The seal-forming structure 3100 may be connected to the chassis portion 3210, either permanently connected or removably connected. The seal-forming structure 3100 may be supported by the chassis portion 3210.

In some forms, the plenum chamber 3200 is formed from a single homogeneous piece of material. In some forms, the plenum chamber 3200 may be formed from a homogenous piece of material fitted with connectors formed from another material.

In some examples, the cushion module 3150 may be formed from a single homogenous piece of material. In some forms, the cushion module 3150 may be formed from a homogenous piece of material fitted with connectors formed from another material.

In further examples, the chassis portion 3210 may be formed from a single homogenous piece of material. In some forms, the chassis portion 3210 may be formed from a homogenous piece of material fitted with connectors formed from another material.

In certain forms of the present technology, such as in the patient interface 3000 of FIGS. 7A-7G, the plenum chamber 3200 does not cover the eyes of the patient in use. In other words, when the patient interface 3000 is donned by the patient, their eyes are outside the pressurised volume defined by the plenum chamber. Such forms tend to be less obtrusive and/or more comfortable for the wearer, which can improve compliance with therapy.

In certain forms of the present technology, the cushion module 3150 is constructed from an at least partially transparent material, e.g. silicone, a thermoplastic elastomer, a transparent polycarbonate or the like. For example, the majority of the cushion module 3150 is formed from silicone in the examples shown in FIGS. 7A-7G, 19A-19F, 25A-25I, 26A-26I, 30A-30E, 31A-31D and 32A-32D. In particular, the chassis portion 3210 and seal-forming structure 3100 are both formed from silicone in those examples. In the example shown in FIGS. 16A-16D the chassis portion 3210 and the anterior side portion of the seal-forming structure 3100 are formed from silicone. The use of a transparent material can reduce the obtrusiveness of the patient interface compared to an opaque material, making a patient feel more comfortable when the patient interface 3000 is donned, and consequently helping improve compliance with therapy. The use of a transparent material may also aid a clinician to observe how the patient interface is located and functioning.

In certain forms of the present technology, the plenum chamber 3200 is constructed from a translucent material. The use of a translucent material can reduce the obtrusiveness of the patient interface 3000, and help improve compliance with therapy.

In some forms of the present technology, the patient interface 3000 does not include a frame formed from a rigid or substantially rigid material (e.g. polycarbonate or the like). In some examples, the patient interface 3000 does not include a rigid frame located anterior to the patient's face in use.

In the exemplary forms of the technology shown in FIGS. 7A-7G, 8A-8H, 19A-19F, 25A-25I, 26A-26I, 30A-30E, 31A-31D and 32A-32D, the cushion module 3150 comprises a chassis portion 3210 and a seal-forming structure 3100. The chassis portion 3210 may be flexible and may be formed from a flexible material. The seal-forming structure 3100 may be formed from the flexible material. In these examples, the chassis portion 3210 and seal-forming structure 3100 are integrally formed and may be formed from the flexible material. The chassis portion 3210 may be formed from an elastomeric material, such as silicone. The seal-forming structure 3100 may be formed from the elastomeric material. The chassis portion 3210 and seal-forming structure 3100 may comprise one piece. In these examples, the chassis portion 3210 and seal-forming structure 3100 are moulded together as a single part formed from an elastomeric material, e.g. silicone. The seal-forming structure 3100 and the chassis portion 3210 (or at least a majority of the chassis portion 3210) may be formed (e.g. constructed, moulded or the like) together from a single homogenous piece of a flexible material, such as an elastomeric material, e.g. silicone. The chassis portion 3210 and the seal-forming structure 3100 may be of unitary construction. In some examples the chassis portion 3210 and seal-forming structure 3100 are moulded together in a single moulding step (e.g. a single shot). In other examples, the chassis portion 3210 and an anterior side portion of the seal-forming structure 3100 may be moulded together as a single first part, after which a posterior side portion of the seal-forming structure 3100 is joined, for example overmoulded or glued, to the single first part.

The wall thickness of the chassis portion 3210 may be in the range of 0.7 mm to 5 mm. In some examples the wall thickness of the majority of the chassis portion may be in the range of 0.7 mm to 1.5 mm, such as 0.9 mm to 1.4 mm, 0.7 mm-1.2 mm, 1.2 mm-1.5 mm, 0.9 mm, or 1.25 mm, as examples. In the examples shown in FIGS. 9A-9H, 16A-16D, 19A-19F, 25A-25I, 26A-26I the majority of chassis portion 3210, including the laterally projecting connection portions 3212 (described below) may have a wall thickness of 1.25 mm. In another example, such as the example shown in FIGS. 31A-31D, the majority of the chassis portion 3210 has a wall thickness of 0.9 mm.

It is also described below that the chassis portion 3210 may comprise chassis superior reinforcing portions 3220, which may have a greater thickness (e.g. 1.7 mm as described below with reference to FIGS. 19A-19F) than most other portions of the chassis portion 3210. Additionally, the chassis portions 3210 may comprise chassis inferior reinforcing portions 3221, which may have a greater thickness (e.g. 3 mm as described below with reference to FIGS. 30A-30E and 31A-31D) than other portions of the chassis portion 3210. Additionally, as described in more detail below, the chassis portion 3210 may comprise an anterior hole 3215 and a lip 3230, the lip having a greater thickness (e.g. 4 mm as described below) than most other portions of the chassis portion 3210.

In a further example of a method of manufacturing a cushion module 3150, the posterior side portion of the seal-forming structure 3100 may be produced and then the chassis portion 3210 and anterior side portion of the seal-forming structure 3100 may be overmoulded to the posterior side portion of the seal-forming structure. The posterior side of the seal-forming structure 3100 may comprise a textile material and, in some forms, may comprise a laminate formed from one or more textile and one or more non-textile layers. A cushion module 3150 produced by one such method is shown in FIGS. 16A-16D.

In other examples of the technology the seal-forming structure 3100 may be removably connected to the chassis portion 3210. The seal-forming structure 3100 may be connected to the chassis portion 3210 by a soft-to-soft, soft-to-hard or a hard-to-hard connection.

The chassis portion 3210, as shown in FIGS. 7A-7G and in isolation in FIGS. 8A-8H, comprises a pair of laterally projecting connection portions 3212. Each laterally projecting connection portion 3212 comprises an inlet configured to receive a flow of air into an interior of the cushion module 3150.

In this example, the cushion module 3150 comprises a pair of connectors 3214 configured to connect with gas delivery tubes 3350 of a positioning and stabilising structure 3300. The connectors 3214 are provided to either lateral side of the chassis portion 3210 in this example. Each connector 3214 in this example is provided to a respective laterally projecting connection portion 3212 of the chassis portion 3210. The connectors 3214, in this example, are provided at the inlets of the laterally projecting connection portions 3212. FIGS. 7A-7G show the gas delivery tubes 3350 connected to the laterally projecting connection portions 3212. The laterally projecting connection portions 3212 are described in more detail below.

The flexible nature of the chassis portion 3210 allows the cushion module 3150 to deform to fit to a wide range of patients. The flexible chassis portion 3210 may enable the cushion module 3150 to fit a wider range of patients than a cushion module 3150 with a rigid chassis portion. For example, the cushion module 3150 may be able to splay out to an extent to fit to a patient with a relatively wide nose, yet allow the sides to be wrapped inward to an extent to fit to a patient with a relatively narrower nose. While the chassis portion 3210 of the cushion module 3150 is flexible to provide these advantageous effects, a certain level of rigidity in the chassis portion 3210 is advantageous for providing stability and support to the seal-forming structure 3100. Accordingly, in some examples a rigidiser is provided to the chassis portion 3210 to make it more rigid (while still being flexible). In some examples, the chassis portion 3210 and the seal-forming structure 3100 are formed from a flexible material (e.g. silicone, TPE or the like) and the chassis portion 3210 comprises a rigidiser. In particular, the patient interface 3000 or cushion module 3150 may comprise a rigidiser. The rigidiser may be provided to the chassis portion 3210. The rigidiser may be configured to rigidise the chassis portion 3210. The rigidisider may be configured to resist deformation of the chassis portion 3210. The rigidiser may be configured to provide support to the chassis portion 3210.

In some examples the rigidiser is a member having a stiffness greater than a stiffness of the chassis portion 3210 of the plenum chamber 3200. The rigidiser may be formed from a different material to the chassis portion 3210. The ridigiser may be formed from a harder and/or stiffer material than a material forming the chassis portion 3210. The rigidiser may be substantially rigid. The rigidiser may be sufficiently rigid that it is not deformable by finger pressure alone. The rigidier may be formed from polycarbonate, polypropylene or nylon for example. The rigidiser may be adhered to the chassis portion 3210 in some examples. In certain examples the rigidiser may be overmoulded to the chassis portion 3210 or the chassis portion 3210 may be overmoulded to the rigidiser. The rigidiser may be removable from the chassis portion 3210. The rigidiser may be provided to one or more sides of the chassis portion 3210. In some examples the rigidiser is provided to an inferior side of the chassis portion 3210. In other examples the rigidiser is provided to an anterior side of the chassis portion 3210. In certain examples the rigidiser is provided externally to the plenum chamber 3200. In other examples the rigidiser is provided internally to the plenum chamber 3200. In some examples the rigidiser partially defines the plenum chamber 3200.

As shown in FIGS. 7A-7G, 30A-30E, 31A-31D and 32A-32D, for example, the cushion module 3150 comprises a vent 3400. In these examples, the chassis portion 3210 comprises a rigidiser in the form of a vent module 3410, i.e.

the vent module acts to add rigidity to the cushion module 3150. The vent module 3410 comprises the vent 3400. The vent 3400 may be provided by multiple vent holes. The rigidising vent module 3410 is provided to the anterior side of the chassis portion 3210. In other examples it may be provided to the inferior side of the chassis portion 3210. In some examples the cushion module 3150 may comprise two vent modules 3410 spaced apart laterally on an anterior side of the chassis portion 3210 or on an inferior side of the chassis portion 3210.

As will be described, the chassis portion 3210 and the seal-forming structure 3100, or more generally the cushion module 3150, may comprise a plurality of regions, one or more regions having a greater stiffness than another region. In general, a greater stiffness of a portion of the cushion module 3150 with respect to another portion of the cushion module 3150 may be provided by one or more of a greater material thickness, a stiffer material (e.g. greater Young's modulus), the presence of a rigidiser, and a shape that provides a greater stiffness. Unless the context requires otherwise, where a first portion of the cushion module 3150 is described as having a greater stiffness than a second portion, each of the above ways in which a portion may be stiffened is to be understood to be disclosed as an option for how the first portion may be stiffer than the second portion. In addition, forms of the technology may combine any one or more of the above ways to render the first portion thicker than the second portion.

Unless the context clearly requires otherwise, references to stiffness of a component or portion/region thereof are to be understood to be references to the stiffness of a structure including the effects on stiffness of both the material from which the component or portion thereof is formed, and the shape (including thickness) of the component or portion thereof. However, unless the context clearly requires otherwise, references to the stiffness of a material, a material having a stiffness, or the like, are to be understood to be references to stiffness as a material property independent of a shape/size (e.g. Young's modulus or the like).

5.3.1.1 Anterior Hole

As shown in FIGS. 8A-8H, 19A-19F, 25A-25I and 26A-26I, in these examples the chassis portion 3210 comprises an anterior hole 3215 configured to receive a rigidiser (rigidiser not shown in FIGS. 8A-8H). As shown in FIGS. 7A-7G, 30A-30E, 31A-31D and 32A-32D the vent module 3410 functioning as a rigidiser is received in the anterior hole 3215 of the chassis portion 3210.

With reference to FIGS. 8A-8H and 11A, the anterior hole 3215 is located centrally in the chassis portion 3210. In use, the anterior hole 3215 is centred in the patient's sagittal plane. In this example, the anterior hole 3215 is located at a partially anterior and partially inferior location in the chassis portion 3210 in use. In use, the anterior hole 3215 may be aligned in the superior-posterior axis with the patient's lip superior. The anterior hole 3215 may be located anterior to the patient's lip superior. The anterior hole 3215 may be located superior to the patient's lower vermillion and/or upper vermillion. In this example, the anterior hole 3215 is located on an opposite side of the chassis portion 3210 to the seal-forming structure. In this example, a superior periphery of the anterior hole 3215 is located adjacent a central portion of an anterior side portion of the seal-forming structure 3100. With reference to FIGS. 9A-9H, 19A-19F, 25A-25I and 26A-26I, the superior periphery of the anterior hole 3215 may be adjacent a central anterior portion 3115 of the seal-forming structure 3100. The inferior periphery of the anterior hole 3215 may be adjacent a lip-superior portion 3116 of the seal-forming structure 3100. The central anterior portion 3115 and the lip-superior portion 3116 are described in more detail below.

In some examples, such as the example illustrated in FIGS. 8A-8H, the anterior hole 3215 opens in a partially anterior and partially inferior direction in use (although in use the anterior hole 3215 contains a vent module 3410). A superior periphery of the anterior hole 3215 may be spaced anteriorly from an inferior periphery of the anterior hole 3215. In use, the anterior hole 3215 may open anteriorly and inferiorly at an angle between 25 degrees and 65 degrees with respect to a horizontal plane, such as the Frankfort horizontal plane. In some examples, the angle may be between 35 degrees and 55 degrees, or between 40 degrees and 50 degrees. In some particular examples the anterior hole 3215 may open inferiorly and anteriorly at an angle of 45 degrees with respect to a horizontal plane.

In some examples, such as the example illustrated in FIGS. 8A-8H, the anterior hole 3215 is wider in the left-right axis than it is tall. In this example, the superior periphery of the anterior hole 3215 comprises a straight portion, the inferior periphery of the anterior hole 3215 comprises a straight portion and the left and right sides of the anterior hole 3215 are curved. In other examples, either or both of the superior and inferior edges of the anterior hole 3215 may be curved. The anterior hole 3215 may be elliptical. In other examples the anterior hole 3215 may be oval, circular, rectangular or square. The anterior hole 3215 may be a generally rectangular or square hole with rounded corners in some examples. In the example shown in FIGS. 8A-8H, the periphery of the anterior hole 3215 is defined by a plane curve (e.g. a curve lying in a single plane and not a space curve).

In some examples, such as the example shown in FIGS. 8A-8H and 11A, the cushion module 3150 comprises a lip 3230. The lip 3230 is part of the chassis portion 3210 in this example. The vent module 3410 is configured to couple with lip 3230. With reference to FIGS. 14A-14D and 15A-15B, the vent module 3410 comprises a peripheral channel 3430. The peripheral channel 3430 is provided around the periphery of the vent module 3410 in this example. In this particular example the peripheral channel is provided around the entire periphery of the vent module. The lip 3230 is configured to be received within the peripheral channel 3430 to secure the vent module 3410 to the plenum chamber 3200. In this example, the lip 3230 defines the anterior hole 3215. The size of the vent module 3410 and depth of the peripheral channel 3430 corresponds to the size of the anterior hole 3215 to enable a secure fit for the vent module 3410 within the anterior hole 3215.

In some examples, such as the example shown in FIGS. 8A-8H, 14A-14D and 15A-15B, the vent module 3410 is inserted into the anterior hole with a snap fit connection. When the vent module 3410 is pressed into the anterior hole 3215, the lip 3230 deforms until it fits into the peripheral channel 3430 of the vent module 3410. The chassis portion 3210 may also deform when vent module 3410 is pressed into the anterior hole 3215. In this example, the anterior hole 3215 is sized such that when the vent module 3410 is received in the chassis portion 3210, the chassis portion 3210 is substantially undeformed. The anterior hole 3215 may have the same size as prior to insertion of the vent module 3410. In other examples the anterior hole 3215 may be slightly stretched after insertion of the vent module 3410 and the vent module 3410 may be slightly larger than the anterior hole 3215. This may facilitate a secure fit.

To remove the vent module 3410 the patient or clinician may push or pull the vent module 3410 out of the anterior hole 3215. The chassis portion 3210 may deform to allow the vent module 3410 to be removed from the anterior hole 3215. The chassis portion 3210 may be configured to allow the user to peel the lip 3230 away from the vent module 3410 to allow the vent module 3410 to be removed. The chassis portion 3210 may be able to be squeezed to aid in the removal of the vent module 3410. In some examples, the patient may be able to squeeze the chassis portion 3210 to at least partially release the lip 3230 from the peripheral channel 3430 of the vent module 3410.

In this example, the cross-sectional profile of the lip 3230 substantially matches the space available within the cross-sectional profile of the peripheral channel 3430 to facilitate a secure fit. The shape of the lip 3230 is complimentary to the shape of the peripheral channel 3430.

In this example of the present technology, the lip 3230 is thicker than adjacent portions of the chassis portion 3210 of the plenum chamber 3200, for example the lip 3230 may be the thickest portion of the chassis portion 3210. The lip 3230 may also be the thickest portion of the cushion module 3150. The lip 3230 may comprise a thickness in the range of 3-5 mm. In some examples of the present technology the thickness of the lip 3230 is within 3.5-4.5 mm. In the illustrated example, the thickness of the lip 3230 is substantially 4 mm.

The lip 3230 may be thick to create a robust connection to the vent module 3410. Additionally, the lip 3230 may be thick to provide rigidity to the chassis portion 3210. A thick lip 3230 may advantageously increase the resistance of the cushion module 3150 to torsion. The cushion module 3150 may receive torsional forces particularly during side sleeping or when the patient moves while sleeping, for example if they turn over. The added stiffness provided by the thickness of the lip 3230 provides resistance to excessive deformation as a result of torsional forces or other forces which could disturb the seal between the seal-forming structure 3100 and the patient's face. Accordingly, in this example the cushion module 3150 comprises a reinforced portion on its anterior side. The reinforced portion resists twisting.

In the illustrated example of the present technology, the lip 3230 is a thick portion of cushion module 3150. The lip 3230 and the remainder of the chassis portion 3210 of the cushion module 3150 are integrally formed in this example. They are formed from a homogenous piece of material. The chassis portion 3210 and the lip 3230 thereof may be moulded together. The lip 3230 may be formed from an elastomeric material, such as silicone, TPE or the like, along with other portions of the chassis portion 3210 in the same moulding process.

In other examples, the lip 3230 may be formed separately from one or more other portions of the chassis portion 3210. In some examples, the lip 3230 is formed from a different material from the remainder of the chassis portions 3210, i.e. the lip 3230 is formed from a first material and the remainder of the chassis portion 3210 may be formed from a second material. In some examples the lip 3230 is overmoulded to the remainder of the chassis portion 3210. In other examples the chassis portion 3210 is overmoulded to the lip 3230.

In some examples, portions of the chassis portion 3210 excluding the lip 3230 are formed from a first silicone material and the lip 3230 is formed from a second silicone material. The second silicone material may have one or more different properties to the first silicone material. The second silicone material may have a greater stiffness than the first silicone material. The second silicone material may have a greater Durometer hardness than the first silicone material.

In some examples the chassis portion 3210 excluding the lip 3230 is formed from an elastomeric material such as silicone, TPE or the like, and the lip 3230 is formed from a more rigid material such as polycarbonate, polypropylene, nylon or the like.

In some examples, the chassis portion 3210 comprises a female feature such as a groove, peripheral channel or the like about the anterior hole 3215, which is configured to receive a complimentary male feature of the vent module 3410, such as a lip, flange or the like. In some examples the vent module 3410 comprises a flange about its periphery, configured to be received within a complementary channel about the periphery of the anterior hole 3215 of the cushion module 3150.

In other forms of the present technology, the chassis portion 3210 of the cushion module 3150 may comprise a rigidising portion (in addition to the rigidising vent module 3410) in the form of a thickened portion spaced from the anterior hole 3215. In one example the chassis portion 3210 may comprise a rigidising portion that spans across an anterior side portion of the cushion module 3150. In other examples, the chassis portion 3210 may comprise a rigidising member. The rigidising member may be formed from a material having a greater stiffness than the material forming the chassis portion 3210 (e.g. silicone). The chassis portion 3210 may be overmoulded to the rigidising member (or vice versa). Alternatively, the rigidising member may be inserted into the chassis portion 3210, snap-fitted to the chassis portion 3210 or otherwise secured to an anterior side portion of the chassis portion 3210.

Sufficient resistance to excessive deformation, especially resulting from torsion, is advantageous. However, some independence between the sides of the cushion module 3150 is advantageous for providing a decoupling effect in which the cushion module 3150 can tolerate forces received at one lateral side without transmitting the forces to the other lateral side. As described above, the chassis portion 3210 may be formed from a flexible material to partially decouple one lateral side of the cushion module 3150 from the other lateral side. For example, the chassis portion 3210 may at least partially decouple movement of one of the laterally projecting connection portions 3212 from the other of the laterally projecting connection portions 3212.

5.3.1.2 Vent Module Locating Features

The cushion module 3150 may comprise one or more features configured to enable easy locating of the vent module 3410 and prevent misalignment thereof. In particular, the cushion module 3150 may comprise one or more locating features 3216 structured and/or arranged to make correct orientation of the vent module 3410 apparent to the user. The chassis portion 3210 may comprise the locating features 3216. The chassis portion 3210 may comprise one or more locating features 3216 which engage or fit with corresponding features of the vent module 3410.

In some examples, such as the example illustrated in FIGS. 8A-8H, the chassis portion 3210 comprises two locating features 3216. One locating feature 3216 is provided to a lateral side of the anterior hole 3215 and another locating feature 3216 is provided to an inferior side of the anterior hole 3215. The locating features 3216 in this example are protrusions which are shaped to fit within correspondingly shaped recesses of the vent module 3410.

In other examples, the cushion module 3150 may comprise a locating feature 3216 at a superior side of the anterior hole 3215. In other examples, the cushion module 3150 may comprise only one locating feature 3216, or may comprise three or more locating features 3216.

The one or more locating features 3216 may prevent the vent module 3410 from being inserted into the anterior hole 3215 incorrectly. The one or more locating features 3216 may prevent the vent module 3410 from being inserted at an incorrect orientation (e.g. upside down or back-to-front). For example, the locating features 3216 may be positioned asymmetrically with respect to the anterior hole 3215.

The shape of the anterior hole 3215 and vent module 3410 in the example illustrated in FIGS. 8A-8H is at least partially asymmetrical to reduce the ability of the user to misalign the vent module 3410. Since the shape of the anterior hole 3215 and vent module 3410 has a greater height than width, the vent module 3410 can only be inserted horizontally into the anterior hole 3215. In some example, the anterior hole 3215 may be asymmetrical in at least one axis and in some examples, the anterior hole 3215 is asymmetrical in multiple axes. In some examples, the anterior hole 3215 is asymmetrical such that the vent module 3410 can fit into the anterior hole 3215 in only one orientation.

In some examples, cushion module 3150 and/or the vent module 3410 comprise guides to indicate the correct orientation of the vent module 3410, such as matching markings, indents or other visual or tactile features to indicate the correct orientation of the vent module 3410.

5.3.1.3 Chassis Superior Reinforcing Portions

In some examples of the present technology, the chassis portion 3210 of the cushion module 3150 comprises a pair of chassis superior reinforcing portions 3220. The cushion modules 3150 shown in FIGS. 19A-19F, 22B, 30A-30E, 31A-31D and 32A-32D comprise chassis superior reinforcing portions 3220. The chassis superior reinforcing portions 3220 are provided to an anterior side of the chassis portion 3210. The chassis superior reinforcing portions 3220 are configured to reinforce the chassis portion 3210. The chassis superior reinforcing portions 3220 and features thereof described with reference to FIGS. 19A-19F, 22B, 30A-30E, 31A-31D and 32A-32D may be applied to the chassis portions 3210 shown in and described with reference to FIGS. 8A-8H, 16A-16D, 25A-25I and 26A-26I, or to chassis portions 3210 of other examples of the present technology.

Each chassis superior reinforcing portion 3220 is provided to a respective lateral and anterior side of the chassis portion 3210. Each chassis superior reinforcing portion 3220 may be spaced medially from a distal end of a respective laterally projecting connection portion 3212. For example, the chassis superior reinforcing portions 3220 may each be spaced medially of a respective one of the laterally projecting connection portions 3212. Each chassis superior reinforcing portion 3220 may have a lateral boundary spaced apart from a distal end of a respective one of the laterally projecting connection portions 3212.

As described above, the chassis portion 3210 may formed from a flexible material, which may be an elastomeric material. The chassis superior reinforcing portions 3220 may be formed from the flexible material forming the chassis portion 3210. The seal-forming structure 3100 may also be formed from the flexible material. The chassis superior reinforcing portions 3220 may be integrally formed with the chassis portion 3210. For example, the chassis superior reinforcing portions 3220 may be moulded together with adjacent portions of the chassis portion 3210 in a single moulding step. The chassis superior reinforcing portions 3220 may partially define the plenum chamber 3200 together with other portions of the chassis portion 3210.

In the illustrated example, the chassis superior reinforcing portions 3220 are each provided at a superior location on the chassis portion 3210, e.g. generally superior to anterior hole 3215. Each chassis superior reinforcing portion 3220 may be stiffer than one or more adjacent portions of the chassis portion 3210. The greater stiffness may result from the chassis superior reinforcing portions 3220 having a wall thickness greater than a wall thickness of one or more adjacent portions of the chassis portion 3210. In some examples the chassis superior reinforcing portions 3220 have a wall thickness between 1 mm and 3 mm. In some examples the wall thickness is between 1.2 mm and 2.5 mm or between 1.5 mm and 2.3 mm. In the examples shown in FIGS. 19A-19F, 22B, and 31A-31D, the chassis superior reinforcing portions 3220 have a wall thickness of 1.7 mm. In the example shown in FIG. 30A-30E, the chassis superior reinforcing portions 3220 have a wall thickness of 2.1 mm.

The chassis superior reinforcing portions 3220 may help increase the stability of the cushion module 3150 and the seal it makes to the patient's face during dynamic movements, for example when the patient moves while sleeping or in bed. The chassis superior reinforcing portions 3220 may also provide greater resistance to excessive flaring out of the seal-forming structure 3100 when the seal-forming structure 3100 is brought into contact with a patient's face having slightly different contours from the seal-forming surface of the seal-forming structure 3100. This flaring may result in leak paths forming where the seal-forming structure 3100 loses contact with the patient's face, due to the otherwise flexible nature of the chassis portion 3210, in examples of the present technology in which the chassis portion 3210 is flexible. The chassis superior reinforcing portions 3220 may also provide added torsion resistance. The chassis superior reinforcing portions 3220 may prevent one side of the cushion module 3150 from twisting away from or with respect to the other side of the cushion module 3150, which could result in loss of contact with the patient's nose and leak paths.

As shown in FIGS. 19A-19F, 30A-30E, 31A-31D and 32A-32D the chassis superior reinforcing portions 3220 are each provided on a lateral side of the anterior hole 3215 at a superior location. Each chassis superior reinforcing portion 3220 is located adjacent a respective superior corner of the anterior hole 3215. A portion of each chassis superior reinforcing portion 3220 may be located on an anterior surface of a respective laterally projecting connection portion 3212.

Each chassis superior reinforcing portion 3220 may be located on the chassis portion 3210 adjacent and anterior to the seal-forming structure 3100. The chassis superior reinforcing portions 3220 may share a boundary with the seal-forming structure 3100. Each chassis superior reinforcing portion 3220 may comprise a superior boundary that meets a portion of an inferior boundary of an anterior portion of the seal-forming structure 3100. As illustrated in FIGS. 19E, 19F, 30A and 31A, each chassis superior reinforcing portion 3220 may have a curved superior surface matching a curvature of an inferior boundary of the seal-forming structure 3100. Each chassis superior reinforcing portion 3220 may have a curved inferior surface matching a curvature of the anterior hole 3215. As shown in FIGS. 19E and 19F, the laterally outward side of each chassis superior reinforcing portion 3220 may comprise a pointed shape towards an outward lateral direction in one example.

In some examples, each chassis superior reinforcing portion 3220 may extend laterally outward to a lateral portion of each connection portion 3212 of the chassis portion 3210, show by of example in FIGS. 30A-30E. In this example each chassis superior reinforcing portion 3220 extends from the anterior hole 3215 in the chassis portion 3210 to a superior ridge 3213 along the respective laterally projecting connection portion 3212. The superior ridges 3213 are described in more detail below. Each chassis superior reinforcing portion 3220 may be provided to a partially anterior-facing portion of the chassis portion 3210 in use. In the example shown in FIGS. 30A-30E each chassis superior reinforcing portion 3220 is provided to the chassis portion 3210 along a boundary between the chassis portion 3210 and the seal-forming structure 3100. Each chassis superior reinforcing portion 3220 may be wider proximate a medial portion of the chassis portion 3210, such as at the anterior hole 3215 or vent module 3410, than at a lateral portion of the chassis portion 3210.

As discussed below in more detail, the seal-forming structure 3100 may comprise mid-lateral anterior portions 3125 each located on a respective lateral side of a central anterior portion 3115, shown in FIGS. 19A-19F, 22B, 30A-30E and 31A-31D. The chassis superior reinforcing portions 3220 may each be located adjacent a respective one of the mid-lateral anterior portions 3125 of the seal-forming structure 3100. In particular, each chassis superior reinforcing portion 3220 may be located inferior to a respective mid-lateral anterior portion 3125. The chassis superior reinforcing portions 3220 may each be located adjacent and/or inferior to a respective inferior portion 3127 of each mid-lateral anterior portion 3125.

In some examples of the present technology, each chassis superior reinforcing portion 3220 has a wall thickness that is the same as the wall thickness of the inferior portion 3127 of the mid-lateral anterior portion 3125 of the seal-forming structure 3100.

In other examples of the present technology, the chassis superior reinforcing portions 3220 may be formed by rigidisers formed by a material stiffer than the material forming the rest of the chassis portion 3210.

5.3.1.4 Chassis Inferior Reinforcing Portions

In some examples of the present technology, the cushion module 3150 may comprise chassis inferior reinforcing portions 3221. A cushion module 3150 may comprise chassis inferior reinforcing portions 3221 in addition, or as an alternative, to chassis superior reinforcing portions 3220. In other examples of the present technology the cushion module 3150 may comprise neither chassis superior reinforcing portions 3220 nor chassis inferior reinforcing portions 3221.

As shown in particular in FIGS. 30E and 31D, the chassis portion 3210 of each cushion module 3150 in the examples shown in FIGS. 30A-30E and 31A-31D comprises a pair of chassis inferior reinforcing portions 3221. The chassis inferior reinforcing portions 3221 may each be provided to an inferior portion of the chassis portion 3210. In these examples the chassis inferior reinforcing portions 3221 are each located adjacent a respective one of the mid-lateral inferior portions 3122 of the seal-forming structure 3100 (described below). The chassis inferior reinforcing portions 3221 are provided on respective lateral sides of a central region on the inferior side of the chassis portion 3210.

Each chassis inferior reinforcing portion 3221 may be spaced medially from a distal end of a respective laterally projecting connection portion 3212. For example, the chassis inferior reinforcing portions 3221 may each be spaced medially of a respective one of the laterally projecting connection portions 3212. Each chassis inferior reinforcing portion 3221 may have a lateral boundary spaced apart from a distal end of a respective one of the laterally projecting connection portions 3212.

As described above, the chassis portion 3210 may formed from a flexible material, which may be an elastomeric material. The chassis inferior reinforcing portions 3221 may be formed from the flexible material forming the chassis portion 3210. The chassis inferior reinforcing portions 3221 may be integrally formed with the chassis portion 3210. For example, the chassis inferior reinforcing portions 3221 may be moulded together with adjacent portions of the chassis portion 3210 in a single moulding step. The chassis inferior reinforcing portions 3221 may partially define the plenum chamber 3200 together with other portions of the chassis portion 3210.

The chassis inferior reinforcing portions 3221 may be elongate. As shown in FIGS. 30E and 31D the chassis inferior reinforcing portions 3221 each extend laterally along the chassis portion 3210 from a medial position proximate the lip superior portion 3116 of the seal-forming structure 3100 (described in more detail below) to a lateral position proximate a lateral posterior region 3141 of the seal-forming structure 3100. As illustrated, the chassis inferior reinforcing portions 3221 have spaced apart medial boundaries. The chassis inferior reinforcing portions 3221 may be shaped to follow a boundary between the chassis portion 3210 and the seal-forming structure.

The chassis inferior reinforcing portions 3221 may each have a greater stiffness than an adjacent portion of the chassis portion 3210. In the example shown in FIGS. 30A-30E, the chassis inferior reinforcing portions 3221 each have a thickness greater than a thickness of an adjacent portion of the chassis portion 3210. The greater thickness provides the greater stiffness in this example. The chassis inferior reinforcing portions 3221 may provide similar advantages to the chassis superior reinforcing portions 3220. The chassis inferior reinforcing portions 3221 may provide stiffness to the chassis portion 3210, facilitating translation of headgear forces into sealing force.

Each chassis inferior reinforcing portion 3221 comprises a thickness of 3 mm in the example shown in FIGS. 30A-30E and, in other examples, may comprise a thickness between 1.5 mm and 4.5 mm. The thickness of the chassis inferior reinforcing portion 3221 in the example shown in FIGS. 31A-31D is also 3 mm. The thickness of the chassis portion 3210 may vary gradually between the chassis inferior reinforcing portions 3221 and adjacent portions. That is, the chassis portion 3210 of the cushion module 3150 may comprise a tapered change in thickness between each chassis inferior reinforcing portion 3221 and one or more adjacent portions. In other examples the chassis portion 3210 may comprise a stepped change in thickness at the boundaries of the chassis inferior reinforcing portions 3221.

5.3.1.5 Laterally Projecting Connection Portions

As discussed above, the chassis portion 3210 may comprise a pair of laterally projecting connection portions 3212. Each of the laterally projecting connection portions 3212 may be configured to connect to and receive a flow of gas from a respective gas delivery tube 3350. Each laterally projecting connection portion 3212 may comprise an inlet to an interior of the chassis portion 3210.

In some examples of the present technology, each laterally projecting connection portion 3212 may define a plenum chamber inlet port.

The angles at which the laterally projecting connection portions 3212 project advantageously orient the seal-forming structure 3100 at an angle which allows the seal-forming structure 3100 to form a stable seal with the patient's face without occluding the patient's nose.

FIGS. 23 and 24A-24C show the angles of the laterally projecting connection portions 3212 in certain forms of the technology. The angles and other features of the laterally projecting connection portions 3212 described with reference to FIGS. 23 and 24A-24C may also be applied to laterally projecting connection portions 3212 of cushion modules 3150 of other examples of the present technology, such as those shown in FIGS. 16A-16D, 19A-19F, 25A-25I, 26A-26I, 30A-30E, 31A-31D and 32A-32D.

FIG. 24A is a cross section view of the cushion module 3150 through the centre of the cushion module 3150 as indicated in FIG. 23. A line L is illustrated in FIG. 24A. Line L is a straight line that is a tangent to two points on the surface of the seal-forming structure 3100 and does not pass through the seal-forming structure 3100. That is, if a line is moved towards the centre of the patient-contacting side of the seal-forming structure 3100 until it contacted a point on the patient contacting side of the seal-forming structure 3100 and then rotated about that point until it contacted a second point on the patient contacting side, the result would be line L. In examples of the technology in which a line cannot be drawn in this manner, or there are multiple possible orientations for such a line, then line L may be a central line drawn over the patient contacting side of the seal-forming structure 3100 generally from the portion of the seal-forming structure 3100 that contacts the patient's lip superior to the portion of the seal-forming structure 3100 that contacts the patient's pronasale.

FIG. 24B shows a line L1, which is a horizontal line perpendicular to line L. Also shown in FIG. 24B is an angle A between the line L1 and a line LA. The line LA indicates the direction in which the connection portion 3212 projects in the plane of the drawing. The angle A is therefore an angle in the plane of the drawing and not a representation of an angle in three-dimensional space. The angle A could be considered a "height" angle. The angle A may be considered an angle of the connection portion 3212 or connector 3214 towards a superior direction.

In some examples of the present technology, the angle A may be between 10 degrees and 30 degrees, such as between 15 degrees and 25 degrees or between 18 degrees and 23 degrees. In one example, the angle A is 21 degrees. In another example, the angle A is 21.5 degrees.

In other examples of the present technology, the angle A may be between 15 degrees and 35 degrees, such as between 20 degrees and 30 degrees or between 23 degrees and 29 degrees. In one example, the angle A is 25 degrees. In another example, the angle A is 27 degrees.

FIG. 24C shows a line L2, which is another horizontal line perpendicular to line L. Also shown in FIG. 24C is an angle B between the line L2 and a line LB. The line LB indicates the direction in which the connection portion projects in the plane of the drawing. The angle B is therefore an angle in the plane of the drawing and not a representation of an angle in three-dimensional space. The angle B could be considered a "depth" angle. The angle B may be considered an angle of the connection portion 3212 or connector 3214 towards a posterior direction.

In some examples of the present technology, the angle B may be between 25 degrees and 45 degrees, such as between 30 degrees and 40 degrees or between 32 degrees and 37 degrees. In one example, the angle B is 34.5 degrees. In another example the angle B is 33 degrees.

In some examples of the present technology, the angle B may be between 20 degrees and 40 degrees, such as between 25 degrees and 35 degrees or between 26 degrees and 30 degrees. In one example, the angle B is 28 degrees.

These particular angles may result in the connection portions 3212, when connected to gas delivery tubes 3350 of a positioning and stabilising structure 3300, holding the seal-forming structure 3100 in a sufficiently splayed out state that it does not squeeze the patient's nose to an excessive extent that results in occlusion of the patient's nasal airways. In examples of the present technology in which the chassis portion 3210 is flexible, the seal-forming structure 3100 may be more likely to fold medially than if the chassis portion 3210 was rigid. Accordingly, connection portion 3212 angles which hold the seal-forming structure 3100 sufficiently open are advantageous for avoiding excessive medial force on the sides of the patient's nose.

The line L shown in FIG. 24A may in use of the patient interface 3000 be oriented with respect to the Frankfort horizontal plane of the patient's head such that a presentation angle of the seal-forming structure 3100 is formed between the line L and the Frankfort horizontal plane. More particularly the presentation angle may be an angle between the line L in use and a line lying in both the Frankfort horizontal plane and also in the sagittal plane of the patient's head. The presentation angle may be formed between the line L in use of the patient interface 3000 and a line at the intersection of the Frankfort horizontal plane and the sagittal plane.

In some particular examples of the present technology, the presentation angle may be between 20 degrees and 40 degrees, such as between 24 and 36 degrees, within the range of 25-32 degrees or within the range of 32-38 degrees. In some examples the seal-forming structure 3100 of a patient interface 3000 may have a presentation angle as defined above within the range of 22-30 degrees. In other examples the seal-forming structure 3100 may have a presentation angle as defined above within the range of 31-39 degrees. The cushion module 3150 shown in FIGS. 24A-24C may have a presentation angle as defined above within the range of 24-29 degrees in use. The cushion module 3150 shown in FIGS. 30A-30E may have a presentation angle as defined above within the range of 33-38 degrees. The cushion module 3150 shown in FIGS. 31A-31D may have a presentation angle within the range of 31-35 degrees.

The presentation angle of the cushion module 3150 shown in FIGS. 30A-30E may be 9 degrees greater than the presentation angle of the cushion module 3150 shown in FIGS. 24A-24C. The presentation angle of the cushion module 3150 shown in FIGS. 31A-31D may be 6.5 degrees greater than the presentation angle of the cushion module 3150 shown FIGS. 24A-24C.

5.3.1.6 Connectors

FIGS. 17A-17E show illustrations of a connector 3214 according to one example of the present technology, FIGS. 27A-27C show illustrations of a connector 3214 according to another example of the present technology and FIGS.

33A-33B show illustrations of a connector 3214 according to yet another example of the present technology. Each of the connectors 3214 described with reference to FIGS. 17A-17E, 27A-27C and 33A-33B may be provided to any of the cushion modules 3150 described herein, such as any of the cushion modules 3150 described with reference to FIGS. 8A-8H, 9A-9H, 16A-16D, 19A-19F, 20, 23, 24A-24C, 25A-25I, 26A-26I, 30A-30E, 31A-31D and 32A-32D, among others. As described above, connectors 3214 may be provided to respective laterally projecting connection portions 3212 of the chassis portion 3210. The connectors 3214, in this example, are provided at inlets of the laterally projecting connection portions 3212. The connectors 3214 may each be configured to connect to a corresponding connector on a respective one of the gas delivery tubes 3350. In particular, the connectors 3214 are each configured to connect a respective one of the laterally projecting connection portions 3212 of the chassis portion 3210 to a respective one of the gas delivery tubes 3350.

In the illustrated examples, the connectors 3214 are rigid. While the chassis portion 3210 may advantageously be formed from a flexible material, the connectors 3214 may be formed from a rigid material. Rigid connectors 3214 may enable a snap fit connection between the cushion module 3150 and the gas delivery tubes 3350. In some examples, the connectors 3214 are formed from polypropylene, nylon, polycarbonate or a similar material.

As illustrated in FIGS. 17A-17E and 27A-27C, each connector 3214 comprises a chassis connection portion 3181. The chassis connection portion 3181 may be the widest part of the connector 3214. The chassis connection portion 3181 of each connector 3214 may be connected to a respective laterally projecting connection portion 3212 of the chassis portion 3210.

Each connector 3214 may be joined to the chassis portion 3210 by an overmoulding process. The overmoulding process may involve forming the connectors 3214, and then moulding the chassis portion 3210 to the connectors 3214. An outwardly facing surface 3181*a* of the chassis connection portion 3181 of each connector 3214 may be bonded to the material forming the chassis portion 3210. The outwardly facing surface 3181*a* may be known as a bonding surface in some examples. The chassis connection portion 3181 of each connector 3214 is, in this example, at a downstream end of the connectors 3214. In other examples the chassis connection portion 3181 may be glued to the chassis portion 3210 or may be mechanically connected, such as by a press fit, snap fit or the like. FIG. 18A shows a cross section view showing a connector 3214 connected to a laterally projecting connection portion 3212.

In cross-section, such as is shown in FIGS. 17C, 17E and 27C, the outwardly facing surface 3181*a* of the chassis connection portion 3181 may be substantially straight. In three dimensions such as is shown in FIGS. 17A and 27A, the chassis connection portion 3181 may be curved around an outward periphery of the connector 3214. The shape of the outwardly facing surface 3181*a* of the chassis connection portion 3181 may correspond to an inwardly facing bonding surface of each laterally projecting connection portion 3212 of the chassis portion 3210.

As shown in FIGS. 17C, 17E and 27C, the chassis connection portion 3181 comprises an inwardly facing surface 3181*b* (labelled in FIG. 27C) opposite the outwardly facing surface 3181*a*. The inwardly facing surface 3181*b* may be shorter in length than the outwardly facing surface 3181*a*. The inwardly facing surface 3181*b*, in cross-section, may be substantially straight and parallel to the length of the connector 3214. The inwardly facing surface of the chassis connection portion 3181 may be parallel, in cross-section, to the outwardly facing surface 3181*a* of the chassis connection portion 3181. The inwardly facing surface of the chassis connection portion 3181 may extend around an internal periphery of the chassis connection portion 3181.

Between the outwardly facing surface 3181*a* and the inwardly facing surface 3181*b* of the chassis connection portion 3181 of each connector 3214 on a downstream side of the connector 3214 (e.g. the side of the connector 3214 interior to the chassis portion 3210) is a substantially flat downstream end surface. The downstream end surface connects the downstream sides of the outwardly facing surface 3181*a* and the inwardly facing surface 3181*b* of the chassis connection portion 3181.

The connectors 3214 each comprise a projecting connector portion 3182. The projecting connector portion 3182 extends away from the chassis portion 3210, in this form of the present technology. The projecting connector portions 3182 each extend in an upstream direction. The projecting connector portions 3182 each extend from the chassis connection portion 3181 from an inward side with respect to the chassis connection portion 3181. In particular, the projecting connector portion 3182 may project away from the chassis connection portion 3181 along a length of the connector 3214. As shown in FIGS. 17E and 27C, each projecting connector portion 3182 is located adjacent the inwardly facing surface 3181*b* of the chassis connection portion 3181 of a respective one of the connectors 3214.

Each projecting connector portion 3182 is configured to engage with a corresponding connector provided to a gas delivery tube 3350. The projecting connector portions 3182, in this example of the present technology, engage with corresponding female connectors provided to respective gas delivery tubes 3350 of the patient interface 3000. In the illustrated examples, with reference to FIGS. 17A, 17E and 27C in particular, the projecting connector portion 3182 of each connector 3214 comprises a pair of recesses 3185. The recesses 3185 are configured to receive and retain corresponding portions of the connectors on the gas delivery tubes 3350 to facilitate a snap fit connection. The connectors on the gas delivery tubes 3350 may be those described in International Application No. PCT/AU2019/050873, the entire contents of which are hereby incorporated herein by reference. The gas delivery tubes 3350 may be those described in International Application No. PCT/AU2019/050874, the entire contents of which are hereby incorporated herein by reference. In some examples of the present technology, each projecting connector portion 3182 may comprise only one recess. In other examples, each projecting connector portion 3182 may comprise more than two recesses 3185.

Between the chassis connection portion 3181 and the projecting connector portion 3182 of each connector 3214 is a bend in cross section, in the examples of the present technology illustrated in FIGS. 17A-17E and 27A-27C. As shown, in particular, in the cross-section views shown in FIGS. 17C, 17E and 27C, the connector 3214 bends in cross-section to transition between the chassis connection portion 3181 and the projecting connector portion 3182. The bend produces a change in width of the connector 3214. Specifically, the projecting connector portion 3182 is narrower than the chassis connection portion 3181.

On either side of the chassis connection portion 3181 and the projecting connector portion 3182, as an outside shoulder 3183 and an inside shoulder 3184. The outside shoulder 3183 and is provided to the outwardly facing side of the connector 3214. The inside shoulder 3184 is provided to the inwardly facing side of the connector 3214.

The outside shoulder 3183 comprises a substantially flat wall 3183*a* perpendicular to the length of the connector 3214, as shown in FIGS. 17E and 27C. The flat wall 3183*a* of the outside shoulder 3183 may be perpendicular to the outwardly facing surface 3181*a* of the chassis connection portion 3181 and/or the inwardly facing surface of the chassis connection portion 3181. The flat wall 3183*a* of the outside shoulder 3183 may be parallel to the downstream end wall of the chassis connection portion 3181 connecting the outwardly facing surface 3181*a* and the inwardly facing surface of the chassis connection portion 3181. As shown in FIGS. 17E and 27C, the projecting connector portion 3182 may comprise an outwardly facing wall that is substantially flat and which is substantially parallel to the outwardly facing surface 3181*a* of the chassis connection portion 3181. The flat wall 3183*a* of the outside shoulder 3183 may be substantially perpendicular to this outwardly facing wall of the projecting connector portion 3182. Between the flat wall 3183*a* of the outside shoulder 3183 and the outwardly facing wall 3183*a* of the projecting connector portion 3182, in cross section, is a curved portion of the outside shoulder 3183. In other examples the transition between the flat wall 3183*a* and the projecting connector portion 3182 may be a sharp corner.

The outside shoulder 3183 may be configured to form a seal in use with the end of a gas delivery tube 3350. Each gas delivery tube 3350 may comprise a substantially flat surface at the downstream end thereof configured to engage with the outside shoulder 3183 of a respective connector 3214 and form a seal therewith. The outside shoulder 3183 extends around the periphery of the connector 3214 and may be configured to engage a sealing surface around a periphery of a corresponding connector of a respective gas delivery tube 3350. The flat wall 3183*a* may be configured to mate with a flat surface of the respective gas delivery tube 3350. The recesses 3185 may be spaced with respect to the outside shoulder 3183 such that when a snap fit is formed between recesses 3185 and corresponding portions of the connectors on the gas delivery tubes 3350, a compliant portion of the gas delivery tube 3350 is held tightly against the outside shoulder 3183.

In some examples, a portion of the projecting connector portion 3182 proximate the outside shoulder 3183 may also form a seal in use with the end of the gas delivery tube 3350. The gas delivery tube 3350 in some examples comprises a radially inwardly projecting lip at the end thereof, which may form a seal with one or more of the projecting connector portion 3182, the chassis connection portion 3181 (e.g. the flat wall 3183*a*) and the outside shoulder 3183.

The gas delivery tubes 3350 may also seal against portions of the chassis portion 3210, such as the ends of the laterally projecting connection portions 3212. Advantageously, the chassis portion 3210 may be formed from a soft material (e.g. silicone, TPE or the like). The gas delivery tubes 3350 may also be formed from a soft material (e.g. silicone, TPE or the like), resulting in a soft-to-soft connection between the gas delivery tubes 3350 and the chassis portion 3210. In other examples, the connection may be a soft-to-hard connection (e.g. if the ends of the gas delivery tubes 3350 are formed by a hard component or the ends of the gas delivery tubes 3350 are soft but they engage with hard portions of the chassis portion 3210, such as hard connectors 3214). In further examples, the connection may be a hard-to-hard connection (e.g. the ends of the gas delivery tubes 3350 are formed by hard components and they connect to hard portions of the chassis portion 3210, such as hard connectors 3214).

The inside shoulder 3184 comprises a gradual curve in cross-section. The inside shoulder 3184 comprises a gradual curved transition between the inwardly facing wall of the chassis connection portion 3181 and an inwardly facing wall of the projecting connector portion 3182. The inwardly facing wall of the projecting connector portion 3182 may be substantially parallel to the inwardly facing wall of the chassis connection portion 3181. The inwardly facing wall of the projecting connector portion 3182 may also be parallel to an outwardly facing wall of the projecting connector portion 3182. The inwardly facing wall of the projecting connector portion 3182 may be perpendicular to the downstream end surface of the chassis connection portion 3181 and/or the flat wall 3183*a* of the outside shoulder 3183. Each recess 3185 of the projecting connector portion 3182 may be recessed relative to the outwardly facing wall of the projecting connector portion 3182.

As shown in FIGS. 17A-17E and 27A-27C, the connectors 3214 in these examples each comprise a clip base portion 3186 and a pair of clip arms 3187. In these examples the projecting connector portion 3182 comprises the clip base portion 3186 and the clip arms 3187.

The clip base portion 3186 is adjacent to the chassis connection portion 3181 of the connector 3214. The clip base portion 3186 may extend from an internal periphery of the chassis connection portion 3181 as shown in FIG. 27C. The clip base portion 3186 may comprise a similar but smaller cross-sectional shape to the chassis connection portion 3181 such that there is a step in the outer surface of the connector 3214 and the boundary between the clip base portion 3186 and the chassis connection portion 3181. The chassis connection portion 3181 and clip base portion 3186 may surround a hole through the connector 3214 through which breathable gas passes in use. For example, the chassis connection portion 3181 and clip base portion 3186 may each be formed in an approximate D-shape when viewed in cross-section along a central axis through the interior of the connector 3214.

The projecting connector portion 3182 may comprise a pair of clip arms 3187 projecting away from the clip base portion 3186. In contrast to clip base portion 3186, each of the clip arms 3187 may only partly surround the hole through the connector 3214 through which breathable gas passes in use. In the examples shown in FIGS. 17A-17E and 27A-27C, each clip arm 3187 comprises a recess 3185 configured to receive a clip projection 3304 (described below) of a tube end connector 3302 of a gas delivery tube 3350 to form a snap-fit connection with the tube end connector 3302. In other examples the connector 3214 may have only one clip arm 3187 or may have three or more clip arms. Each clip arm 3187 may comprise a respective recess 3185 configured to receive a respective clip projection 3304.

FIG. 29 shows a tube end 3314 of a gas delivery tube 3350 of the patient interface 3000 shown in FIGS. 7A-7G. The connectors 3214 shown in FIGS. 17A-17E and 27A-27C are configured to connect to this tube end 3314. In particular, the projecting connector portion 3182 of the connector 3214 is configured to be received within the tube end 3314 and connect to a tube end connector 3302 within the tube end 3314. In the example shown in FIG. 29, the tube end connector 3302 is overmoulded to a clip overmould 3318, which itself is overmoulded within the tube end 3314. In other examples, the clip is overmoulded directly to the flexible material forming the gas delivery tube 3350 at the tube end 3314.

When a snap fit connection is made between a connector 3214 and a corresponding tube end connector 3302 provided to the tube end 3314 of a gas delivery tube 3350, the clip arms 3187 in these examples deform to allow clip projections 3304 of the tube end connector 3302 to slide over the outwardly facing surfaces of the clip arms 3187 and then fit into the recesses 3185 to form the snap fit connection. In order to facilitate the snap fit connection, the clip arms 3187 may each bend inwardly towards a central axis of the connector 3214. In some examples of the present technology the tube end connector 3302 may also deform during the snap-fit connection to the connector 3214. The tube end 3314 also comprises a lip 3324 to form a seal with the connector 3214. The lip 3324 may seal to one or more of the projecting connector portions 3182, the outside shoulder 3183, the flat wall 3183*a* of the outside shoulder 3183 and the connection portion 3212 of the chassis portion 3210.

FIG. 28A shows a partial side view of the connector 3214 shown in FIGS. 17A-17E with some dimensions indicated. FIG. 28B shows a partial side view of the connector 3214 shown in FIGS. 27A-27C with some dimensions indicated.

The location of the recess 3185 within the connector 3214 corresponds with the location of the clip projection 3304 of the tube end connector 3302, as the recess 3185 receives the clip projection 3304 when the tube end 3314 is connected to the connector 3214. The distance C1 labelled in FIG. 28A is the distance of the recess 3185 from the chassis connection portion 3181 in the connector 3214 shown in FIGS. 17A-17E. The distance C2 labelled in FIG. 28B is the distance of the recess 3185 from the chassis connection portion 3181 in the connector 3214 shown in FIG. 27A-27C. The distances C1 and C2 may be substantially equal to each other and may be substantially equal to the distance of the clip projection 3304 from the end wall of the tube end 3314. Accordingly, when the clip projection 3304 fits into the recess 3185 of the connector 3214 shown in either FIG. 28A or 28B, the distal-most end of the tube wall 3314 abuts the chassis connection portion 3181 of the connector 3214 or connection portion 3212 of the chassis portion 3210.

With reference to FIG. 28A, the distance C1 of the recess 3185 from the chassis connection portion 3181 is divided into two labelled distances CB1 and CA1. The distance CB1 is a length of the clip base portion 3186 along the length of the connector 3214 and the distance CA1 is a length of the clip arms 3187 between the clip base portion 3186 and the recess 3185.

With reference to FIG. 28B, the distance C2 of the recess 3185 from the chassis connection portion 3181 is divided into two labelled distances CB2 and CA2. The distance CB2 is a length of the clip base portion 3186 along the length of the connector 3214 and the distance CA2 is a length of the clip arms 3187 between the clip base portion 3186 and the recess 3185.

The applicant has found that, without modifying the spacing between the recess 3185 and the chassis connection portion 3181 (e.g. distances C1 and C2), the lengths of the clip base portion 3186 and clip arms 3187 can be tailored to achieve an advantageous retention force of the connector 3214 when connected to the gas delivery tube 3350. In use of the patient interface 3000 the gas delivery tubes 3350 hold the cushion module 3150 in a sealing position. It is advantageous for the force required to disconnect the gas delivery tubes 3350 to be sufficiently high that the gas delivery tubes 3350 are not disconnected inadvertently, for example during setup when the patient pulls on the gas delivery tubes 3350 to don or adjust the patient interface 3000, or during use when the patient moves while sleeping. Additionally, it is advantageous that the force required to connect and disconnect the gas delivery tubes 3350 is not so high that it is difficult for a patient to disassemble and reassemble the patient interface 3000, for example for cleaning or replacement of the cushion module 3150.

The length of the clip arms 3187 is a factor in the force required to sufficiently deflect the clip arms 3187 during the snap-fit connection to the tube end connector 3302. Longer clip arms 3187 will result in a lower force being required to be applied to the free ends of the clip arms 3187 to deflect the free ends by a particular amount. During connection and disconnection of a gas delivery tube 3350 to/from a connector 3214, the tube end connector 3302 will apply a force on each clip arm 3187 inwardly with respect to the connector 3214. A particular amount of deflection of each clip arm 3187 is required to allow connection and disconnection of the gas delivery tubes 3350 from the connectors 3214. Accordingly, a longer clip arm 3187 will result in a lower force required to connect or disconnect the gas delivery tubes 3350 to/from the connectors 3214. Similarly, a shorter clip arm 3187 will result in a greater force required to connect or disconnect the gas delivery tubes 3350 to/from the connectors 3214.

Accordingly, for a given spacing between the recess 3185 and chassis connection portion 3181 (e.g. C1 in FIG. 28A and C2 in FIG. 28B), the length of the clip base portion 3186 (e.g. CB1 in FIG. 28A and CB2 in FIG. 28B) and the length of the clip arms 3187 between the clip base portion 3186 and the recess 3185 (e.g. CA1 in FIG. 28A and CA2 in FIG. 28B) can be tailored to achieve a retention force of the connector 3214 which balances the requirement of the connector 3214 to remain connected to the gas delivery tube 3350 in use with the ability for a patient to disconnect the connector 3214 from the gas delivery tube 3350 from time to time.

In one form of the present technology, such as in the connector 3214 shown in FIGS. 17A-17E and 28A, the length CB1 of the clip base portion 3186 is less than the length CA1 of the clip arms 3187 between the clip base portion 3186 and the recess 3185 along the length of the connector 3214. The applicant has found that a cushion module 3150 including this connector 3214 can be connected to gas delivery tubes 3350 and be held in connection with a retention force sufficiently high to provide a sufficiently stable connection in use.

In another form of the present technology, such as in the connector 3214 shown in FIGS. 27A-27C and 28B, the length CB2 of the clip base portion 3186 is greater than the length CA2 of the clip arms 3187 between the clip base portion 3186 and the recess 3185 along the length of the connector 3214.

The applicant has found that a length of the clip base portion 3186 along the length of the connector 3214 which is equal to or greater than the length of the clip arms 3187 between the clip base portion 3186 and the recess 3185 along the length of the connector 3214 results in a particularly advantageous retention force. The retention force (e.g. the separation force that the connection can withstand before separating) is sufficiently high that there is a low chance of unintentional disconnection during setup or use, but not excessively high that it is too difficult for patients to intentionally disconnect the cushion module 3150 from the gas delivery tubes 3350.

Accordingly, in some examples of the present technology, the length of the clip base portion 3186 is greater than the length of the clip arm 3187 between the clip base portion 3186 and the recess 3185. The relationship between the length of the clip base portion 3186 and the length of the clip arm 3187 between the clip base portion 3186 and the recess 3185 may also be expressed as a ratio. In some examples, the ratio of the length of the clip base portion 3186 to the length of the clip arm 3187 between the clip base portion 3186 and the recess 3185 is equal to or greater than 1.2:1 or 1.3:1. In further examples, the ratio is greater than about 1.5:1, 1.7:1 or 1.9:1. In the example shown in FIG. 28B, the ratio is about 2:1.

In some examples of the present technology, a force required to disconnect each connector 3214 of the cushion module 3150 from the tube end connector 3302 of a respective gas delivery tube 3350 may be greater than 12N. In further examples the force required may be greater than 20N, 25N or greater than 30N. In some examples the force required is within the range of 12N-50N. In further examples the force required is within the range of 20N-40N, such as within the range of 20N-30N or within the range of 30N-40N. In some examples the force required is in the range of 25N-35N. In some examples of a patient interface 3000 according to the present technology, a cushion module 3150 may be separable from a gas delivery tube 3350 of the patient interface 3000 upon application of a force as specified above or within a range specified above, yet may comprise one or more connectors 3214 of a design other than those shown in FIG. 17A-17E, 27A-27C or 28A-28B.

With reference to FIGS. 33A-33B, the clip arms 3187 of the connectors 3214 comprise clip arm corners 3188. Each clip arm 3187 may comprise a pair of clip arm corners 3188 at a distal end of the clip arm 3187 opposite to the chassis connection portion 3181 of the connector 3214. In this example the clip arm corners 3188 are rounded. Rounded clip arm corners 3188 may reduce stress in the clip arm corners 3188 during connection of the connector 3214 to the gas delivery tube 3350. Excessive stress in the clip arm corners 3188 may reduce the service life of the cushion module 3150 or its reliability. Clip arm corners 3188 shaped in the manner described below may advantageously provide for connectors 3214 with a low risk of chipping, cracking or otherwise breaking or failing in use.

FIG. 33A shows a view of a connector 3214 from a first side in which an anterior clip arm 3187 and its clip arm corners 3188 are visible and labelled. The first side may be an anterior side of the connector 3214 in use. In other examples the first side may be a posterior side of the connector 3214 in use and the clip arm 3187 shown may be a posterior clip arm 3187. Each clip arm corner 3188 may be shaped in an arc. The arc may have a transverse dimension CR1 orthogonal to a longitudinal axis of the connector 3214 (the longitudinal axis being substantially parallel to the direction of the flow of gas through the connector 3214 in use) and a longitudinal dimension CR2 parallel to the longitudinal axis of the connector 3214.

The transverse dimension CR1 of the arc of the clip arm corners 3188 of the anterior clip arm 3187 may be within the range of 2-5 mm, for example within the range or 2.5-4 mm. In the example shown in FIG. 33A the dimension CR1 is 3 mm. The longitudinal dimension CR2 of the arc of the clip arm corners 3188 of the anterior clip arm 3187 may be the same as the transverse dimension CR1. In other examples the longitudinal dimension CR2 may be different from the transverse dimension CR1. The longitudinal dimension CR2 of the arc of the clip arm corners 3188 of the anterior clip arm 3187 may be within the range of 2-5 mm, for example within the range or 2.5-4 mm. In the example shown in FIG. 33A the dimension CR2 is 3 mm.

FIG. 33B shows a view of a connector 3214 from a second side in which a posterior clip arm 3187 and its clip arm corners 3188 are visible and labelled. The second side may be a posterior side of the connector 3214 in use. In other examples the second side may be an anterior side of the connector 3214 in use and the clip arm 3187 shown may be an anterior clip arm 3187. Each clip arm corner 3188 may be shaped in an arc. The arc may have a transverse dimension CR3 orthogonal to a longitudinal axis of the connector 3214 and a longitudinal dimension CR4 parallel to the longitudinal axis of the connector 3214.

The transverse dimension CR3 of the arc of the clip arm corners 3188 of the posterior clip arm 3187 may be within the range of 1-4 mm, for example within the range or 1.5-3 mm. In the example shown in FIG. 33B the dimension CR3 is 2 mm. The longitudinal dimension CR4 of the arc of the clip arm corners 3188 of the posterior clip arm 3187 may be different from the transverse dimension CR3. In other examples the longitudinal dimension CR4 may be the same as the transverse dimension CR3. The longitudinal dimension CR4 of the arc of the clip arm corners 3188 of the posterior clip arm 3187 may be within the range of 2-5 mm, for example within the range or 2.5-4 mm. In the example shown in FIG. 33B the dimension CR4 is 3 mm.

5.3.1.7 Connection Between Connectors and Laterally Projecting Connection Portions FIG. 18A shows a cross section view through the chassis portion 3210 to illustrate the connection of the connectors 3214 to the laterally projecting connection portions 3212. As illustrated, the end of the laterally projecting connection portion 3212 is bonded to the chassis connection portion 3181 of the connector 3214. The projecting connector portion 3182 projects outwardly away from the laterally projecting connection portion 3212.

As illustrated in FIG. 18A, each laterally projecting connection portion 3212 may comprise a superior portion which is convex when viewed from a superior direction and an inferior portion which is concave when viewed from an inferior direction. Each of the laterally projecting connection portions 3212 may curve towards an inferior direction away from the seal-forming structure 3100. This is also evident from FIGS. 8D and 8H.

As illustrated in FIG. 21, each laterally projecting connection portion 3212 comprises a superior ridge 3213. Each superior ridge 3213 may extend transversely across the length of the respective laterally projecting connection portion 3212. Each superior ridge 3213 may extend longitudinally along the length of the respective laterally projecting connection portion 3212. In this example of the present technology, each superior ridge 3213 extends both transversely across and longitudinally along a respective one of the laterally projecting connection portions 3212. One end of each superior ridge 3213 may be located at a superior and anterior location with respect to the laterally projecting connection portion 3212. The other end of each superior ridge 3213 may be located adjacent the seal-forming structure 3100 at a superior and posterior side of the laterally projecting connection portion 3212, as illustrated in FIG. 21.

5.3.2 Positioning and Stabilising Structure

The seal-forming structure 3100 of the patient interface 3000 of the present technology may be held in sealing position in use by the positioning and stabilising structure 3300. Positioning and stabilising structure 3300 may comprise and function as "headgear" since it engages the patient's head in order to hold the patient interface 3000 in a sealing position. In some examples of the present technology, the positioning and stabilising structure 3300 may comprise any one or more of the features described in International Application No. PCT/AU2019/050874, the entire contents of which are hereby incorporated herein by reference.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face, in some examples in combination with other straps or other structures. In an example the strap may be configured as a tie.

A tie will be understood to be a structure designed to resist tension. In use, a tie is part of the positioning and stabilising structure 3300 that is under tension. Some ties will impart an elastic force as a result of this tension, as will be described. A tie may act to maintain the seal-forming structure 3100 in a therapeutically effective position on the patient's head.

In one form of the present technology, the positioning and stabilising structure 3300 comprises a first tie, the first tie being constructed and arranged so that in use at least a portion of an inferior edge thereof passes superior to an otobasion superior of the patient's head and overlays a portion of a parietal bone and/or frontal bone. The first tie may be provided, for example, as part of a patient interface that comprises a cradle cushion, nasal pillows, nasal cushion or full-face cushion (either an under-the-nose full-face cushion or a full-face cushion that seals to the patient's nose superior to the pronasale).

In some examples of the present technology, the first tie of the positioning and stabilising structure 3300 comprises a superior first tie portion and an inferior first tie portion. The superior first tie portion may overlay a portion of a parietal bone and/or the frontal bone. The inferior first tie portion may overlay or lie inferior to the occipital bone of the patient's head. The first tie may be bifurcated. The first tie may bifurcate into the superior first tie portion and the inferior first tie portion. The first tie may comprise an anterior portion configured to overlay the side of the patient's head/face and a bifurcated portion configured to overlay the lateral, superior to and/or posterior sides to the patient's head. The anterior portion may be formed integrally with the superior first tie portion. The inferior first tie portion may connect to a junction between the anterior portion and the superior first tie portion.

For example, as shown in FIGS. 7A-7G, the positioning and stabilising structure 3300 comprises a first tie, being the portion which connects to the cushion module 3150 and in use lies alongside the patient's head and over the superior surfaces of the patient's head and the posterior surfaces of the patient's head. The first tie bifurcates into a superior first tie portion and an inferior first tie portion. The superior first tie portion is provided by the superior portion of each gas delivery tube 3350 and the inferior first tie portion is provided by the strap 3310 shown in FIG. 7A.

In one form of the present technology, the positioning and stabilising structure 3300 includes a second tie, the second tie being constructed and arranged so that in use at least a portion of a superior edge thereof passes inferior to an otobasion inferior of the patient's head and overlays or lies inferior to the occipital bone of the patient's head. The second tie may pass below the patient's ears. The second tie may be provided, for example, as part of a patient interface that comprises a full-face cushion (which may or may not leave the patient's pronasale uncovered) or a nasal cushion. In other examples the second tie may be provided as part of a patient interface that comprises a cradle cushion or nasal pillows cushion. The second tie may overlay the lateral and/or posterior sides of the patient's neck in use and connect to an inferior portion of a frame of the positioning and stabilising structure 3300, to an inferior portion of a cushion module 3150 or to an inferior portion of a plenum chamber 3200.

In one form of the present technology, the positioning and stabilising structure 3300 includes a third tie that is constructed and arranged to interconnect the first tie and the second tie to reduce a tendency of the first tie and the second tie to move apart from one another. The third tie may be provided as part of a patient interface that comprises a full-face cushion (which may or may not leave the patient's pronasale uncovered) or a nasal cushion. In other examples the third tie may be provided as part of a patient interface that comprises a cradle cushion or nasal pillows cushion.

In certain forms of the present technology, a positioning and stabilising structure 3300 comprises a strap that is bendable and e.g. non-rigid. An advantage of this aspect is that the strap is more comfortable for a patient to lie upon while the patient is sleeping. As shown in FIGS. 7A-7G, the positioning and stabilising structure 3300 comprises a pair of gas delivery tubes 3350 which are non-rigid. Additionally, the positioning and stabilising structure 3300 comprises a strap 3310 which is non-rigid.

As shown in FIGS. 7A-7G, the positioning and stabilising structure 3300 comprises a pair of tabs 3320. In use, the strap 3310 (shown in FIG. 7A), can be connected between the tabs 3320. The strap 3310 may be sufficiently flexible to pass around the back of the patient's head and lie comfortably against the patient's head, even when under tension in use.

In certain forms of the present technology, a positioning and stabilising structure 3300 comprises a strap constructed to be breathable to allow moisture vapour to be transmitted through the strap. The strap 3310 of the positioning and stabilising structure 3300 of the exemplary patient interface 3000 shown in FIGS. 7A-7G is constructed from a foam material covered in a textile material. In other examples the strap 3310 may be formed solely from a foam material, a textile material or another material such as a flexible plastic material.

In certain forms of the present technology, a system is provided comprising more than one positioning and stabilizing structure 3300, each being configured to provide a retaining force to correspond to a different size and/or shape range. For example, the system may comprise one form of positioning and stabilizing structure 3300 suitable for a large sized head, but not a small sized head, and another. suitable for a small sized head, but not a large sized head.

5.3.2.1 Headgear Tubing

In some forms of the present technology, the positioning and stabilising structure 3300 comprises one or more tubes 3350 that deliver pressurised air received from the air circuit 4170 to the plenum chamber 3200 and then the patient's airways, for example through the cushion module 3150 and seal-forming structure 3100. The tubes 3350 may receive a pressurised flow of gas from a conduit forming part of the air circuit 4170. The conduit may be connected to an RPT device 4000.

In the form of the present technology illustrated in FIGS. 7A-7G, the positioning and stabilising structure 3300 comprises two gas delivery tubes 3350 that deliver air to the plenum chamber 3200 from the air circuit 4170. In this example, the tubes 3350 removably connect to the cushion module 3150. In other examples, the tubes 3350 may be permanently connected to a cushion module 3150 of the patient interface 3000 at least partially forming the plenum chamber 3200. The tubes 3350 are an integral part of the positioning and stabilising structure 3300 of the patient interface 3000, forming part of headgear to position and stabilise the seal-forming structure 3100 of the patient interface to the appropriate part of the patient's face (for example, the nose and/or mouth). This allows the conduit of air circuit 4170 providing the flow of pressurised air to connect to a connection port 3600 of the patient interface 3000 in a position other than in front of the patient's face which may be unsightly to some people.

Since air can be contained and passed through headgear tubing 3350 in order to deliver pressurised air from the air circuit 4170 to the patient's airways, the positioning and stabilising structure 3300 may be described as being inflatable. It will be understood that an inflatable positioning and stabilising structure 3300 does not require all components of the positioning and stabilising structure 3300 to be inflatable. For example, in the example shown in FIGS. 7A-7G, the positioning and stabilising structure 3300 comprises headgear tubes 3350, which are inflatable, and the strap 3310, which is not inflatable.

In certain forms of the present technology, the patient interface 3000 may comprise a connection port 3600 located proximal a top, side or rear portion of a patient's head. For example, in the form of the present technology illustrated in FIGS. 7A-7G, the connection port 3600 is located on top of the patient's head. In this example the patient interface 3000 comprises an elbow 3610 to which the connection port 3600 is provided. The elbow 3610 may swivel with respect to the positioning and stabilising structure 3300 and order to decouple movement of a conduit connected to the connection port 3600 from the positioning and stabilising structure 3300. The elbow 3610 is configured to fluidly connect with a conduit of an air circuit 4170.

Patient interfaces in which the connection port is not positioned in front of the patient's face may be advantageous as some patients find a conduit that connects to a patient interface in front of the face to be unsightly and obtrusive. For example, a conduit connecting to a patient interface in front of the face may be prone to being tangled up in bedclothes or bed linen, particularly if the conduit extends downwardly from the patient interface in use. Forms of the technology with a patient interface with a connection port positioned proximate the top of the patient's head in use may make it easier or more comfortable, compared to other types of patient interface, for a patient to lie or sleep in one or more of the following positions: in a side or lateral position; in a supine position (i.e. on their back, facing generally upwards); and in a prone position (i.e. on their front, facing generally downwards). Moreover, connecting a conduit to the anterior side of a patient interface may exacerbate a problem known as tube drag, wherein the conduit may provide an undesired drag force upon the patient interface thereby causing dislodgement away from the face.

In some examples, at least one tube 3350 extends between the plenum chamber 3200 and the connection port 3600 across the patient's cheek region and above the patient's ear. A portion of the tube 3350 that connects to cushion module 3150 overlays a maxilla region of the patient's head in use and a portion of the tube 3350 overlays a region of the patient's head superior to the otobasion superior on the patient's head. Each of the one or more tubes 3350 may also lie over the patient's sphenoid bone and/or temporal bone and either or both of the patient's frontal bone and parietal bone. The elbow 3610 may be located in use over the patient's parietal bone, frontal bone or the junction therebetween.

In the form of the present technology illustrated in FIGS. 7A-7G, the positioning and stabilising structure 3300 comprises two tubes 3350. Each tube 3350 is positioned in use on a different side of the patient's head and extends from the plenum chamber 3200 across a respective cheek region, above the respective ear (superior to the otobasion superior on the patient's head) to the connection port 3600 on top of the head of the patient 1000. This form of technology may be advantageous because, if a patient sleeps with their head on its side and one of the tubes is compressed to block or partially block the flow of gas along the tube, the other tube remains open to supply pressurised gas to the patient. In other examples of the technology, the patient interface 3000 may comprise a different number of tubes, for example one tube, or three or more tubes. In one example in which the patient interface has one tube 3350, the single tube 3350 is positioned on one side of the patient's head in use (e.g. across one cheek region) and a strap forms part of the positioning and stabilising structure 3300 and is positioned on the other side of the patient's head in use (e.g. across the other region) to assist in securing the patient interface 3000 on the patient's head.

In the form of the technology shown in FIGS. 7A-7G the two tubes 3350 are fluidly connected at their upper ends to each other and to connection port 3600. In one form, the two tubes are integrally formed while in other forms the tubes are separate components that are connected together in use and may be disconnected, for example for cleaning, storage or replacement. Where separate tubes are used they may be indirectly connected together, for example each may be connected to an intermediary conduit, for example a T-shaped conduit having two conduit arms each fluidly connectable to the tubes 3350 and a third conduit arm or opening acting as the connection port 3600 and connectable in use to the air circuit 4170.

The tubes 3350 may be formed of a semi-rigid material such as an elastomeric material, e.g. silicone. The tubes 3350 may have a natural, preformed shape and be able to be bent or moved into another shape if a force is applied to the tubes. For example, the tubes may be generally arcuate or curved in a shape approximating the contours of a patient's head between the top of the head and the nasal or oral region.

As described in U.S. Pat. No. 6,044,844, the contents of which are incorporated herein, the tubes 3350 may be crush resistant to avoid the flow of breathable gas through the tubes if either is crushed during use, for example if it is squashed between a patient's face and pillow. Crush resistant tubes may not be necessary in all cases as the pressurised gas in the tubes may act as a splint to prevent or at least restrict crushing of the tubes 3350 during use. A crush resistant tube may be advantageous where only a single tube 3350 is present as if the single tube becomes blocked during use the flow of gas would be restricted and therapy will stop or reduce in efficacy.

More features of positioning and stabilising structures 3300 according to some examples of the present technology are described in U.S. Provisional Patent Application No. 62/764,995, the entire contents of which are hereby incorporated by reference herein.

In certain forms of the present technology the patient interface 3000 is configured such that the connection port 3600 can be positioned in a range of positions across the top of the patient's head so that the patient interface 3000 can be positioned as appropriate for the comfort or fit of an individual patient. Movement of an upper portion of the patient interface 3000 may be decoupled from a lower portion of the patient interface 3000. This may enable the cushion module 3150 to form an effective seal with the patient's face irrespective of the position of the connection port 3600 on the patient's head. Such de-coupling can be achieved using, for example, mechanisms that allow parts of the headgear tubes 3350 to easily move or flex relative to other parts of the patient interface 3000. Examples of such mechanisms will be described below.

In a certain form of the present technology, the patient interface 3000 is configured such that the connection port 3600 is positioned approximately at a top point of the patient's head in use. The connection port 3600 may be positioned in the sagittal plane and aligned with the otobasion superior points in a plane parallel to the coronal plane.

As described above, in some examples of the present technology the patient interface 3000 comprises a seal-forming structure 3100 in the form of a cradle cushion which lies generally under the nose and seals to an inferior periphery of the nose. The positioning and stabilising structure 3300 may be structured and arranged to pull the seal-forming structure 3100 into the patient's face under the nose with a sealing force vector that has a posterior and superior direction (e.g. a posterosuperior direction). A sealing force vector with a posterosuperior direction may facilitate the seal-forming structure 3100 forming a good seal to both the inferior periphery of the patient's nose and the anterior-facing surfaces of the patient's face on either side of the patient's nose and the upper lip.

5.3.2.1.1 Headgear Tube Fluid Connections

The two tubes 3350 are fluidly connected at their inferior ends to the plenum chamber 3200.

Examples of laterally projecting connection portions of the cushion module 3150 to which gas delivery tubes 3350 connect in certain forms of the technology have been described above. In these forms, the gas delivery tubes 3350 are configured to engage with such connection portions of the cushion module 3150.

In certain forms of the technology, the connection between the tubes 3350 and the cushion module 3150 is achieved by connection of two rigid components so that the patient can easily connect the two components together in a reliable manner. The tactile feedback of a 're-assuring click' or like sound may be easy for a patient to use or for a patient to know that the tube has been correctly connected to the cushion module 3150. In one form, the tubes 3350 are formed from silicone and the lower end of each of the silicone tubes 3350 is overmolded to a rigid connector made, for example, from polypropylene, polycarbonate, nylon or the like. The rigid connector may comprise a female mating feature configured to connect with a male mating feature on the cushion module 3150. Alternatively, the rigid connector may comprise a male mating feature configured to connect to a female mating feature on the cushion module 3150.

In another embodiment a compression seal is used to connect each tube 3350 to the cushion module 3150. For example, a resiliently flexible (e.g. silicone) tube 3350 without the rigid connector may need to be squeezed slightly to reduce its diameter so that it can be jammed into a port in the cushion module 3150 and the inherent resilience of the silicone pushes the tube 3350 outwards to seal the tube 3350 in the port in an air-tight manner. In a hard-to-hard type engagement between the tube 3350 and port, a pressure activated seal such as a peripheral sealing flange may be used. When pressurised gas is supplied through the tubes 3350 the sealing flange is urged against the join between the tubes and the inner circumferential surface of the port of the cushion module 3150 to enhance the seal between them. If the port is soft and a rigid connector is provided to the tube 3350, the pressure activated seal as described earlier may also be used to ensure the connection is air-tight. In another example, each tube 3350 is formed from a resiliently flexible (e.g. silicone) material which is over moulded to a rigid connector such that the resiliently flexible material fits over the rigid connector and itself functions as a gasket to seal the connection between the tube 3350 and the cushion module 3150 around a periphery of an air flow passage from the tube 3350 into the cushion module 3150.

5.3.2.1.2 Extendable Concertina Structure

The patient interface 3000 may comprise one or more extendable tube sections. In some examples, an extendable tube section comprises an extendable concertina structure. The patient interface 3000 may comprise a positioning and stabilising structure 3300 including at least one gas delivery tube comprising a tube wall having an extendable concertina structure. For example, the patient interface 3000 shown in FIGS. 7A-7G comprises tubes 3350, the superior portions of which comprise extendable tube sections each in the form of an extendable concertina structure 3362. In other examples of the present technology the patient interface 3000 comprises a single tube 3350 having an extendable concertina structure 3362. In general, any features described herein of a tube 3350 may be applied to a patient interface 3000 having a single tube 3350 or may be applied to each tube 3350 of a patient interface having a plurality of tubes 3350.

Each extendable concertina structure 3362 may comprise a portion of the tube 3350 having one or more folding portions, pleats, corrugations or bellows to form an extendable portion of the tube 3350. In the example shown in FIGS. 7A-7G, the extendable concertina structures 3362 each take the form of an extendable concertina structure. The extendable concertina structures 3362 are separated by the elbow 3610 and connection port 3600. The extendable concertina structures 3362 are able to change in length. In particular, each extendable concertina structure 3362 is able to extend or contract in order to change the length of the respective tube 3350.

5.3.2.1.3 Non-Extendable Headgear Tubing

The patient interface 3000 may comprise one or more non-extendable tube sections 3363. For example, the patient interface 3000 shown in FIGS. 7A-7G comprises tubes 3350 The inferior portion of each tube 3350 comprises a non-extendable tube section 3363. The non-extendable tube sections 3363 are configured to overlie the patient's cheeks and may be configured to contact the patient's face inferior to the patient's cheekbones. Each non-extendable tube section 3363 may lie on a curve extending inferiorly from the connection between the respective headgear tube 3350 and then extending in a partially anterior and partially medial direction towards the plenum chamber 3200 in order to avoid the patient's cheek bones.

The cross-sectional shape of the non-extendable tube sections 3363 of the tubes 3350 may be circular, elliptical, oval, D-shaped or a rounded rectangle, for example as described in U.S. Pat. No. 6,044,844. A cross-sectional shape that presents a flattened surface of tube on the side that faces and contacts the patient's face or other part of the head may be more comfortable to wear than, for example a tube with a circular cross-section.

In some examples of the present technology, the non-extendable tube sections 3363 connect to the plenum chamber 3200 from a low angle. The headgear tubes 3350 may extend inferiorly down the sides of the patient's head and then curve anteriorly and medially to connect to the plenum chamber 3200 in front of the patient's face. The tubes 3350, before connecting to the plenum chamber 3200, may extend to a location at the same vertical position as or, in some examples, inferior to the connection with the plenum chamber 3200. That is, the tubes 3350 may project in an at least partially superior direction before connecting with the plenum chamber 3200. A portion of the tubes 3350 may be located inferior to the plenum chamber 3200 and/or the seal forming structure 3100. The low position of the tubes 3350 in front of the patient's face facilitates contact with the patient's face below the patient's cheekbones.

Each non-extendable tube portion 3363 may permanently or removably connect to a cushion module 3150 of the patient interface at least partially forming the plenum chamber 3200.

5.3.2.2 Headgear Straps

In certain forms of the present technology, the positioning and stabilising structure 3300 comprises at least one headgear strap acting in addition to the tubes 3350 to position and stabilise the seal-forming structure 3100 to the entrance to the patient's airways. As shown in FIG. 7A, the patient interface 3000 comprises a strap 3310 forming part of the positioning and stabilising structure 3300. The strap 3310 may be known as a back strap or a rear headgear strap, for example. In other examples of the present technology, one or more further straps may be provided. For example, a patient interface 3000 according to an example of the present technology having a full face or oro-nasal cushion module may have a second, lower, strap configured to overlie the back of the patient's neck.

In the example shown in FIG. 7A, strap 3310 of the positioning and stabilising structure 3300 is connected between the two tubes 3350 positioned on each side of the patient's head and passing around the back of the patient's head, for example overlying or lying inferior to the occipital bone of the patient's head in use. The strap 3310 connects to each tube above the patient's ears. In other embodiments, for example as part of an oro-nasal patient interface, the positioning and stabilising structure 3300 comprises an upper strap similar to strap 3310 and at least one additional lower headgear strap that connects between the tubes and/or cushion module and passes below the patient's ears and around the back of the patient's head. Such a lower headgear strap may also be connected to an upper strap (e.g. a similar to strap 3310).

5.3.3 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an exterior surface of the seal-forming structure 3100.

In certain forms of the present technology, the seal-forming structure 3100 is constructed from a biocompatible material, e.g. silicone rubber, a textile material or a combination of such materials.

A seal-forming structure 3100 in accordance with some examples of the present technology may be constructed from a soft, flexible, resilient material such as silicone.

A seal-forming structure 3100 in accordance with some examples of the present technology may comprise non-patient contacting portions and patient contacting portions. In some examples, a seal-forming structure 3100 may comprise anterior-facing, lateral-facing, superior-facing and/or inferior-facing portions which may not be in contact with the patient's face.

A seal-forming structure 3100 in accordance with further examples of the present technology may be constructed from a textile material. In some examples an anterior side of the seal-forming structure 3100 may be formed form an elastomeric material such as silicone of TPE while a posterior side may formed from a textile material.

Where the seal-forming structure 3100 comprises a textile or textile portion, the textile may comprise a material formed of a network of fibres and being adapted such that it is air impermeable. For example, the textile can have an air impermeable film on at least one surface thereof.

In some forms, the seal-forming structure 3100 is constructed so as to stretch elastically in at least one dimension. For example, when a textile seal-forming structure is constructed from a network of fibres, the seal-forming structure may be capable of elongating in either, or both of, a longitudinal warp direction or a lateral weft direction across the textile. In some forms, a textile seal-forming structure 3100 is constructed so as to elongate elastically to an extent greater than that achievable by conventional silicone seal-forming structure.

In some forms, the seal-forming structure 3100 is constructed so as to be substantially inelastic in at least one dimension. For example, when a textile seal-forming structure is constructed from a woven textile, the seal-forming structure may be capable of substantially resisting elongation in either, or both of, a longitudinal warp direction or a lateral weft direction across the textile.

The seal-forming structure 3100 can be made from either a single layer or a plurality of layers. In forms where a plurality of layers are utilised, the individual layers can be formed using the same material, or a variety of different materials, each with unique material properties.

In some forms, the textile seal-forming structure 3100 can comprise at least one layer that exhibits substantially air-impermeable characteristics, whilst maintaining the material characteristics necessary for comfort and minimal pressure points. In some forms a textile seal-forming structure 3100 may comprise an air impermeable material formed on an inner surface of the textile material. The air impermeable material can in some forms be laminated onto the textile material. The air impermeable material and textile material can in some forms be selected such that the resulting textile material can exhibit a predetermined overall elasticity, or a resistance to elasticity, as required.

In some forms, the textile seal-forming structure 3100 can exhibit a low spring constant (i.e. high compliance) in both warp and weft. In such forms, unlike conventional designs where a fixed cushion may cause the skin of a patient's face to distort to form an effective seal, the textile material of the seal-forming structure 3100 can have a material spring constant and spring length such that the textile seal-forming structure 3100 is more compliant than the patient's skin that engages the seal-forming structure 3100. This may advantageously improve the comfort of the mask, and reduce the formation of localized pressure "hot spots".

In some forms, the surface of the textile material of the seal-forming structure 3100 that contacts the patient's face can have low friction characteristics. This may advantageously improve the comfort of the surface texture of the textile seal-forming structure 3100 and reduce friction relative to the patient's face. In some forms, higher friction textiles may cause the seal-forming structure 3100 to grip or rub against contacted regions of the patient's face 1300, in use. Such rubbing or gripping may cause the seal-forming structure to be distorted or deformed thereby reducing the effectiveness of the seal and allowing air to leak undesirably from the device.

In some forms, the textile material of the seal-forming structure 3100 has an overall thickness of 0.275 mm or less.

FIG. 16A-16D shows a cushion module 3150 comprising a seal-forming structure 3100 comprising a textile material. The seal-forming structure 3100 in this particular example comprises a textile material in the central portion 3111 of the patient-facing part of the seal-forming structure (i.e. a posterior side). Other portions of the seal-forming structure 3100, such as the anterior- and superior-facing surfaces, may also be formed from silicone. In other examples, the entire seal-forming structure 3100 may be formed from a textile material. Advantageously, a seal-forming structure 3100 having a textile surface that contacts and seals to the patient's face may have benefits in enhanced tactile comfort and may also be more stretchable than silicone (for example by the use of a weaving pattern selected for stretchability). Additionally, a textile seal-forming structure 3100 or seal-forming surface thereof may provide less friction than silicone, which may improve comfort and allow the seal to slidably and sealingly conform to complex surfaces of the patient's face. In a seal-forming structure 3100 comprising both a silicone portion and a textile portion, the silicone portion may advantageously function as an easily moulded support for the textile portion which makes sealing contact with the patient's face.

The textile seal-forming structure 3100 shown in FIGS. 16A-16D is described in more detail below.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.3.1 Sealing Mechanisms

In one form, the seal-forming structure 3100 includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface, and/or having a higher coefficient of friction compared to other surfaces.

In certain forms of the present technology, a seal-forming structure may comprise one or more of a pressure-assisted sealing flange, a compression sealing portion, a gasket sealing portion, a tension portion, and a portion having a tacky or adhesive surface.

In some forms of the present technology, a seal-forming structure 3100 may comprise a low-friction surface in one or more regions. The low friction surface may enable the seal-forming structure 3100 to slide over the patient's skin to fit to surfaces of the patient's face comprising complex geometry, such as proximate the nasolabial sulcus and the concavities often present at the location where the ala of the patient's nose meets the patient's face.

5.3.3.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.3.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.3.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.3.5 Nasal Pillows

In one form the seal-forming structure 3100 of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frustro-cone, at least a portion of which forms a seal on an underside of the patient's nose, a stalk, a flexible region on the underside of the frustro-cone and connecting the frustro-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frustro-cone and the structure to which the nasal pillow is connected. For example, the frustro-cone may be axially displaced towards the structure to which the stalk is connected.

5.3.3.6 Nasal Mask Cushion

In one form, the non-invasive patient interface 3000 comprises a seal-forming portion that forms a seal in use on an upper lip region (that is, the lip superior), a nasal bridge region and a cheek region of the patient's face. This is the case, for example, with the patient interface 3000 shown in FIG. 1B. This seal-forming portion delivers a supply of air or breathable gas to both nares of patient 1000 through a single orifice. This type of seal-forming structure may be referred to as a "nasal cushion" or "nasal mask". In some examples of the present technology, the positioning and stabilising structure 3300 shown in FIGS. 7A-7G may be utilised to hold a nasal cushion in sealing position on a patient's face.

5.3.3.7 Full-Face Mask Cushion

In one form the patient interface 3000 comprises a seal-forming portion that forms a seal in use on a chin-region, a cheek region and either a nasal bridge region or an under the nose region of the patient's face. This is the case, for example, with the patient interface 3000 shown in FIG. 1C. This seal-forming portion delivers a supply of air or breathable gas to both nares and mouth of patient 1000 through a single orifice or through separate orifices. This type of seal-forming structure may be referred to as a "full-face mask" or "ultra compact full face mask". In some examples of the present technology, the positioning and stabilising structure 3300 shown in FIGS. 7A-7G may be utilised to hold a full-face cushion in sealing position on a patient's face. Portions of the seal-forming structure 3100 described below may be incorporated into a full-face mask cushion or a chassis for supporting a full-face mask.

5.3.3.8 Nasal Cradle

In one form of the present technology, for example as shown in FIGS. 7A-7G, the seal-forming structure 3100 of the patient interface 3000 is configured to form a seal in use with the underside of the nose around the nares. In this example, the seal-forming structure 3100 is also configured to form a seal in use with the lip superior of the patient 1000. This type of seal-forming structure may be referred to as a "cradle", "nasal cradle cushion", "under-the-nose cushion" or "sub-nasal cushion". The shape of the seal-forming structure 3100 may be configured to match or closely follow the underside of the patient's nose. In one form of nasal cradle cushion, the seal-forming structure 3100 comprises a bridge portion defining two orifices, each of which, in use, supplies air or breathable gas to a different one of the patient's nares. The bridge portion may be configured to contact or seal against the patient's columella in use. In some forms of the technology, the seal-forming structure 3100 is configured to form a seal on an underside of the patient's nose without contacting a nasal bridge region of the patient's nose.

In certain forms of the present technology, the seal-forming structure 3100 comprises a central portion configured to form a seal to inferior surfaces of the patient's nose. The central portion may seal to an inferior periphery of the patient's nose (e.g., surrounding the patient's nares and to the patient's lip superior). In examples, the seal-forming structure 3100 may be configured to contact the patient's face below the bridge of the nose or below the pronasale.

The seal-forming structure 3100 may be configured to not enter the patient's nares in use. For example, the seal-forming structure 3100 may seal to the patient's face without entering the patient's nares. The seal-forming structure 3100 may be configured to form a seal with a region of the patient's face surrounding the patient's nares without entering the patient's nares. In some examples, the seal-forming structure 3100 is configured to form a seal which surrounds the patient's nares and columella. The seal-forming structure 3100 may form a single contiguous seal that surrounds both nares.

The seal-forming structure 3100 may be configured to seal to anterior and/or inferior surfaces of the patient's nose tip in use. The seal-forming structure 3100 may seal against lateral and/or inferior surfaces of the patient's nasal alae in use. The seal-forming structure 3100 may be configured to seal to any one or more of the patient's subnasale, inferior surfaces of the patient's nose between the patient's nares and upper lip and/or the patient's upper lip.

In some examples the seal-forming structure 3100 is configured to leave the patient's nose tip uncovered in use. The seal-forming structure 3100 may be configured to leave the patient's nasal bridge uncovered in use. In some forms the seal-forming structure 3100 may not seal to any surfaces of the patient's face superior to the lateral cartilage of the patient's nose (identified in FIG. 2H). In further forms, the seal-forming structure 3100 may not seal to any surfaces of the patient's face superior to the greater alar cartilage of the patient's nose (also identified in FIG. 2H). The seal-forming structure 3100 may be configured not to engage the bridge of the patient's nose in use. In some examples, the seal-forming structure 3100 may be configured to not engage the patient's nose superior to the pronasale in use. The patient interface 3000 may be configured to leave the patient's mouth uncovered in use.

FIGS. 8A-8H show the cushion module 3150 in isolation and FIGS. 9A-9H show the cushion module 3150 with certain portions identified. FIGS. 19A-19F, 25A-25I, 26A-26I, 30A-30E, 31A-31D and 32A-32D show cushion modules 3150 according to further examples of the present technology. The connectors 3214 are not shown in FIG. 9A-9H or 19A-19F. Features of cushion modules 3150 according to these and other examples of the present technology are described below.

5.3.3.8.1 Central Portion

The seal-forming structure 3100 comprises a central portion 3111 configured to seal in use to the patient's face at inferior portions of the patient's nose. In some examples of the present technology, the central portion 3111 is configured to seal in use against at least the patient's pronasale, nasal alae and lip superior. The central portion 3111 may be configured to seal to an inferior periphery of the patient's nose in use surrounding the patient's nares and against the patient's lip superior. The central portion 3111 is provided to a posterior side of the seal-forming structure 3100. The central portion 3111 may be bisected by a plane that is parallel to the patient's sagittal plane in use. FIGS. 9A-9H, 11A, 11B, 19A-19F, 25A-25I, 26A-26I, 30A-30E, 31A-31D and 32A-32D show examples of seal-forming structures 3100 having a central portion 3111 among other portions.

Most of the contact with the patient's nose may be made by the central portion 3111. Some contact may also be made by mid-lateral portions 3121, which are described below. In some examples, a majority of the seal formed by the seal-forming structure 3100 to the inferior periphery of the patient's nose may be made by the central portion 3111.

It will be appreciated that the actual amount of contact made by the seal-forming structure 3100 to the patient's face will depend on the particular implementation of the present technology and the anatomy of a particular patient, among other things, such as the way the patient has setup the patient interface.

The cushion module 3150 comprises two holes 3272 configured to allow a flow of air at therapeutic pressure to be delivered to the patient's nares. The holes 3272 are identified in FIGS. 8D-8F. Each hole 3272 aligns in use with a respective nare of the patient. In some examples the cushion module 3150 may comprise a single hole 3272 configured to allow the flow of air to be delivered to both nares of the patient. The holes 3272 are formed in the seal-forming structure 3100 of cushion module 3150. In some examples, the holes 3272 are formed in the central portion 3111 of the seal-forming structure 3100.

In some examples, the central portion 3111 may comprise a wall thickness of between 0.15 mm and 0.4 mm. In some examples, the wall thickness of the central portion 3111 may be between 0.2 mm and 0.35 mm. In some examples the wall thickness of the central portion 3111 may be substantially 0.25 mm.

5.3.3.8.1.1 Lip Superior Portion

In one form, the patient interface 3000 comprises a seal-forming structure 3100 that forms a seal in use on an upper lip region (that is, the lip superior) of the patient's face. In one form, the seal-forming structure 3100 includes a saddle-shaped region constructed to form a seal in use on an upper lip region of the patient's face.

In the examples shown in FIGS. 9A-9H, 19A-19F, 25A-25I, 26A-26I, 30A-30E, 31A-31D and 32A-32D the seal-forming structure 3100 also comprises a lip superior portion 3116. The lip superior portion 3116 may be provided within the central portion 3111 and may make contact with inferior surfaces of the patient's nose along with the patient's lip superior.

In some examples the lip superior portion 3116 has the same stiffness as the rest of the central portion 3111. The cushion module 3150 shown in FIGS. 9A-9H, includes a seal-forming structure 3100 in which the lip superior portion 3116 and other portions of the central portion 3111 have substantially the same stiffness.

The central portion 3111 and the lip superior portion 3116 thereof may have a lower stiffness than most or all other portions of the seal forming structure 3100. In some examples of the present technology the lower stiffness is provided by a lower wall thickness than other portions of the seal forming structure 3100. The pronasale, the inferior surfaces of the patient's nose and the lip superior, can have complex geometry and can also be very sensitive to pressure. Accordingly, it is advantageous for the areas of the plenum chamber 3200 that will contact or seal against these locations to be flexible and compliant, to avoid exerting excessive pressure on the face at these regions.

A low stiffness of certain portions of the seal-forming structure 3100, which may be provided by a low wall thickness, enables the seal-forming structure 3100 to readily deform to seal against the surfaces on the underside of the patient's nose, e.g., against the pronasale towards the anterior direction, the nasal ala on either lateral side and the lip superior.

In some examples of the present technology, the central portion 3111 may have a greater stiffness in the lip superior portion 3116 than in other regions of the central portion 3111. For example, the lip superior portion 3116 may be stiffer than the portion of the central portion 3111 surrounding the holes 3272. FIGS. 25A-25I show a cushion module 3150 having a lip superior portion 3116 which is stiffer than other portions of the central portion 3111. The greater stiffness may be provided by a greater wall thickness.

The cushion module 3150 shown in FIGS. 25A-25I is wider than the cushion modules 3150 shown in FIGS. 9A-9H. While the lip superior portion 3116 of the cushion module 3150 shown in FIGS. 9A-9H has a wall thickness that is the same as the wall thickness of adjacent portions of the central portion 3111. The lip superior portion 3116 of the cushion module 3150 shown in FIGS. 25A-25I has a wall thickness greater than the wall thickness of adjacent portions of the central portion 3111. Because the cushion module 3150 shown in FIGS. 25A-25I and its lip superior portion 3116 are wider than the other cushion modules 3150, the lip superior portion 3116 may be more susceptible to buckling or creasing due to its increased width. Extra thickness in the lip superior portion 3116 of the cushion module 3150 may reduce the susceptibility of bucking and may result in good stability in use.

5.3.3.8.1.2 Anterior and Posterior Portions of the Lip Superior Portion

In some examples of the present technology, such as the example shown in FIGS. 19A-19F and 22A and the examples shown in FIGS. 25A-25I, 26A-26I, 30A-30E and 31A-31D the lip superior portion 3116 comprises an anterior portion 3133 and a posterior portion 3134. The anterior portion 3133 is located adjacent the chassis portion 3210 and may be posterior to the chassis portion 3210 or at least posterior to a central portion of the chassis portion 3210, since the chassis portion 3210 curves towards a posterior direction on either lateral side of the chassis portion 3210. The posterior portion 3134 is configured to seal in use against the patient's lip superior.

The anterior portion 3133 of the lip superior portion 3116 may have a stiffness greater than a stiffness of the posterior portion 3134 of the lip superior portion 3116. In the examples shown in FIGS. 19A-19F, 22A, 25A-26I, 26A-26I, 30A-30E and 31A-31D, the greater stiffness is provided by a greater wall thickness of the seal-forming structure 3100. In these examples, the anterior portion 3133 of the lip superior portion 3116 has a thickness greater than a thickness of the posterior portion 3134 of the lip superior portion 3116. In other examples of the present technology, the cushion module 3150 may comprise a rigidiser provided to the anterior portion 3133 of the lip superior portion 3116 to provide an increased stiffness. The rigidiser may be a part formed from a stiffer material than other portions of the seal-forming structure 3100 and may be overmoulded to the anterior portion 3133.

The thickness of the posterior portion 3134 of the lip superior portion 3116 may the same thickness as that of one or more portions of the central portion 3111 adjacent to the lip superior portion 3116. In the examples shown in FIGS. 19A-19F and 26A-26I, the thickness of the posterior portion 3134 is the same as the thickness of the rest of the central portion 3111.

In other examples, the thickness of the posterior portion 3134 of the lip superior portion 3116 may be greater than the thickness of one or more portions of the central portion 3111 adjacent to the lip superior portion 3116. In the example shown in 25A-25I, the thickness of the posterior portion 3134 is greater than other portions of the central portion 3111.

The thickness of the posterior portion 3134 of the lip superior portion 3116 may be in the range of 0.1 mm to 1 mm, such as between 0.2 mm-0.8 mm, 0.3 mm-0.7 mm, 0.4 mm-0.6 mm, 0.15 mm-0.35 mm or 0.2 mm-0.3 mm. In particular examples the thickness of the posterior portion 3134 may be 0.25 mm or 0.5 mm. In the examples illustrated in FIGS. 19A-19F, 26A-26I, 30A-30E and 31A-31D, the posterior portion 3134 has a thickness of 0.25 mm. In the example illustrated in FIGS. 25A-25I, the thickness of the posterior portion 3134 is 0.5 mm.

The thickness of the anterior portion 3133 of the lip superior portion 3116 may be in the range of 0.4 mm-2 mm, such as between 0.5 mm-1.6 mm, 0.9 mm-1.3 mm, or 1.4 mm-1.6 mm. In particular examples the thickness of the anterior portion 3133 may be 1.5 mm, 1.2 mm, 1.15 mm or 0.5 mm. In the example illustrated in FIGS. 19A-19F, the thickness of the anterior portion 3133 of the lip superior portion 3116 is 1.5 mm. In the example illustrated in FIGS. 31A-31D, the thickness of the anterior portion 3133 is 1.2 mm and in the examples illustrated in FIGS. 25A-25I and 26A-26I, the thickness of the anterior portion 3133 is 1.15 mm. In the example shown in FIGS. 30A-30E, the anterior portion 3133 of the lip superior portion 3116 is 0.5 mm.

As described below in more detail, the seal-forming structure 3100 may comprise a pair of lateral posterior regions 3141 on respective lateral posterior sides of the lip superior portion 3116. In the example illustrated in FIGS. 19A-19F and 22A, the thickness of the posterior portion 3134 of the lip superior portion 3116 is less than a thickness of the lateral posterior regions 3141. In particular, the thickness of the posterior portion 3134 of the lip superior portion 3116 is less than the thickness of both a decoupling portion 3142 and a peripheral portion 3143 of each lateral posterior region 3141. The decoupling portion 3142 and peripheral portion 3143 are described in detail below.

In the example illustrated in FIGS. 19A-19F, the thickness of the anterior portion 3133 of the lip superior portion 3116 is substantially the same as a thickness of the lateral posterior regions 3141. In particular, the thickness of the anterior portion 3133 of the lip superior portion 3116 is substantially the same as the thickness of the peripheral portions 3143 of the lateral posterior regions 3141. The thickness of the anterior portion 3133 of the lip superior portion 3116 is in this example greater than the thickness of the decoupling portion 3142. The anterior portion 3133 of the lip superior portion 3116 may be contiguous with the lateral posterior regions 3141.

In the examples illustrated in FIGS. 25A-25I and 26A-26I, the thickness of the anterior portion 3133 of the lip superior portion 3116 is substantially the same as a thickness of the lateral posterior regions 3141. In particular, the thickness of the anterior portion 3133 is substantially the same as a posterior portion of each lateral posterior region 3141. An anterior portion of each lateral posterior region 3141 may have a greater thickness then the anterior portion 3133 of the lip superior portion 3116.

As shown in FIGS. 19A-19F, 22A, 25A-25I, 26A-26I, 30A-30E and 31A-31D, the boundary between the anterior portion 3133 and the posterior portion 3134 of the lip superior portion 3116 is curved with the central part of the curve being more anterior than the ends of lateral portions of the curve. This boundary may be curved to correspond approximately to the curvature of the patient's lip superior. The cushion module 3150 may comprise a junction between the anterior portion 3133 of the lip superior portion 3116 and the chassis portion 3210. This junction may be curved. The curvature of this junction may have a larger radius of curvature than the boundary between the anterior portion 3133 and the posterior portion 3134 of the lip superior portion 3116. This junction may be a portion of a longer junction between the chassis portion 3210 and the seal-forming structure 3100. In other examples the boundary between the anterior portion 3133 and the posterior portion 3134 of the lip superior portion 3116 may comprise a more gradual curve or may be straight.

The difference in thickness between the anterior portion 3133 and the posterior portion 3134 of the lip superior portion 3116 may be produced by a sharp or stepped change in thickness. The change in thickness may be produced by a step formed in the material forming the seal-forming structure 3100, the step being formed in an internal surface of the seal-forming structure 3100.

The greater thickness in the anterior portion 3133 with respect to the posterior portion 3134 of the lip superior portion 3116 may advantageously provide additional crease resistance to the seal-forming structure 3100 than if these portions had the same thickness as each other and/or the rest of the central portion 3111. The anterior portion 3133 may prevent or at least resist creasing and the seal-forming structure 3100 proximate the junction between the seal-forming structure 3100 and the chassis portion 3210. The increased thickness of the anterior portion 3133 may also stiffen the chassis portion 3210 proximate the lip superior portion 3116 and may improve dynamic seal at the upper lip (e.g. improve the stability of the seal formed with the patient's upper lip during movement of the patient's head).

5.3.3.8.1.3 Central Saddle Portion

The central portion 3111 is contiguous with a central anterior portion 3115 in this example. The central anterior portion 3115 is an anterior-facing portion of the seal-forming structure 3100. In use the central anterior portion 3115 may be located proximate and inferior to the patient's pronasale.

In the examples shown in FIGS. 9A-9H and 19A-19F, the seal-forming structure 3100 has a central saddle portion 3112 which may seal to anterior or inferior areas of the patient's pronasale in addition to the central portion 3111. The central saddle portion 3112 or a portion thereof comprises the same or similar low stiffness as the central portion 3111 and central anterior portion 3115, in this example. The central saddle portion 3112 connects the central portion 3111 and the central anterior portion 3115. In the examples shown in FIGS. 25A-25I and 26A-26I the seal-forming structure 3100 may also have a central saddle portion 3112 (shown in FIGS. 25A and 26A). The central saddle portion 3112 in these examples has less curvature than the central saddle portion 3112 of the seal-forming structures 3100 shown in FIGS. 9A-9H and 19A-19F. In these examples the central portion 3111 or a central saddle portion 3112 may seal to inferior and/or anterior surfaces of the patient's pronasale.

The central portion 3111 of the seal-forming structure 3100 may be configured to inflate to conform to inferior surfaces and periphery of the patient's nose. The thin wall of the seal-forming structure 3100 in the superior-facing central portion 3111 is advantageous in creating a good seal to the complex geometry under and around the nose. The thin wall can deform and inflate under pressure from breathable gas in the plenum chamber 3200, conforming to the surfaces of the patient's face to create an effective and yet comfortable seal.

While there is an advantage for comfort in keeping the wall thickness low in the regions configured to contact the sensitive pronasale and lip superior regions, in examples of the present technology the wall thickness in these regions is not reduced to the extent that the seal-forming structure 3100 is no longer able to maintain a stable seal to the patient's face. If the wall thickness is too low in these regions, the seal-forming structure 3100 could be prone to creasing, which can break the seal and create a leak path through which air can flow to the surroundings between the patient's face and the cushion.

5.3.3.8.1.4 Central Anterior Portion

In some examples of the present technology, the central anterior portion 3115 comprises a superior portion 3114 and an inferior portion 3113, as shown in FIGS. 19A-19F and 21A-21B.

The central anterior portion 3115 is on an anterior side of the seal-forming structure 3100, which may be a non-patient contact side. It is located proximate and inferior to the patient's pronasale in use. The central anterior portion 3115 may be at least partially anterior facing. For example, the central anterior portion 3115 may comprise an at least partially anterior-facing surface. At least a majority of the central anterior portion 3115 may be on an anterior side of the seal-forming structure 3100. A portion of the central anterior portion 3115 may be configured not to contact the patient's face in use. The inferior portion 3113 of the central anterior portion 3115 may be configured not to contact the patient's face in use. In some examples the superior portion 3114 may be configured not to contact the patient's face in use.

In the examples of the present technology shown in FIGS. 19A-19F and 21A-21B, the inferior portion 3113 of the central anterior portion 3115 has a stiffness greater than a stiffness of the superior portion 3114 of the central anterior portion 3115. In this example the inferior portion 3113 of the central anterior portion 3115 has a wall thickness greater than a wall thickness of the superior portion 3114 of the central anterior portion 3115. The inferior portion 3113 may also be known as a rigidising portion or rigidising band. The inferior portion 3113 may span across an anterior side of the seal-forming structure 3100. The inferior portion 3113 may be provided adjacent a junction between the seal-forming structure 3100 and the chassis portion 3210.

The central anterior portion 3115 is an otherwise thin and relatively flexible portion of the seal-forming structure 3100 in comparison to other portions of the seal-forming structure. For example, in the examples shown in FIGS. 9A-9H and 19A-19F, the central anterior portion 3115 is one of the thinnest and most flexible portions of the seal-forming structure. Being flexible, the central anterior portion 3115 allows the seal-forming structure 3100 to conform to the inferior periphery of the patient's nose. However, due to high flexibility the central anterior portion 3115 may be prone to creasing. The inferior portion 3113 of the central anterior portion 3115 is stiffer than the superior portion 3114 to provide support to the central anterior portion 3115. The inferior portion 3113 of the central anterior portion 3115 may provide crease resistance to the central anterior portion 3115.

In the examples shown in FIGS. 19A-19F and 22A-22B, the superior portion 3114 of the central anterior portion 3115 has substantially the same stiffness and wall thickness as the central portion 3111 on the posterior side of the seal-forming structure 3100.

In the examples shown in FIGS. 19A-19F and 22A-22B, the inferior portion 3113 of the central anterior portion 3115 comprises a portion of the seal-forming structure 3100 having a greater wall thickness than one or more adjacent portions of the seal-forming structure 3100. The inferior portion 3113 of the central anterior portion 3115 may have a wall thickness of between 0.3 mm and 1 mm. In some examples the inferior portion 3113 has a wall thickness of between 0.4 and 0.7 mm. In the example illustrated in FIGS. 19A-19F the inferior portion 3113 has a wall thickness of substantially 0.5 mm. The superior portion 3114 may have a wall thickness of between 0.1 mm and 0.5 mm, such as between 0.2 mm and 0.3 mm, or 0.25 mm in the example illustrated in FIGS. 19A-19F.

In other examples of the present technology, the inferior portion 3113 of the central anterior portion 3115 may comprise a rigidising member, a portion of the seal-forming structure formed from a stiffer material or another appropriate stiffening means.

As shown in FIG. 22A, the central anterior portion 3115 has a step change in thickness between the inferior portion 3113 and the superior portion 3114. In other examples the central anterior portion 3115 may comprise a taper in thickness between the inferior portion 3113 and the superior portion 3114.

More generally, any difference in thickness between two portions of the seal-forming structure 3100 or chassis portion 3210 exemplified herein by a step change in thickness may in other examples comprise a taper in thickness. Likewise any difference in thickness exemplified by a taper in thickness may in other examples comprise a step change in thickness.

In some examples of the present technology, an inferior portion 3113 having a greater stiffness and/or thickness than a superior portion 3114 may be provided to the central anterior portions 3115 of the cushion modules 3150 shown in FIGS. 25A-25I and 26A-26I. In the forms of these cushion modules 3150 illustrated in FIGS. 25A-25I and 26A-26I, the central anterior portion 3115 is of substantially uniform thickness.

5.3.3.8.2 Mid-Lateral Portions

As shown in FIGS. 9A-9H, 19A-19F, 25A-25I, 26A-26I, 30A-30E and 31A-31D the seal-forming structure 3100 may also comprise a pair of mid-lateral portions 3121. The mid-lateral portions 3121 may be configured to be located against or proximate the ala of the patient's nose in use. The mid-lateral portions 3121 may be provided to the posterior side of the seal-forming structure 3100. Each mid-lateral portion 3121 may be provided on a respective lateral side of the central portion 3111 and may each be configured to lie alongside a respective nasal ala of the patient's nose in use. As shown in FIGS. 9A-9H, 19A-19F, 25A-25G, 26A-26G, 30A-30E and 31A-31D, each of the mid-lateral portions 3121 may be located between the central portion 3111 and a lateral periphery of the seal-forming structure 3100.

As shown in FIGS. 9A, 9F and 19A in particular, each mid-lateral portion 3121 may have a crescent-like shape. Each mid-lateral portion 3121 comprises a medial boundary and a lateral boundary. Each medial boundary may comprise a three-dimensional curve (e.g. a space curve) which, from a perspective of moving generally anteriorly along the curve, curves towards an inferior and medial direction at the anterior side of the cushion module 3150 proximate the central saddle portion 3112. Each lateral boundary may also comprise a three-dimensional curve which, from a perspective of moving generally anteriorly along the curve, curves towards a medial direction at the anterior side of the cushion module 3150. The mid-lateral portions 3121 may comprise a surface curvature to follow curvature of the inferior periphery of the patient's nose.

As a result of the curvature of the boundaries of the mid-lateral portions 3121, each mid-lateral portions 3121 as a whole may comprise a curved shape which, from a perspective of moving generally anteriorly, curves towards a medial direction proximate the anterior side of the seal-forming structure 3100.

The curves of the mid-lateral portions 3121 and their boundaries may result in the mid-lateral portions 3121 following the shape of the inferior periphery of the patient's nose. The mid-lateral portions 3121 may be concave with respect to the patient's nose proximate the widest portion of the patient's nose (e.g. proximate the alar wings). Each mid-lateral portion 3121 may curve towards an inferior and/or medial direction proximate the posterior corner portions 3131 (described below) and/or lip superior portion 3116, from a perspective of moving along the curve of the mid-lateral portion in a generally posterior direction.

Each of the mid-lateral portions 3121 may extend such that one end is proximate the lip superior portion 3116 and the other end is proximate an anterior-most portion of the central portion 3111. In the examples shown in FIGS. 9A-9H and 19A-19F, one end of each of the mid-lateral portions 3121 extends to the central saddle portion 3112. The central saddle portion 3112 may be located between anterior-most portions of the mid-lateral portions. In this example, the anterior-most portion of each mid-lateral portion 3121 is pointed. An anterior junction between the medial boundary and lateral boundary of each mid-lateral portion 3121 comprises a pointed shape. The medial boundary and lateral boundary meet forming a pointed corner. In this example the anterior junction of the medial boundary and the lateral boundary of each mid-lateral portion 3121 tapers to a point.

In this example, the lateral boundary of each mid-lateral portion is located between a medial-facing side portion of the seal-forming structure 3100 and a lateral-facing side-portion of the seal-forming structure 3100. The seal-forming structure 3100 may comprise a superior ridge 3117 (shown in FIGS. 8A-8H) separating the medial- and posterior-facing side portions of the seal-forming structure 3100 from laterally- and anterior-facing side portions. The superior ridge 3117 may include the central saddle portion 3112. The lateral boundary of each mid-lateral portion 3121 may be located proximate the superior ridge 3117. The lateral boundary of each mid-lateral portion 3121 may be located proximate to, and medially from, the superior ridge 3117.

In the examples shown in FIGS. 25A-I and 26A-26I, the mid-lateral portions 3121 are approximately C-shaped, as shown in particular in FIGS. 25G and 26G. In these examples, the central anterior portion 3115 and central saddle portion 3112 is wider than in the examples shown in FIGS. 9A-9H and 19A-19F. As shown in FIGS. 25G and 26G the central saddle portion 3112 may comprise portions on the superior-facing (e.g. patient-contacting) portion of the seal-forming structure 3100 such that in the seal-forming structure 3100 there is a junction between the central saddle portion 3112, central portion 3111 and a respective one of the mid-lateral portions 3121.

The mid-lateral portions 3121 may be located around some or all of the inferior periphery of the patient's nose in use. For example, the mid-lateral portions 3121 may be configured to lie just outside of a patient's nose at the base of the nose, e.g., proximate or in contact with the ala.

The mid-lateral portions 3121 of the seal-forming structure 3100 may comprise a pair of exterior walls facing towards partially medial and partially superior directions (e.g., having external or exterior surfaces facing in medial and superior directions) and in some examples also partially posteriorly.

Each mid-lateral portion 3121 may have a stiffness greater than a stiffness of the central portion 3111. The seal-forming structure 3100 may comprise a greater wall thickness in the mid-lateral portions 3121 than in the central portion 3111. The greater wall thickness in the mid-lateral portions 3121 in comparison to the central portion 3111 may provide the greater stiffness of the mid-lateral portions 3121.

In some examples, the mid-lateral portions 3121 of the seal-forming structure 3100 reinforce the central portion 3111 of the seal-forming structure 3100. In further examples, the mid-lateral portions 3121 are configured to resist creasing in the seal-forming structure. This crease resistance is provided in the illustrated examples due to an increased thickness of the seal-forming structure 3100 in the mid-lateral portions. In some forms, the mid-lateral portions provide a barrier to creases and prevent leak paths forming in the seal-forming structure 3100. The mid-lateral portions 3121 may be configured to prevent creases in the central portion 3111 of the seal-forming structure 3100 from forming leak paths through which gas can leak through the crease from the interior of the plenum chamber 3200 to ambient.

Accordingly, the mid-lateral portions 3121 may act as a barrier to creases that closely follow the shape of the patient's nose, by being configured to lie at or proximate the edges of the patient's ala around the base of the nose.

Additionally, the mid-lateral portions 3121 may provide for flexible support against sideward loading on the plenum chamber 3200 to help prevent breaking the seal under lateral forces. The mid-lateral portions 3121 may be flexible to deform under lateral forces while being thicker than the central portion 3111 to support the central portion 3111 in sealed contact against the underside of the patient's nose.

5.3.3.8.2.1 Mid-Lateral Anterior Portions

On either side of the central anterior portion 3115 (discussed above) is a mid-lateral anterior portion 3125, in some examples of the present technology, such as in the cushion module 3150 shown in FIGS. 9A-9H, 19A-19F, 25A-25H, 26A-26H, 30A-30E and 31A-31D. The mid-lateral anterior portions 3125 may be located on an anterior side of the seal-forming structure 3100. Some contact with the patient's nose may be made by the central anterior portion 3115 and the mid-lateral anterior portions 3125, depending on anatomy and setup. These mid-lateral anterior portions 3125 have a wall thickness greater than the wall thickness of the mid-lateral portions 3121 on the posterior side of the central portion 3111. They also have a wall thickness greater than the central anterior portion 3115. The mid-lateral anterior portions 3125 may have a stiffness and/or wall thickness greater than the superior portion 3114 of the central anterior portion 3115. The mid-lateral anterior portions 3125 may have a stiffness and/or wall thickness greater than the inferior portion 3113 of the central anterior portion 3115.

In other examples, the mid-lateral anterior portions 3125 have substantially the same wall thickness as the mid-lateral portions 3121 on the patient-contacting side of the seal-forming structure 3100.

The mid-lateral anterior portions 3125 may each comprise a superior portion 3126 and an inferior portion 3127. The mid-lateral anterior portions 3125 may be at least partially anterior facing and at least partially laterally facing. For example, the mid-lateral anterior portions 3125 may each comprise a surface facing at least partially anteriorly and at least partially laterally. At least a majority of the mid-lateral anterior portions 3125 may be on an anterior side of the seal-forming structure 3100. A portion of each mid-lateral anterior portion 3125 may be configured not to contact the patient's face in use. The inferior portions 3127 of each mid-lateral anterior portion 3125 may be configured not to contact the patient's face in use. In some examples the superior portion 3126 may be configured not to contact the patient's face in use.

The inferior portions 3127 of each mid-lateral anterior portion 3125 may have a stiffness greater than a stiffness of the superior portions 3126 of the mid-lateral anterior portion 3125. As shown in FIGS. 19A-19F and FIG. 22B, the cushion module 3150 according to some examples comprises mid-lateral anterior portions 3125 each having an inferior portion 3127 that comprises a wall thickness greater than a wall thickness of a respective superior portion 3126. The cushion modules shown in FIGS. 30A-30E and 31A-31D also include mid-lateral anterior portions 3125 having superior portions 3126 and inferior portions 3127. The mid-lateral anterior portions 3125 of the cushion modules 3150 shown in FIGS. 30A-30E and 31A-31D are described separately below, but unless the context requires otherwise, features of the mid-lateral anterior portions 3125 described with reference to FIGS. 19A-19F and FIG. 22B may be applied to the cushion modules 3150 shown in FIGS. 30A-30E and 31A-31D, and vice versa. The cushion module 3150 shown in FIGS. 32A-32D may also be provided with mid-lateral anterior portions 3125 in some examples.

The stiffness of the inferior portions 3127 of the mid-lateral anterior portions 3125 may help increase the stability of the cushion module 3150 and the seal it makes to the patient's face during dynamic movements, for example when the patient moves while sleeping or in bed. The stiffness and thickness of the inferior portions 3127 may also provide greater resistance to excessive flaring out of the seal-forming structure 3100 resulting in leak paths through loss of contact with the patient's nose, due to the otherwise flexible nature of the seal-forming structure 3100. Finally, the stiffness of the inferior portions 3127 of the mid-lateral anterior portions 3125 may provide added torsion resistance. The inferior portions 3127 may prevent one side of the cushion module 3150 from twisting away from or with respect to the other side of the cushion module 3150, which could result in loss of contact with the patient's nose and leak paths. The inferior portions 3127 of the mid-lateral anterior portions 3125 and the chassis superior reinforcing portions 3220 may together provide the above advantages, in cushion modules 3150 in which both the stiffer inferior portions 3127 and the chassis superior reinforcing portions 3220 are provided.

In the example shown in FIGS. 19A-19F, each inferior portion 3127 of the mid-lateral anterior portions 3125 has a stiffness greater than the stiffness of the central portion 3111 of the seal-forming structure 3100. Each inferior portion 3127 also has a stiffness greater than the stiffness of the central anterior portion 3115 of the seal-forming structure 3100. Additionally, the stiffness of each inferior portion 3127 is greater than the stiffness of both the superior portion 3114 and the inferior portion 3113 of the central anterior portion 3115 of the seal-forming structure 3100. The stiffness of each inferior portion 3127 is also greater than the stiffness of the mid-lateral portions 3121 on the posterior side of the seal-forming structure 3100. The relatively higher stiffnesses and thicknesses of the superior portion 3126 and the inferior portion 3127 of the mid-lateral anterior portions 3125 may provide advantages as described above.

Each superior portion 3126 of the mid-lateral anterior portions 3125, in the example shown in FIGS. 19A-19F, has a greater stiffness than the stiffness of the central portion 3111. The stiffness of each superior portion 3126 is greater than the stiffness of the central anterior portion 3115 as well. In this example the stiffness of each superior portion 3126 is greater than the stiffness of each of the superior portion 3114 and the inferior portion 3113 of the central anterior portion 3115. In addition, the stiffness of each superior portion 3126 is greater than the stiffness of each of the mid-lateral portions 3121 on the posterior side of the seal-forming structure.

In the example shown in FIGS. 19A-19F, the greater stiffnesses are provided by greater wall thicknesses. In other examples the greater stiffnesses are provided by the application of stiffer materials and/or additional rigidising parts.

In the example shown in FIGS. 19A-19F, the inferior portion 3127 of each mid-lateral anterior portion 3125 is located adjacent the chassis portion 3210. That is, the mid-lateral anterior portion 3125 is directly superior to the junction between the chassis portion 3210 and the anterior side portion of the seal-forming structure 3100. The inferior boundary of each mid-lateral anterior portion 3125 is also a portion of the superior boundary of the chassis portion at an anterior side portion of the cushion module 3150. As described above, the chassis portion 3210 may comprise chassis superior reinforcing portions 3220. The inferior portions 3127 may have a wall thickness that is the same as the wall thickness of the chassis superior reinforcing portions 3220.

In some examples the inferior portions 3127 have a wall thickness between 1 mm and 3 mm. In some examples the wall thickness is between 1.2 mm and 2.5 mm or between 1.5 mm and 2 mm. In the example shown in FIGS. 19A-19F and 22B the inferior portions 3127 have a wall thickness of 1.7 mm.

In the example illustrated in FIGS. 19A-19F, the inferior portions 3127 of the mid-lateral anterior portions 3125 have a wall thickness that is substantially the same as the wall thickness of the anterior portions 3162 of the rigidising portions 3161 (described below). In such examples the inferior portions 3127 of the mid-lateral anterior portions 3125 may be considered contiguous with the rigidising portions 3161.

In some examples of the present technology, the seal-forming structure may comprise mid-lateral anterior portions 3125 having a tapering thickness from a greater thickness in an inferior portion to a lesser thickness in a superior portion of each mid-lateral anterior portion 3125. More generally, in examples of the present technology, any non-patient contacting portion of the seal-forming structure 3100 may have a thickness that tapers from a greater thickness in a region proximate the chassis portion 3210 to a lesser thickness proximate the central portion 3111.

5.3.3.8.2.2 Medial/Lateral Portions of Mid-Lateral Anterior Portions

In some examples of the present technology, the seal-forming structure 3100 of a cushion module 3150 may comprise mid-lateral anterior portions 3125 comprising medial portions 3128 and lateral portions 3129. In the cushion modules 3150 shown in FIGS. 30A-30E and 31A-31D, the seal-forming structure 3100 comprises a pair of mid-lateral anterior portions 3125 each comprising a medial portion 3128 and a lateral portion 3129, the lateral portion 3129 being located laterally of the medial portion 3128. In these particular examples the medial portion 3128 of each mid-lateral anterior portion 3125 has a stiffness greater than a stiffness of the lateral portion 3129 of the mid-lateral anterior portion 3125.

The stiffness of each of the medial portions 3128 of the mid-lateral anterior portions 3125 may be greater than a stiffness of the central anterior portion 3115. In these examples, the wall thickness of each medial portion 3128 is greater than the wall thickness of the central anterior portion 3115. The greater stiffness is provided by the greater thickness in this example. In other examples a greater stiffness may be provided by a rigidiser or by forming the medial portion 3128 from a stiffer material.

The medial portions 3128 may also have a greater stiffness than the mid-lateral portions 3121 on the patient-contacting side of the seal-forming structure 3100, or at least a greater stiffness than the central portion 3111. In the examples shown in FIGS. 30A-30E and 31A-31D, the medial portions 3128 have a greater wall thickness than the central portion 3111 and the mid-lateral portions 3121.

In some examples of the present technology, the mid-lateral anterior portions 3125 may each comprise a superior portion 3126 and an inferior portion 3127. The lateral portions 3129 of the mid-lateral anterior portions 3125 may comprise the superior portion 3126 and the inferior portion 3127. In the examples shown in FIGS. 30A-30E and 31A-31D, each the mid-lateral anterior portions 3125 comprises a superior portion 3126 and an inferior portion 3127, the inferior portion 3127 having a stiffness greater than the superior portion 3126. The greater stiffness may be provided by a greater wall thickness. In this example, the wall thickness of the inferior portion 3127 of the lateral portion 3129 of each mid-lateral portion 3125 is greater than the wall thickness of the superior portion 3126.

Additionally, the wall thickness of the medial portion 3128 is greater than the wall thickness of the superior portion 3126 of the lateral portion 3129 of each mid-lateral anterior portion 3125. In this example, the wall thickness of the medial portion 3128 is less than the wall thickness of the inferior portion 3127 of the lateral portion 3129 each mid-lateral anterior portion 3125. The differences in wall thickness may provide corresponding differences in stiffnesses.

The additional stiffness and/or thickness provided to the medial portion 3128 may resist creasing in the central and/or mid-lateral portions of the anterior side of the seal-forming structure. Additionally, the additional stiffness and/or thickness may help provide structure to the seal-forming structure 3100 to maintain its overall shape in use, allowing patient-contacting surfaces of the seal-forming structure 3100 to be thin to conform to the surfaces of the patient's face and create a good seal in use. The additional stiffness and/or thickness in the medial portion 3128 may be particularly advantageous in cushion modules 3150 of the present technology in which the chassis portion 3210 is formed from a flexible material, such as from silicone. The inferior portion 3127 of the lateral portion 3129 of each mid-lateral anterior portion 3125 may provide similar advantages to the cushion module 3150.

Also as illustrated in FIGS. 30A-30E and 31A-31D, the chassis portion 3210 of the cushion module 3150 may comprise a pair of chassis superior reinforcing portions 3220 each provided to a respective lateral and anterior side of the chassis portion 3210, the chassis superior reinforcing portions 3220 each having a greater stiffness than one or more adjacent portions of the chassis portion 3210. The chassis superior reinforcing portions 3220 are described in greater detail above.

In these examples the chassis superior reinforcing portions 3220 are located adjacent the seal-forming structure 3100 and, in this particular example, are each located adjacent a respective one of the mid-lateral anterior portions 3125. Each chassis superior reinforcing portion 3220 in the cushion modules 3150 shown in FIGS. 30A-30E and 31A-31D is located adjacent a respective one of the inferior portions 3127 of the mid-lateral anterior portions 3125.

Each chassis superior reinforcing portion 3220 may comprise a greater wall thickness than a wall thickness of the mid-lateral anterior portions 3125. The greater wall thickness provides the greater stiffness in this particular example. Additionally, each chassis superior reinforcing portion 3220 may comprise a greater wall thickness than the wall thickness of the medial portions 3128 of the mid-lateral anterior portions 3125.

In the example shown in FIGS. 30A-30E, the central anterior portion 3115 comprises a wall thickness of 0.6 mm and, in other examples of the present technology, may comprise a wall thickness between 0.25 mm and 1 mm. The medial portions 3128 of the mid-lateral anterior portions 3125 may comprise a wall thickness of 1.4 mm and, in other examples, may comprise a thickness between 1 mm and 2 mm. The inferior portions 3127 may comprise a thickness of 2.25 mm and, in other examples, may comprise a thickness between 1 mm and 3 mm. The superior portions 3126 may comprise a thickness of 0.7 mm and, in other examples may comprise a thickness between 0.2 mm and 2 mm. The chassis superior reinforcing portions 3220 in this example may have a thickness of 2.1 mm and, in other examples may comprise a thickness between 1.5 and 3.5 mm. In further examples the thicknesses of the seal-forming structure 3100 may differ from the above exemplary thicknesses.

It is to be understood that the cushion module 3150 may comprise gradual changes in thickness between adjacent portions, such as a tapering thickness rather than a stepped change in thickness. A smooth transition may help prevent creases and leak paths forming when a load is applied. Sudden changes in geometry may also be more likely to be felt by the patient while a smoother change is more comfortable. Smooth changes may also make the cushion module 3150 easier to mould and demould.

5.3.3.8.2.3 Mid-Lateral Inferior Portions

In some examples of the present technology the seal-forming structure 3100 may comprise a pair of mid-lateral inferior portions 3122. As illustrated in particular in FIGS. 30E and 31D, the cushion modules 3150 shown in FIGS. 30A-30E and 31A-31D include mid-lateral inferior portions 3122 located on either lateral inferior side of the lip superior portion 3116 of the central portion 3111. The mid-lateral inferior portions 3122 may be lateral to the lip superior portion 3116 and medial to lateral posterior regions 3141. The mid-lateral inferior portions 3122 may be adjacent the chassis portion 3210, for example provided adjacent the boundary between the seal-forming structure 3100 and the chassis portion 3210 on the inferior side of the chassis portion 3210. The mid-lateral inferior portions 3122 may be adjacent to the chassis inferior reinforcing portions 3221 of the chassis portion 3210. The chassis inferior reinforcing portions 3221 are described in greater detail above.

Also as shown in FIGS. 30E and 31D each mid-lateral inferior portion 3122 in these examples comprises an anterior portion 3123 and a posterior portion 3124. The anterior portion 3123 is provided adjacent the chassis portion 3210. The posterior portion 3124 is provided posterior to the anterior portion 3123 (e.g. closer to the patient's face in use). As shown by way of example in FIG. 30E, the chassis inferior reinforcing portions 3221 and the anterior portions 3123 of the mid-lateral inferior portions 3122 may be substantially equal in length. Additionally, the ends of the chassis inferior reinforcing portions 3221 may be aligned with the ends of the mid-lateral inferior portions 3122.

5.3.3.8.2.3.1 Anterior Portions of Mid-Lateral Inferior Portions Stiffer than Posterior Portions of Mid-Lateral Inferior Portions In the examples of the present technology shown in FIGS. 30A-30E and 31A-31D, the anterior portions 3123 of the mid-lateral inferior portions 3122 are stiffer than the posterior portions 3124 of the mid-lateral inferior portions 3122. In the examples illustrated in FIGS. 30A-30E and 31A-31D, the anterior portions 3123 of the mid-lateral inferior portions 3122 each have a thickness that is greater than a thickness of the posterior portions 3124 of the mid-lateral inferior portions 3122. In these examples the greater stiffness of the anterior portions 3123 is provided by the greater thickness. In other examples the greater stiffness may be provided by a rigidiser attached to the seal-forming structure 3100 in the region of the anterior portions 3123. In further examples the anterior portions 3123 may be formed from a stiffer material than the posterior portions 3124.

5.3.3.8.2.3.2 Anterior Portion of Lip Superior Portion Stiffer than Posterior Portion of Lip Superior Portion As described above, the lip superior portion 3116 of the cushion module 3150 shown in FIGS. 30A-30E includes an anterior portion 3133 adjacent the chassis portion 3210 and a posterior portion 3134 configured to seal in use against the patient's lip superior. In this example, the anterior portion 3133 of the lip superior portion 3116 is stiffer than the posterior portion 3134 of the lip superior portion. More particularly, in this example the anterior portion 3133 of the lip superior portion 3116 has a thickness greater than a thickness of the posterior portion 3134 of the lip superior portion 3116. The greater stiffness is in this example provided by the greater thickness. In other examples the greater stiffness may be provided by a rigidiser attached to the seal-forming structure 3100 in the region of the anterior portion 3133 of the lip superior portion 3116. In further examples the anterior portion 3133 may be formed from a stiffer material than the posterior portion 3134.

5.3.3.8.2.3.3 Anterior Portions of Mid-Lateral Inferior Portions Stiffer than Anterior Portion of Lip Superior Portion The anterior portions 3123 of the mid-lateral inferior portions 3122 may be stiffer than the anterior portion 3133 of the lip superior portion 3116. In the examples shown in FIGS. 30A-30E and 31A-31D, the thickness of the anterior portions 3123 of the mid-lateral inferior portions 3122 is greater than the thickness of the anterior portion 3133 of the lip superior portion 3116. The greater stiffness is in this example provided by the greater thickness. In other examples the greater stiffness may be provided by a rigidiser attached to the seal-forming structure 3100 in the region of the anterior portions 3123. In further examples the anterior portions 3123 of the mid-lateral inferior portions 3122 may be formed from a stiffer material than the anterior portion 3133 of the lip superior portion 3116.

5.3.3.8.2.3.4 Anterior Portions of Mid-Lateral Inferior Portions Stiffer than Posterior Portion of Lip Superior Portion The anterior portions 3123 of the mid-lateral inferior portions 3122 may be stiffer than the posterior portion 3134 of the lip superior portion 3116. In the examples shown in FIGS. 30A-30E and 31A-31D, the thickness of the anterior portions 3123 of the mid-lateral inferior portions 3122 is greater than the thickness of the posterior portion 3134 of the lip superior portion 3116. In this example, the greater stiffness is provided by the greater thickness. In other examples the greater stiffness may be provided by a rigidiser attached to the seal-forming structure 3100 in the region of the anterior portions 3123. In further examples the anterior portions 3123 of the mid-lateral inferior portions 3122 may be formed from a stiffer material than the posterior portion 3134 of the lip superior portion 3116.

5.3.3.8.2.3.5 Posterior Portions of Mid-Lateral Inferior Portions Stiffer than Posterior Portion of Lip Superior Portion The posterior portions 3124 of the mid-lateral inferior portions 3122 may be stiffer than the posterior portion 3134 of the lip superior portion 3116. In the examples shown in FIGS. 30A-30E and 31A-31D, the thickness of the posterior portions 3124 of the mid-lateral inferior portions 3122 is greater than the thickness of the posterior portion 3134 of the lip superior portion 3116. The greater stiffness is in this example provided by the greater thickness. In other examples the greater stiffness may be provided by a rigidiser attached to the seal-forming structure 3100 in the region of the posterior portions 3124. In further examples the posterior portions 3124 of the mid-lateral inferior portions 3122 may be formed from a stiffer material than the posterior portion 3134 of the lip superior portion 3116.

In some examples of the present technology, the thickness of the posterior portions 3124 of the mid-lateral inferior portions 3122 is substantially the same as the thickness of the anterior portion 3133 of the lip superior portion 3116.

The greater stiffness and/or thickness of the anterior portions 3123 of the mid-lateral inferior portions 3122, relative to the posterior portions 3124 of the mid-lateral inferior portions 3122, has been found to facilitate a cushion module 3150 which may form a particularly robust seal to the patient's face in use. Likewise the applicant has found that the greater stiffness and/or thickness of the anterior portions 3123 of the mid-lateral inferior portions, relative to the posterior portion 3134 of the lip superior portion 3116, may facilitate a particularly robust seal in use. Cushion modules 3150 according to other examples of the present technology which do not incorporate the above described relative stiffnesses/thicknesses, may also provide an acceptably robust seal in use.

5.3.3.8.2.3.6 Exemplary Thicknesses of Seal-Forming Structure in Mid-Lateral Inferior Portions In the example illustrated in FIGS. 30A-30E, the anterior portion 3123 of each mid-lateral inferior portion 3122 comprises a thickness of 3 mm and, in other examples, may comprise a thickness of between 1.5 mm and 4.5 mm. The posterior portion 3124 of each mid-lateral inferior portion 3122 comprises a thickness of 1.35 mm and, in other examples, may comprise a thickness of between 0.75 mm and 2 mm. The posterior portion 3134 of the lip superior portion 3116 comprises a thickness of 0.25 mm. The anterior portion 3133 of the lip superior portion 3116 comprises a thickness of 0.5 mm. In other examples, the thicknesses in the seal-forming structure 3100 may differ from the above exemplary thicknesses. Other suitable thicknesses for the anterior portion 3133 and the posterior portion 3134 of the lip superior portion 3116 are described above in description of the central portion 3111.

It is to be understood that the cushion module 3150 may comprise gradual changes in thickness between adjacent portions, such as a tapering thickness rather than a stepped change in thickness. A smooth transition may help prevent creases and leak paths forming when a load is applied. Sudden changes in geometry may also be more likely to be felt by the patient while a smoother change is more comfortable. Smooth changes may also make the cushion module 3150 easier to mould and demould.

For example, the seal-forming structure 3100 may comprise a gradual transition in thickness (e.g. a taper) between the anterior portion 3133 and the posterior portion 3134 of the lip superior portion 3116. The seal-forming structure 3100 may comprise a gradual change in thickness, rather than a stepped change, between any two or more of the anterior portion 3133 of the lip superior portion 3116, the posterior portion 3134 of the lip superior portion 3116, the anterior portions 3123 of the mid-lateral inferior portions 3122, the posterior portions 3124 of the mid-lateral inferior portions 3122, the chassis inferior reinforcing portions 3221 and the lateral posterior portion 3141.

In the example shown in FIGS. 31A-31D, the anterior portion 3123 of each mid-lateral inferior portion 3122 comprises a thickness of 2.4 mm. The posterior portion 3124 of each mid-lateral inferior portion 3122 comprises a thickness of 1.35 mm. The posterior portion 3134 of the lip superior portion 3116 comprises a thickness of 0.25 mm. The anterior portion 3133 of the lip superior portion 3116 comprises a thickness of 1.2 mm. In other examples, the thicknesses in the seal-forming structure 3100 may differ from the above exemplary thicknesses.

5.3.3.8.3 Posterior Corner Portions

In some examples, such as those shown in FIGS. 9A-9H, 19A-19F, 25A-25I, 26A-26I, 30A-30E and 31A-31D, the seal-forming structure 3100 comprises posterior corner portions 3131. The posterior corner portions 3131 are portions of the seal-forming structure 3100 that support the cushion module on the patient's face. The posterior corner portions 3131 may advantageously fit into the space between the patient's nose and nasolabial sulci in use, assisting in preventing leaks through this region. The posterior corner portions 3131 may be particularly thick portions of the seal-forming structure 3100, providing support to the plenum chamber 3200 on the patient's face.

The posterior corner portions 3131 may be configured to resist creasing in the seal-forming structure 3100. The crease resistance may be provided by a greater stiffness and/or thickness of the posterior corner portions 3131 than adjacent portions of the seal-forming structure 3100. For example, if a crease occurs in the central portion 3111 of the seal-forming structure 3100, the posterior corner portions 3131 may limit the size of the crease to prevent it from continuing past the seal forming surface (e.g. past the periphery of the patient's nose).

In examples of the present technology, a greater stiffness in regions of the seal-forming structure 3100 compared to other regions of the seal-forming structure 3100 may be provided by a greater wall thickness, a stiffer material (e.g., higher durometer silicone or other material), a reinforcing structure such as a tie or a rib, an undercushion, portion of a chassis, or the like, across various examples of the present technology.

5.3.3.8.4 Lateral Posterior Regions

The seal-forming structures 3100 of the plenum chambers 3200 shown in FIGS. 9A-9H, 19A-19F, 25A-25I, 26A-26I, 31A-31D and 32A-32D also comprise a pair of lateral posterior regions 3141. The lateral posterior regions 3141 are provided on respective lateral posterior sides of the seal-forming structure 3100. The lateral posterior regions 3141 may be provided to non-patient contacting sides of the seal-forming structure 3100. The lateral posterior regions 3141 may each face at least partially in a lateral direction.

In some examples, the lateral posterior regions 3141 may also comprise sub-regions which face in one or more of an at least partially inferior, an at least partially posterior, an at least partially superior, an at least partially anterior and an at least partially medial direction, in addition to facing in a lateral direction. In the examples illustrated in FIGS. 9A-9H, 19A-19F, 25A-25I, 26A-26I, 30A-30E, 31A-31D and 32A-32D, the posterior corner portions 3131 are provided within the lateral posterior regions 3141.

The lateral posterior regions 3141 may comprise a stiffness greater than a stiffness of the central portion 3111. The thickness of the lateral posterior regions 3141 may be greater than the thickness of the central portion 3111. The greater thickness of the lateral posterior regions 3141 may provide the greater stiffness. The lateral posterior regions 3141 may comprise sufficient stiffness to provide form to the seal forming structure 3100 and support the more flexible portions of the seal forming structure 3100, such as the central portion 3111.

As shown in FIGS. 9A-9H, 19A-19F, 25A-25I, 26A-26I, 30A-30E and 31A-31D, the lateral posterior regions 3141 may be located adjacent to the laterally projecting connection portions 3212 of the chassis portion 3210 of the cushion module 3150, for example medially and/or posteriorly adjacent to the laterally projecting connection portions 3212. In some examples the lateral posterior regions 3141 may be located at least partially superior to the laterally projecting connection portions 3212.

Each of the lateral posterior regions 3141 may partially encircle a respective one of the laterally projecting connection portions 3212, for example having a shape that follows the curvature of the laterally projecting connection portion 3212. Each of the lateral posterior regions 3141 may comprise an anterior boundary matching the posterior shape of a respective laterally projecting connection portion 3212. Each of the lateral posterior regions 3141 may be located in the seal-forming structure 3100 at a junction between the seal-forming structure 3100 and a respective laterally projecting connection portion 3212. Each of the lateral posterior regions 3141 may be provided at least partially around a respective one of the laterally projecting connection portions 3212.

Each lateral posterior region 3141 may be approximately C- or crescent-shaped when viewed from the side, as shown in FIGS. 9B, 19B, 25E, 26E, 30D and 31C.

As shown in FIGS. 9A, 9C, 9D, 19A, 19C, 19D, 25D, 25F, 25G, 26D, 26F and 26G, each lateral posterior region 3141 extends medially across the seal-forming structure 3100 in the posterior corner portion 3131 from a lateral side of the seal-forming structure 3100 to a lateral side of the lip superior portion 3116. Each lateral posterior region 3141 may also have an inferior facing portion connecting a laterally-facing portion of the lateral posterior region 3141 to the lip superior portion 3116.

With reference to the examples shown in FIGS. 9A-9H, 19A-19F, 25A-25I and 26A-26I, in the superior regions of the seal-forming structure 3100, the medial boundary of each lateral posterior region 3141 may be the lateral boundary of a respective mid-lateral portion 3121. In the inferior regions, the medial boundary of each lateral posterior region 3141 may be a lateral boundary of the lip superior portion 3116. As shown in FIGS. 30E and 31D, in these cushion modules 3150 in the inferior regions the medial boundary of each lateral posterior region 3141 is a lateral boundary of a respective mid-lateral inferior portion 3122. Each mid-lateral inferior portion 3122 may be located between the lip superior portion 3116 and a respective one of the lateral posterior regions 3141.

In some examples, such as those shown in FIGS. 25A-25I and 26A-26I, the wall thickness of the seal-forming structure 3100 in the lateral posterior regions 3141 is greater proximate the chassis portion 3210 than proximate the central portion 3111. The thickness may taper in the lateral posterior regions 3141 between the chassis portion 3210 and the patient-contacting side of the seal-forming structure 3100. Increased thickness proximate the chassis portion 3210 may advantageously provide support to the structure of the seal-forming structure 3100 while a reduced thickness closer to and at the patient-contacting portions may provide for a comfortable seal and good conformance to the geometry of the surface of the patient's face.

5.3.3.8.4.1 Anterior/Posterior Portions of Lateral Posterior Regions

In some examples of the present technology, the lateral posterior regions 3141 may comprise a plurality of portions comprising differing properties. In the examples shown in FIGS. 30A-30E and 31A-31D, the seal-forming structure 3100 comprises a pair of lateral posterior regions 3141 provided on respective lateral posterior sides of the non-patient contacting side of the seal-forming structure 3100.

Each lateral posterior portion 3141 in this example comprises an anterior portion 3147 and a posterior portion 3146. The anterior portion 3147 has a greater stiffness than the posterior portion 3146. In this example, the anterior portion 3147 has a wall thickness greater than a wall thickness of the posterior portion 3146. The greater wall thickness provides the anterior portion 3147 with a greater stiffness than the posterior portion 3146.

The additional stiffness and/or thickness in the anterior portion 3147 may help provide structure to the seal-forming structure 3100 to maintain the shape of the non-patient contacting side of the seal-forming structure 3100 in use, allowing the patient-contacting surfaces of the seal-forming structure 3100 to be thin to conform to the surfaces of the patient's face and create a good seal in use. The additional stiffness and/or thickness in the anterior portions 3147 of the lateral posterior regions 3141 may be particularly advantageous in cushion modules 3150 of the present technology in which the chassis portion 3210 is formed from a flexible material, such as from silicone.

5.3.3.8.4.2 Superior/Inferior Portions of Anterior Portions of Lateral Posterior Regions The anterior portion 3147 of each lateral posterior region 3141 itself may comprise sub-portions having differing properties. In some examples of the present technology, the anterior portion 3147 of each lateral posterior region 3141 comprises a superior portion 3148 and an inferior portion 3149. The superior portion 3148 may have a greater stiffness than the inferior portion 3149. In the examples shown in FIGS. 30A-30E and 31A-31D, each anterior portion 3147 of each lateral posterior region 3141 comprises a superior portion 3148 having a wall thickness greater than a wall thickness of the inferior portion 3149 of the anterior portion 3147. The greater wall thickness of the superior portion 3148 provides the greater stiffness in this example. In other examples the seal-forming structure 3100 may comprise a rigidiser in the superior portion 3148 or the superior portion 3148 may be formed from a stiffer material than the inferior portion 3149 and/or posterior portion 3146.

In the example shown in FIGS. 30A-30E, the superior portion 3148 of the anterior portion 3147 of each lateral posterior region 3141 has a wall thickness of 2.5 mm and, in other examples, may have a wall thickness of between 1.5 mm and 3.5 mm. The inferior portion 3149 of the anterior portion 3147 has a wall thickness of 1.5 mm and, in other examples, may have a wall thickness of between 1 mm and 2 mm. The posterior portion 3146 has a wall thickness of 1.25 mm and, in other examples the posterior portion 3146 may have a wall thickness between 0.7 mm and 1.8 mm. In further examples the thicknesses in the lateral posterior regions 3141 may differ from these exemplary thicknesses.

It is to be understood that the cushion module 3150 may comprise gradual changes in thickness between adjacent portions, such as a tapering thickness rather than a stepped change in thickness. A smooth transition may help prevent creases and leak paths forming when a load is applied. Sudden changes in geometry may also be more likely to be felt by the patient while a smoother change is more comfortable. Smooth changes may also make the cushion module 3150 easier to mould and demould.

As discussed above, the seal-forming structure 3100 in the examples shown in FIGS. 30A-30E and 31A-31D comprises a pair of mid-lateral anterior portions 3125 on the non-patient contacting side of the seal-forming structure 3100 each located on a respective lateral side of the seal-forming structure 3100. The mid-lateral anterior portions 3125 may have a stiffness and/or thickness greater than a stiffness of the central portion 3111 of the seal-forming structure 3100.

In these examples, each of the anterior portions 3147 of the lateral posterior regions 3141 have a greater wall thickness than a wall thickness of the mid-lateral anterior portions 3125. In other examples, the anterior portions 3147 may have substantially the same wall thickness as a thickness within the mid-lateral anterior portions 3125.

In these examples, the superior portion 3148 of the anterior portion 3147 of each of the lateral posterior regions 3141 has a wall thickness greater than a wall thickness of each mid-lateral anterior portion 3125. In other examples the superior portion 3148 may have substantially the same thickness as some or all of the mid-lateral anterior portion 3125.

As discussed above, each mid-lateral anterior portion 3125 comprises a superior portion 3126 and an inferior portion 3127 in the cushion module 3150 shown in FIGS. 30A-30E and 31A-31D, the inferior portion 3127 of the mid-lateral anterior portion 3125 being stiffer than the superior portion 3126 of the mid-lateral anterior portion 3125. The inferior portion 3127 of each mid-lateral anterior portion 3125 in this example has a wall thickness greater than a wall thickness of the superior portion 3126 of each mid-lateral anterior portion 3125.

Additionally, the stiffness of the inferior portion 3127 of each mid-lateral anterior portion 3125 may be substantially the same as the stiffness of the superior portion 3148 of the anterior portion 3147. In the examples shown in FIGS. 30A-30E and 31A-31D, the inferior portion 3127 of each mid-lateral anterior portion 3125 has a wall thickness that is substantially the same as the superior portion 3148 of the anterior portion 3147 of each lateral posterior region 3141.

As shown in FIGS. 30D and 31C, a boundary between the superior portion 3148 and the inferior portion 3149 of the anterior portion 3147 of each lateral posterior region 3141 is located at a longest portion of the lateral posterior region 3141 in an anterior-posterior direction. The longest portion of the lateral posterior region 3141 in the anterior-posterior direction may appear as the widest part of the lateral posterior region 3141 as visible from the lateral side as shown in FIGS. 30D and 31C. The boundary between the superior portion 3148 and the inferior portion 3149 of the anterior portion 3147 of each lateral posterior region 3141 may be located approximately at a mid-point of the boundary between the laterally projecting connection portion 3212 of the chassis portion 3210 and the seal-forming structure 3100 on the posterior side of the laterally projecting connection portion 3212.

Accordingly, as shown in FIGS. 30C and 31D in particular, the seal-forming structure 3100 comprises a thickened region in the central anterior portion 3115 and extending towards each lateral side along the non-patient contacting side of the seal-forming structure 3100 through the mid-lateral anterior portions 3125 and into the lateral posterior regions 3141. In these examples, this thickened region may be provided to substantially all of the central anterior portion 3115. Additionally, in these examples the thickened region may be provided to inferior portions 3127 of the mid-lateral anterior portions 3125. Finally, the thickened region may occupy an anterior portion 3147 of the lateral posterior regions 3141 and, in particular, may be provided to a superior portion 3148 of the anterior portion 3147 of each lateral posterior region 3141. In these examples the thickened portion extends laterally from the central anterior portion 3115 and terminates at the longest portion of the lateral posterior region 3141 in an anterior-posterior direction.

5.3.3.8.5 Decoupling Portions

In some examples of the present technology, the cushion module 3150 comprises one or more decoupling portions 3142. The decoupling portions 3142 may be configured to at least partially decouple seal-forming surfaces of the seal-forming structure 3100 from movement of, or forces receive by, other portions of the cushion module 3150. In some examples, the seal-forming structure 3100 comprises decoupling portions 3142. In other examples the chassis portion 3210 comprises decoupling portions 3142.

5.3.3.8.5.1 Decoupling Portions Provided to the Seal-Forming Structure

As described above, the seal-forming structure 3100 comprises a pair of lateral posterior regions 3141 provided on respective lateral posterior sides of the seal-forming structure 3100. As shown in FIGS. 9A-9H and 19A-19F, each lateral posterior region 3141 comprises a decoupling portion 3142. In these examples, each lateral posterior region 3141 also comprises a peripheral portion 3143 provided around at least part of the decoupling portion 3142. Each peripheral portion 3143 is provided adjacent a respective decoupling portion 3142. In each of the lateral posterior regions 3141, at least part of the peripheral portion 3143 is located posterior to the decoupling portion 3142. The decoupling portions 3142 may also be known as gussets, for example by being portions configured to deform (e.g. by a lower stiffness or thickness) to allow at least some relative movement between two other portions. Each decoupling portion 3142 may be located in a portion of a respective lateral posterior region 3141 that is configured to face away from and not contact the patient's face during use. Each decoupling portion 3142 may be provided to a non-patient contacting portion or side of the seal-forming structure 3100. The lateral posterior regions 3141 may each have a surface at/over a respective decoupling portion 3142 configured to face away from and not contact the patient's face during use.

Each decoupling portion 3142 is configured to at least partially decouple the posterior side of the seal-forming structure 3100 from the chassis portion 3210 so that forces applied to one component are not wholly transmitted to the other component. Additionally or alternatively, movement of one component does not result in the same movement to the other component. In particular, each decoupling portion 3142 is configured to at least partially decouple the central portion 3111 of the seal-forming structure 3100 from a respective one of the laterally projecting connection portions 3212. The decoupling portions 3142 may at least partially decouple the central portion 3111 from movement of the laterally projecting connection portions 3212 and/or forces applied to the laterally projecting connection portions 3212.

As illustrated, the decoupling portions 3142 are provided to the non-patient-contacting side of the seal-forming structure 3100. In this example they are located proximate the connections to the headgear conduits made by the laterally projecting connection portions 3212.

The decoupling portion 3142 may have a decoupling property due to having a lower stiffness and/or thickness in comparison to adjacent portions of the seal-forming structure 3100 to allow at least some relative movement between the adjacent portions.

The stiffness of each decoupling portion 3142 is less than a stiffness of each peripheral portion 3143. In this example, the stiffness of the peripheral portion 3143 is greater than a stiffness of the central portion 3111 of the seal-forming structure 3100. Additionally, the stiffness of each decoupling portion 3142 is greater than the stiffness of the central portion 3111 of the seal-forming structure 3100. The lateral-facing posterior portions 3141 are therefore stiffer than the central portion 3111.

The decoupling portions 3142 may be regions having a low wall thickness and may also be known as thin wall zones. As discussed above, a portion of the seal-forming structure 3100 may have a greater stiffness due to having a greater material thickness. The wall thickness of the peripheral portion 3143 of each lateral posterior region 3141 may be greater than a wall thickness of the central portion 3111 of the seal-forming structure 3100. Additionally, the wall thickness of the peripheral portion 3143 of each lateral posterior region 3141 may be greater than a wall thickness of the decoupling portion 3142 of each lateral posterior region 3141. Furthermore, the wall thickness of the decoupling portion 3142 of each lateral posterior region 3141 may be greater than the wall thickness of the central portion 3111 of the seal-forming structure 3100.

In some examples of the present technology, the decoupling portions 3142 each comprise a wall thickness of between 0.3 mm and 0.7 mm, and in some examples the wall thickness is between 0.4 mm and 0.6 mm. In some examples, the peripheral portions 3143 each comprise a wall thickness of between 1.2 mm and 1.6 mm, and in some examples the wall thickness is between 1.3 mm and 1.5 mm. In the example illustrated in FIGS. 9A-9H, each decoupling portion 3142 comprises a wall thickness of approximately 0.5 mm Each peripheral portion 3143 comprises a wall thickness of approximately 1.4 mm. As described above, the central portion 3111 comprises a wall thickness of approximately 0.25 mm.

FIG. 13A shows a cross section view of the cushion module 3150 according to one example of the present technology, in a somewhat horizontal plane through a superior portion of the seal-forming structure 3100. As shown, the decoupling portions 3142 are portions of the seal-forming structure 3100 having a low wall thickness located anterior to thicker peripheral portions 3143. Also shown in this view are rigidising portions 3161 located anterior to the superior portions of the decoupling portions 3142. The rigidising portions 3161 are described in more detail below.

FIG. 13B shows a cross section view of the cushion module 3150 shown in FIG. 13A, in a generally horizontal plane approximately centred between the superior and the inferior portions of the cushion module 3150. As illustrated, the decoupling portions 3142 are portions of the seal-forming structure 3100 having a low wall thickness in comparison to peripheral portions 3143. In this example, each lateral posterior region 3141 comprises a decoupling portion 3142 and a peripheral portion 3143 on each of the anterior and posterior sides of the decoupling portion 3142.

FIG. 11C shows another cross-section view of a cushion module 3150 according to one example of the present technology. In this example, a portion of a rigidising portion 3161 (which will be described in more detail below) is located superior to a portion of the decoupling portion 3142 on each side of the seal-forming structure 3100. Also visible in this view is a mid-lateral portion 3121 and the central portion 3111 on the patient contacting side of the seal-forming structure 3100. In some examples of the present technology, portions of each decoupling portion 3142 may be located directly adjacent portions of the laterally projecting connection portions 3212. As shown in FIG. 11C, a superior portion of the decoupling portion 3142 is located directly adjacent a superior portion of a laterally projecting connection portion 3212. No inferior portion of the decoupling portion 3142 is visible in this view because in this example, the superior portion of each decoupling portion 3142 includes a portion spaced anteriorly relative to the inferior-most portion of the decoupling portion 3142.

The decoupling portions 3142 may each be C-shaped, U-shaped or the like when viewed from a lateral side of the seal-forming structure. The decoupling portions 3142 are provided between the connection portions 3212 and the patient-contacting side of the seal-forming structure 3100. Each decoupling portion 3142 may have a curvature that follows the curvature of the posterior-most portions of the seal-forming structure 3100. Each decoupling portion 3142 may have a curvature corresponding to curvature of the seal-forming structure 3100 at the posterior corner portions 3131 when viewed from the side.

As described above, the peripheral portions 3143 may each be provided adjacent to, posterior to and/or surrounding, a respective one of the decoupling portions 3142 and may have a greater stiffness and/or thickness than the decoupling portions 3142. Each peripheral portion 3143 may partially or fully surround a respective decoupling portion 3142. Each peripheral portion 3143 may be located between a respective decoupling portion 3142 and posterior-most portion of the seal-forming structure 3100. The peripheral portions 3143 may each have a shape that matches the shape of a respective one of the decoupling portions 3142. The peripheral portions 3143 may each be C-shaped, U-shaped or the like when viewed from the side. The peripheral portions 3143 may comprise a curvature that follows the curvature of the decoupling portions 3142, the posterior-most portions of the seal-forming structure 3100 and/or the posterior corner portions 3131.

The decoupling portions 3142 may each have a posterior boundary and an anterior boundary. The posterior boundary of each decoupling portion 3142 may be curved. As shown in FIGS. 9B and 19B, a superior portion of the posterior boundary is located more anteriorly than a midpoint of the posterior boundary. An inferior portion of the posterior boundary is also located more anteriorly than the midpoint of the posterior boundary. The anterior boundary of each decoupling portion 3142 also may be curved. As shown in FIGS. 9B and 19B, a superior portion of the anterior boundary is located more anteriorly than a midpoint of the anterior boundary. An inferior portion of the anterior boundary is also located more anteriorly than the midpoint of the anterior boundary. Either or both of the posterior boundary and the anterior boundary of each decoupling portion 3142 may be C-shaped, U-shaped or the like when viewed from the side. The interior boundary of each decoupling portion 3142 may curve around the posterior side of a respective laterally projecting connection portion 3212.

Each peripheral portion 3143 or a portion thereof may comprise an anterior boundary matching a posterior boundary of a respective one of the decoupling portions 3142. As shown in FIGS. 9B and 19B, a posterior portion of the peripheral portion 3143 has an anterior boundary which matches the posterior boundary of the decoupling portion 3142. In this example, each peripheral portion 3143 is located posterior, inferior and anterior to a respective one of the decoupling portions 3142. As visible in FIGS. 9B and 19B, there is a portion of the peripheral portion 3143 located between the decoupling portion 3142 and the laterally projecting connection portion 3212. In other examples, the decoupling portions 3142 are each located directly posterior to a respective one of the laterally projecting connection portions 3212. Each peripheral portion 3143 may widen at a region inferior to a respective decoupling portion 3142 of the seal forming structure 3100. As shown in FIGS. 9B and 19B, each peripheral portion 3143 may widen as it curves towards an anterior and superior direction around the inferior portion of a respective decoupling portion 3142.

In the examples shown in FIGS. 9B and 19B, a rigidising portion 3161 is located anterior to the superior portions of each of the decoupling portion 3142 and the peripheral portion 3143, on each side of the seal-forming structure 3100. The rigidising portions 3161 are described in more detail below. In some examples, the peripheral portion 3143 comprises a portion located anterior to a superior portion of the decoupling portion 3142, on each side of the seal-forming structure 3100. In other examples, a mid-lateral anterior portion 3125 is located directly anterior to a superior portion of each of the decoupling portion 3142 and peripheral portion 3143, on each side of the seal-forming structure 3100.

The seal-forming structure 3100 is flexible in general due to the use of thin walls and/or flexible materials, however the decoupling portions 3142 allow extra movement of the connection portions 3212 with respect to the patient-contacting side of the seal-forming structure 3100 and in particular with respect to the central portion 3111. This further decouples the connection portions 3212 from the sealing surfaces, enabling the cushion module 3150 to tolerate some force received at the connection portions 3212 without transferring that force to the sealing surfaces, or at least without transferring as much force as would be transferred without the decoupling portions 3142.

Decoupling of the connection portions 3212 from the sealing surface may be particularly advantageous because the connectors 3214 and the corresponding connectors on the tubes 3350 are substantially rigid, meaning they may have minimal inherent decoupling effect and are efficient at transferring forces to the chassis portion 3210 and seal-forming structure 3100. Additionally, as the laterally projecting connection portions 3212 are connections between the headgear conduits and the cushion module 3150, some forces may be received by the headgear conduits and passed on to the connection portions 3212. For example, the connection portions 3212 may be particularly susceptible to receiving external forces during side sleeping, since the seal-forming structure 3100 and/or the tubes 3350 of the positioning and stabilising structure 3300 may be in contact with the patient's pillow. Sleeping movements, such as the patient turning over or onto their side, may result in forces being received at the connection portions 3212. The decoupling portions 3142 may reduce the extent to which these forces are transmitted to the posterior side of the seal-forming structure 3100.

Additionally, the decoupling portions 3142 add flexibility to the non-patient contacting side of the seal forming structure 3100, helping it to expand to accommodate wider noses. This may enable the patient interface 3000 to fit comfortably and securely to a wider range of the population.

In the example shown in FIGS. 8A-8H and 9A-9H, each decoupling portion 3142 is formed in the seal-forming structure 3100 by a recess in an internal surface of the seal-forming structure 3100. Forming the decoupling portions 3142, or any other thinner portions, by a recess in an internal surface of the seal-forming structure 3100 allows for a change in thickness while leaving an exterior surface of the seal-forming structure 3100 smooth. Patients may find a smooth exterior surface of the seal-forming structure 3100 to be comfortable, easy to clean and/or aesthetically pleasing.

5.3.3.8.5.2 Decoupling Portions Provided to the Chassis Portion

In some examples of the present technology, the chassis portion 3210 may comprise one or more decoupling portions 3142 in addition or as an alternative to one or more decoupling portions 3142 of the seal-forming structure 3100. In some examples the laterally projecting connection portions 3212 may comprise decoupling portions. Decoupling portions may be provided to an anterior side of the chassis portion 3210. In one example, the cushion module 3150 comprises a decoupling portion provided to an anterior side of each one of the pair of laterally projecting connection portions 3212.

FIG. 20 shows a cushion module 3150 according to one such example of the present technology, in which decoupling portions 3142 are provided to the chassis portion 3210. The chassis portion 3210 in this example comprises a pair of decoupling portions 3142 each provided to a respective lateral side of the chassis portion 3210. Each decoupling portion 3142 has a lesser stiffness than one or more adjacent portions of the chassis portion 3210. As shown, the decoupling portions 3142 are provided to an anterior side of each one of the laterally projecting connection portions 3212. Like the decoupling portions 3142 provided to the seal-forming structure 3100, the decoupling portion 3142 provided to the chassis portion 3210 are configured to decouple the posterior side of the seal-forming structure 3100 from movements of the laterally projecting connection portions 3212 and/or forces received by the laterally projecting connection portions 3212. This decoupling effect is provided by a lower wall thickness of the seal-forming structure 3100 in the decoupling portions 3142 in the FIG. 20 example.

As described above, the decoupling portions 3142 may comprise a lower stiffness in comparison to other portions of the cushion module 3150, such as the peripheral portions 3143 and the laterally projecting connection portions 3212. In other examples of the present technology, the decoupling portions 3142 may comprise a shape that allows flexibility, such as a fold or concertina structure.

FIGS. 32A-32D show a cushion module 3150, according to another example of the present technology, which includes decoupling portions 3142*a* and 3142*b* in a chassis portion 3210. The cushion module 3150 comprises a chassis portion 3210 and a seal-forming structure 3100. The chassis portion 3210 and seal-forming structure 3100 both partially form a plenum chamber 3200. The chassis portion 3210 comprises a pair of laterally projecting connection portions 3212 configured to connect to gas delivery tubes 3350, such as those described herein. The chassis portion 3210 is in this example formed from a flexible material, such as silicone, TPE or the like. The chassis portion 3210 and seal-forming structure 3100 may have any one or more of the features described in relation to any of the other examples.

In general, a cushion module 3150 according to the present technology may comprise a chassis portion 3210 comprising a pair of decoupling portions 3142 each provided to a respective lateral side of the chassis portion 3210 and each having a lesser stiffness than one or more adjacent portions of the chassis portion 3210. The decoupling portions 3142 may be configured to at least partially decouple the central portion 3111 of the seal-forming structure 3100 from forces applied to the chassis portion 3210. The decoupling portions 3142 may be configured to at least partially decouple the posterior (e.g. patient-contacting) side of the seal-forming structure 3100 from forces applied to the chassis portion 3210.

In the FIG. 32A-32D example, the chassis portion 3210 comprises two pairs of decoupling portions 3142: a pair of lateral decoupling portions 3142*a* and a pair of medial decoupling portions 3142*b*. The lateral decoupling portions 3142*a* are each provided to a respective lateral side of the chassis portion 3210 and the medial decoupling portions 3142*b* are each provided to a respective lateral side of the chassis portion 3210. The lateral decoupling portions 3142*a* and the medial decoupling portions 3142*b* may each have a lesser stiffness than one or more adjacent portions of the chassis portion 3210. The lateral decoupling portions 3142*a* and the medial decoupling portions 3142*b* may each be configured to at least partially decouple the central portion 3111 of the seal-forming structure 3100 from forces applied to the chassis portion 3210. The lateral decoupling portions 3142*a* and the medial decoupling portions 3142*b* may be configured to at least partially decouple the posterior (e.g. patient-contacting) side of the seal-forming structure 3100 from forces applied to the chassis portion 3210.

The medial decoupling portions 3142*b* and the lateral decoupling portions 3142*a* may not be features of a cushion module 3150 that are inextricably linked to each other. In some examples, the cushion module 3150 comprises a pair of medial decoupling portions 3142*b* and no lateral decoupling portions. In other examples, the cushion module 3150 comprises a pair of lateral decoupling portions 3142*a* and no medial decoupling portions. While features of the medial decoupling portions 3142*b* and lateral decoupling portions 3142*a* may be described herein in the context of a cushion module 3150 having both pairs of decoupling portions 3142*a* and 3142*b*, it is to be understood that a cushion module 3150 may have only a single pair of decoupling portions 3142. It is to be understood that the single pair of decoupling portions 3142 may have some or all of the features described with reference to the medial decoupling portions 3142*b*. Alternatively, or additionally, the single pair of decoupling portions 3142 may have some or all of the features described with reference to the lateral decoupling portions 3142*a*.

As shown in FIGS. 32A-32D, each decoupling portions 3142 is located on an anterior side of the chassis portion 3210 (e.g. a non-patient facing side). The decoupling portions 3142 may be provided to an anterior-facing surface of the cushion module 3150. The decoupling portions 3142 may face partially anteriorly and partially inferiorly in use.

Each decoupling portion 3142 of the cushion module 3150 shown in FIGS. 32A-32D has a lesser thickness than one or more adjacent portions of the chassis portion 3210. In this example, the lesser thickness provides the decoupling portions 3142 with the lesser stiffness than the one or more adjacent portions.

The lesser stiffness/thickness may allow the decoupling portions 3142 to deform more readily than adjacent portions of the chassis portion 3210, which may allow the decoupling portions 3142 to absorb forces applied to the chassis portion 3210. The chassis portion 3210 is sufficiently stiff that is able to support the seal-forming structure 3100 and hold its shape while transferring force from the positioning and stabilising structure 3300 to the seal-forming structure 3100 to hold the seal-forming structure 3100 in sealing engagement with the patient's face. While the chassis portion 3210 may transfer a force from the positioning and stabilising structure 3300 to the seal-forming structure 3100 for sealing purposes, the decoupling portions 3142 may prevent other forces applied to the chassis portion 3210 from being transmitted to the seal-forming structure 3100 and disrupting the seal, for example forces from the patient's pillow or bed sheets. The decoupling portions 3142 (e.g. medial decoupling portions 3142*b* and/or lateral decoupling portions 3142*a*) may allow localised controlled deformation of the chassis portion 3210 to partially or fully absorb disruptive forces received by the chassis portion 3210. Advantageously, absorption by the chassis portion 3210 of force applied to the chassis portion 3210 may prevent disruptive forces from being transferred to the seal-forming structure 3100 and disrupting the seal. FIG. 32D shows a cushion module 3150 with a deformed lateral decoupling portion 3142*a*. The lateral decoupling portion 3142*a* is able to deform into the illustrated state to absorb a force applied to the chassis portion 3210, reducing the magnitude of force transmitted through to the seal-forming structure 3100 from the chassis portion 3210.

It is to be understood that a decoupling portion 3142 configured to at least partially decouple the seal-forming structure 3100 or the central portion 3111 thereof from forces applied to the chassis portion 3210 may not decouple the seal-forming structure 3100 from all force applied to the chassis portion 3210. For example, the positioning and stabilising structure 3300 may apply a force to the chassis portion 3210 to hold the cushion module 3150 in place on the patient's face and may apply force sufficient to hold the seal-forming structure 3100 in sealing engagement with the patient's face while the plenum chamber 3200 is pressurised. The decoupling portions 3142 may not decouple the seal-forming structure 3100 from those forces, but may decouple the seal-forming structure 3100 from additional unwanted forces.

The decoupling portions 3142 may also advantageously deform to stabilise the cushion module during movement of the patient's head during sleep. When the patient moves, forces could disrupt the seal formed by the seal-forming structure 3100. The decoupling portions 3142 may provide for deformation of the cushion module 3150 in the chassis portion 3210 rather than in the seal-forming structure 3100, which may prevent some or all of the disruptive forces from affecting the seal formed by the seal-forming structure 3100 with the patient's face.

In some examples of the present technology, each decoupling portion 3142 may have a thickness within the range of 0.25 mm-1 mm, for example between 0.35 mm-0.8 mm or 0.4 mm-0.6 mm. In the FIG. 32A-32D example, each decoupling portion 3142 (e.g. each medial decoupling portion 3142*b* and lateral decoupling portion 3142*a*) has a thickness of 0.5 mm. The chassis portion 3210 has a thickness of 0.9 mm (e.g. a thickness of 0.9 mm in one or more portions other than the decoupling portions 3142). In other examples, the chassis portion 3210 has a thickness within the range of 0.7 mm-1.5 mm, such as 0.9 mm-1.4 mm, 0.7 mm-1.2 mm, 1.2 mm-1.5 mm, as examples.

As shown in FIGS. 32A-32D, each decoupling portion 3142 extends from a superior side of the chassis portion 3210 to an inferior side of the chassis portion 3210. Each decoupling portion 3142 may have an upper end and a lower end. The upper end may be located at a superior region of the chassis portion 3210. The lower end may be located at an inferior region of the chassis portion 3210. Decoupling portions 3142 that extend from a superior side to an inferior side may be able to decouple the seal-forming structure 3100 from forces applied to the chassis portion 3210 in a range of directions. In other examples the decoupling portions 3142 may be provided to a smaller region of the chassis portion, for example between a superior side and a superior-anterior midpoint, or between an anterior side and a superior-anterior midpoint.

In some examples, such as the example shown in FIGS. 32A-32D, the decoupling portions 3142 are integrally formed in the chassis portion 3210. The decoupling portions 3142 may be formed from the same material as chassis portion 3210 and may be moulded together with the chassis portion 3210. For example, the decoupling portions 3142 may be moulded together with adjacent portions of the chassis portion 3210 in a single moulding step. The decoupling portions 3142 may partially define the plenum chamber 3200 together with other portions of the chassis portion 3210.

In some examples, a pair of decoupling portions 3142 may each be located medially adjacent a distal end of a respective laterally projecting connection portion 3212. In other examples, each one of a pair of decoupling portions 3142 may be spaced from a distal end of a respective laterally projecting connection portion 3212. For example, each one of a pair of decoupling portions 3142 may comprise a lateral boundary spaced apart from a distal end of a respective laterally projecting connection portion 3212.

5.3.3.8.5.3 Lateral and Medial Decoupling Portions

As described above, the chassis portion 3210 shown in FIGS. 32A-32D comprises two decoupling portions 3142 on each lateral side of the chassis portion 3210. The chassis portion 3210 comprises two decoupling portions 3142 provided to either side of the vent module 3410.

In this example, on each lateral side of the chassis portion 3210, the chassis portion 3210 comprises a medial decoupling portion 3142*b* and a lateral decoupling portion 3142*a*. On each lateral side, the lateral decoupling portion 3142*a* is located laterally of the medial decoupling portion 3142*b*.

The lateral decoupling portion 3142*a* and the medial decoupling portion 3142*b* may decouple the seal-forming structure 3100 from different types of forces.

In this example, the lateral decoupling portions 3142*a* are configured to at least partially decouple the seal-forming structure 3100 from forces applied to the laterally projecting connection portions 3212. For example, the lateral decoupling portions 3142*a* may be configured to decouple the seal-forming structure 3100 from forces applied to the laterally projecting connection portions 3212 and/or gas delivery tubes 3350 when the patient turns their head on to its side while lying on a pillow. The lateral decoupling portions 3142*a* may deform to absorb such forces and prevent the forces from disrupting the seal between the seal-forming structure 3100 and the patient's face, or at least reduce the magnitude of force that reaches the seal-forming structure 3100. The lateral decoupling portions 3142*a* may be proximate or adjacent to the connectors 3214. In the illustrated example, the decoupling effects provided by the lateral decoupling portions 3142*a* may be provided by proximity to the distal ends of the laterally projecting connection portions 3212 and a lesser stiffness than adjacent portions of the chassis portion 3210.

FIG. 32D shows a cushion module 3150 with a deformed lateral decoupling portion 3142*a*. As illustrated in FIG. 32D, the lateral decoupling portion 3142*a* has deformed to allow for an amount of relative movement between the connector 3214 and other portions of the chassis portion 3210 and cushion module 3150, such as the seal-forming structure 3100. In this way, the lateral decoupling portion 3142*a* is able to at least partially decouple the seal-forming structure 3100 from forces applied to the laterally projecting connection portion 3212 by a gas delivery tube 3350 connected to the connector 3214 in use.

The medial decoupling portions 3142*b* are configured to at least partially decouple the seal-forming structure 3100 from forces applied to a central region of the anterior side of the chassis portion 3210 (e.g. a medial region of the anterior/non-patient facing side of the chassis portion 3210). For example, the medial decoupling portions 3142*b* may be configured to decouple the seal-forming structure 3100 from forces applied to the central region of the anterior side of the chassis portion 3210 when the patient turns their face towards a pillow or if the central region of the chassis portion 3210 contacts bedsheets, a mattress, the patient's hand/arm/shoulder or the like. The medial decoupling portions 3142*b* may deform to absorb such forces and prevent the forces from disrupting the seal between the seal-forming structure 3100 and the patient's face, or at least reduce the magnitude of force that reaches the seal-forming structure 3100.

In the example illustrated in FIGS. 32A-32D, the cushion module 3150 comprises a vent module 3410 comprising a vent 3400. The vent module 3410 is located in the central/medial region of the anterior side of the chassis portion 3210. In this particular example, the medial decoupling portions 3142*b* are configured to at least partially decouple the seal-forming structure 3100 from forces applied to the vent module 3410. The vent module 3410 may be formed from a rigid material (e.g. a material not readily deformable by finger pressure), for example to rigidly form vent holes of the vent 3400. A rigid vent module 3410 may not itself have any ability to deform to absorb forces and may instead pass on forces to the chassis portion 3210. Advantageously, the medial decoupling portions 3142*b* may decouple or at least partially decouple the seal-forming structure 3100 from these forces.

The medial decoupling portions 3142*b* may be proximate or adjacent to the vent module 3410. In the illustrated example, the decoupling effects provided by the medial decoupling portions 3142*b* may be provided by proximity to the vent module 3410 or centre of the chassis portion 3210 and a lesser stiffness than adjacent portions of the chassis portion 3210.

As shown in FIGS. 32A-32D, the lateral decoupling portions 3142*a* are D-shaped. In other examples the lateral decoupling portions 3142*a* may have another shape, such as a crescent shape, C-shape, a rectangular shape, an S-shape, a concertina structure or any other suitable shape or structure to at least partially decouple the seal-forming structure 3100 from disruptive forces. Each lateral decoupling portion 3142*a* may have a lateral side proximate a distal end of the respective lateral projecting connection portion 3212. Each lateral decoupling portion 3142*a* may also have a medial side opposite the lateral side. The medial side may have a greater curvature than the lateral side. As shown in FIGS. 32A-32D by way of example, the lateral side of each lateral decoupling portion 3142*a* may be shaped to match a shape of the respective distal end of the laterally projecting connection portion 3212.

As shown in FIGS. 32A-32D, the medial decoupling portions 3142*b* are crescent shaped. In other examples the medial decoupling portions 3142*b* may have another shape, such as a D-shape, C-shape, a rectangular shape, an S-shape, a concertina structure or any other suitable shape or structure to at least partially decouple the seal-forming structure 3100 from disruptive forces. Each medial decoupling portion 3142*b* may have a medial side proximate the vent module 3410 or central region of the anterior side of the chassis portion 3210. Each medial decoupling portion 3142*b* may also have a lateral side opposite the medial side. The lateral side may have a greater curvature than the medial side. As shown in FIGS. 32A-32D, the medial side of each medial decoupling portion 3142*b* is curved to follow a curvature of the vent module 3410.

5.3.3.8.5.4 Peripheral Portions Adjacent Decoupling Portions Provided to the Chassis Portion In some examples, each decoupling portion 3142 may be at least partially surrounded by a peripheral portion 3143 having a greater stiffness than both the decoupling portion 3142 and an adjacent portion of the chassis portion 3210. In the example shown in FIGS. 32A-32D, each decoupling portion 3142 is partially surrounded by a peripheral portion 3143 of the chassis portion 3210. Each peripheral portion 3143 has a greater thickness than both the respective decoupling portion 3142 and an adjacent portion of the chassis portion 3210 to the peripheral portion 3143. The greater thickness provides the greater stiffness in this particular example.

The decoupling portions 3142 are more flexible than other portions of the chassis portion 3210 and the peripheral portions 3143, having less flexibility, advantageously compensate for any overall strength of the chassis portion 3210 that may be lost in the flexible decoupling portions 3142. Advantageously the decoupling portions 3142 may readily deform in a localised controlled manner, decoupling the seal-forming structure 3100 from disruptive forces, while the peripheral portions 3143 together with other portions of the chassis portion 3210 provide sufficient strength to the overall structure of the chassis portion 3210 that the chassis portion 3210 is able to support the seal-forming structure 3100 in sealing position.

As shown in FIGS. 32A-32D, on each lateral side of the chassis portion 3210, the chassis portion 3210 comprises a first peripheral portion 3143*a* located medially adjacent to the lateral decoupling portion 3142*a*. The chassis portion 3210 in this example also comprises a second peripheral portion 3143*b* located laterally adjacent to the medial decoupling portion 3142*b*.

In this example, on each lateral side of the chassis portion 3210, the first peripheral portion 3143*a* is curved to follow the curvature of the medial side of the lateral decoupling portion 3142*a*. Also on each lateral side of the chassis portion 3210, the second peripheral portion 3143*b* is curved to follow the curvature of the lateral side of the medial decoupling portion 3142*b*. The first peripheral portion 3143*a* and the second peripheral portion 3143*b* may share respective boundaries with the lateral decoupling portion 3142*a* and the medial decoupling portion 3142*b*. The first peripheral portion 3143*a* and the second peripheral portion 3143*b* may each have a shape that matches a shape of a side of a respective one of the lateral decoupling portion 3142*a* and the medial decoupling portion 3142*b*. In other examples of the present technology, either of the first peripheral portion 3143*a* and the second peripheral portion 3143*b* may have a different shape, such as a straight shape. As shown in FIGS. 32A-32D, on each lateral side of the chassis portion 3210, the first peripheral portion 3143*a* and the second peripheral portion 3143*b* are closest at or proximate a midpoint of the anterior side of the chassis portion 3210. The first peripheral portion 3143*a* and the second peripheral portion 3143*b* may be spaced further apart at superior and/or inferior sides of the chassis portion 3210.

In the example shown in FIGS. 32A-32D there are two peripheral portions 3143 each corresponding to a respective one of two decoupling portions 3142. In other examples of the present technology a cushion module 3150 may have a different number of decoupling portions 3142 and peripheral portions 3143. There may not be an even number of decoupling portions 3142 and peripheral portions 3143.

More generally, a cushion module 3150 may comprise one or more decoupling portions 3142, each decoupling portion 3142 being at least partially surrounded by a peripheral portion 3143 of the chassis portion 3210. The peripheral portion 3143 may have a greater stiffness than both the decoupling portion 3142 and an adjacent portion of the chassis portion 3210 to the peripheral portion 3143. Each peripheral portion 3143 may have a greater thickness than both an adjacent portion of the chassis portion 3210 to the peripheral portion 3143.

Each peripheral portion may have a thickness within the range of 1 mm-5 mm, for example 1.2 mm-3.5 mm, 1.4 mm-2.5 mm, 1.5 mm-2 mm. In some examples each peripheral portion 3143 has a thickness of 1.75 mm.

5.3.3.8.5.5 Other Decoupling Portion Examples

The cushion modules 3150 illustrated in FIGS. 25A-25I and 26A-26I do not include decoupling portions 3142 in lateral posterior regions 3141 of the seal-forming structure 3100 in the same manner as the cushion modules 3150 shown in FIGS. 9A-9H or FIG. 19A-19F or on the anterior side of the chassis portion 3210 as shown in FIG. 20 or 32A-32D. In other examples of the present technology, the cushion modules 3150 illustrated in FIGS. 25A-25I and 26A-26I comprise decoupling portions 3142 in the lateral posterior regions 3141 and/or decoupling portions 3142 in the chassis portion 3210.

In some examples of the present technology, the seal-forming structure 3100 may comprise a decoupling portion in the form of a bridge 3118 between holes 3272 which supply a flow of gas to the patient's nares. With reference to FIGS. 8D-8F, the cushion module 3150 comprises a bridge 3118 separating a pair of holes 3272 and connecting a superior portion of the central portion 3111 and the lip superior portion 3116. The length of the bridge 3118 is configured so that the bridge 3118 is slack when the patient interface 3000 is not being worn by a patient and, when a patient dons the patient interface 3000, the slack bridge 3118 allows the superior portion of the central portion 3111 to move relative to the lip superior portion 3116 to accommodate the length of the patient's nose. This aspect of the bridge 3118 as described in International Application No. PCT/AU2019/050278 the entire contents of which are incorporated herein by reference.

5.3.3.8.6 Rigidising Portions

The cushion module 3150, and in some examples the seal-forming structure 3100, may comprise one or more rigidising portions 3161.

The seal-forming structure 3100 shown in FIGS. 9A-9H and 19A-19F comprises a pair of rigidising portions 3161. The rigidising portions 3161 may be provided to the cushion modules 3150 shown in FIGS. 25A-25I, 26A-26I, 30A-30E, 31A-31D and 32A-32D in some examples. The rigidising portions 3161 are provided to posterior, superior and anterior sides of the seal forming structure 3100, in this example. Each rigidising portion 3161 is located on a respective lateral side of the seal-forming structure 3100. Due to these locations, the rigidising portions 3161 are positioned alongside the patient's nasal ala in use to reinforce the seal-forming structure 3100 alongside the nasal ala and increase the overall stability of the seal.

In some examples, each rigidising portion 3161 is provided to only the posterior side of the seal-forming structure 3100. In other examples, each rigidising portion 3161 is provided to only the anterior side of the seal-forming structure 3100. In some examples the rigidising portions 3161 are provided at a superior side of the seal-forming structure 3100, on either or both of an anterior and posterior side of the seal-forming structure. In some examples, the seal-forming structure 3100 comprises two rigidising portions 3161 on each lateral side thereof, one rigidising portion 3161 on an anterior side and one on a posterior side of the seal-forming structure 3100. In some examples the seal-forming structure 3100 comprises a single rigidising portion 3161 on each lateral side of the seal-forming structure 3100, each rigidising portion 3161 having an anterior portion and a posterior portion integrated to form a single rigidising portion 3161.

As shown in FIGS. 9A-9H and 19A-19F, rigidising portions 3161 are provided to opposing superior portions of the patient-contacting side of the seal-forming structure 3100. In this example, each rigidising portion 3161 extends from the posterior side of the seal-forming structure 3100 to an anterior side of the seal-forming structure 3100 configured to face away from the patient's face in use. Providing the rigidising portions 3161 on the anterior side of the seal-forming structure 3100 and also over the superior ridge 3117 and into the posterior side of the seal-forming structure 3100 adds further stiffness and stability to the seal-forming structure 3100. In this example, each rigidising portion 3161 has negative curvature along a first path from the posterior side of the seal-forming structure 3100 to the anterior side of the seal-forming structure. Each rigidising portion 3161 may have zero curvature or negative curvature along a second path that is perpendicular to the first path.

Each rigidising portion 3161 may have a stiffness greater than the stiffness of the mid-lateral portions 3121 of the seal-forming structure 3100. The rigidising portions 3161 add stiffness to the seal-forming structure 3100, enhancing stability. The rigidising portions 3161 may help the seal-forming structure 3100 remain sealed to the sides of the inferior periphery of the patient's nose. The rigidising portions 3161 may help prevent leaks occurring, particularly when the seal-forming structure 3100 receives external forces, for example when the patient moves. In use, each rigidising portion 3161 may lie proximate and/or in contact with the nasal ala of the patient's nose.

As shown in FIGS. 9A-9H, each rigidising portion 3161 comprises an anterior portion 3162 and a posterior portion 3163. The anterior portion 3162 is provided to an anterior side of the seal-forming structure 3100. The posterior portion 3163 is provided to a posterior side of the seal-forming structure 3100. In this example, the anterior portion 3162 has a stiffness greater than a stiffness of the posterior portion 3163. More particularly, the anterior portion 3162 comprises a thickness greater than a thickness of the posterior portion 3163. That is, the thickness of the seal-forming structure 3100 in the anterior portion 3162 is greater than the thickness of the seal-forming structure 3100 in the posterior portion 3163. The greater thickness provides the greater stiffness. In this example, each rigidising portion 3161 comprises a tapered increase in thickness between the posterior portion 3163 and the anterior portion 3162. In other examples the rigidising portions 3161 may comprise a more abrupt increase in thickness such as a stepped increase in thickness.

In this example, the stiffness of the anterior portion 3162 of each rigidising portion 3161 is greater than a stiffness of an adjacent portion of the seal-forming structure 3100 on the anterior side thereof. More particularly, the thickness of the anterior portion 3162 of each rigidising portion 3161 is greater than a thickness of adjacent portions of the seal-forming structure 3100 on the anterior side thereof.

Additionally, the stiffness of the posterior portion 3163 of each rigidising portion 3161 is greater than a stiffness of an adjacent portion of the posterior side of the seal forming structure 3100. More particularly, the thickness of the posterior portion 3163 of each rigidising portion 3161 is greater than a thickness of adjacent portions of the posterior side of the seal-forming structure 3100.

In other examples, the seal-forming structure 3100 may comprise a stiffer material forming the rigidising portions 3161 than forming adjacent portions. Further still, the rigidising portions 3161 may be rigidised with a rigidising part, such as an insert or a relatively rigid member moulded into or otherwise provided to the seal-forming structure 3100. In the example shown in FIGS. 8A-8H, 9A-9H and 19A-19F, the rigidising portions 3161 are formed from silicone or another elastomeric material. The rigidising portions 3161 may be moulded together with the seal-forming structure 3100.

While each rigidising portion 3161 comprises a greater wall thickness than adjacent portions of the seal-forming structure 3100, the exterior surface on the posterior side of the seal-forming structure 3100 may comprise a smooth surface. The exterior surface on the anterior side of the seal-forming structure 3100 also comprises a smooth surface. The greater wall thickness is provided to an internal surface of the seal-forming structure 3100. This enables a smooth exterior surface of the seal-forming structure 3100, which may be more comfortable, easy to wash and/or aesthetically pleasing for a patient compared to a non-smooth exterior surface.

As described above, in use, each rigidising portion 3161 is located proximate a respective one of the patient's nasal ala. The rigidising portions 3161 stiffen the seal-forming structure 3100 in the areas which are proximate to, or in contact with, the patient's nasal ala. Additionally, each rigidising portion 3161 is located proximate a respective one of the laterally projecting connection portions 3212 of the plenum chamber 3200.

With reference to FIGS. 9A, 9B, 9F, 9G, 19A, 19B, 19E and 19F, in these examples the two rigidising portions 3161 are spaced laterally apart. They are each confined to a region proximate to the patient's nasal ala while being located partially lateral to and partially anterior to the patient's nasal ala. The rigidising portions 3161 in these examples are spaced laterally from the central saddle region 3112. The rigidising portions 3161 in these examples are located posterior to the chassis portion 3210. The rigidising portions 3161 are also superior to the chassis portion 3210. The rigidising portions 3161 in these examples are provided directly adjacent to the chassis portion 3210. That is, the rigidising portions 3161 form part of the boundary between the chassis portion 3210 and the seal-forming structure. The anterior portion 3162 of each rigidising portion 3161 is not spaced apart from the chassis portion 3210. The anterior portion 3162 comprises an inferior boundary that matches a superior boundary of the chassis portion 3210.

In the example illustrated in FIGS. 19A-19F and 22B the anterior portions 3162 of the rigidising portions 3161 have a wall thickness that is substantially as the wall thickness of the inferior portions 3127 of the mid-lateral anterior portions 3125.

The cushion modules 3150 illustrated in FIGS. 25A-25I, 26A-26I and 30A-30E do not include rigidising portions 3161 in the seal-forming structure 3100 in the same manner as the cushion modules 3150 shown in FIGS. 9A-9H or FIGS. 19A-19F. In other examples of the present technology, the cushion modules 3150 illustrated in FIGS. 25A-25I, 26A-26I, 30A-30E, 31A-31D and 32A-32D may comprise rigidising portions 3161.

5.3.3.8.7 Mid-Lateral Posterior Support Portions

With reference to FIGS. 9A-9H, 19A-19F and in particular to FIGS. 9A, 9D, 9F and 9H, the seal-forming structures 3100 according to these particular examples of the present technology comprise mid-lateral posterior support portions 3171. The mid-lateral posterior support portions 3171 as described herein may also be applied to the cushion modules 3150 shown in FIGS. 30A-30E, 31A-31D and 32A-32D, in some examples of the present technology. The mid-lateral posterior support portions 3171 are provided to the posterior side of the seal-forming structure 3100. Each of the mid-lateral posterior support portions 3171 is provided proximate a junction between the central portion 3111, a respective mid-lateral portion 3121 and a respective lateral posterior region 3141. The mid-lateral posterior support portions 3171 are each located at the junction between the central portion 3111 and a respective mid-lateral portion 3121 and are proximate to a respective posterior corner portion 3131. Each mid-lateral posterior support portion 3171 is configured to lie proximate a respective lateral posterior corner of the base of the patient's nose in use. The base of the patient's nose may comprise the inferior periphery of the patient's nose. The lateral posterior corners of the base of the patient's nose are the posterior ends of the nasal ala. The lateral posterior corners of the nasal base may be the lateral locations at which the nasal ala meet the patient's cheeks (or at least meet the region of the patient's face between the nasolabial sulci and the nasal ala). The mid-lateral posterior support portions 3171 in the illustrated examples are located symmetrically about the sagittal plane of the patient's head in use.

The mid-lateral posterior support portions 3171 may be located laterally with respect to the central portion 3111. For example, each mid-lateral posterior support portion 3171 may be located on a respect lateral side of the central portion 3111. The mid-lateral posterior support portions 3171 may be located medially to the posterior corner portions 3131 and/or lateral posterior regions 3141. In some examples the mid-lateral posterior support portions 3171 may be located superior to the posterior corner portions 3131 and/or lateral posterior regions 3141. The mid-lateral posterior support portions 3171 may be located at posterior and/or inferior ends of the mid-lateral portions 3121. The mid-lateral posterior support portions 3171 may be located inferior to a majority of the central portion 3111. The mid-lateral posterior support portions 3171 may be located anterior and/or superior to the lip superior portion 3116.

Each mid-lateral posterior support portion 3171 has a stiffness greater than the stiffness of the central portion 3111. Due to the higher stiffness of the mid-lateral posterior support portions 3171, the mid-lateral posterior support portions 3171 provide crease-resistance to the seal-forming structure 3100. Similarly to the way that the mid-lateral portions 3121 provide crease resistance (as described above), the mid-lateral posterior support portions 3171 also resist the formation of creases in the seal-forming structure 3100, which could result in the leak paths forming. The mid-lateral posterior support portions 3171 may limit the size of creases forming the seal-forming structure 3100.

In some forms of the present technology, the stiffness of each mid-lateral posterior support portion 3171 is less than the stiffness of the mid-lateral portions 3121. In the illustrated examples, each mid-lateral portion 3121 has a greater thickness than the thickness of the mid-lateral posterior support portions 3171.

As described above, the seal-forming structure 3100 may comprise a pair of posterior corner portions 3131 configured to engage with the patient's face proximate and/or medially of the patient's nasolabial sulci, such as between the nasolabial sulci and the nasal ala. In some forms, the stiffness of each mid-lateral posterior support portion 3171 is less than the stiffness of the posterior corner portions 3131.

As described above, each mid-lateral portion 3121 may comprise a thickness greater than the thickness of the central portion 3111. In the illustrated examples, the thickness of each mid-lateral posterior support portion 3171 is also greater than the thickness of the central portion 3111. However, in these examples the thickness of each mid-lateral posterior support portion 3171 is less than the thickness of the mid-lateral portions 3121. Additionally, the thickness of each posterior corner portion 3131 is greater than the thickness of the mid-lateral portions 3121.

The thickness of each mid-lateral posterior support portion 3171 may be tapered. In some forms, the thickness of each mid-lateral posterior support portion 3171 is tapered and increases in thickness towards the respective adjacent mid-lateral portion 3121. In this example, the tapered thickness of each mid-lateral posterior support portion 3171 increases to the thickness of the respective adjacent mid-lateral portion 3121.

In some forms of the present technology, the thickness of each mid-lateral posterior support portion 3171 may be between 0.3-0.7 mm. In particular examples, the thickness may be between 0.4-0.6 mm.

In other examples of the present technology, the additional stiffness of the mid-lateral posterior support portions 3171 is provided by another means. For example, the mid-lateral posterior support portions 3171 may comprise a different material to adjacent portions of the seal-forming structure 3100, such as a silicone material with a higher durometer hardness value or another material stiffer than the central portion 3111.

In some examples of the present technology, the mid-lateral posterior support portions 3171 are wedge-shaped. As shown in FIGS. 9A-9H and 19A-19F, each of the pair of mid-lateral posterior support portions 3171 has a wedge shape. The mid-lateral posterior support portions 3171 may have one or more curved sides. The curvature of the sides of each mid-lateral posterior support portion 3171 may match the curvature of corresponding sides of a respective mid-lateral portion 3121. Each mid-lateral posterior support portion 3171 may have a medial side that is narrower than a lateral side, for example the medial side may terminate in a point. This point may be a junction between the mid-lateral posterior support portion 3171, the central portion 3111 and the respective lateral posterior region 3141.

The mid-lateral posterior support portions 3171 may be wedge-shaped, triangular, tear-drop-shaped, circular or another suitable shape.

The cushion modules 3150 illustrated in FIGS. 25A-25I, 26A-26I, 30A-30E, 31A-31D and 32A-32D do not include mid-lateral posterior support portions 3171 in the seal-forming structure 3100 in the same manner as the cushion modules 3150 shown in FIGS. 9A-9H or FIGS. 19A-19F. In other examples of the present technology, the cushion modules 3150 illustrated in FIGS. 25A-25I, 26A-26I, 30A-30E, 31A-31D and 32A-32D may comprise mid-lateral posterior support portions 3171.

5.3.3.8.8 Textile Portion

In the example cushion modules 3150 illustrated in FIGS. 7A-7H, 8A-8H, 9A-9H, 19A-19F, 25A-25I, 26A-26I, 30A-30E, 31A-31D and 32A-32D, the central portion 3111 of the seal-forming structure 3100 is formed from silicone. In other examples the central portion of the seal-forming structure 3100 is formed from a textile. FIGS. 16A-16D show a cushion module 3150 comprising a seal-forming structure 3100 having a posterior side formed from a textile. The anterior and lateral side portions of the seal-forming structure 3100 are formed from silicone and function as a support structure for the textile sealing surface of the seal-forming structure 3100, in this example of the present technology.

The textile material may comprise a laminate formed by one or more layers of non-textile material and a textile layer. In some examples the laminate may comprise an air-impermeable layer, which may be formed from silicone, TPE, TPU or the like, and a textile layer for contacting the patient's face. The textile material may be formed from a microfibre or polyurethane, for example. The textile material and textile seal may be as described in Australian Patent Application No. 2018903752 or Australian Patent Application No. 2018904886, for example, the entire contents of each of which are incorporated by reference.

In some forms, the textile may comprise a material formed of a network of fibres and being adapted such that it is air impermeable. For example, the textile can have an air impermeable film on at least one surface thereof.

In use, the textile portion of the seal-forming structure 3100 may be maintained in sealing contact with the patient's face by 1) a resilient stretch characteristic of the material; 2) a reactive stress of the support structure; and/or 3) air pressure within the plenum chamber 3200 against an inside surface of the textile portion. Each of these factors may contribute to the textile portion being under constant tension such that the textile portion complies to the anthropometric contours of the patient's face, thereby minimizing wrinkles or blow-out and maximizing the contact area of the textile portion.

In some examples, the textile portion of the seal-forming structure 3100 may be a thin, compliant, stretchable, elastic material (e.g., microfiber or polyurethane). The textile portion may be held taut and in tension by the support structure prior to and during use. The textile portion may be molded or otherwise attached (e.g., adhered, glued) to the support structure so that the textile portion is pre-tensioned (slightly stretched) so that there are no wrinkles in the material of the textile portion. This may be advantageous in ensuring that the textile portion forms a smooth and continuous seal on the patient's face without any folded sections through which air may leak. Further, the textile portion may be shaped or have curvature imparted thereto, e.g., by thermoforming, so that the textile portion holds its own shape.

The textile portion of the seal-forming structure 3100 may be constructed from a single or a plurality of layers of material (e.g., textile and non-textile materials). The material of the textile portion may exhibit a low spring constant (i.e., highly compliant) in both warp and weft. Unlike conventional masks (e.g., silicone sealing membrane), where a fixed cushion may cause a patient's skin to distort to form an effective seal, the material of the textile portion may have a material spring constant and spring length (i.e., the amount of material available to stretch) such that the material is more compliant than the patient's skin so as to more readily conform to the patient's facial features. This may improve comfort of the mask and reduce formation of localized pressure "hot spots" on the patient's face.

Compared to conventional silicone membranes and compression foam seals, the textile portion of the seal-forming structure 3100 of the present technology has a more flexible structural stiffness and therefore has a dynamic spring back characteristic that enables the textile portion to recover more quickly when disturbed by an external force. Further, due to the lower structural stiffness a smaller seal force is required allowing the sealing portion to be more comfortable and create less facial marks during use.

The material of the textile portion may exhibit variable tension forces across the material (e.g., less tension forces proximal to holes or in wider stretches of material). In some forms, the surface of the material of the textile portion that contacts the patient's face may have low friction characteristics (e.g., a low friction finish), which may advantageously improve compliance of the material with the patient's face while also improving patient comfort.

The material of the textile portion of the seal-forming structure 3100 may also comprise at least one layer that exhibits substantially air-impermeable characteristics, while maintaining the resilient stretch characteristics necessary for comfort and minimal pressure points. That is, a membrane layer or laminate film layer (e.g., a polymer such as silicone, polyurethane, polyester, nylon, etc.) may be applied to the textile material to provide a substantially air-tight material. In an alternative example, the fibers of a textile may be tightly weaved to create a substantially air impermeable material.

In some forms, the material of the sealing portion may have a thickness of 0.275 or less (e.g., 0.275 to 0.075 mm, 0.275 to 0.175 mm, 0.25 mm or less, 0.225 mm or less, 0.225 to 0.09 mm, 0.225 to 0.095 mm, 0.225 mm, or 0.25 mm). The membrane layer may have a thickness of 0.03 to 0.01 mm (e.g., 0.015, 0.02 mm, or 0.025 mm). The material of the sealing portion with the membrane layer may have an overall thickness of 0.305 mm or less (e.g., 0.305 to 0.085 mm, 0.305 to 0.185 mm, 0.28 mm or less, 0.255 mm or less, 0.255 to 0.10 mm, 0.255 to 0.105 mm, 0.25 mm, or 0.275).

Tensile forces may also be transferred to the textile portion as a result of the stiffness and resilient properties of the support structure provided by the anterior and lateral side portions of the seal-forming structure 3100. The support structure in various forms may be formed from a variety of materials, including silicone, foam (e.g., polyurethane foam), polyurethane solid material, thermoplastic elastomers (TPE) (e.g., thermoplastic polyurethane (TPU)), and suitable plastic materials. The support structure may be configured so as to create a number of different cushion configurations, including a single air assisted sealing portion (e.g., textile membrane) and a sealing portion with underlying cushion support layer(s) such as a double air assisted sealing portion (e.g., dual textile membranes), a sealing portion with compression support (e.g., open cell foam, polyurethane foam, gel), a sealing portion with TPU, TPE or silicone support, or a double air assisted sealing portion with additional support (e.g., dual textile membranes wherein the inner membrane has a foam laminate layer (e.g., open cell, polyurethane) or a TPU, TPE, polyurethane or silicone moulded layer thereon).

The underlying cushion layer(s) may assist in optimizing the textile portion contact surface area with the patient's face. Further, in examples where the sealing portion is constructed from a breathable material (e.g., a breathable textile), the underlying cushion layer(s) may provide sufficient contact area behind the sealing portion to adequately seal the sealing portion against the patient's face and prevent leakage.

In some forms of the present technology, in use, engagement of the patient's face with the textile portion may create a temporary strain force that tends to pull the lateral side walls of the support structure toward one another. The support structure will respond to the strain force with an outwardly pulling reaction force. The reaction force transfers more tension to the sealing portion by preferentially stretching the more compliant textile portion which creates a resultant spring force in the textile portion that is exerted on the patient's face. This may increase the ability for the textile portion to conform to, and form a good seal with, the patient's face.

In some examples, the support structure may comprise a gusset that utilizes the internal air pressure to dynamically support the support structure and sealing portion. A gusset in this context may be a portion of the support structure which is deformable either in response to external forces such as resulting from tube drag, the patient putting their face partially into their pillow or movement of the patient's head during sleep, and/or forces resulting from air pressure within the plenum chamber 3200. This type of gusset may comprise a folded portion configured to be at least partially unfolded by air pressure acting on the interior of the folded portion. This may advantageously provide further support of the sealing portion when under dynamic loads (e.g., tube drag).

The air pressure within the plenum chamber 3200 and acting against the inside surface of the textile portion of the seal-forming structure 3100 may also create tension in the textile portion such that the central portion 3111 may substantially fill depressed contours of a patient's face (e.g., around the sides of the nose). This may enable the compliant central portion 3111 to form a larger seal contact area on the patient's face. The tension in the textile portion created by the plenum chamber 3200 air pressure may also be advantageous in providing a continuous seal even when the mask is partially displaced from an optimal positioning on the patient's face, as the textile portion may partially inflate (i.e., a "hovercraft effect") due to the counter-force from the internal air pressure.

In examples where the material of the textile portion of the seal-forming structure 3100 is not under constant tension and is non-elastic, the sealing portion may still be maintained in sealing contact with the patient's face by the air pressure within the plenum chamber 3200 and form an improved air assisted seal with the patient's face that conforms dynamically to alterations/movements (i.e., "hovercraft effect") due to the sealing portion being thinner and having a lower structural stiffness than the support structure formed by the anterior and lateral sides of the seal-forming structure 3100.

The textile portion of the seal-forming structure 3100 may be integrated with the support structure of the seal-forming structure 3100 by molding or otherwise attaching the textile portion to the inner edge of the support structure. Thus, for example, an outer perimeter of the textile portion may be attached to the inner edge of the support structure such that the textile portion extends radially inwardly of the seal-forming structure beyond or to a further extent than the support structure. The inner edge of the support structure may be curved such that the textile portion may be slightly angled inwardly toward the mask interior. By attaching the sealing portion along the inner edge of the support structure, the sealing portion does not need to be folded or cut to blend around the corners of the support structure. This may advantageously reduce the occurrence of protruding folds or wrinkles in the textile portion, which may cause leakage, thereby improving the performance of the seal.

In some forms, the textile portion may have a removable or modular structure. For example, the textile portion may be attached to a more rigid supporting frame structure along its perimeter. The supporting frame may be removably attached as a module to a support structure formed by the seal-forming structure 3100 or chassis portion 3210. The textile portion may be attached to the supporting frame so as to reduce the occurrence of protruding folds or wrinkles in the textile surface. The modular arrangement may also substantially simplify the manufacturing of the sealing portion (e.g., textile sealing portion) as complex bonding can be done in a simple unstressed state. While the textile portion may be treated to have substantially self-cleaning properties, the use of a modular sealing portion may also provide a cheaper and more hygienic alternative.

The textile portion of the seal-forming structure 3100 may have underlying cushion support layer(s) (e.g., second, third or more cushion layers) incorporated therein. The underlying cushion layer(s) may provide additional flexibility and allow the cushion to be suitable for use by most patient faces (e.g., one size fits most). For example, the textile portion may be structured as a double air assisted sealing portion (e.g., dual textile membranes), a textile portion with compression support layer(s) (e.g., open cell foam, polyurethane foam, gel), a textile portion with TPU, TPE or silicone support layer(s), or a double air assisted textile portion with additional support layer(s) (e.g., dual textile membranes wherein the inner membrane has a foam laminate layer (e.g., open cell, polyurethane) or a TPU, TPE, polyurethane or silicone molded layer thereon).

In some examples, the support layers may be supported by a rigid structure such as plastic, e.g., polypropylene (PP), polycarbonate (PC), polyamide (PA), or polyethylene terephthalate (PET).

In some forms, the seal-forming structure 3100 is constructed so as to stretch elastically in at least one dimension. For example, when a textile seal-forming structure is constructed from a network of fibres, the seal-forming structure may be capable of elongating in either, or both of, a longitudinal warp direction or a lateral weft direction across the textile. In some forms, a textile seal-forming structure 3100 is constructed so as to elongate elastically to an extent greater than that achievable by conventional silicone seal-forming structure.

In some forms, the seal-forming structure 3100 is constructed so as to be substantially inelastic in at least one dimension. For example, when a textile seal-forming structure is constructed from a woven textile, the seal-forming structure may be capable of substantially resisting elongation in either, or both of, a longitudinal warp direction or a lateral weft direction across the textile.

Illustrated in FIGS. 16A-16D is an example cushion module 3150 in which the central portion 3111 of the cushion module 3150 is formed from a textile material. The lateral and anterior sides of the cushion module 3150 are formed from silicone, in this example. The chassis portion 3210 is formed from silicone. The anterior-facing and lateral-facing surfaces of the seal-forming structure 3100 are formed from silicone, which supports the more flexible textile material. In general, the patient contacting surfaces are formed from a textile material and the non-patient contacting surfaces are formed from a silicone material.

The silicone portions of the cushion module 3150 shown in FIGS. 16A-16D may include any one or more of the features of the cushion module described with reference to FIGS. 8A-8H, 9A-9H, 19A-19F, 20, 25A-25I, 26A-26I, 30A-30E, 31A-31D and 32A-32D such as one or more of the decoupling portions 3142, rigidising portions 3161, thick posterior corner portions 3131, inferior portion 3113 and superior portion 3114 of a central anterior portion 3115, superior portion 3126 and inferior portion 3127 of mid-lateral anterior portions 3125, anterior portion 3133 and posterior portion 3134 of a lip superior portion 3116 and/or chassis superior reinforcing portions 3220. The cushion module 3150 shown in FIGS. 16A-16D may also comprise a vent module 3410 defining one or more vent(s) 3400 (not shown in FIGS. 16A-16D) having any one or more of the features described with reference to the vent module 3410 and vents 3400 of the cushion module 3150 shown in FIGS. 8A-8H and 14A-14D. In some examples, the textile portion of the seal-forming structure 3100 shown in FIGS. 16A-16D may be provided to any of the cushion modules 3150 shown in FIGS. 8A-8H, 9A-9H, 19A-19F, 25A-25I, 26A-26I, 30A-30E, 31A-31D and 32A-32D. In some examples the textile portion may occupy the regions occupied by the central portion 3111 and mid-lateral portions 3121 of the seal-forming structure 3100 shown in FIGS. 8A-8H, 9A-9H, 19A-19F, 25A-25I, 26A-26I, 30A-30E, 31A-31D and 32A-32D.

5.3.4 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use. The vent 3400 may provide a continuous vent flow of gas from the interior of the plenum chamber 3200 to ambient throughout the patient's respiratory cycle.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel such as elbow 3610. In the example shown in FIGS. 7A-7G, the patient interface 3000 comprises a plurality of vents 3400. In particular, the patient interface 3000 comprises at least one vent 3400 in the plenum chamber 3200 and at least one vent in the elbow 3610. Each vent 3400 may comprise an array of holes. The vents 3400 of the patient interface 3000 are sized and configured to provide sufficient gas washout throughout a range of therapeutic pressures.

5.3.4.1 Vent Module

As discussed above, the chassis portion 3210 may be rigidised with a vent module 3410 which comprises a vent 3400. A vent module may be a part of the patient interface 3000 that acts to vent exhaled gases to atmosphere. The vent module may be removable from the other parts of the patient interface 3000 for cleaning, replacement, storage and/or inspection or for any other reason the patient or clinician may need to separate a part of the patient interface 3000 comprising a vent 3400 from the rest of the patient interface 3000.

In some examples, the patient interface 3000 may comprise multiple vents 3400, each provided by a separate vent module 3410. In other examples of the present technology, the patient interface 3000 may comprise a single vent 3400 provided in a single vent module 3410. In further examples, the patient interface 3000 may comprise at least two vents 3400, one of which is provided in a vent module 3410 and another of which is not. For example, the patient interface 3000 may comprise a vent module 3410 comprising a first vent 3400, and the patient interface 3000 may comprise a second vent 3400 elsewhere on the patient interface 3000.

In some examples of the present technology, a vent module 3410 may serve more than one function. In some examples a vent module 3410 may allow gas washout, and may also function as a rigidiser. In some examples a vent module 3410 may comprise multiple parts. The multiple parts may or may not be separable. In other examples, a vent module 3410 may be formed from a single part.

In some examples of the present technology, the vent module 3410 of the patient interface 3000 may be configured to diffuse the flow of exhaust gas through the vent 3400. The vent module 3410 may comprise a diffuser.

FIGS. 14A-14D show a vent module 3410 according to one example of the present technology. The vent module 3410 comprises a vent 3400 of the patient interface 3000. In this example, the cushion module 3150 comprises the vent module 3410. The vent module 3410 is coupled to the chassis portion 3210 of the vent module 3410. The vent module 3410 is provided to an anterior side portion of the chassis portion 3210. The chassis portion 3210 of the cushion module 3150 is formed from a flexible material. The vent module 3410 in this example, rigidises the chassis portion 3210 of the cushion module 3150 in the sense that, when the vent module 3410 is provided to the chassis portion 3210, the chassis portion 3210 is made more rigid although still retains a level of flexibility in order to deform to an extent when the patient interface 3000 is donned by a patient. As discussed above, some flexibility in the chassis portion 3210 is desirable as it may enable the cushion module 3150 to fit to a wider range of patients than if the chassis portion 3210 is substantially inflexible. The vent module 3410 may make the chassis portion 3210 stiffer than it would be if the entire chassis portion 3210 was formed from silicone or another elastomeric material. The vent module may be formed from a substantially rigid material such as polycarbonate, polypropylene, nylon or the like.

As shown in FIGS. 8A-8H and discussed above, the chassis portion 3210 of the cushion module 3150 comprises an anterior hole 3215. The anterior hole 3215 is configured to receive the vent module 3410. The vent 3400 is formed in the vent module 3410. The cushion modules 3150 shown in FIGS. 19A-19F, 25A-25I and 26A-26I also comprise an anterior hole 3215 and are also configured to receive the vent module 3410.

As shown in FIGS. 14A-14D, the vent 3400 comprises a plurality of vent holes through which a continuous flow of gases exhaled by the patient pass from the interior of the plenum chamber 3200 to ambient. In this example, the vent holes of the vent 3400 are formed in the vent module 3410. In this example, the plurality of vent holes comprises upstream vent holes 3411 and downstream vent holes 3412, 3414. An exhaust flow of gas through the vent 3400 passes through the upstream vent holes 3411 and then the downstream vent holes 3412, 3414. The plurality of downstream vent holes may comprise one or more superior vent holes 3412 and one or more inferior vent holes 3414. In other examples of the present technology, the vent module 3410 may not comprise both upstream and downstream vent holes and may comprise a single vent hole or multiple vent holes in parallel with each other rather than in series.

The superior vent holes 3412 may be configured to direct exhaust gas in a direction 3416 at an angle towards the superior with respect to an axis 3415, as shown in FIG. 14D, which may be identified as an upward angle. The axis 3415 may be normal to an anterior face of the vent module 3410. The inferior vent holes 3414 may be configured to direct exhaust gas in a direction 3417 at an angle towards the inferior with respect to the axis 3415, which may be identified as a downward angle. The angle towards the superior, between the direction 3416 and the axis 3415, may be larger than the angle towards the inferior, between the direction 3417 and the axis 3415.

The sum of the angle towards the superior and the angle towards the inferior may be within the range of 60-100 degrees. In some forms, the sum of the angle towards the superior and the angle towards the inferior is within the range of 70-90 degrees. For the vent module 3014 shown in FIGS. 14A-14D, the sum of the angle towards the superior and the angle towards the inferior is substantially 80 degrees.

A large angle between the direction at which the superior vent holes 3412 discharge exhaust gas and the direction at which the inferior vent holes 3414 discharge exhaust gas may advantageously allow for good dispersion of the exhaust gas, avoid all of the exhaust gas being discharged in the same direction and reduce noise. The larger angle towards the superior between the direction 3416 and the axis 3415 in comparison to the angle towards the inferior between the direction 3417 and the axis 3415 minimises the amount of exhaust gas impinging on the patient's lips, which could be irritating.

As shown in FIGS. 14A and 14B, the plurality of downstream vent holes comprises a pair of superior vent holes 3412. Additionally, the plurality of downstream vent holes comprises a pair of inferior vent holes 3414. In other examples of the present technology, there may be only one superior vent hole 3412 and only one inferior vent hole 3414. In further examples there may be three or more superior and inferior vent holes on the downstream side of the vent module 3410. In some examples the vent module 3410 may comprise only one upstream vent hole. Additionally, in some examples the vent module 3410 may comprise only one downstream vent hole.

The vent module 3410 may comprise a diffuser configured to diffuse the exhaust flow of gas and/or muffle the vent 3400. As shown in FIG. 14D, the vent module 3410 supports a diffuser 3420 through which the continuous flow of gases exhaled by the patient is able to pass when flowing to ambient. The vent module 3410 is configured to allow the continuous flow of gases exhaled by the patient from the interior of the plenum chamber 3200 to ambient to pass into and out of the diffuser 3420 after passing through the upstream vent holes 3411. Additionally, the vent module 3410 is configured to allow the continuous flow of gases exhaled by the patient from the interior of the plenum chamber 3200 to ambient to pass into and out of the diffuser before passing through the downstream vent holes 3412, 3414. Additionally, the vent module 3410 is configured to allow the continuous flow of gases exhaled by the patient from the interior of the plenum chamber 3200 to ambient to pass by the diffuser 3420 without flowing through the diffuser 3420. Advantageously, as the exhaust gases need not flow through the diffuser 3420 to pass through the downstream vent holes, the exhaust gas is still able to pass through the downstream vent holes if the diffuser 3420 becomes clogged. This allows for exhaust gas washout even if the diffuser 3420 is clogged and does not allow gas to flow therethrough.

The diffuser 3420 may be formed from felt, foam or any suitable network of fibres configured to allow gas to flow therethrough but force the gas to flow through a torturous path.

As described above, the vent module 3410 is configured to be fitted to the chassis portion 3210 of the cushion module 3150.

In other examples of the present technology the vent module 3410 may comprise a plurality of vent holes but no diffuser material. In further examples the vent module 3410 may comprise a meshed structure through which the exhaust gas is able to flow, with or without diffuser material.

5.3.5 Conduit Decoupling Structure(s)

In one form the patient interface 3000 includes at least one conduit decoupling structure, for example, a swivel or a ball and socket to decouple a conduit connected to the patient interface 3000 from components of the patient interface 3000. In one example, the conduit decoupling structure decouples a conduit from the positioning and stabilising structure 3300. The conduit decoupling structure may advantageously at least partially decouple the patient interface 3000 from tube drag forces during use. This may result in greater comfort and stability than if no conduit decoupling structure is provided.

For example, the patient interface 3000 shown in FIGS. 7A-7G comprises an elbow 3610 configured the swivel with respect to the positioning and stabilising structure 3300. In this example the elbow 3610 is configured to swivel about an axis concentric with a circular opening in the positioning and stabilising structure 3300. In some examples of the present technology, the elbow 3610 may form part of a ball and socket joint to the positioning and stabilising structure 3300. For example, a ring having a partially spherical inner surface may be provided to the positioning and stabilising structure 3300 and may be configured to receive the elbow 3610. The elbow 3610 may have partially spherical outer surface complimentary to the partially spherical inner surface of the ring, thereby enabling the elbow 3610 to swivel with respect to the ring in a plurality of axes.

5.3.6 Connection Port

Connection port 3600 allows for connection to the air circuit 4170. In the exemplary patient interface 3000 shown in FIGS. 7A-7G, the connection port 3600 is provided to the elbow 3610. The elbow 3610, as a decoupling structure, decouples movement of the air circuit 4170 from the positioning and stabilising structure 3300 in order to reduce tube drag on the positioning and stabilising structure 3300.

5.3.7 Forehead Support

In one form, the patient interface 3000 includes a forehead support 3700. In other forms, the patient interface 3000 does not include a forehead support. Advantageously, the exemplary patient interface 3000 shown in FIGS. 7A-7G comprises a positioning and stabilising structure 3300 that is able to hold the seal forming structure 3100 in sealing position without connection to a forehead support or any frame or strap members that lie in front of the patient's face at eye level.

5.3.8 Anti-Asphyxia Valve

In one form, the patient interface 3000 includes an anti-asphyxia valve. In some examples, the patient interface 3000 includes a plurality of anti-asphyxia valves.

5.3.9 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

5.4 RPT Device

An RPT device 4000 in accordance with one aspect of the present technology comprises mechanical, pneumatic, and/or electrical components and is configured to execute one or more algorithms, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 $cmH_2O$, or at least 10$cmH_2O$, or at least 20 $cmH_2O$.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller, a therapy device controller, a pressure generator 4140, one or more protection circuits, memory, transducers 4270, data communication interface and one or more output devices. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The impellers may be located in a volute. The blower 4142 may be supported in a blower housing 4100. The blower may be capable of delivering a supply of air, for example at a rate of up to about 120 litres/minute, at a positive pressure in a range from about 4 $cmH_2O$ to about 20 $cmH_2O$, or in other forms up to about 30 $cmH_2O$. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller.

In other forms, a pressure generator 4140 may be a piston-driven pump, a pressure regulator connected to a high pressure source (e.g. compressed air reservoir), or a bellows.

Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller. One example of an air circuit 4170 comprising a heated wire circuit is described in U.S. Pat. No. 8,733,349, which is incorporated herewithin in its entirety by reference.

5.4.2 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.5 Humidifier 5.5.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.5.2 Humidifier Components 5.5.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.5.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.5.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

5.5.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

In one form of the present technology, an anti-spillback valve 4160 is located between the humidifier 5000 and the pneumatic block 4020. The anti-spillback valve is constructed and arranged to reduce the risk that water will flow upstream from the humidifier 5000, for example to the motor 4144.

5.6 Breathing Waveforms

FIG. 6 shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak −0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.7 Glossary

For the purposes of the present technology disclosure, in certain forms of the present technology, one or more of the following definitions may apply. In other forms of the present technology, alternative definitions may apply.

5.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. ‘Flow rate’ is sometimes shortened to simply ‘flow’ or ‘airflow’.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient’s respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient’s face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, g-f/$cm^2$ and hectopascal. 1 $cmH_2O$ is equal to 1 g-f/$cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.7.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.7.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

- 'Soft' materials may include silicone or thermo-plastic elastomer (TPE), and may, e.g. readily deform under finger pressure.
- 'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.7.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

5.7.3 Anatomy 5.7.3.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion.

5.7.3.2 Anatomy of the Skull

Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.7.3.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.7.4 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a nonairtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.7.5 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.7.5.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.7.5.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical-topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.7.5.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.7.5.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.8 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.9 REFERENCE SIGNS LIST

1000 Patient
1100 Bed partner
3000 Patient interface
3100 Sealing or seal-forming structure
3111 Central portion
3112 Saddle portion
3113 Inferior portion of the central anterior portion
3114 Superior portion of the central anterior portion
3115 Central anterior portion
3116 Lip superior portion
3117 Superior ridge of the seal-forming structure
3118 Bridge portion
3121 Mid-lateral portion
3122 Mid-lateral inferior portion
3123 Anterior portion of the mid-lateral inferior portion
3124 Posterior portion of the mid-lateral inferior portion
3125 Mid-lateral anterior portion
3126 Superior portion of the mid-lateral anterior portion
3127 Inferior portion of the mid-lateral anterior portion
3128 Medial portion of the mid-lateral anterior portion
3129 Lateral portion of the mid-lateral anterior portion
3131 Posterior corner portion
3133 Anterior portion of the lip superior portion
3134 Posterior portion of the lip superior portion
3141 Lateral posterior region
3142 Decoupling portion
**3142*a*** Lateral decoupling portion
**3142*b*** Medial decoupling portion
3143 Peripheral portion
**3143*a*** First peripheral portion
**3143*b*** Second peripheral portion
3146 Posterior portion of the lateral posterior region
3147 Anterior portion of the lateral posterior region
3148 Superior portion of the anterior portion of the lateral posterior region
3149 Inferior portion of the anterior portion of the lateral posterior region
3150 Cushion module
3161 Rigidising portion
3171 Mid-lateral support portion
3181 Chassis connection portion
**3181*a*** Outwardly facing surface of the chassis connection portion
**3181*b*** Inwardly facing surface of the chassis connection portion
3182 Projecting connector portion
3183 Outside shoulder

3183*a* Flat wall of the outside shoulder
3184 Inside shoulder
3185 Recess
3186 Clip base portion
3187 Clip arm
3188 Clip arm corner
3200 Plenum chamber
3210 Chassis portion
3212 Connection portion
3213 Superior ridge of the chassis portion
3214 Connector
3215 Anterior hole
3216 Locating feature
3220 Chassis superior reinforcing portion
3221 Chassis inferior reinforcing portion
3230 Lip
3241 Superior point
3242 Inferior point
3243 Chord
3272 Hole
3300 Positioning and stabilising structure/headgear
3302 Tube end connector
3304 Clip projection
3310 Strap
3314 Tube end
3318 Clip overmould
3320 Tab
3324 Lip
3350 Gas delivery tubes
3362 Extendable concertina structure
3363 Non-extendable tube section
3400 Vent
3410 Vent module
3411 Upstream vent hole
3412 Superior vent hole
3414 Inferior vent hole
3415 Axis
3416 Direction at an angle towards the superior
3417 Direction at an angle towards the inferior
3420 Diffuser
3430 Peripheral channel
3600 Connection port
3610 Elbow
4000 RPT device
4010 External housing
4012 Upper portion
4014 Lower Portion
4015 Panel
4016 Chassis
4018 Handle
4020 Pneumatic block
4100 Blower housing
4110 Air filter
4112 Inlet air filter
4114 Outlet air filter
4120 Muffler
4122 Inlet muffler
4124 Outlet muffler
4140 Pressure generator
4142 Blower
4144 Motor
4160 Anti spillback valve
4170 Air circuit
4180 Supplementary oxygen
4200 Electrical components
4202 Printed Circuit Board Assembly (PCBA)
4210 Electrical power supply
4220 Input devices
4270 Transducers
4272 Pressure sensors
4274 Flow rate sensors
5000 Humidifier
5002 Humidifier inlet
5004 Humidifier outlet
5006 Humidifier base
5110 Humidifier reservoir
5120 Conductive portion
5130 Humidifier reservoir dock
5135 Locking lever
5150 Water level indicator
5240 Heating element

The invention claimed is:

1. A cushion module for a patient interface comprising:

a chassis portion partially forming a plenum chamber pressurisable to a therapeutic pressure of at least 6 cmH2O above ambient air pressure, the chassis portion comprising a pair of laterally projecting connection portions, and each of the laterally projecting connection portions being configured to connect to one of a pair of gas delivery tubes and being sized and structured to receive a flow of air at the therapeutic pressure for breathing by a patient; and a seal-forming structure connected to the chassis portion and partially forming the plenum chamber, the seal-forming structure being constructed and arranged to seal with a region of the patient's face surrounding an entrance to the patient's airways, the seal-forming structure having at least one hole therein to deliver the flow of air at the therapeutic pressure to at least an entrance to the patient's nares, and the seal-forming structure is constructed and arranged to maintain the therapeutic pressure in the plenum chamber throughout the patient's respiratory cycle in use;

wherein the seal-forming structure comprises:

a central portion configured to seal in use against at least the patient's pronasale, nasal alae, and lip superior; and a pair of lateral posterior regions, each lateral posterior region positioned on a respective lateral posterior side of the seal-forming structure, each lateral posterior region comprising:

a decoupling portion positioned in a portion of the lateral posterior region that is configured to face away from and not contact the patient's face during use; and a peripheral portion positioned adjacent the decoupling portion such that, in use, at least part of the peripheral portion is positioned posterior to the decoupling portion and at least part of the peripheral portion is positioned anterior to at least part of the decoupling portion, wherein the decoupling portion is less stiff than the peripheral portion, and wherein each decoupling portion is positioned between the laterally projecting connection portion and the peripheral portion on a corresponding lateral posterior side of the seal-forming structure to at least partially decouple the central portion of the seal-forming structure from force applied by a corresponding one of the laterally projecting connection portions.

2. The cushion module of claim 1, wherein each peripheral portion is stiffer than the central portion of the seal-forming structure.

3. The cushion module of claim 1, wherein the decoupling portion of each lateral posterior region is stiffer than the central portion of the seal-forming structure.

4. The cushion module of claim 1, wherein a wall thickness of the peripheral portion of each lateral posterior region is greater than a wall thickness of the central portion of the seal-forming structure.

5. The cushion module of claim 4, wherein the wall thickness of the peripheral portion of each lateral posterior region is greater than a wall thickness of the decoupling portion of each lateral posterior region.

6. The cushion module of claim 5, wherein the wall thickness of the decoupling portion of each lateral posterior region is greater than the wall thickness of the central portion of the seal-forming structure.

7. The cushion module of claim 1, wherein the decoupling portion of each lateral posterior region is C-shaped when viewed from a lateral side of the seal-forming structure.

8. The cushion module of claim 1, wherein each of the peripheral portions partially or fully surrounds a respective decoupling portion.

9. The cushion module of claim 1, wherein each decoupling portion is recessed into an internal surface of the seal-forming structure within a respective lateral posterior region.

10. A patient interface comprising:

the cushion module of claim 1; and a positioning and stabilising structure comprising a strap and the pair of gas delivery tubes configured to provide a force to hold the seal-forming structure in a therapeutically effective position on the patient's head.

11. The cushion module of claim 1, wherein the chassis portion and the seal-forming structure are formed from a unitary piece of silicone.

12. The cushion module of claim 11, wherein the silicone comprises two silicones having different durometers.

13. The cushion module of claim 1, wherein the seal-forming structure is configured to leave the patient's mouth uncovered during use.

14. The cushion module of claim 1, wherein each lateral posterior region comprises a posterior corner portion configured to engage with the patient's face proximal to the patient's nasolabial sulci in use, and each posterior corner portion being positioned adjacent a respective one of the peripheral portions.

15. The cushion module of claim 14, wherein each of the decoupling portions has a curvature corresponding to a curvature of the seal-forming structure at a respective one of the posterior corner portions when viewed from a lateral side.

16. The cushion module of claim 14, wherein each of the peripheral portions comprises a curvature that follows a curvature of a respective one of the decoupling portions and a respective one of the posterior corner portions.

17. The cushion module of claim 1, wherein the chassis portion is formed from an elastomeric material, and wherein each laterally projecting connection portion comprises a first connector that is more rigid than the chassis portion and is configured to connect to a second connector on a respective one of the gas delivery tubes that is more rigid than the chassis portion.

18. The cushion module of claim 1, further comprising a vent module that is removably attachable to the chassis portion, the vent module comprising vent holes configured to allow a flow of gases exhaled by the patient from an interior of the plenum chamber to ambient, and the vent holes being sized and shaped to maintain the therapeutic pressure in the plenum chamber in use.

19. The cushion module of claim 18, wherein the vent module is configured to be more rigid than the chassis portion.

20. The cushion module of claim 1, wherein the central portion is configured to seal on an underside of the patient's nose without contacting a nasal bridge region of the patient's nose.

21. The patient interface of claim 10, wherein each gas delivery tube is configured to convey the flow of air from atop the patient's head to an interior of the chassis portion in use.

22. The cushion module of claim 1, wherein the chassis portion is formed from a flexible material.

23. The patient interface of claim 10, wherein the cushion module is removable from the positioning and stabilising structure.

* * * * *